United States Patent
Kim et al.

(10) Patent No.: US 9,831,445 B2
(45) Date of Patent: Nov. 28, 2017

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Haejin Kim, Yongin (KR); Samil Kho, Yongin (KR); Kwanghyung Kim, Yongin (KR); Youngkook Kim, Yongin (KR); Seokhwan Hwang, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 357 days.

(21) Appl. No.: 14/724,357

(22) Filed: May 28, 2015

(65) Prior Publication Data

US 2016/0172594 A1 Jun. 16, 2016

(30) Foreign Application Priority Data

Dec. 12, 2014 (KR) .................. 10-2014-0179366

(51) Int. Cl.
*H01L 51/00* (2006.01)
*C07F 5/02* (2006.01)
(Continued)

(52) U.S. Cl.
CPC ............ *H01L 51/008* (2013.01); *C07F 5/027* (2013.01); *C09K 11/06* (2013.01); *H01L 51/006* (2013.01);
(Continued)

(58) Field of Classification Search
None
See application file for complete search history.

(56) References Cited

U.S. PATENT DOCUMENTS 7,053,255 B2 5/2006 Ikeda et al.
7,233,019 B2 6/2007 Ionkin et al.
(Continued)

FOREIGN PATENT DOCUMENTS

EP 1142895 A1 10/2001
JP 2000-294373 A 10/2000
(Continued)

*Primary Examiner* — Robert S Loewe
(74) *Attorney, Agent, or Firm* — Lee & Morse, P.C.

(57) ABSTRACT

A condensed cyclic compound and an organic light-emitting device, the compound being represented by Formula 1 below:

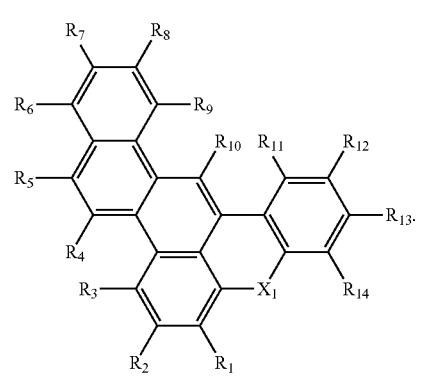

20 Claims, 1 Drawing Sheet

(51) Int. Cl.
*C09K 11/06* (2006.01)
*H01L 51/50* (2006.01)

(52) U.S. Cl.
CPC .. *H01L 51/0073* (2013.01); *C09K 2211/1007* (2013.01); *C09K 2211/1014* (2013.01); *C09K 2211/1088* (2013.01); *C09K 2211/188* (2013.01); *H01L 51/5012* (2013.01)

(56) References Cited

U.S. PATENT DOCUMENTS

| | | | |
|---|---|---|---|
| 8,324,802 B2 | 12/2012 | Matsuura et al. | |
| 2003/0157366 A1* | 8/2003 | Matsuura | C09K 11/06 428/690 |
| 2005/0156164 A1 | 7/2005 | Sotoyama | |
| 2005/0238910 A1 | 10/2005 | Ionkin et al. | |
| 2006/0052641 A1 | 3/2006 | Funahashi | |
| 2007/0237984 A1 | 10/2007 | Matsuura et al. | |
| 2009/0004485 A1 | 1/2009 | Zheng et al. | |
| 2010/0032658 A1 | 2/2010 | Lee et al. | |
| 2010/0052526 A1 | 3/2010 | Je et al. | |
| 2010/0277061 A1 | 11/2010 | Matsuura et al. | |
| 2011/0006289 A1 | 1/2011 | Mizuki et al. | |
| 2012/0056165 A1 | 3/2012 | Kawamura et al. | |
| 2013/0306958 A1 | 11/2013 | Ito et al. | |
| 2014/0346482 A1 | 11/2014 | Mizuki et al. | |
| 2015/0171337 A1* | 6/2015 | Jung | H01L 51/0058 257/40 |

FOREIGN PATENT DOCUMENTS

| | | |
|---|---|---|
| JP | 2007-123863 A | 5/2007 |
| JP | 4221050 B2 | 11/2008 |
| JP | 2013-63930 A | 4/2013 |
| JP | 2013-63931 A | 4/2013 |
| KR | 10-2005-0086518 A | 8/2005 |
| KR | 10-2006-0006760 A | 1/2006 |
| KR | 10-2009-0111355 A | 10/2009 |
| KR | 10-2010-0007780 A | 1/2010 |
| KR | 10-2010-0097182 A | 9/2010 |
| KR | 10-2011-0015213 A | 2/2011 |
| KR | 10-2011-0094271 A | 8/2011 |
| KR | 10-1132635 B1 | 4/2012 |
| WO | WO 2012/070226 A1 | 5/2012 |

* cited by examiner

| 10 |
|---|
| 190 |
| 150 |
| 110 |

CONDENSED CYCLIC COMPOUND AND ORGANIC LIGHT-EMITTING DEVICE INCLUDING THE SAME

CROSS-REFERENCE TO RELATED APPLICATION

Korean Patent Application No. 10-2014-0179366, filed on Dec. 12, 2015, in the Korean Intellectual Property Office, and entitled: "Condensed Cyclic Compound and Organic Light-Emitting Device Including The Same," is incorporated by reference herein in its entirety.

BACKGROUND

1. Field

Embodiments relate to a condensed cyclic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, may be recombined in the emission layer to produce excitons. These excitons change from an excited state to a ground state, thereby generating light.

SUMMARY

Embodiments are directed to a condensed cyclic compound and an organic light-emitting device including the same An aspect provides a condensed cyclic compound represented by Formula 1 below:

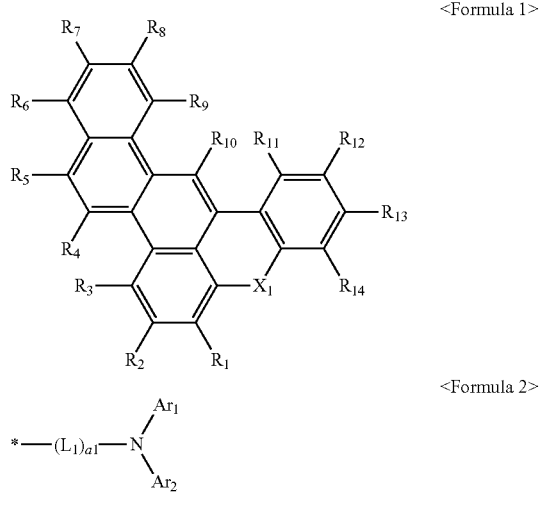

<Formula 1>

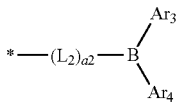

<Formula 3> wherein in Formulae 1 to 3, $X_1$ is O or S;

$L_1$ and $L_2$ are each independently selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

a1 and a2 may be each independently selected from 0, 1, 2 and 3, when a1 is 2 or more, two or more $L_1$ may be identical or different, and when a2 is 2 or more, two or more $L_2$ may be identical or different.

$Ar_1$ to $Ar_4$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

$R_1$ to $R_{14}$ may be each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

at least one selected from $R_1$ to $R_{14}$ is a group represented by Formula 2, and at least one selected from $R_1$ to $R_{14}$ is a group represented by Formula 3:

at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$cycloalkyl group, a $C_1$-$C_{10}$ heterocycloalkyl group, a $C_3$-$C_{10}$cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

Another aspect provides an organic light-emitting device that includes: a first electrode; a second electrode facing the first electrode; and an organic layer that is disposed between the first electrode and the second electrode and includes an emission layer, wherein the organic layer includes at least one of the condensed cyclic compound described above.

BRIEF DESCRIPTION OF THE DRAWING

Features will be apparent to those of skill in the art by describing in detail exemplary embodiments with reference to the attached drawings in which:

FIG. 1 illustrates is a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

A condensed cyclic compound according to an embodiment may be represented by Formula 1 below.

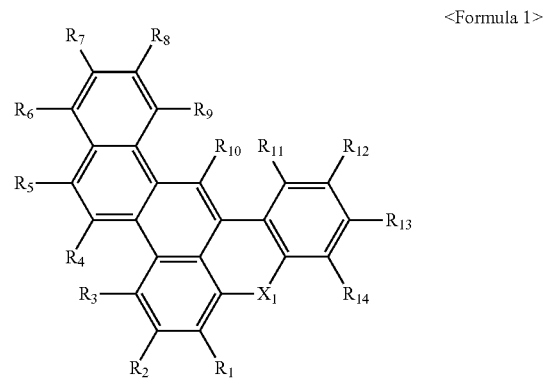

<Formula 1>

$X_1$ in Formula 1 may be, e.g., O or S. In an implementation, $X_1$ may be O.

$R_1$ to $R_{14}$ in Formula 1 may each independently be selected from or include, e.g., a group represented by Formula 2, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$).

In an implementation, at least one of $R_1$ to $R_{14}$ in Formula 1 may be a group represented by the following Formula 2, and at least one of $R_1$ to $R_{14}$ may be a group represented by the following Formula 3.

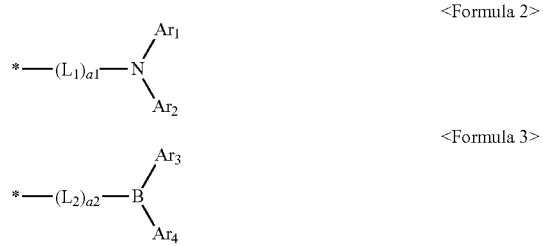

In Formulae 2 and 3, $L_1$ and $L_2$ may each independently be selected from or include, e.g., a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group.

For example, $L_1$ to $L_2$ in Formulae 2 and 3 may each independently be selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

In an embodiment, $L_1$ and $L_2$ in Formulae 2 and 3 may each independently be a group represented by one of the following Formulae 3-1 to 3-35.

Formula 3-1
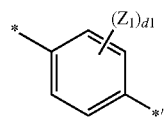

Formula 3-2
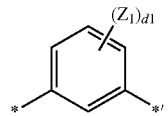

Formula 3-3
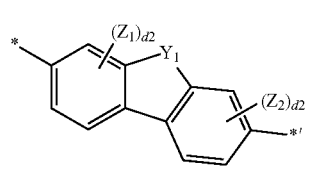

Formula 3-4
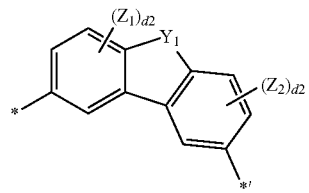

Formula 3-5
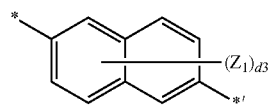

Formula 3-6
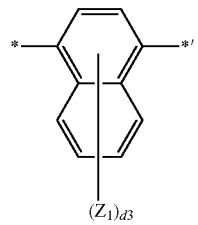

Formula 3-7
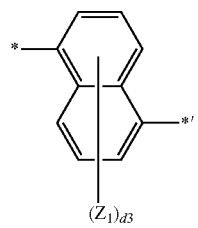

Formula 3-8
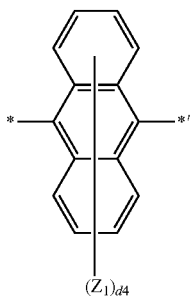

Formula 3-9
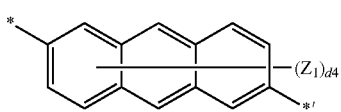

Formula 3-10
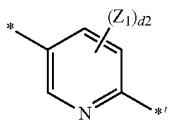

Formula 3-11
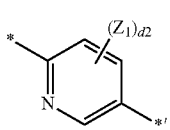

Formula 3-12
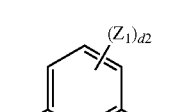

Formula 3-13
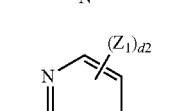

Formula 3-14
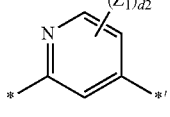

Formula 3-15
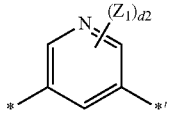

Formula 3-16
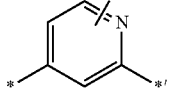

Formula 3-17

Formula 3-18
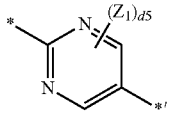

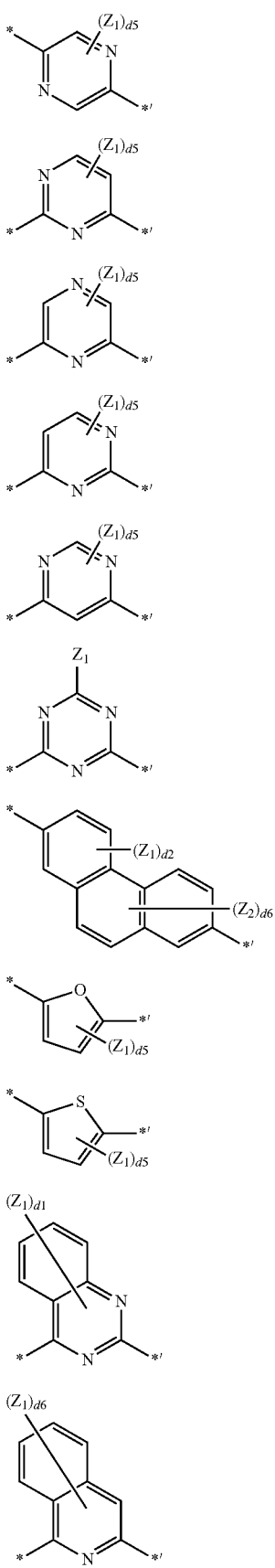
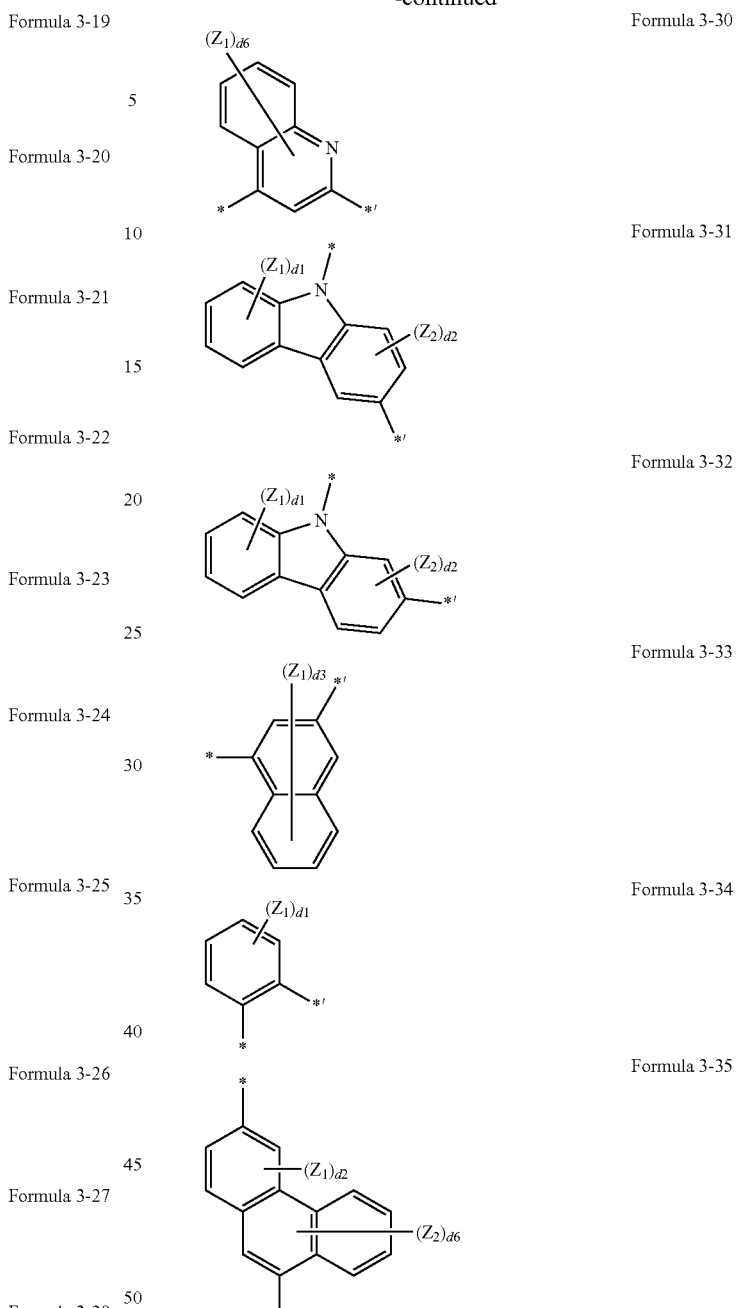

In Formulae 3-1 to 3-35, $Y_1$ may be, e.g., O, S, $C(Z_3)(Z_4)$, $N(Z_5)$, or $Si(Z_6)(Z_7)$;

$Z_1$ to $Z_7$ may each independently be selected from, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, d1 may be an integer selected from 1, 2, 3, and 4, d2 may be an integer selected from 1, 2, and 3, d3 may be an integer selected from 1, 2, 3, 4, 5, and 6, d4 may be an integer selected from 1, 2, 3, 4, 5, 6, 7, and 8, d5 may be 1 or 2, d6 may be an integer selected from 1, 2, 3, 4, and 5, and * and *' indicate binding sites to a neighboring atom.

In some embodiments, $L_1$ and $L_2$ in Formulae 2 and 3 may each independently be selected from:

a phenylene group, a naphthylene group, a pyridinylene group, a dibenzofuranylene group, and a dibenzothiophenylene group; and a phenylene group, a naphthylene group, a pyridinylene group, a dibenzofuranylene group, and a dibenzothiophenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C1-C10 alkyl group, a phenyl group, a naphthyl group, a pyridinyl group, a pyrimidinyl group, and a triazinyl group.

In some embodiments, $L_1$ and $L_2$ in Formulae 2 and 3 may each independently be a group represented by one of the following Formulae 4-1 to 4-29.

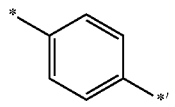

Formula 4-1


Formula 4-2

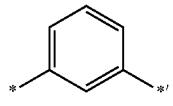

Formula 4-3

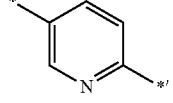

Formula 4-4

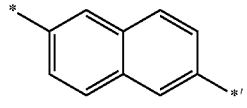

Formula 4-5

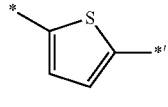

Formula 4-6

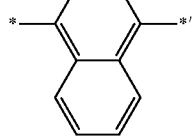

Formula 4-7

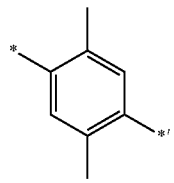

Formula 4-8

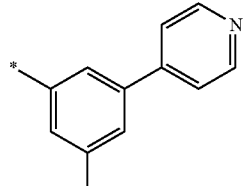

Formula 4-9

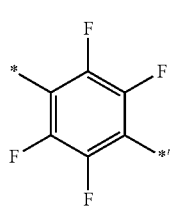

Formula 4-10

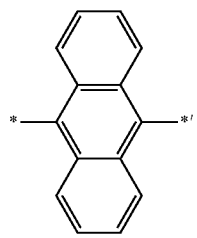

Formula 4-11

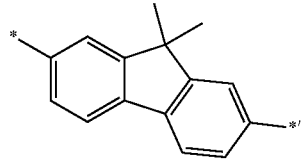

Formula 4-12

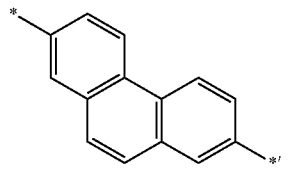

Formula 4-13

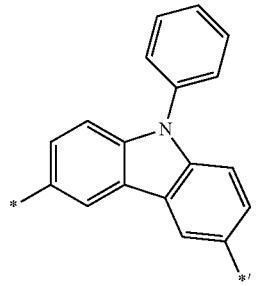

Formula 4-14

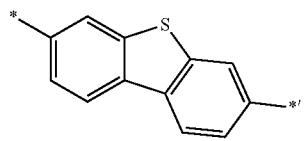

Formula 4-15

-continued

Formula 4-16
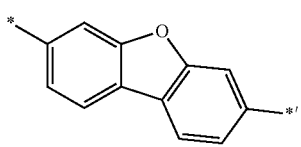

Formula 4-17
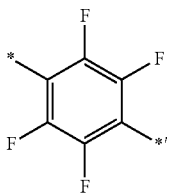

Formula 4-18
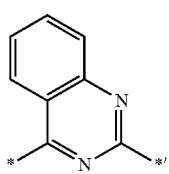

Formula 4-19
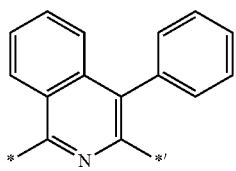

Formula 4-20
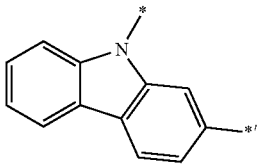

Formula 4-21
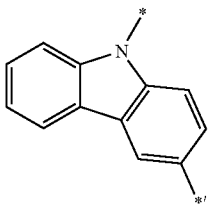

Formula 4-22
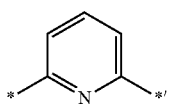

Formula 4-23
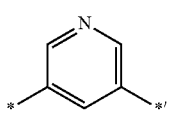

Formula 4-24
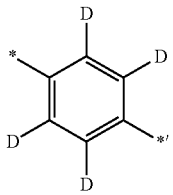

Formula 4-25
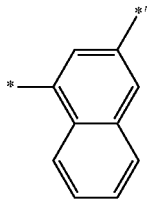

Formula 4-26
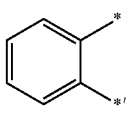

Formula 4-27
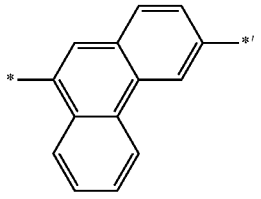

Formula 4-28
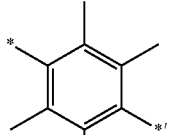

Formula 4-29
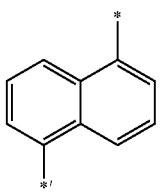

* and *' in Formulae 4-1 to 4-29 each indicate a binding site to a neighboring atom.

a1 and a2 in Formulae 2 and 3 may be selected from 0, 1, 2, and 3. a1 indicates the number of $L_1$ in Formula 2, and when a1 is 2 or more, a plurality of $L_1$ may be identical or different. For example, when a1 is 0, *-$(L_1)_{a1}$-*' is a single bond. a2 indicates the number of $L_2$ in Formula 3, and when a2 is 2 or more, a plurality of $L_2$ may be identical or different. When a2 is 0, *-$(L_2)_{a2}$-*' is a single bond. In some embodiments, a1 and a2 may be each independently 0, 1, or 2. In some embodiments, a1 and a2 may be each independently 0 or 1.

$Ar_1$ to $Ar_4$ in Formulae 2 and 3 may each independently be selected from or include, e.g., a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group.

For example, $Ar_1$ to $Ar_4$ in Formulae 2 and 3 may each independently be selected from:

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group), a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzosilolyl group), a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, a thiadiazolyl group, an imidazopyridinyl group, an imidazopyrimidinyl group, and —Si($Q_{31}$)($Q_{32}$)($Q_{33}$); and $Q_{31}$ to $Q_{33}$ may each independently be selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

In some embodiments, $Ar_1$ to $Ar_4$ in Formulae 2 and 3 may each independently be selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), $Q_{31}$ to $Q_{33}$ may each independently be selected from a $C_1$-$C_{10}$ alkyl group, a $C_1$-$C_{10}$ alkoxy group, a phenyl group, and a naphthyl group.

In some embodiments, $Ar_1$ to $Ar_4$ in Formulae 2 and 3 may each independently be selected from:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), $Q_{31}$ to $Q_{33}$ may each independently be selected from a $C_1$-$C_{10}$ alkyl group, a $C_1$-$C_{10}$ alkoxy group, a phenyl group, and a naphthyl group.

In an implementation, $R_1$ to $R_{14}$ in Formula 1 may each independently be selected from:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ may be each independently selected from a $C_1$-$C_{10}$ alkyl group, a $C_1$-$C_{10}$ alkoxy group, a phenyl group, and a naphthyl group.

For example, $R_1$ to $R_{14}$ in Formula 1 may each independently be selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;

a phenyl group, a naphthyl group, a pyrimidinyl group, and a triazinyl group;

a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si(Q)($Q_2$)($Q_3$), wherein $Q_1$ to $Q_3$ and $Q_{31}$ to $Q_{33}$ may each independently be selected from a $C_1$-$C_{10}$ alkyl group, a $C_1$-$C_{10}$ alkoxy group, a phenyl group, and a naphthyl group.

In an implementation, $Ar_1$ to $Ar_4$ may each independently be a group represented by one of the following Formulae 5-1 to 5-43.

In an implementation, $R_1$ to $R_{14}$ may each independently be selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), and a group represented by one of Formulae 5-1 to 5-43, and $Q_1$ to $Q_3$ may each independently be selected from a $C_1$-$C_{10}$ alkyl group, a $C_1$-$C_{10}$ alkoxy group, a phenyl group, and a naphthyl group.

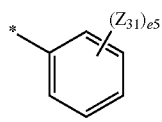

Formula 5-1

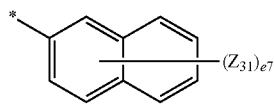

Formula 5-2

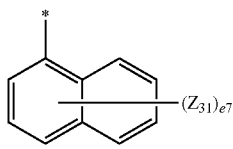

Formula 5-3

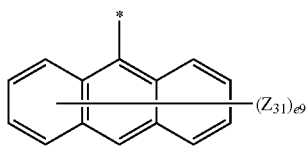

Formula 5-4

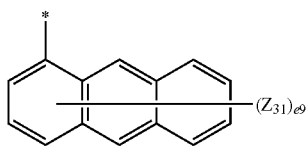

Formula 5-5

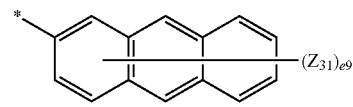

Formula 5-6

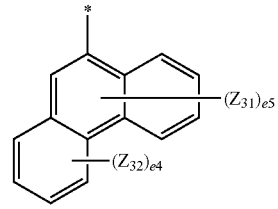

Formula 5-7

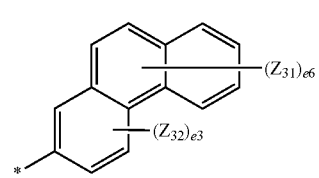

Formula 5-8

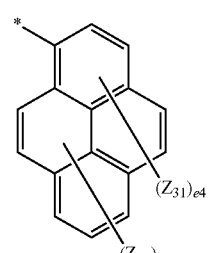

Formula 5-9

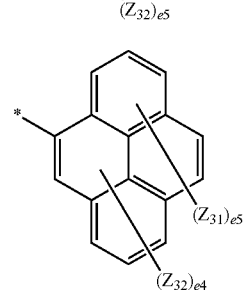

Formula 5-10

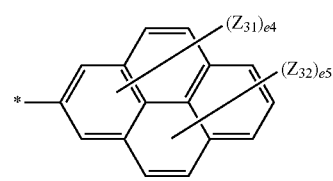

Formula 5-11

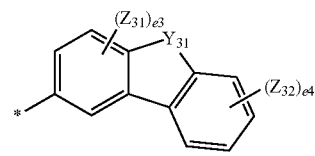

Formula 5-12

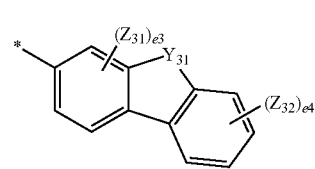

Formula 5-13

-continued
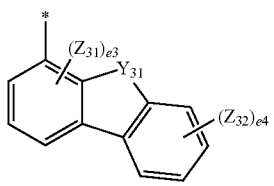
Formula 5-14
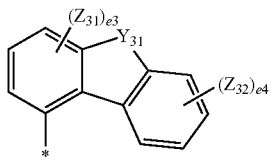
Formula 5-15
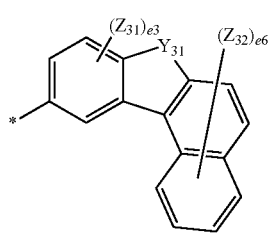
Formula 5-16
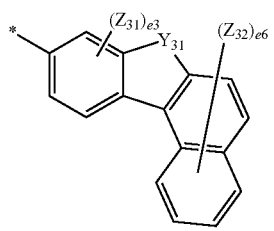
Formula 5-17
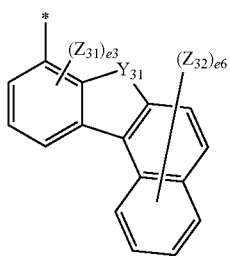
Formula 5-18
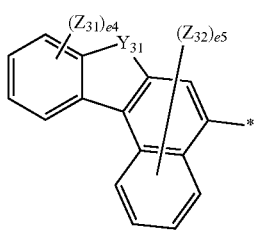
Formula 5-19
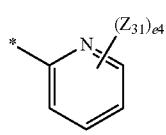
Formula 5-20
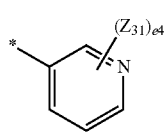
Formula 5-21
-continued
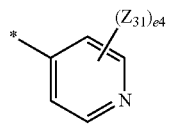
Formula 5-22
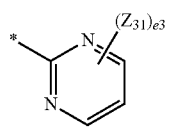
Formula 5-23
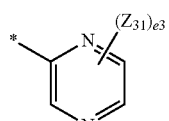
Formula 5-24
Formula 5-25
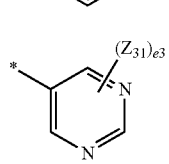
Formula 5-26
Formula 5-27
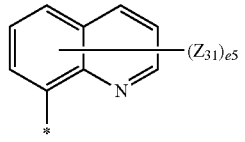
Formula 5-28
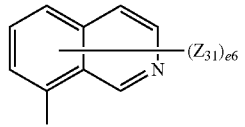
Formula 5-29
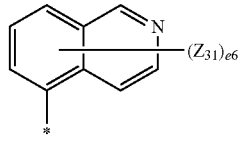
Formula 5-30
Formula 5-31
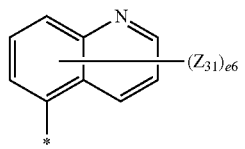
Formula 5-32

Formula 5-33

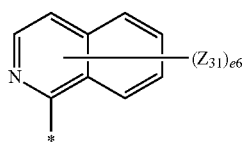
Formula 5-34

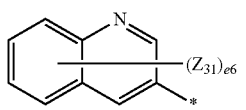
Formula 5-35

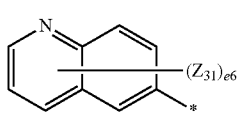
Formula 5-36

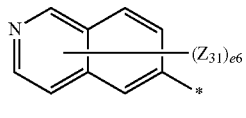
Formula 5-37

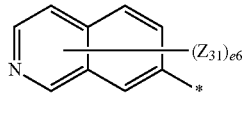
Formula 5-38

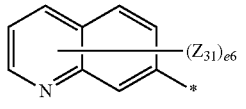
Formula 5-39

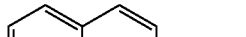
Formula 5-40

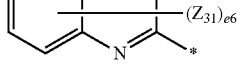
Formula 5-41

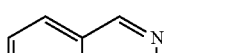
Formula 5-42

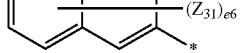
Formula 5-43

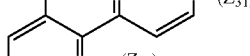

In Formulae 5-1 to 5-43, $Y_{31}$ may be O, S, $C(Z_{33})(Z_{34})$, $N(Z_{35})$, or $Si(Z_{36})(Z_{37})$;

$Z_{31}$ to $Z_{37}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e3 may be an integer selected from 1, 2, and 3, e4 may be an integer selected from 1, 2, 3, and 4, e5 may be an integer selected from 1, 2, 3, 4, and 5, e6 may be an integer selected from 1, 2, 3, 4, 5, and 6, e7 may be an integer selected from 1, 2, 3, 4, 5, 6, and 7, e8 may be an integer selected from 1, 2, 3, 4, 5, 6, 7, and 8, e9 may be an integer selected from 1, 2, 3, 4, 5, 6, 7, 8, and 9, and * indicates a binding site to a neighboring atom.

In some embodiments, regarding Formulae 1 to 3, $Ar_1$ to $Ar_4$ may each independently be a group represented by one of the following Formulae 6-1 to 6-40, and $R_1$ to $R_{14}$ may each independently be selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —$Si(Q_1)(Q_2)(Q_3)$, a phenyl group, a naphthyl group, a pyridinyl group, a pyrimidinyl group, and a triazinyl group, and $Q_1$ to $Q_3$ may be each independently selected from a $C_1$-$C_{10}$ alkyl group, a $C_1$-$C_{10}$ alkoxy group, a phenyl group, and a naphthyl group.

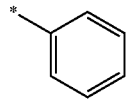
Formula 6-1

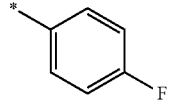
Formula 6-2

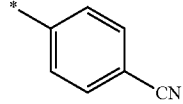
Formula 6-3

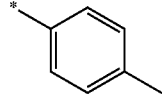
Formula 6-4

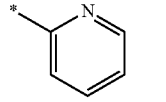
Formula 6-5

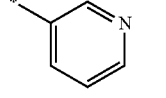
Formula 6-6

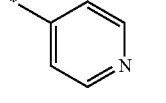
Formula 6-7

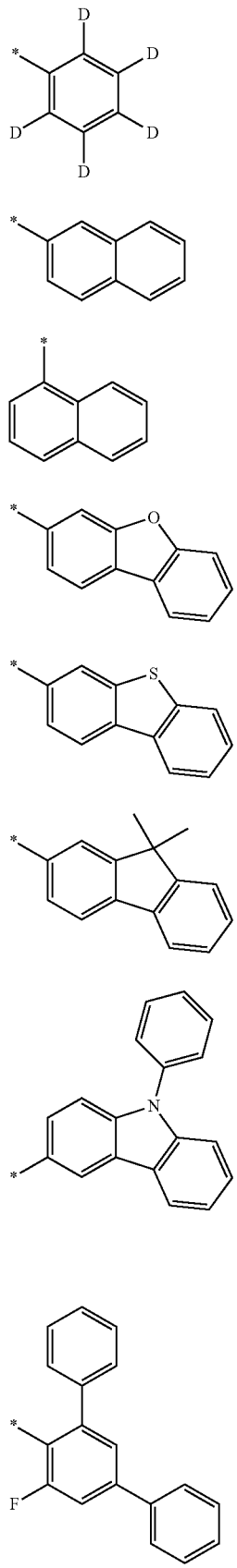
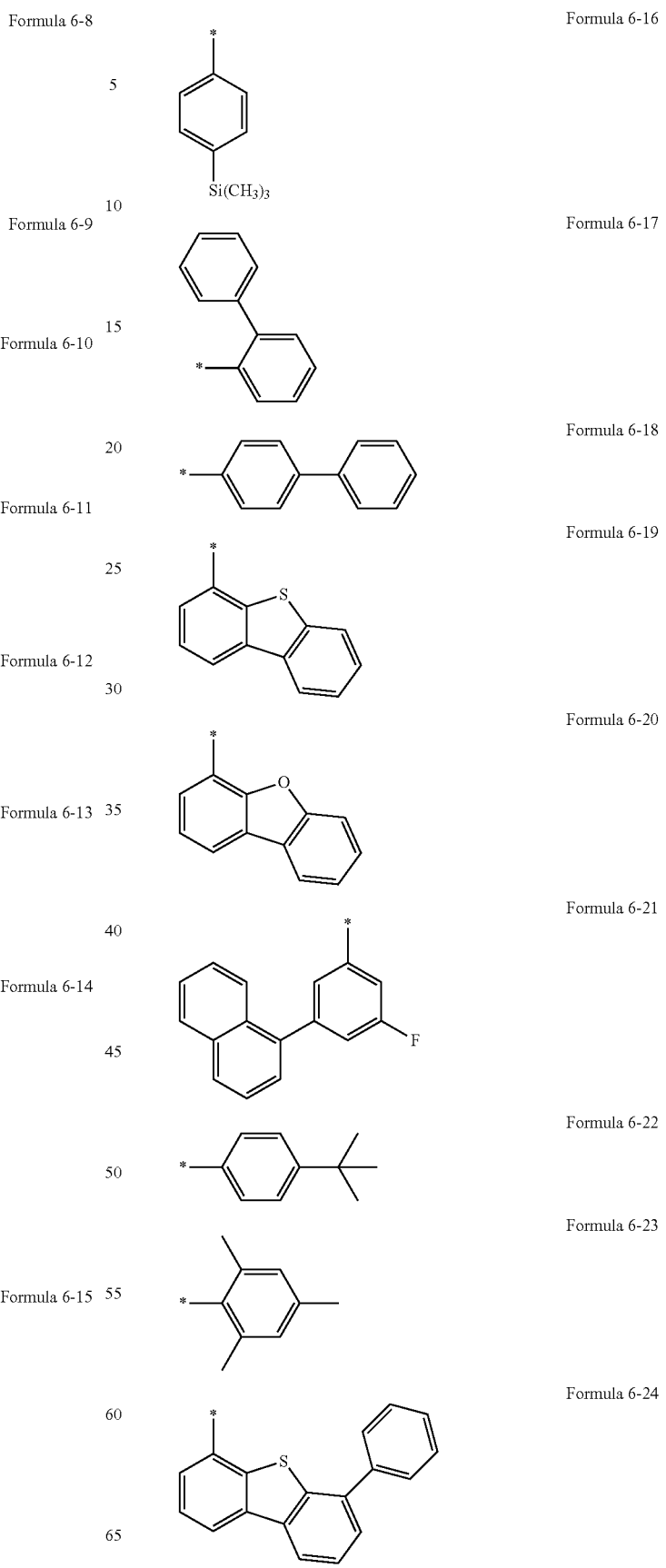

Formula 6-25 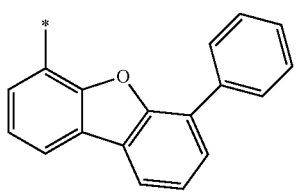

Formula 6-26 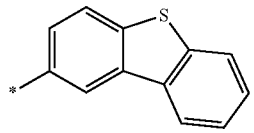

Formula 6-27 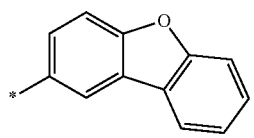

Formula 6-28 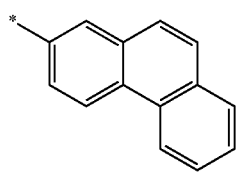

Formula 6-29 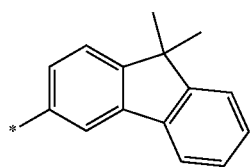

Formula 6-30 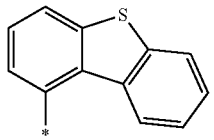

Formula 6-31 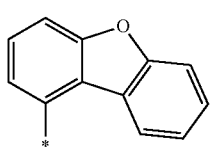

Formula 6-32 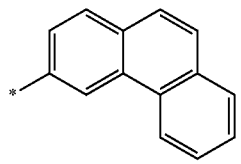

Formula 6-33 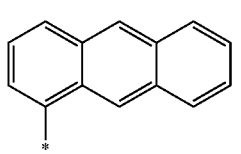

Formula 6-34 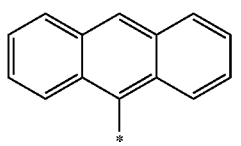

Formula 6-35 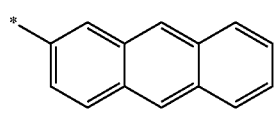

Formula 6-36 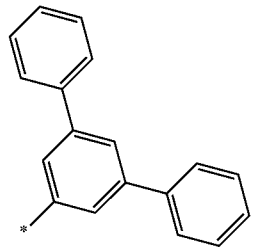

Formula 6-37 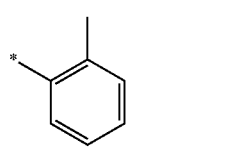

Formula 6-38 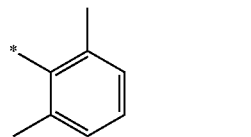

Formula 6-39 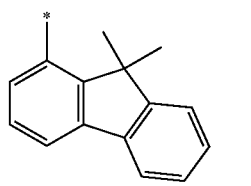

Formula 6-40 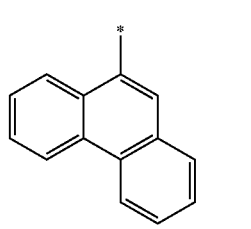

* in Formulae 6-1 to 6-40 indicates a binding site to a neighboring atom.

In an implementation, two substituents of $R_1$ to $R_{12}$ in Formula 1 may each independently be selected from a group represented by Formula 2 and a group represented by Formula 3.

For example, the condensed cyclic compound represented by Formula 1 may be represented by one of the following Formulae 1-1 to 1-8.

<Formula 1-1>
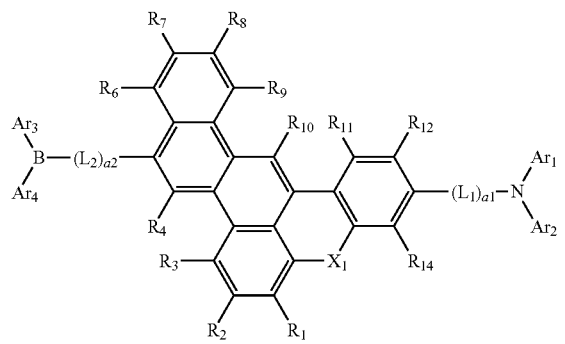
<Formula 1-2>
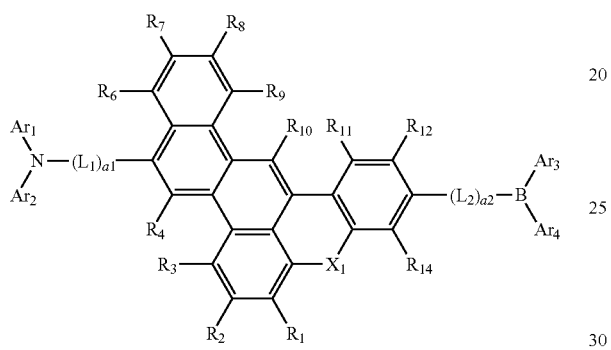
<Formula 1-3>
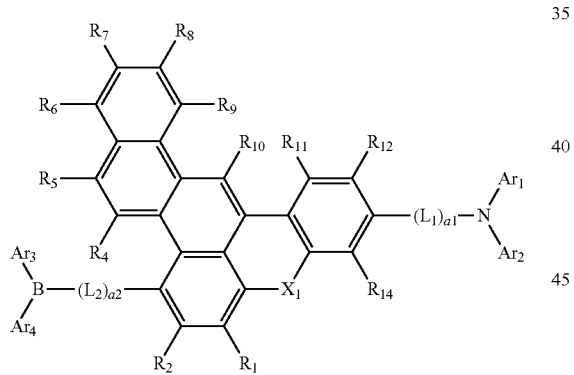
<Formula 1-4>
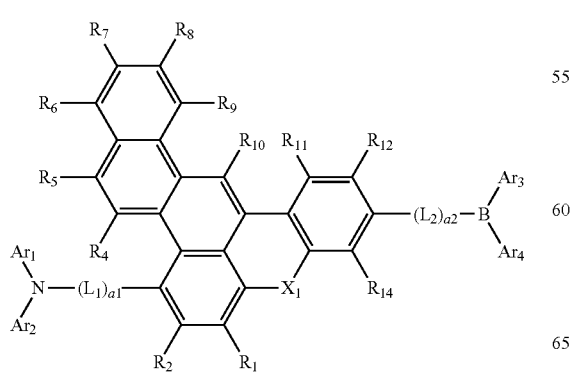
<Formula 1-5>
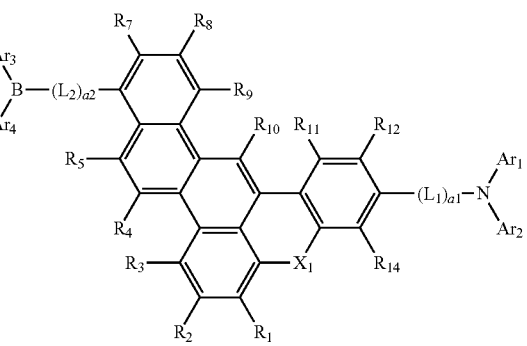
<Formula 1-6>
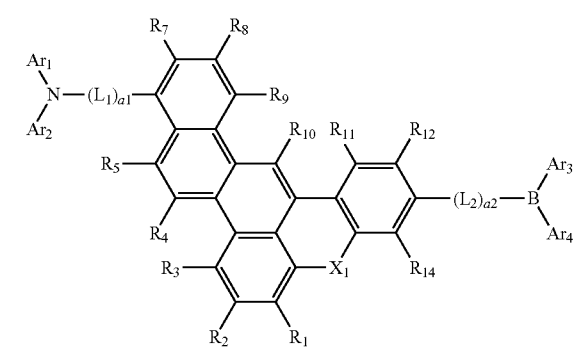
<Formula 1-7>
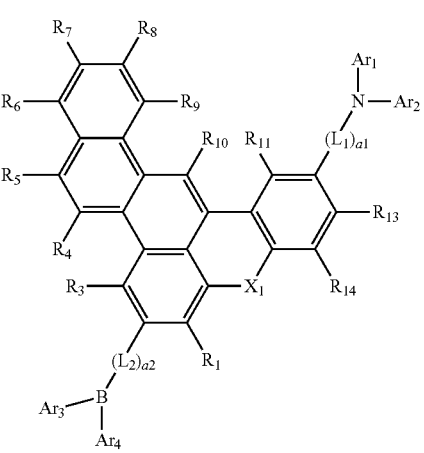

-continued

<Formula 1-8>

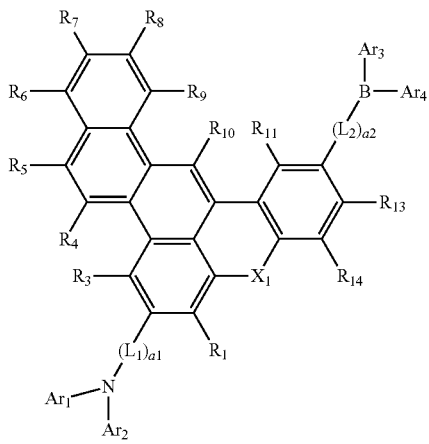

<Formula 1-1(1)>

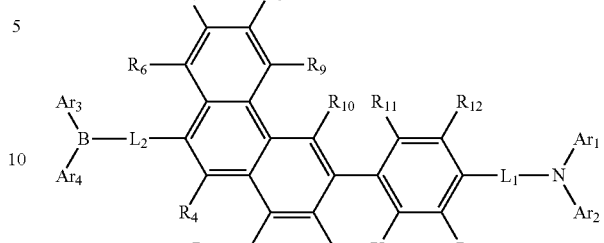

<Formula 1-1(2)>

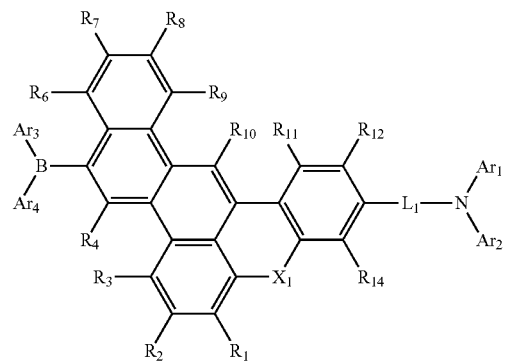

<Formula 1-1(3)>

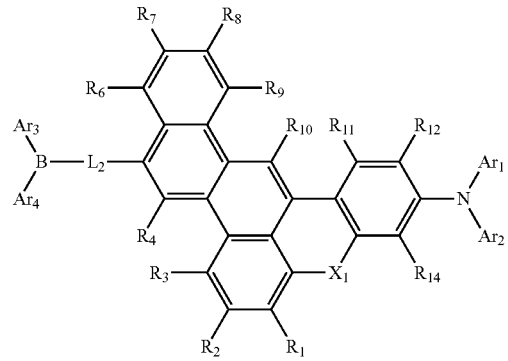

<Formula 1-1(4)>

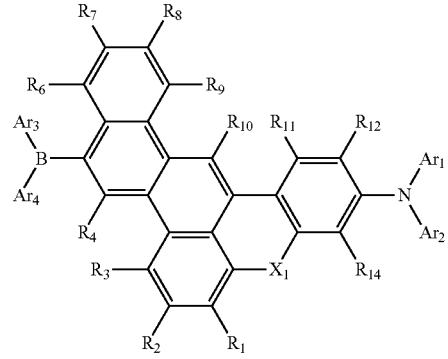

Descriptions of $X_1$, $L_1$, $L_2$, $a_1$, $a_2$, $Ar_1$ to $Ar_4$, and $R_1$ to $R_{14}$ in Formula 1-1 to Formula 1-8 may be the same as described above.

In some embodiments, regarding Formulae 1-1 to 1-8,
a1 may be 0 and a2 may be 0;
a1 may be 0 and a2 may be 1 or 2;
a1 may be 1 or 2 and a2 may be 0;
a1 may be 1 and a2 may be 1;
a1 may be 1 and a2 may be 2;
a1 may be 2 and a2 may be 1; or
a1 may be 2 and a2 may be 2.

In some embodiments, regarding Formulae 1-1 to 1-8,
a1 may be 0 and a2 may be 0;
a1 may be 0 and a2 may be 1;
a1 may be 1 and a2 may be 0; or
a1 may be 1 and a2 may be 1.

In some embodiments, regarding Formulae 1-1 to 1-8,
$Ar_1=Ar_2=Ar_3=Ar_4$
$Ar_1=Ar_3$ and, $Ar_2=Ar_4$ and, $Ar_2 \neq Ar_3$;
$Ar_1=Ar_3$ and, $Ar_2 \neq Ar_4$ and, $Ar_2 \neq Ar_3$; or
$Ar_1 \neq Ar_2 \neq Ar_3 \neq Ar_4$.

In some embodiments, regarding Formulae 1-1 to 1-8, $R_1$ to $R_{14}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ may each independently be a group represented by one of Formulae 3-1 to 3-35,
a1 and a2 may each independently be 0, 1, or 2;
$Ar_1$ to $Ar_4$ may each independently be a group represented by one of Formula 5-1 to 5-43.

In some embodiments, regarding Formulae 1-1 to 1-8,
$R_1$ to $R_4$, $R_6$ to $R_{12}$, and $R_{14}$ may be hydrogens,
$L_1$ and $L_2$ may each independently be a group represented by one of Formulae 4-1 to 4-29,
a1 and a2 may each independently be 0 or 1,
$Ar_1$ to $Ar_4$ may each independently be a group represented by one of Formula 6-1 to 6-40.

In some embodiments, the condensed cyclic compound represented by Formula 1 may be represented by one of Formulae 1-1(1) to 1-1(4) below.

Descriptions of $X_1$, $L_1$, $L_2$, $Ar_1$ to $Ar_4$, $R_1$ to $R_4$, $R_6$ to $R_{12}$ and $R_{14}$ in Formulae 1-1(1) to 1-1(4) may be the same as described above.

For example, the condensed cyclic compound represented by Formula 1 may be one of Compounds 1 to 104 below.
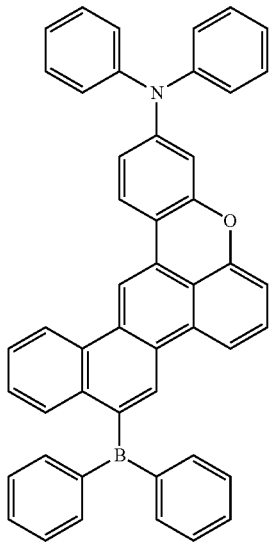
1
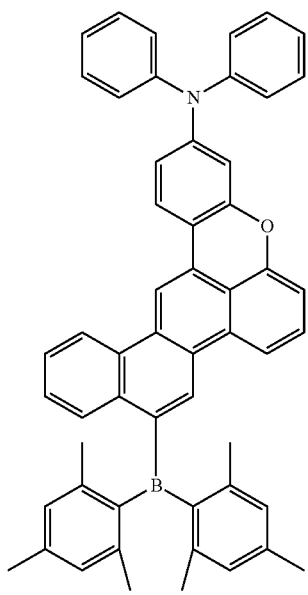
2
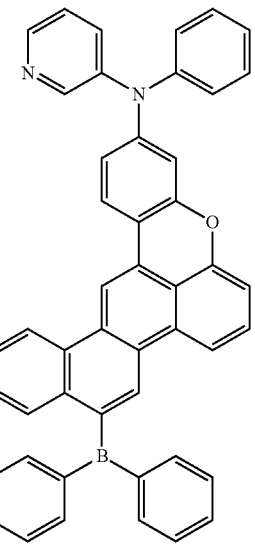
3
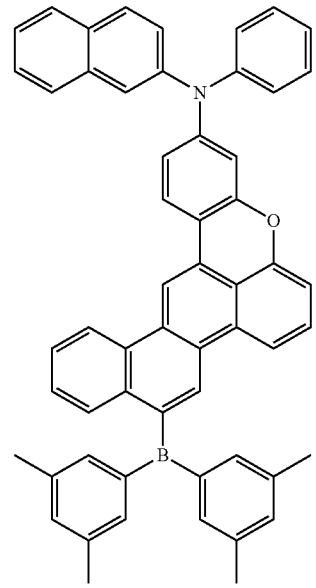
4

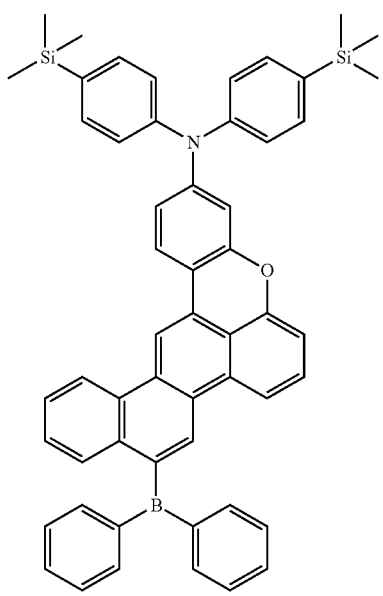
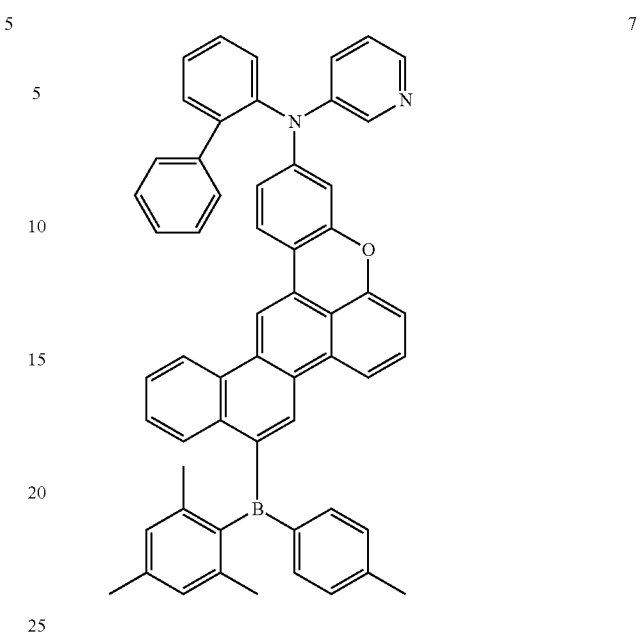
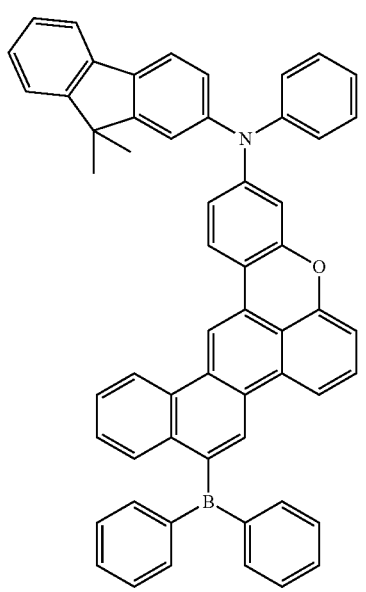
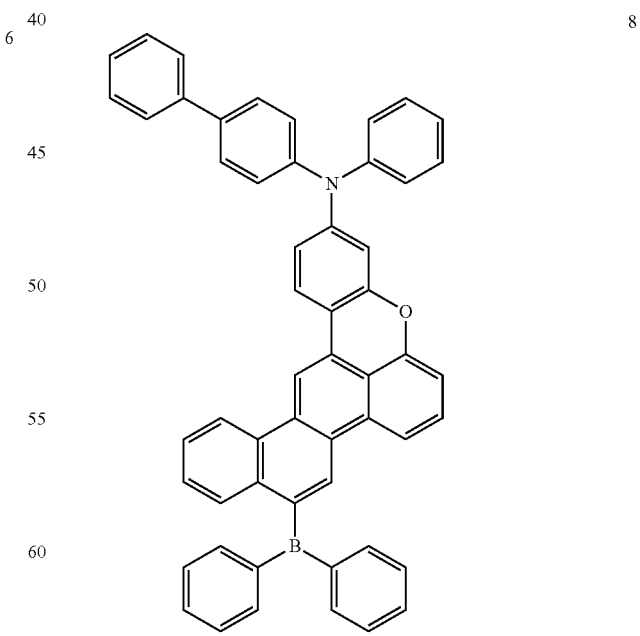

-continued
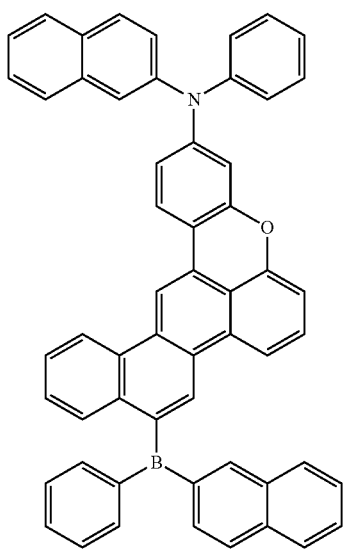
9
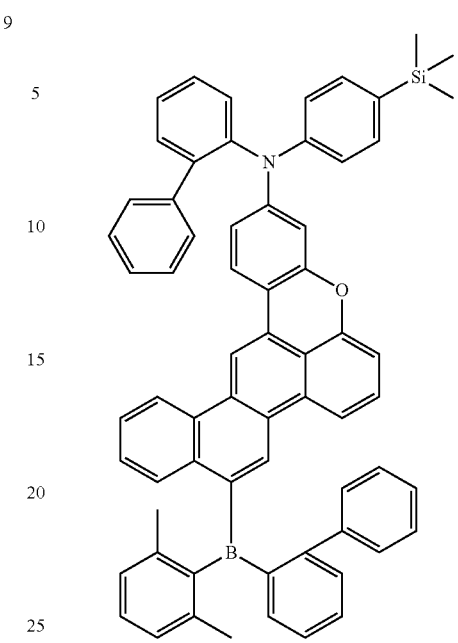
-continued
10
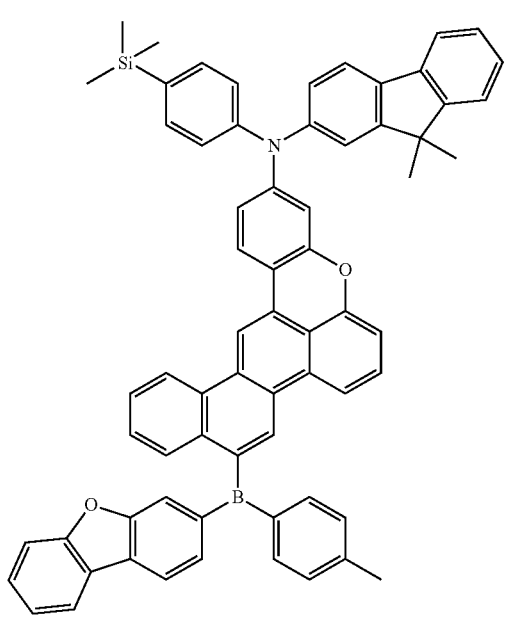
11
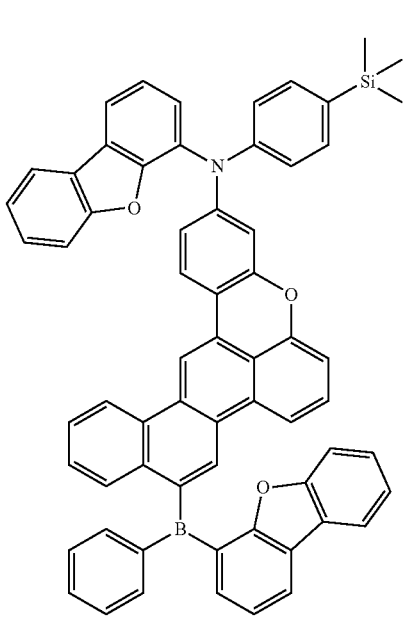
12

13
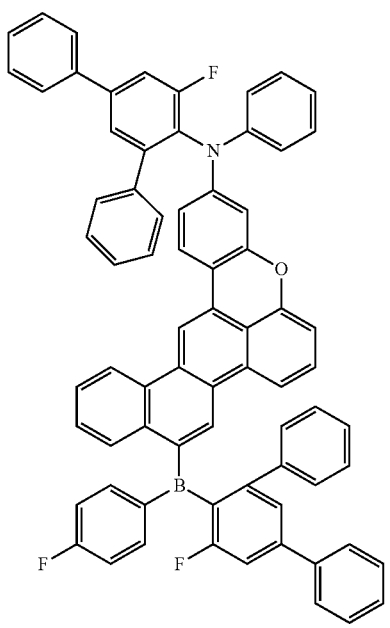
14
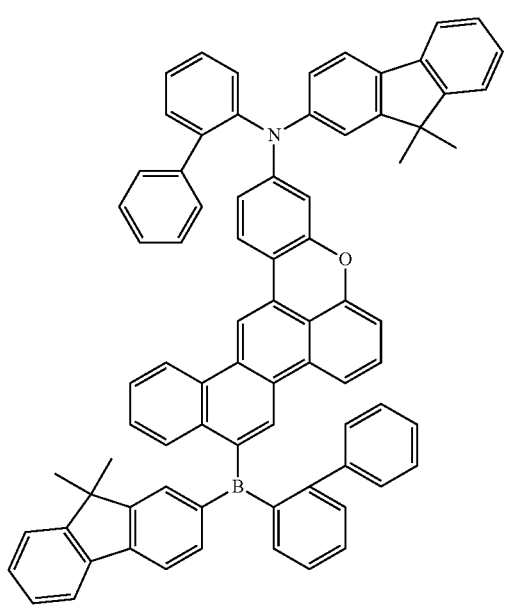
15
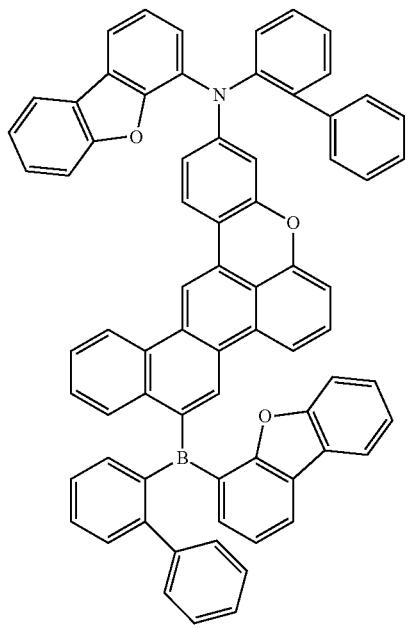
16
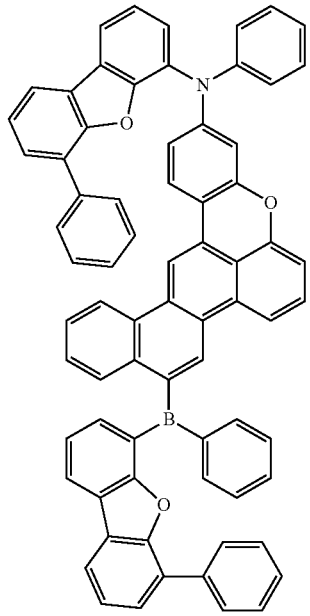

41
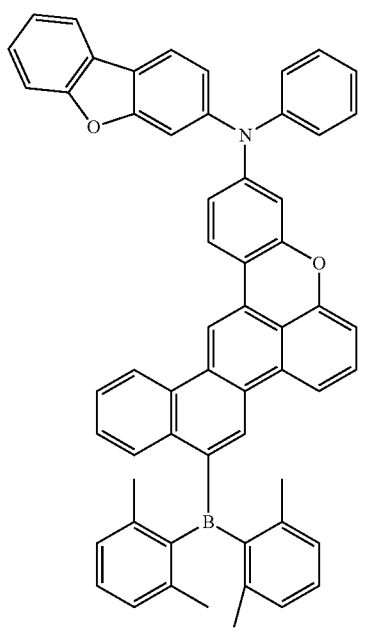
17
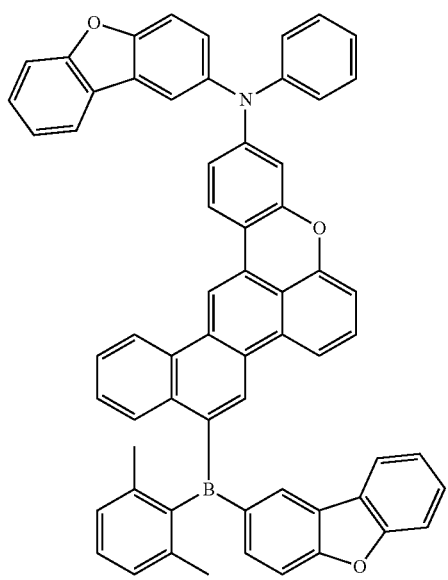
19
18
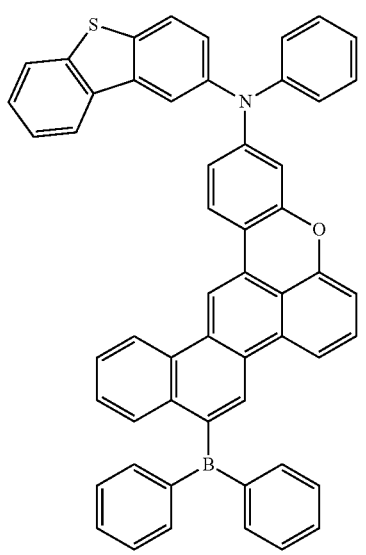
20
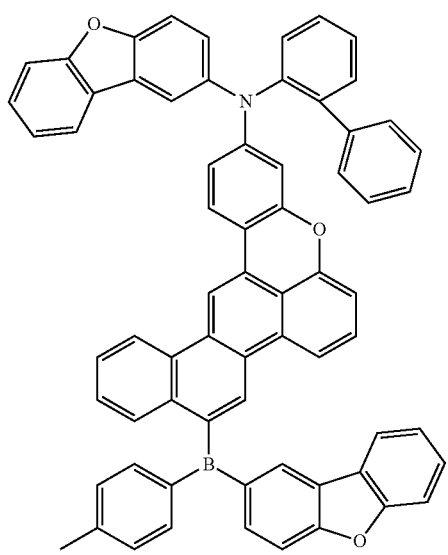

21
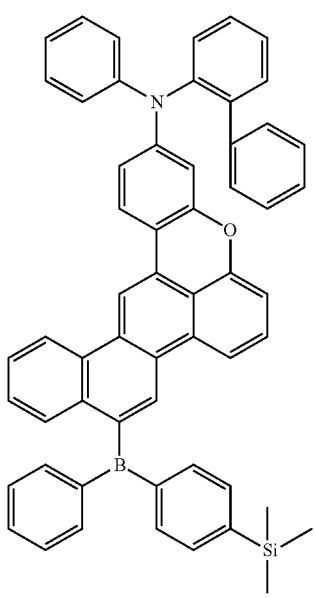
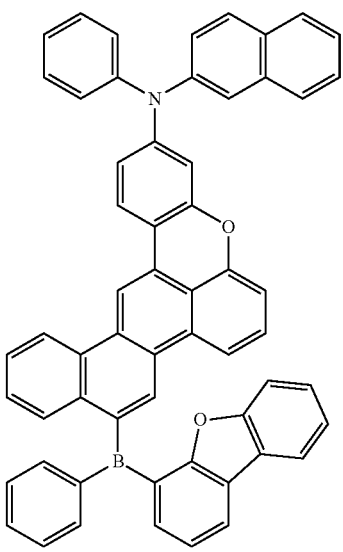
22
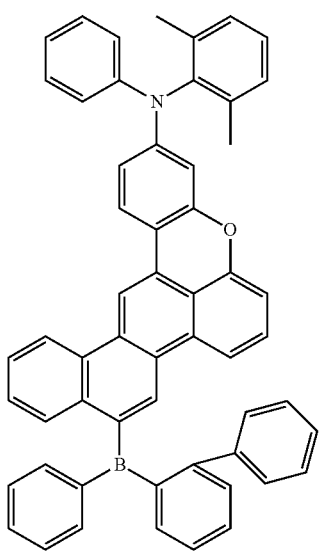
23
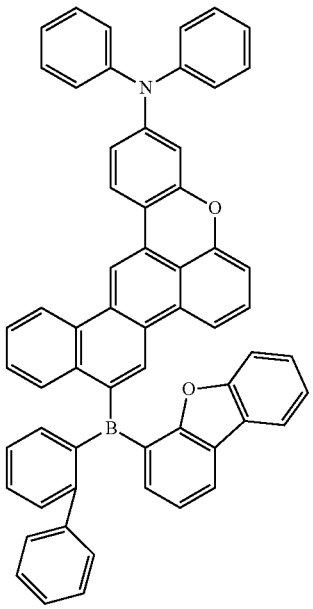
24

25
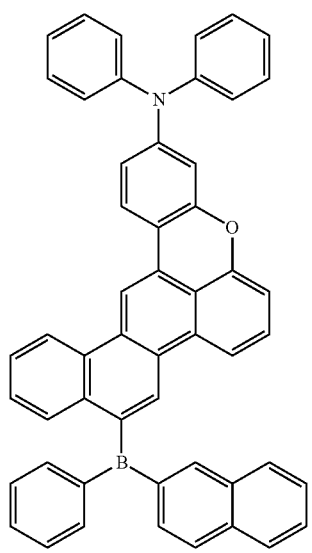
27
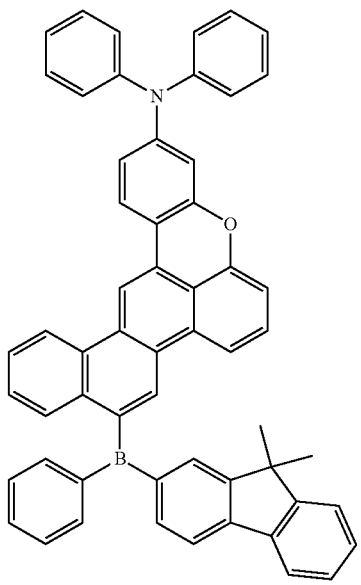
26
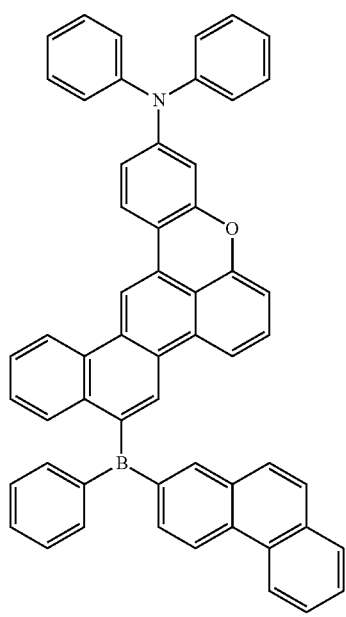
28
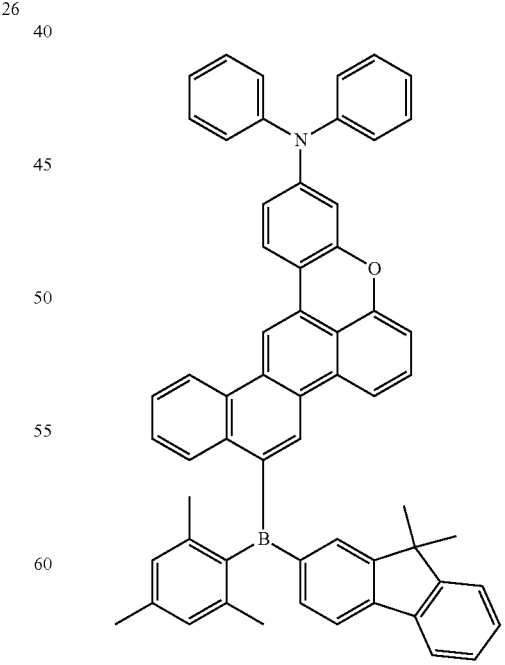

29
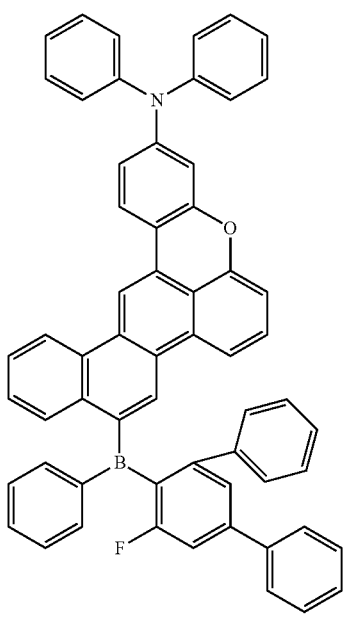
31
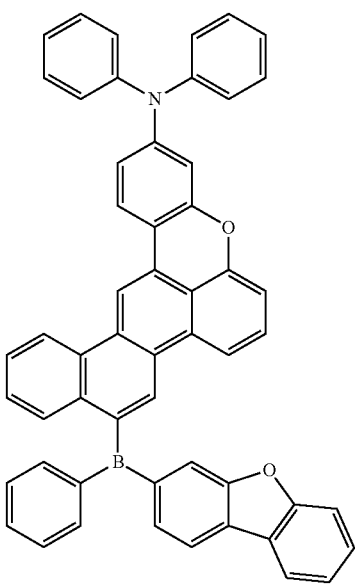
30
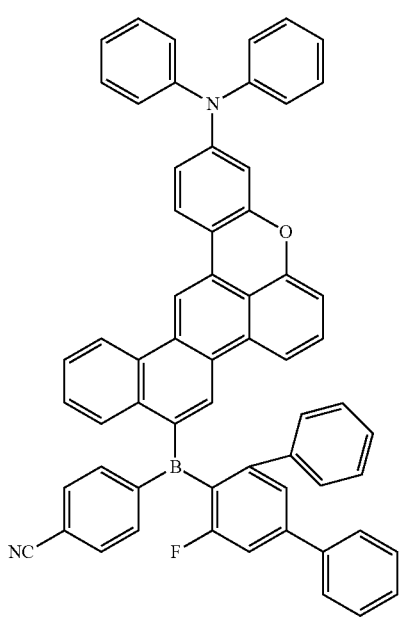
32
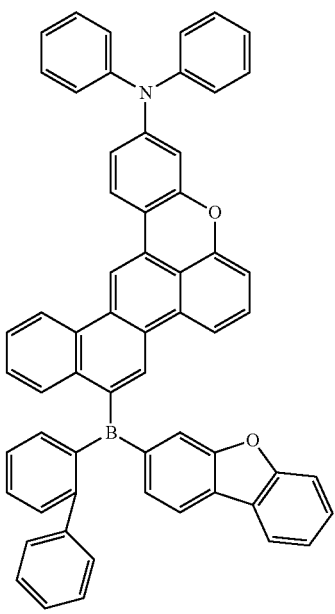

-continued
33
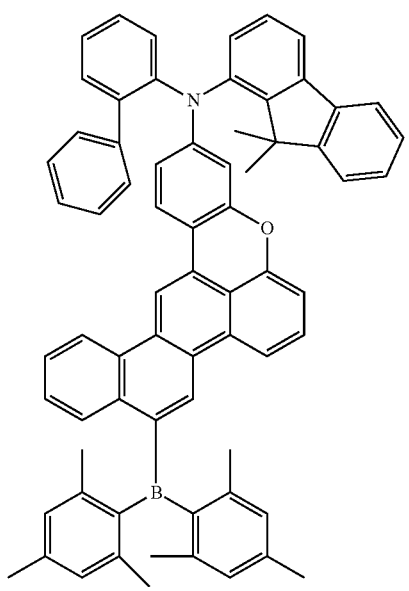
34
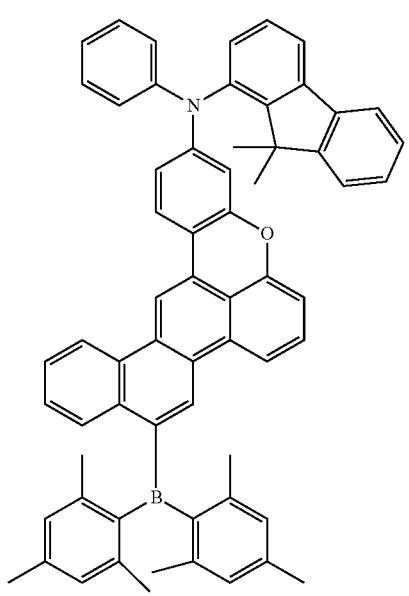
-continued
35
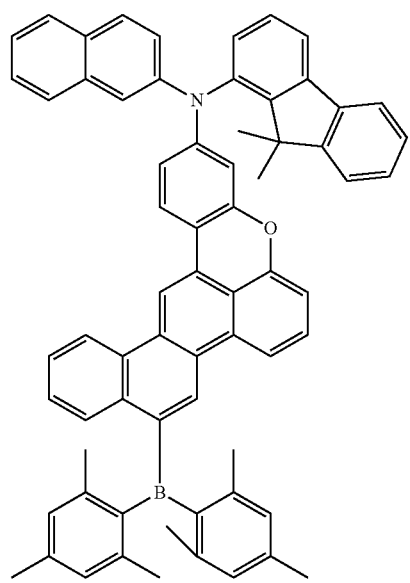
36
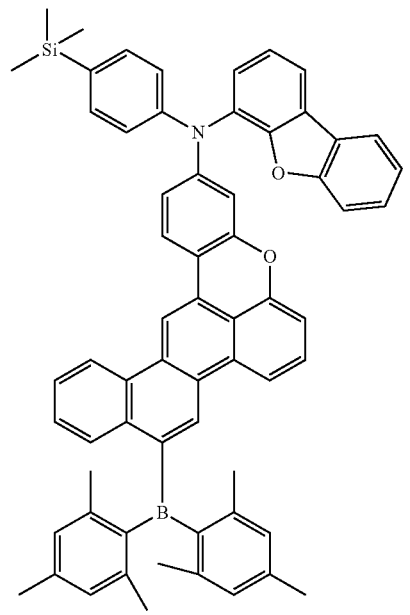

37
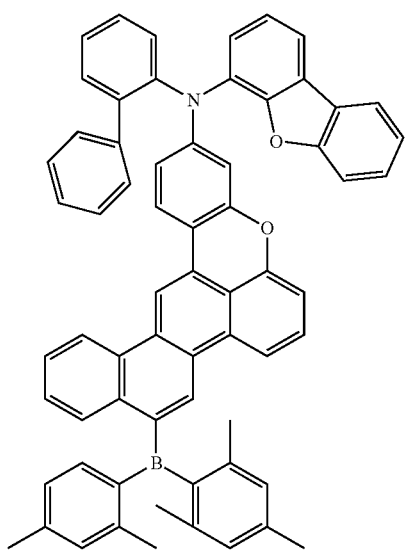
38
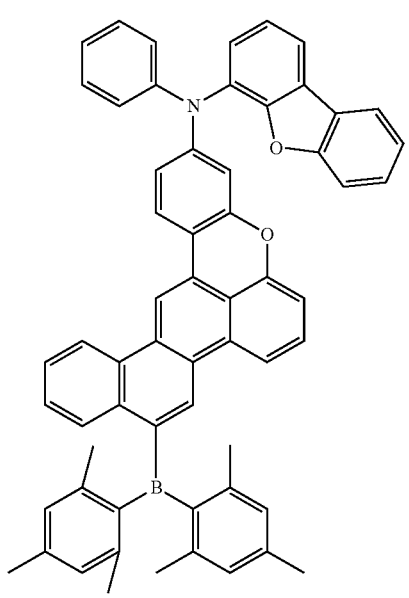
39
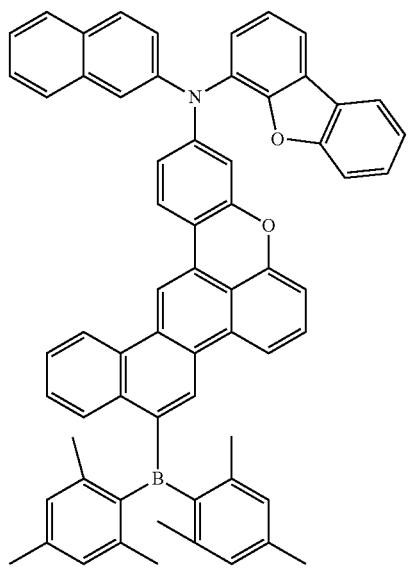
40
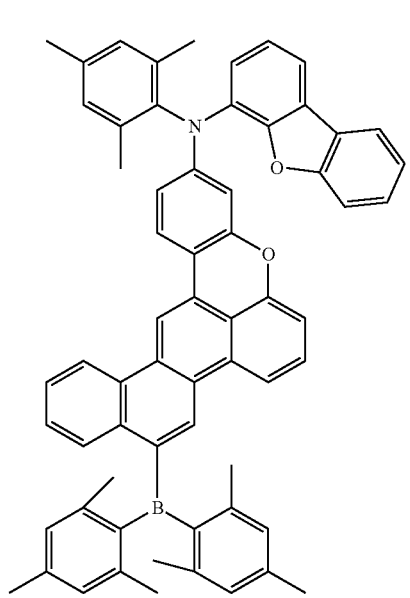

41
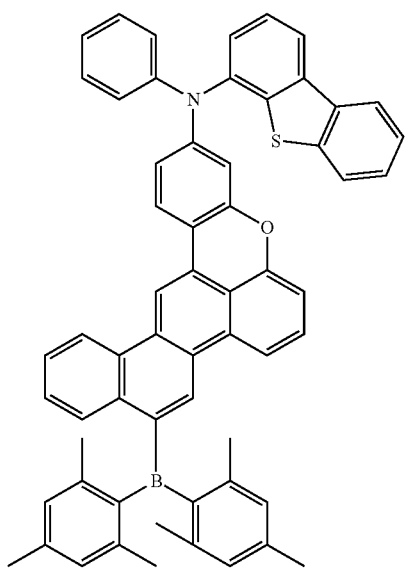
42
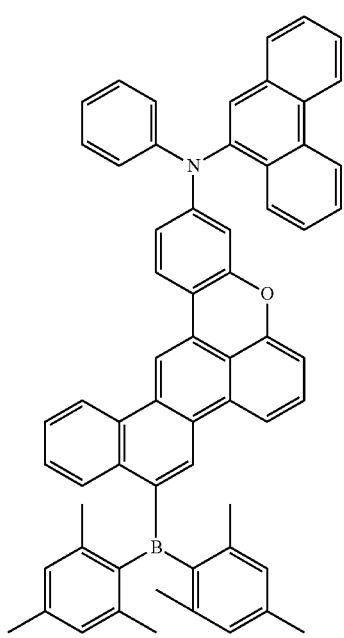
43
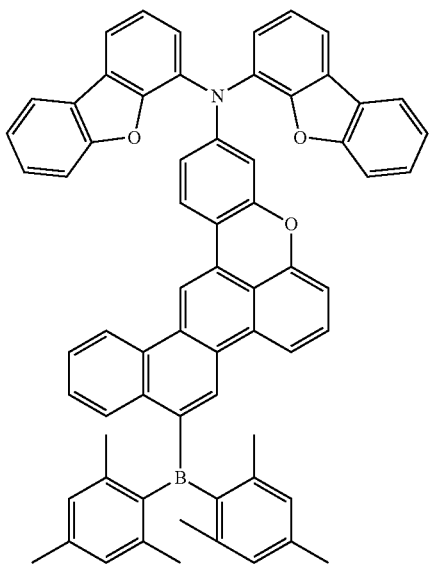
44
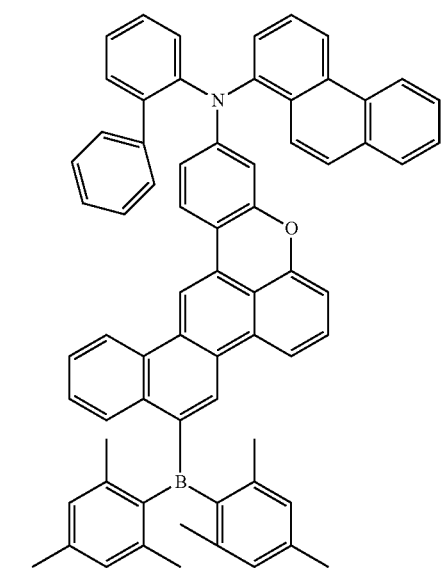

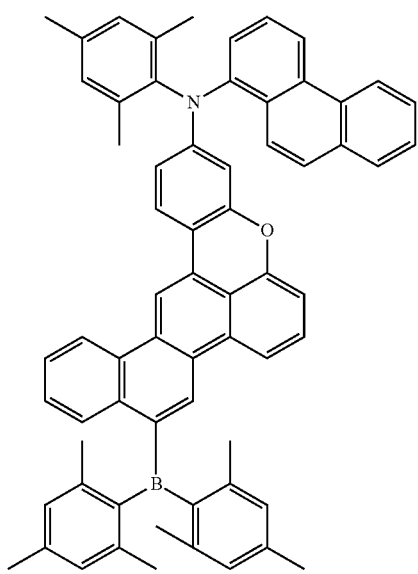
45
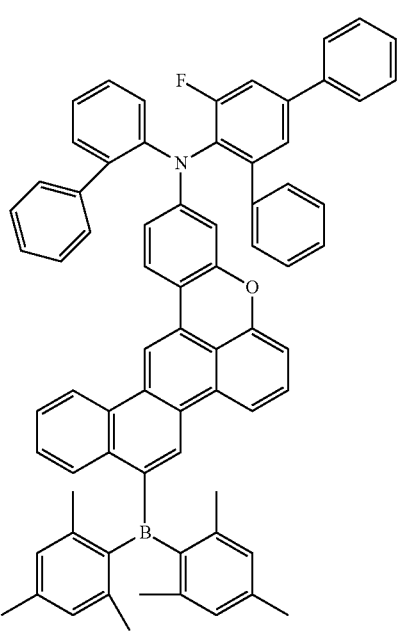
46
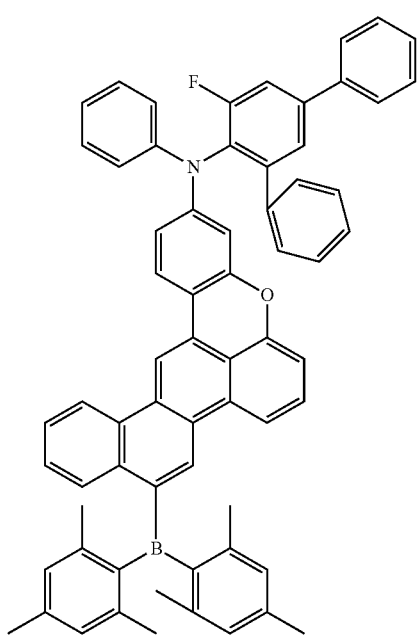
47
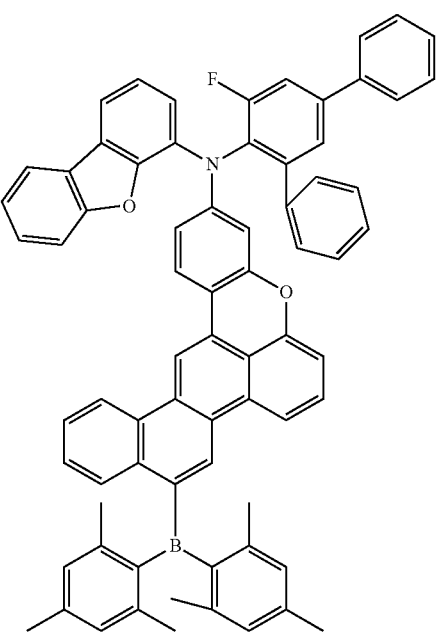
48

49
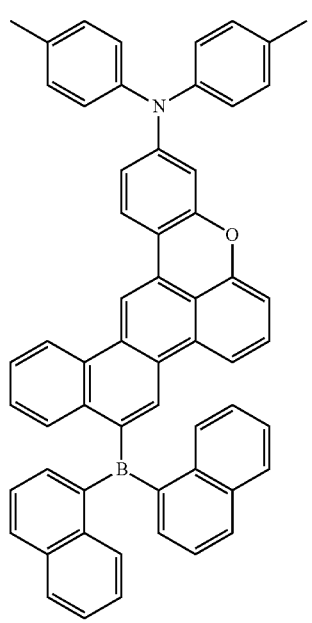
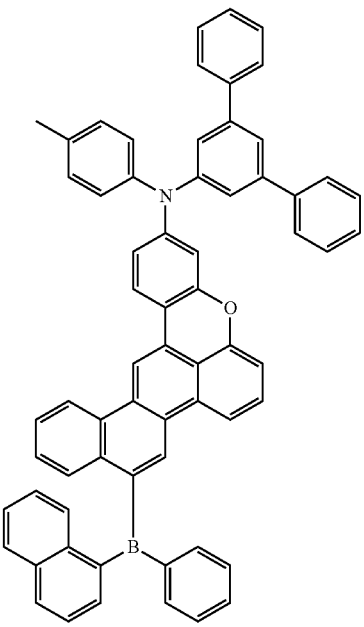
51
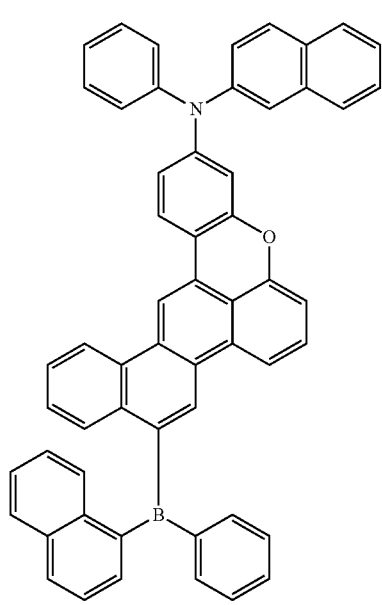
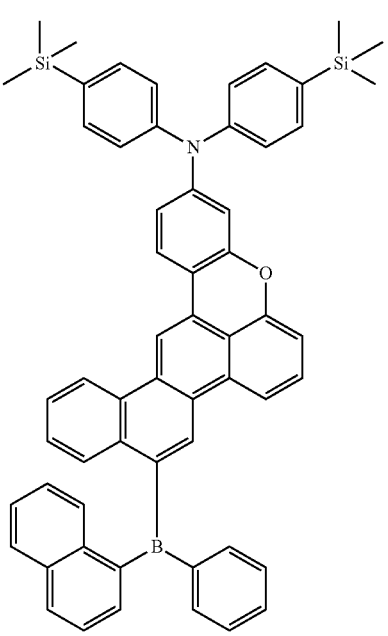
52

53
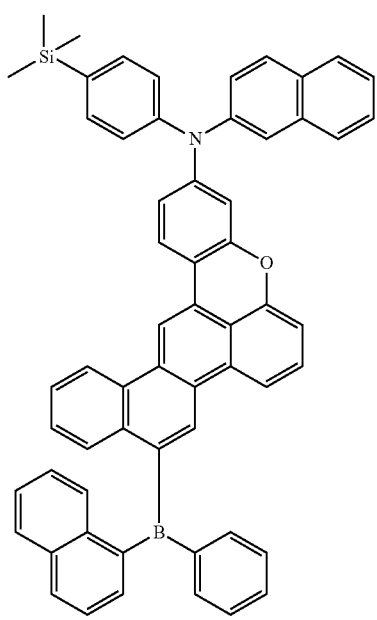
54
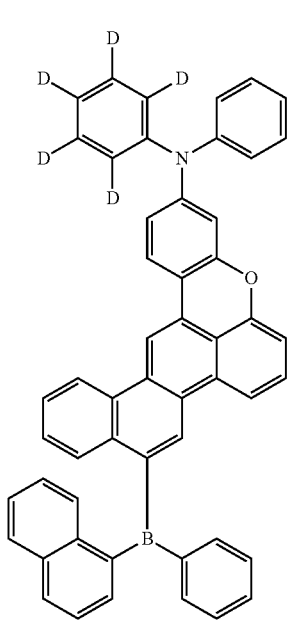
55
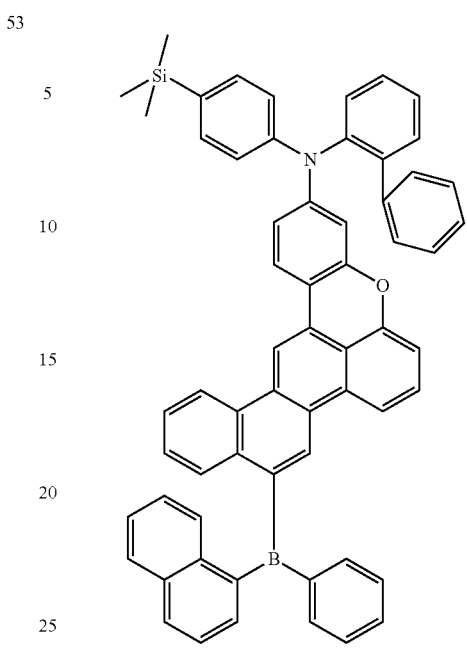
56
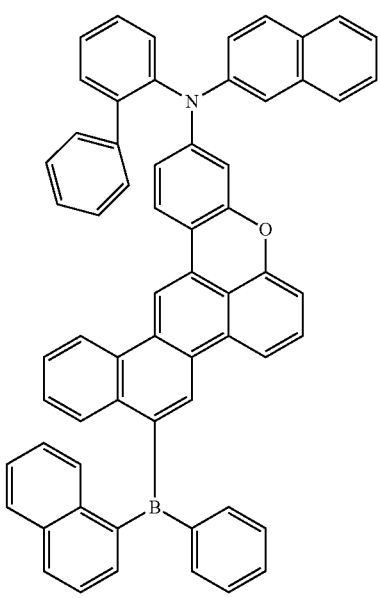

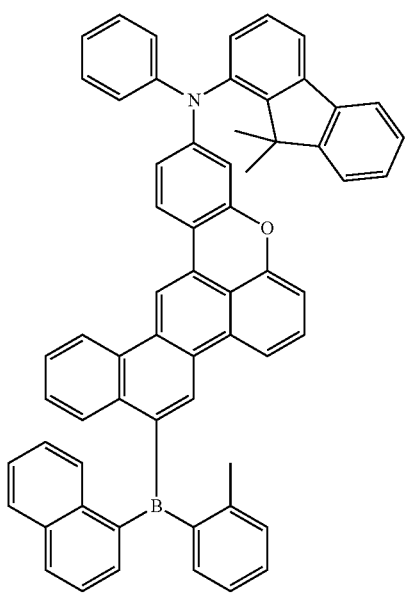
57
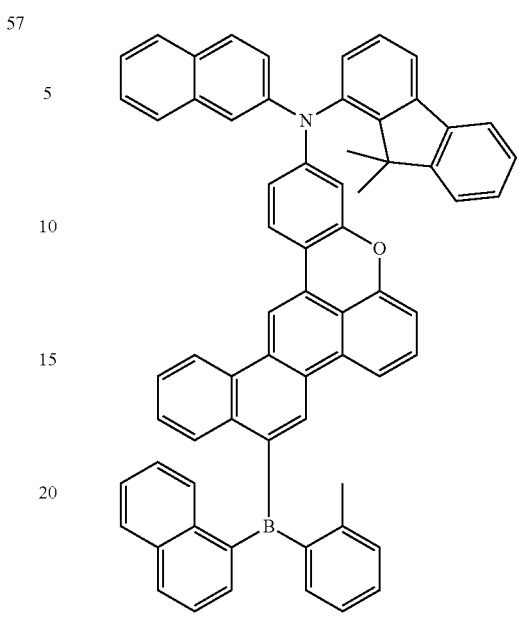

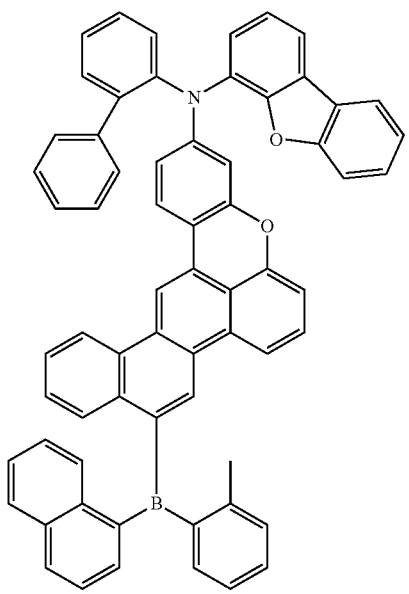
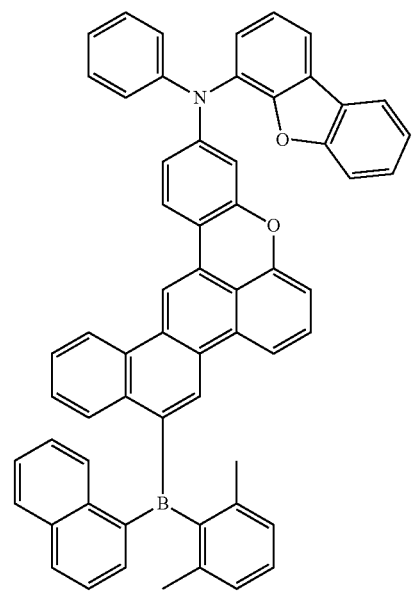
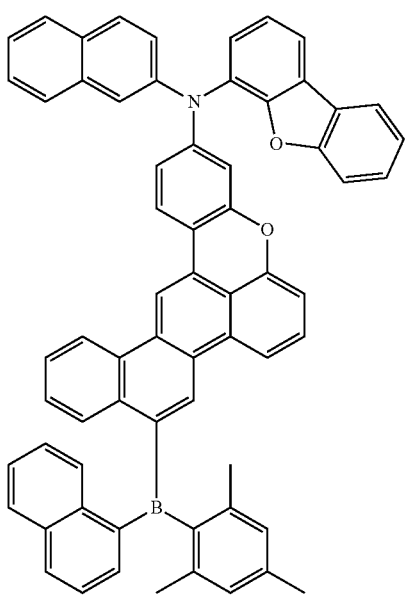
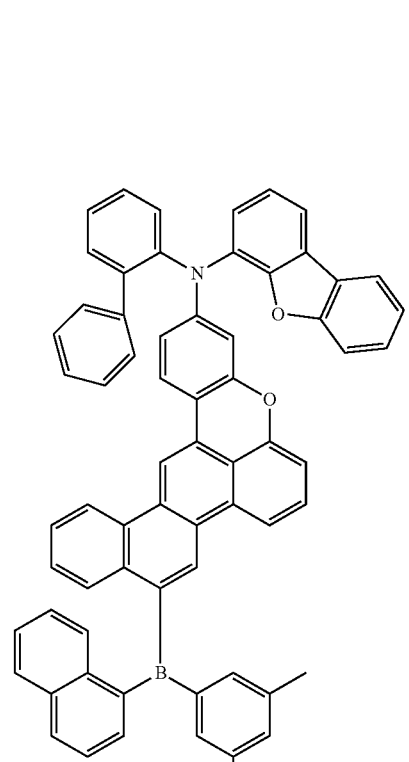

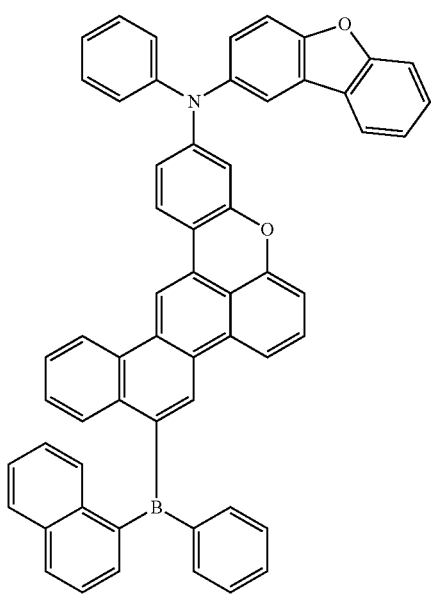
65
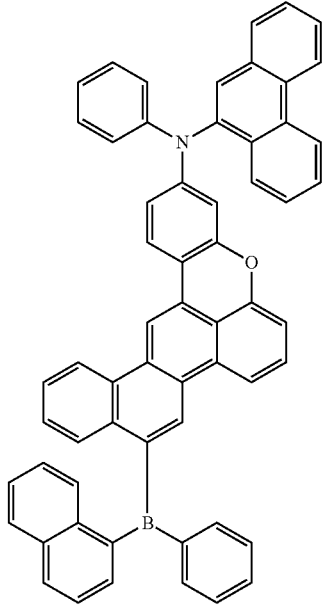
67
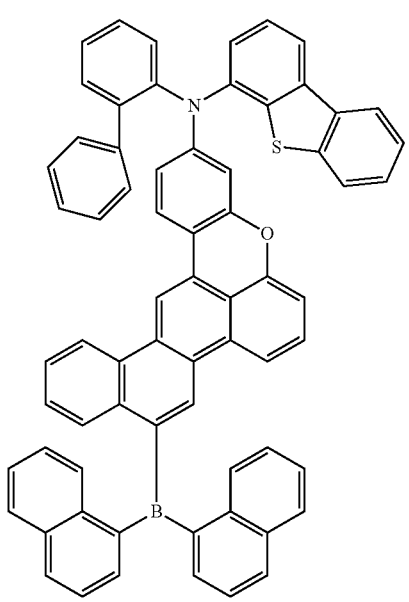
66
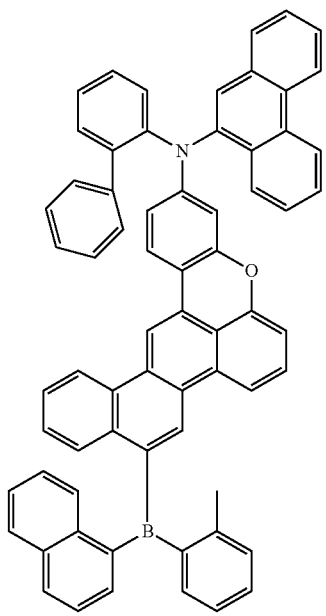
68

67
-continued
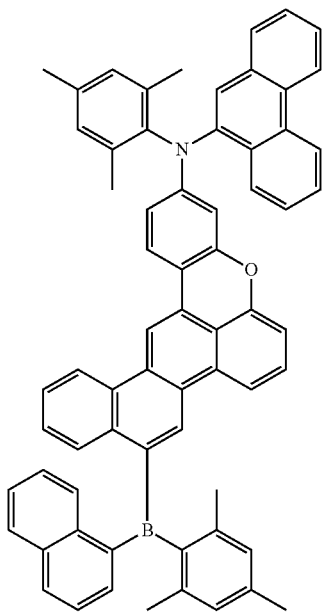
69
68
-continued
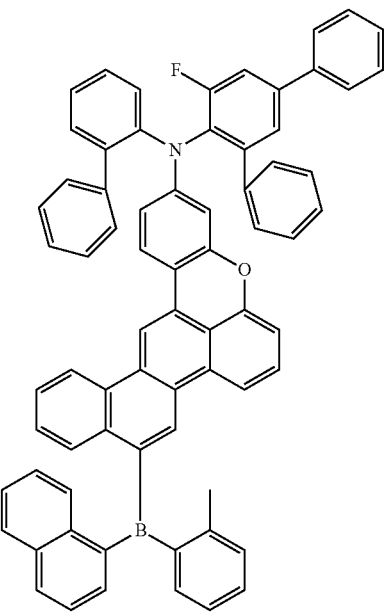
71
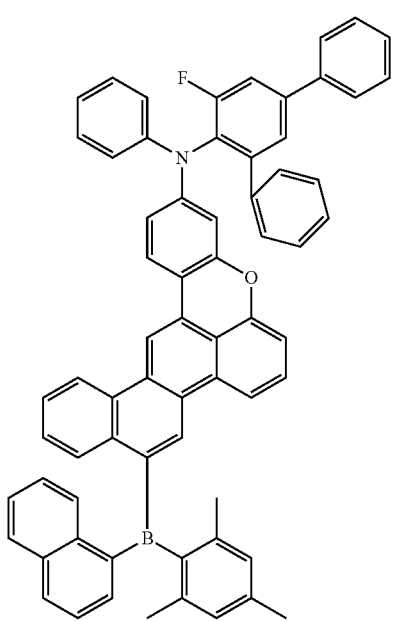
70
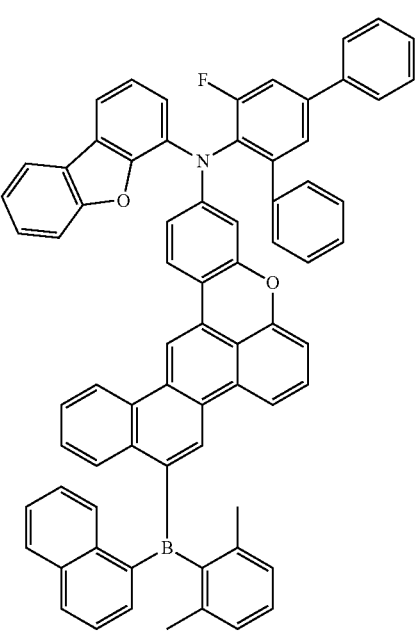
72

73
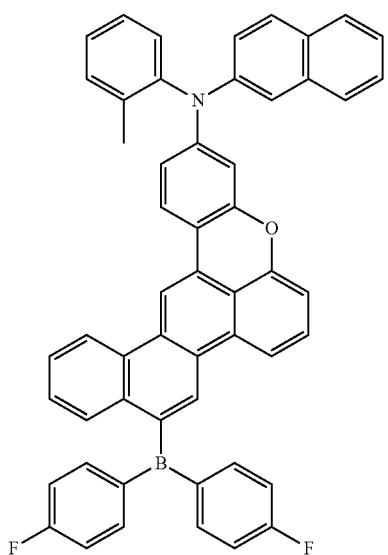
74
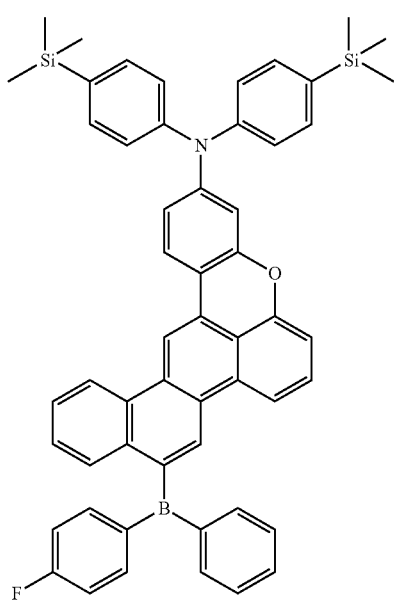
75
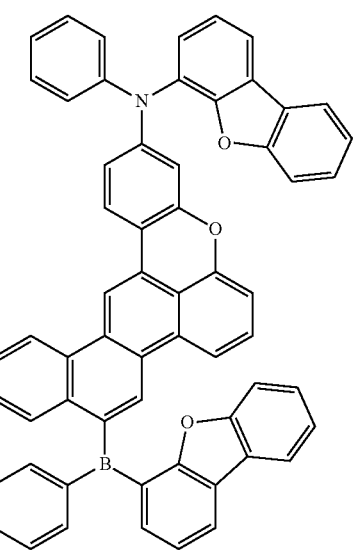
76
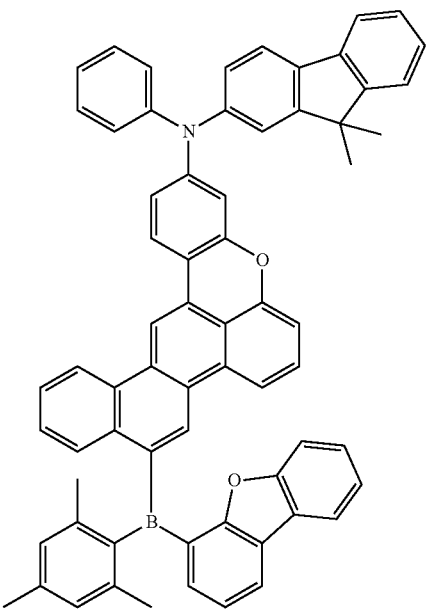

77
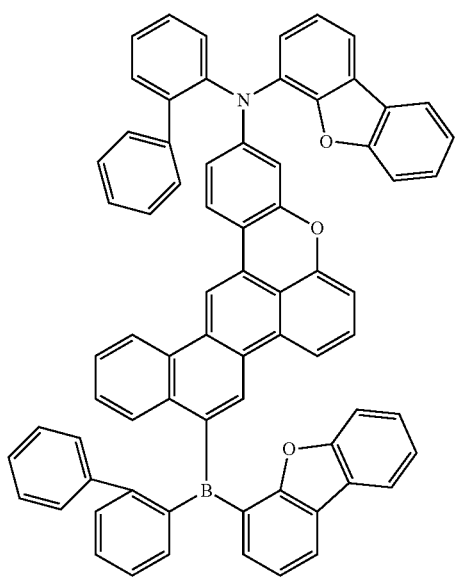
78
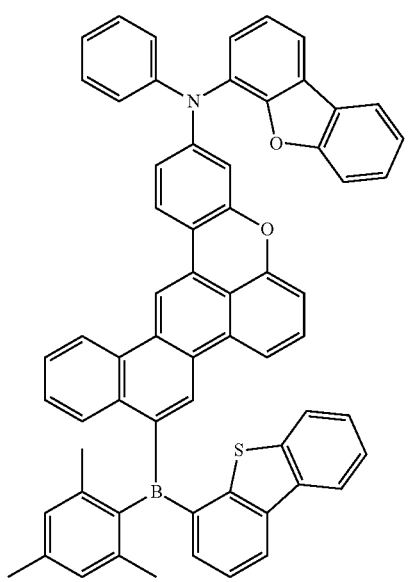
79
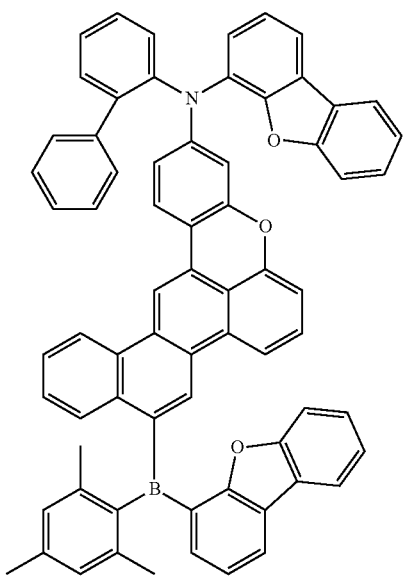
80

81
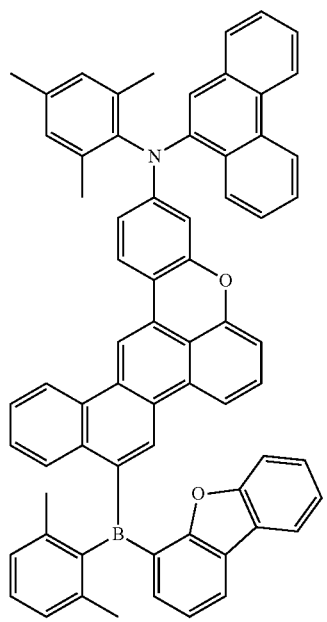
82
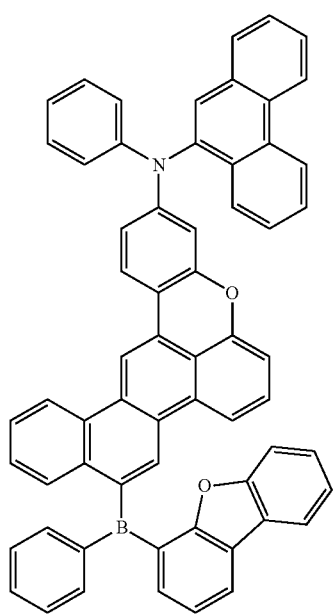
83
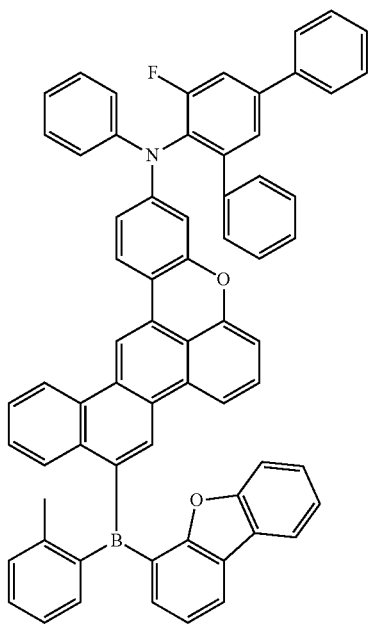
84
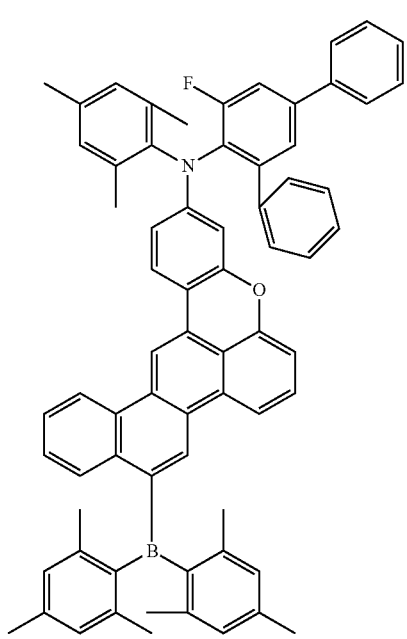

75
-continued
85
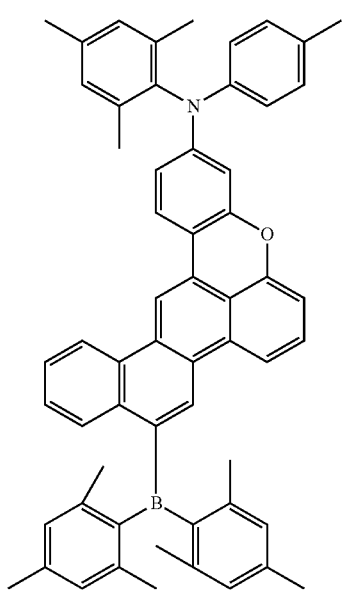
86
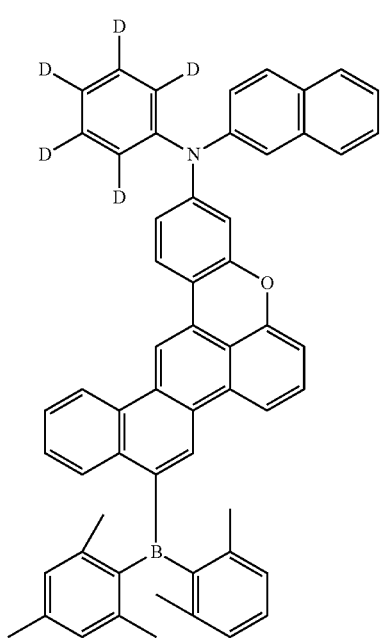
76
-continued
87
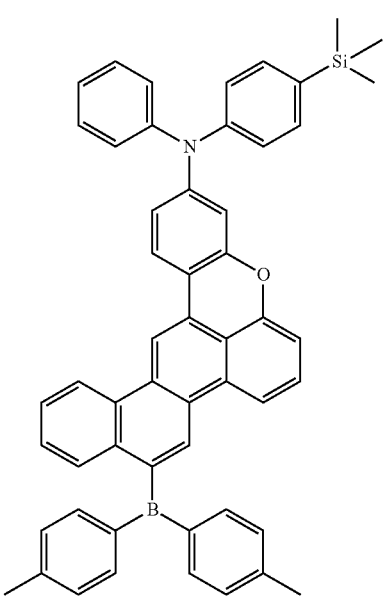
88
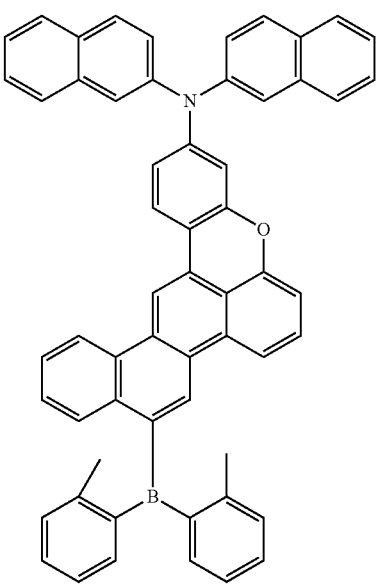

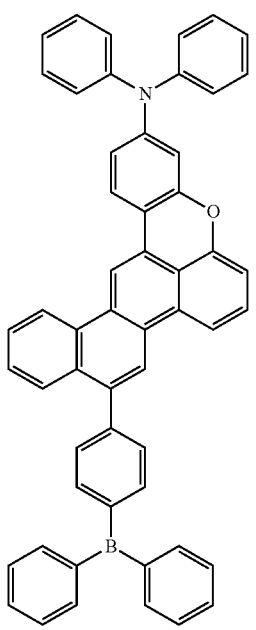
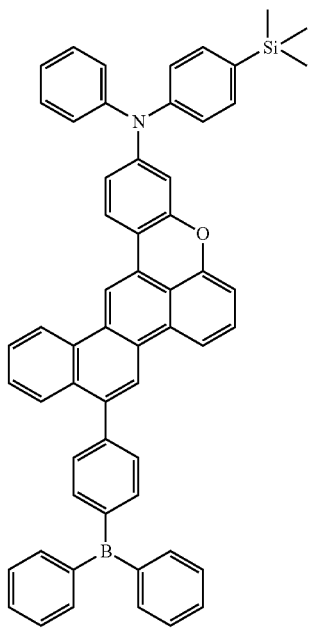
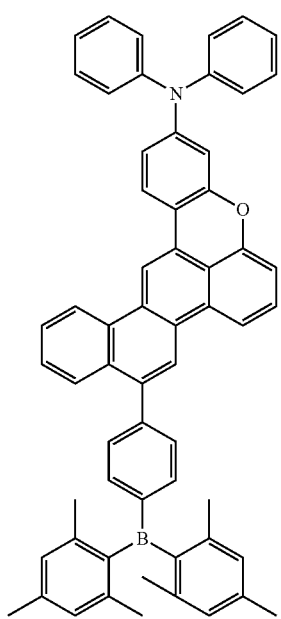
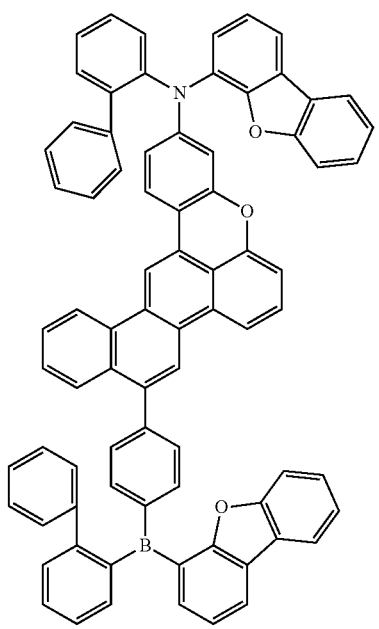

93
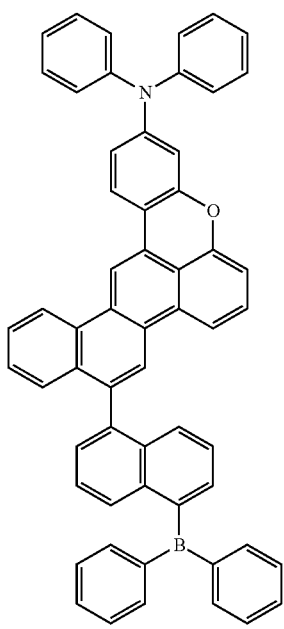
94
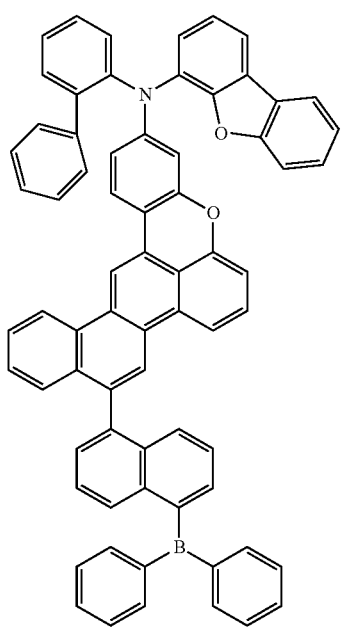
95
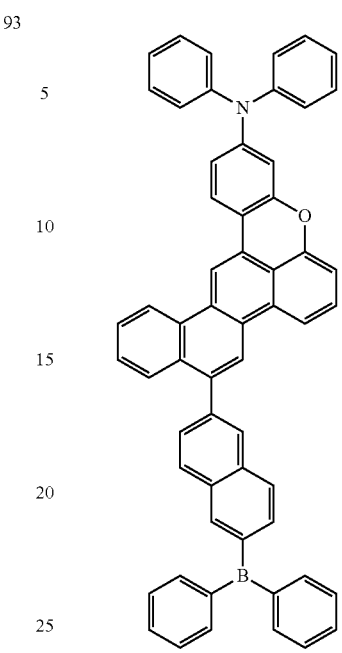
96
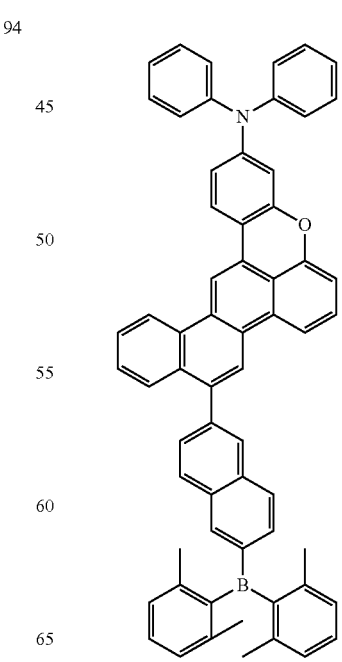

97
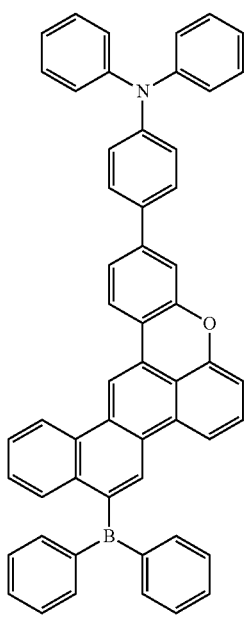
98
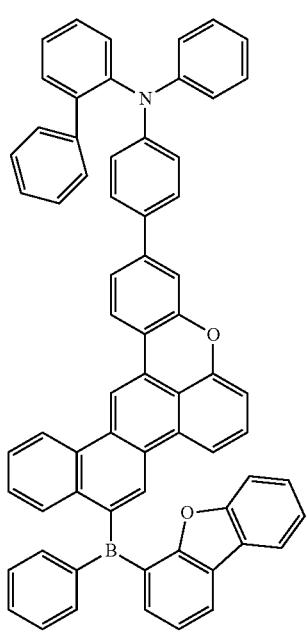
99
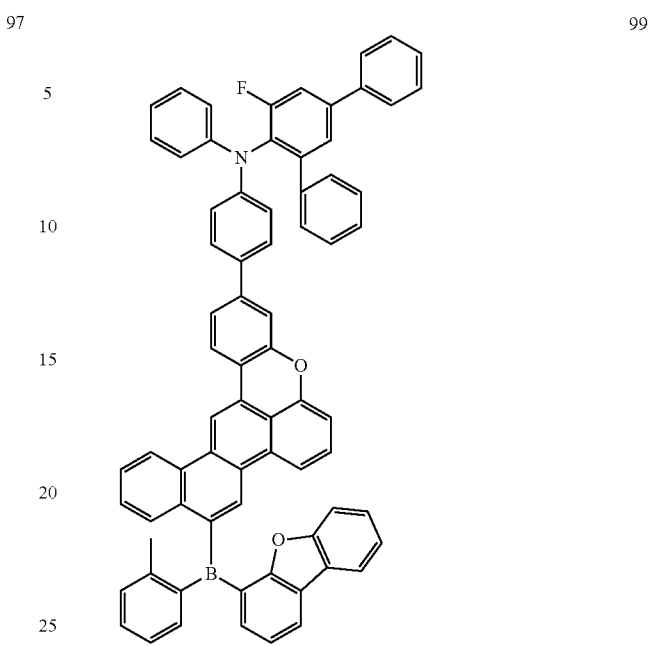
100
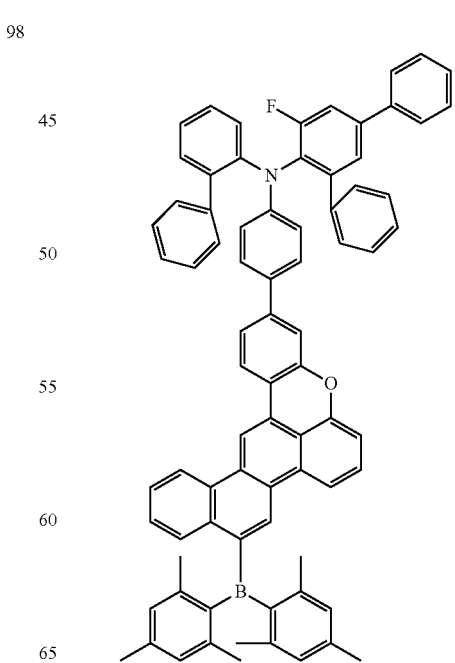

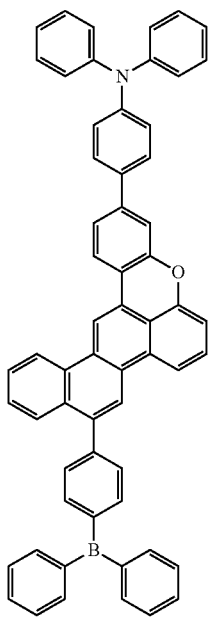

101

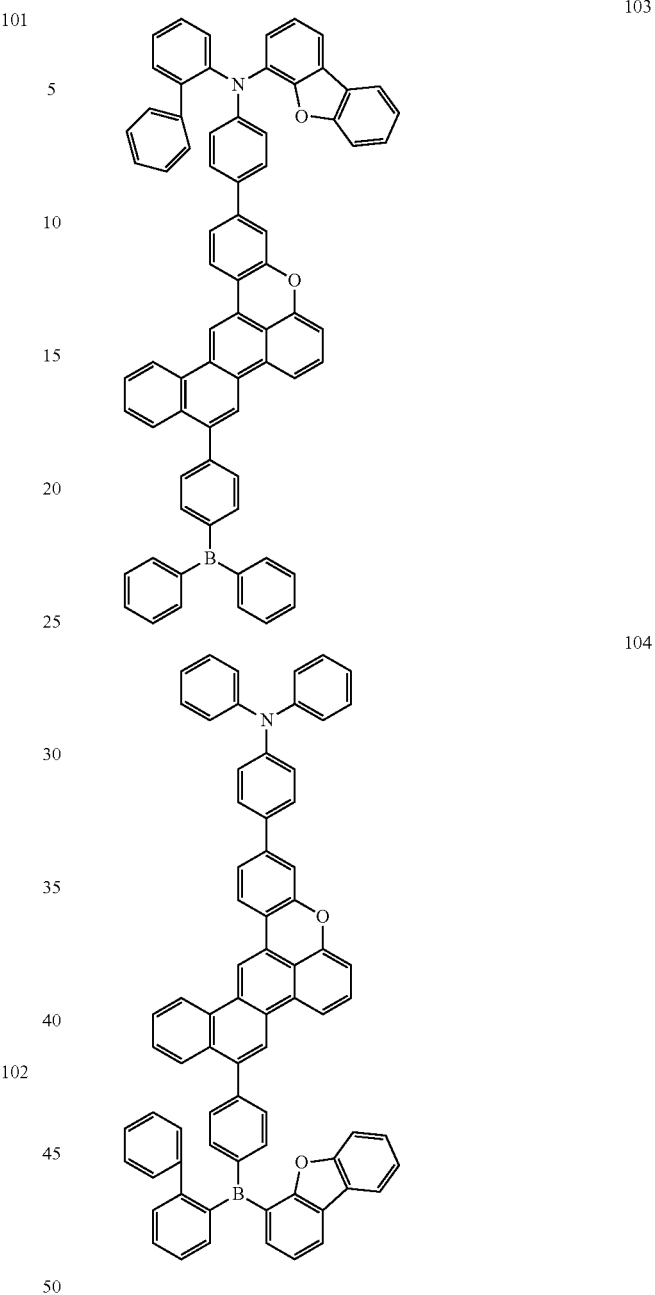

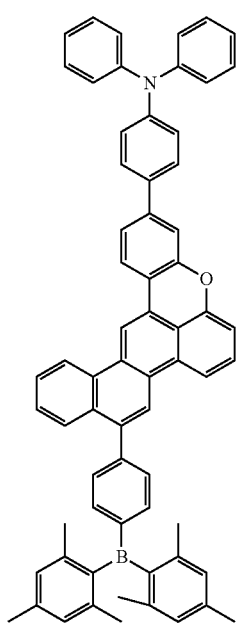

The condensed cyclic compound represented by Formula 1 may have an amine group and a boryl group in its molecular structure. Due to the inclusion of these groups, the condensed cyclic compound may have a high glass transition temperature (Tg) or a high melting point. Accordingly, a heat resistance to Joule heat (which may occur inside an organic layer or between an organic layer and an electrode) and a resistance to high temperature environments may increase, and thus, an organic light-emitting device including the condensed cyclic compound represented by Formula 1 may have high durability during preserving and driving.

A boron atom has an empty p orbital. Accordingly, an electron withdrawing property of the condensed cyclic compound represented by Formula 1 having a boryl group in its molecular structure may be increased, and thus, an electron injection capability and an electron transport capability may be increased. Thus, an organic light-emitting device including the condensed cyclic compound may have high luminescent efficiency.

A core of the condensed cyclic compound represented by Formula 1 may have many n-conjugation systems. Accordingly, the condensed cyclic compound may have high luminescent efficiency. Also, the core of the condensed cyclic compound represented by Formula 1 may include an oxygen atom (which is a hetero atom), and due to the interaction with a boryl group or an amine group, the electron injection capability and an electron transport capability may all be increased.

The condensed cyclic compound represented by Formula 1 may be synthesized by using a suitable organic synthetic method. A synthesis method of the condensed cyclic compound may be recognizable in view of the following embodiments.

At least one of the condensed cyclic compound of Formula 1 may be used or included between a pair of electrodes of an organic light-emitting device. In some embodiments, the condensed cyclic compound may be included in a hole transport region, e.g., a hole transport layer. In some embodiments, the condensed cyclic compound may be included in an emission layer. Accordingly, an organic light-emitting device according to an embodiment may include, e.g., a first electrode; a second electrode facing the first electrode; and an organic layer that is disposed between the first electrode and the second electrode and includes an emission layer, wherein the organic layer includes at least one of the condensed cyclic compounds described above.

The expression that "(an organic layer) includes at least one condensed cyclic compound" used herein may include a case in which "(an organic layer) includes identical condensed cyclic compounds represented by Formula 1 and a case in which (an organic layer) includes two or more different condensed cyclic compounds represented by Formula 1.

For example, the organic layer may include, as the condensed cyclic compound, only Compound 1. In this regard, Compound 1 may exist in an emission layer of the organic light-emitting device. In some embodiments, the organic layer may include, as the condensed cyclic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in a hole transport layer and Compound 2 may exist in an emission layer).

The organic layer may include, e.g., i) a hole transport region that is disposed between the first electrode (anode) and the emission layer and includes at least one of a hole injection layer, a hole transport layer, a buffer layer, and an electron blocking layer, and ii) an electron transport region that is disposed between the emission layer and the second electrode (cathode) and includes at least one selected from a hole blocking layer, an electron transport layer, and an electron injection layer. At least one of the hole transport region and the emission layer may include at least one of the condensed cyclic compound represented by Formula 1. For example, the hole transport region may include the hole transport layer, and the hole transport layer may include at least one of the condensed cyclic compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 may include a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water-resistance.

The first electrode 110 may be formed by depositing or sputtering a material for forming the first electrode on the substrate. When the first electrode 10 is an anode, the material for the first electrode may be selected from materials with a high work function to facilitate hole injection. The first electrode 110 may be a reflective electrode or a transmissive electrode. The material for the first electrode may be a transparent and highly conductive material, and examples of such a material may include indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 may be disposed on the first electrode 110. The organic layer 150 may include an emission layer.

The organic layer 150 may further include a hole transport region disposed between the first electrode and the emission layer, and an electron transport region disposed between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, for example, the vacuum deposition may be performed at a temperature of a deposition temperature of about 100 to about 500° C. at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be determined by referring to the deposition and coating conditions for the hole injection layer.

The hole transport region may include the condensed cyclic compound represented by Formula 1. For example, the hole transport region may include the hole transport layer, wherein the hole transport layer includes the condensed cyclic compound represented by Formula 1.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4"-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (PANI/CSA), (polyaniline)/poly(4-styrenesulfonate) (Pani/PSS), a compound represented by Formula 201 below, and a compound represented by Formula 202 below:

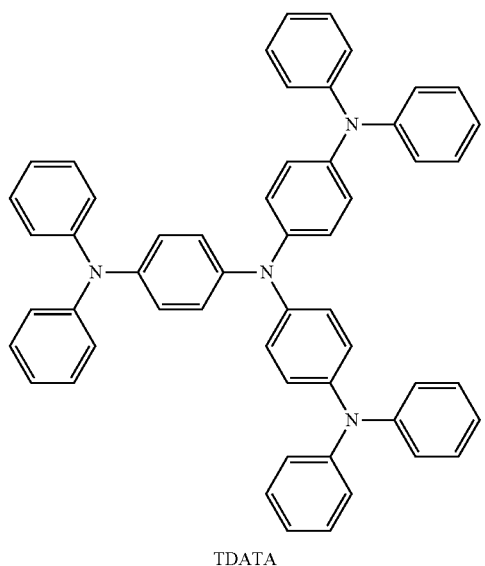

TDATA

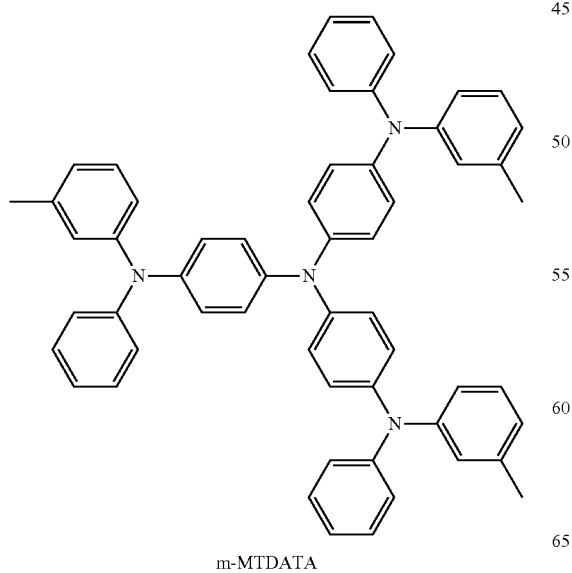

m-MTDATA

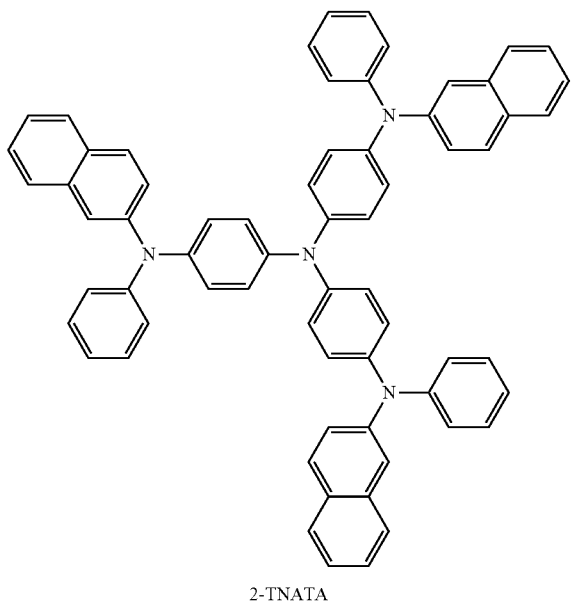

2-TNATA

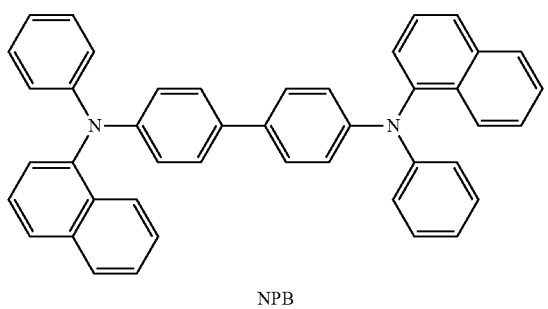

NPB

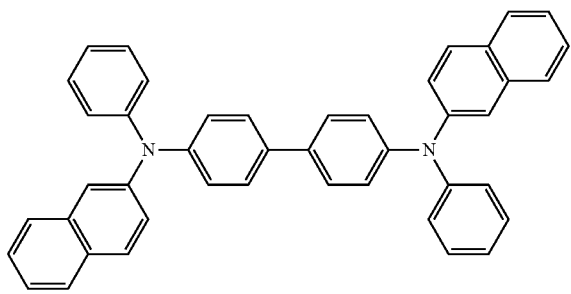

β-NPB

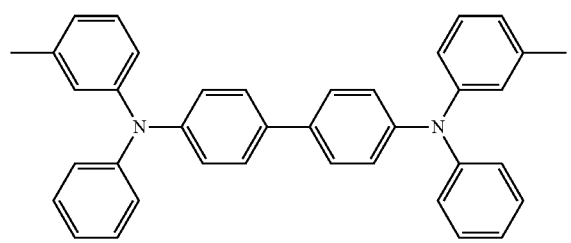

TPD

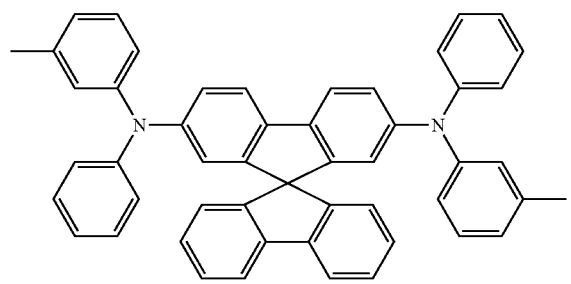

Spiro-TPD

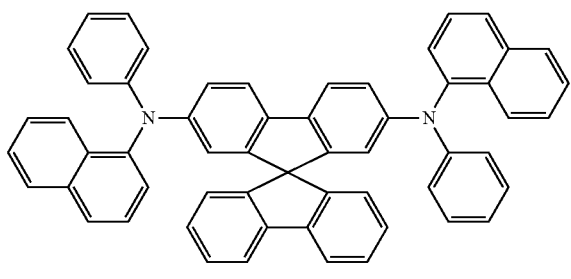

Spiro-NPB

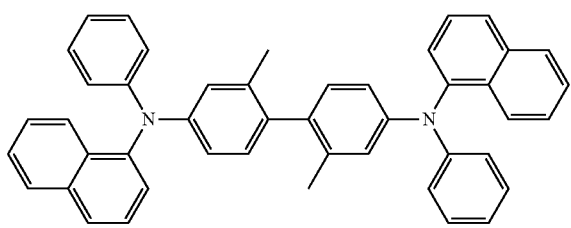

methylated NPB

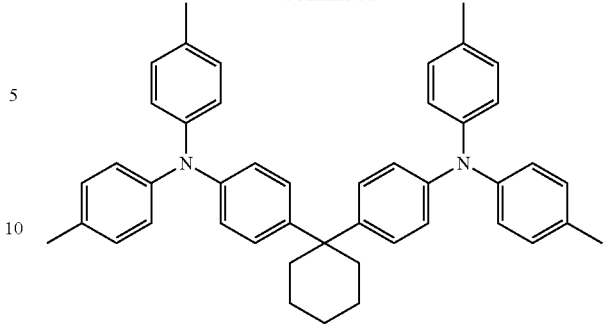

TAPC

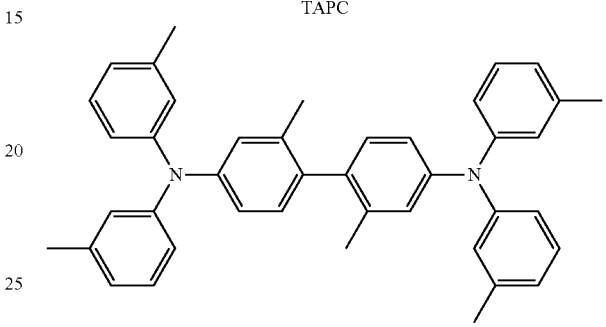

HMTPD

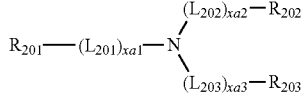

<Formula 201>

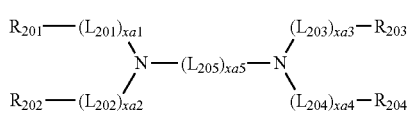

<Formula 202>

In Formulae 201 and 202, $L_{201}$ to $L_{205}$ may be the same as explained in connection with $L_1$;

xa1 to xa4 may each independently be selected from 0, 1, 2, and 3;

xa5 may be selected from 1, 2, 3, 4, and 5; and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2;

xa5 may be 1, 2, or 3;

$R_{201}$ to $R_{204}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but they are not limited thereto.

The compound represented by Formula 201 may be represented by Formula 201A:

<Formula 201A>

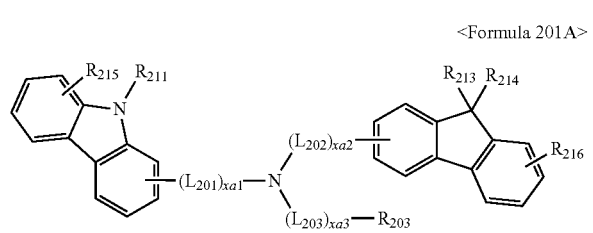

For example, the compound represented by Formula 201 may be represented by Formula 201A-1 below:

<Formula 201A-1>

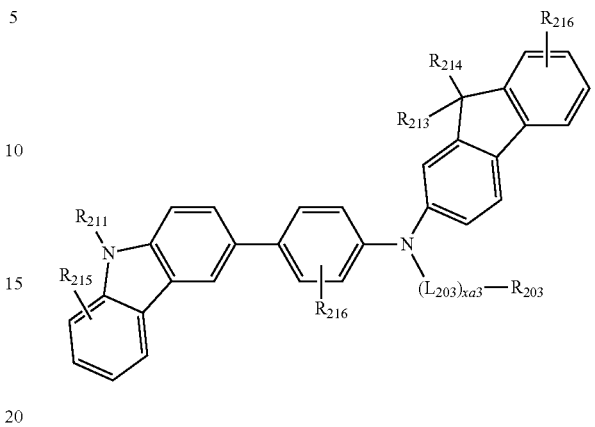

For example, the compound represented by Formula 202 may be represented by Formula 202A below:

<Formula 202A>

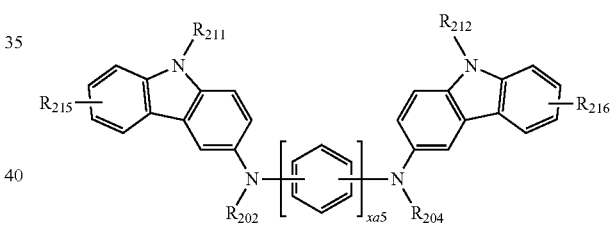

Descriptions of $L_{201}$ to $L_{203}$, xa1 to xa3, xa5, and $R_{202}$ to $R_{204}$ in Formulae 201A, 201A-1, and 202A are the same as described above, a description of $R_{211}$ is the same as defined in connection with $R_{203}$, and $R_{213}$ to $R_{216}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monvalent non-aromatic condensed polycyclic group, and a monvalent non-aromatic condensed heteropolycyclic group.

The compound represented by Formula 201, and the compound represented by Formula 202 may each include compounds HT1 to HT20 illustrated below.

HT1
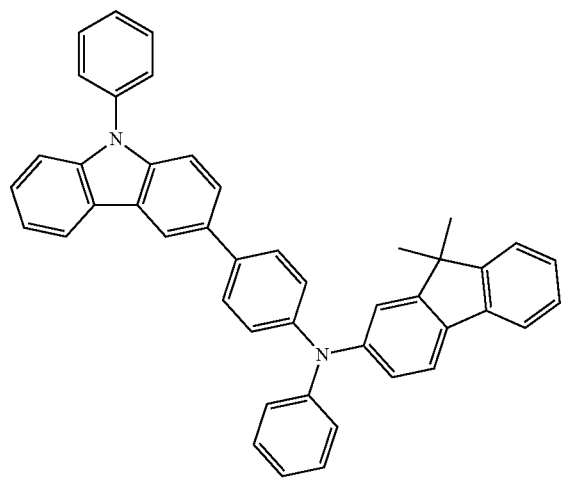
HT2
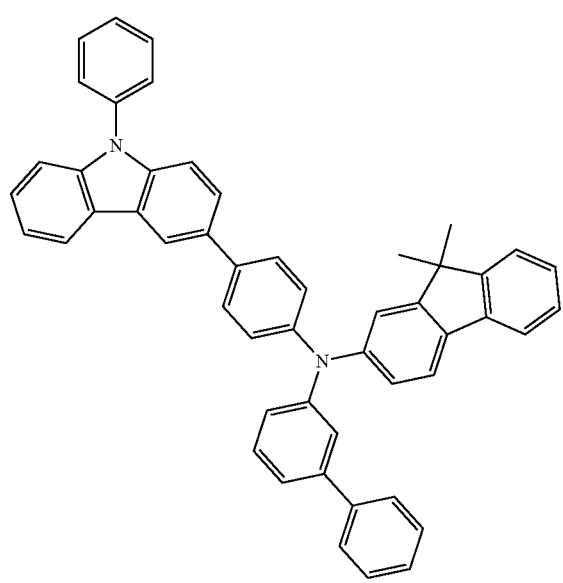
HT3
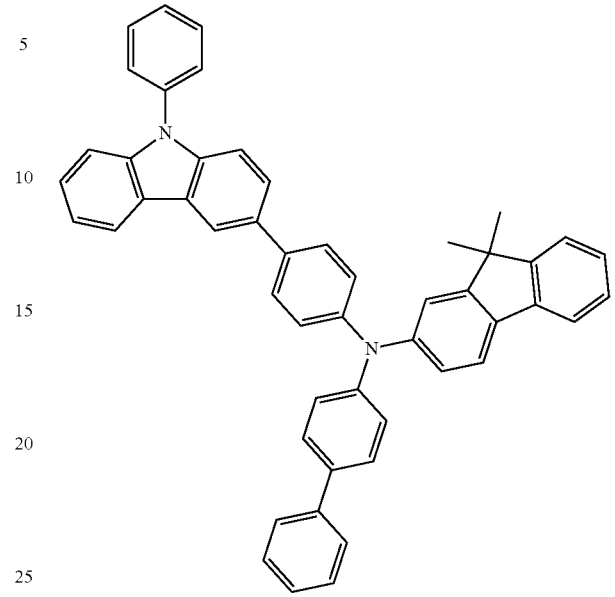
HT4
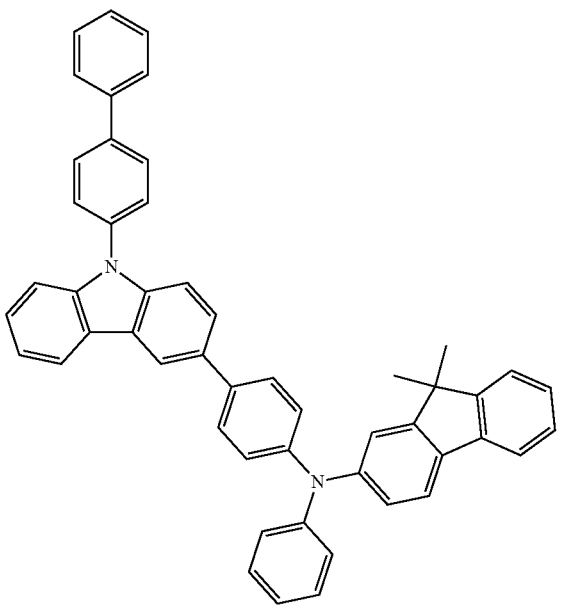

HT5
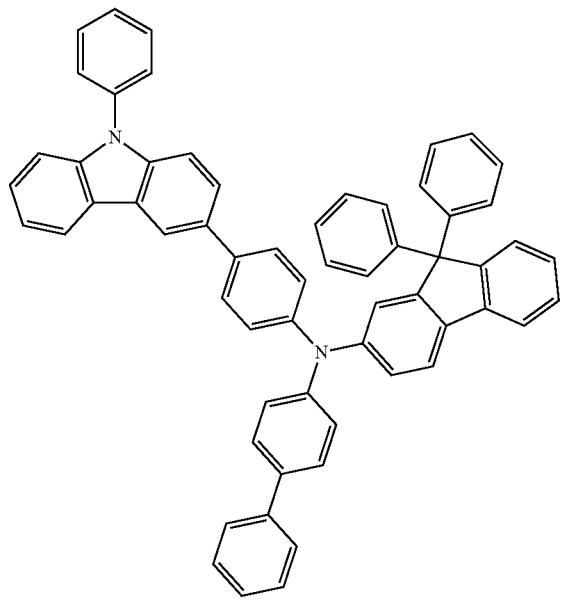
HT7
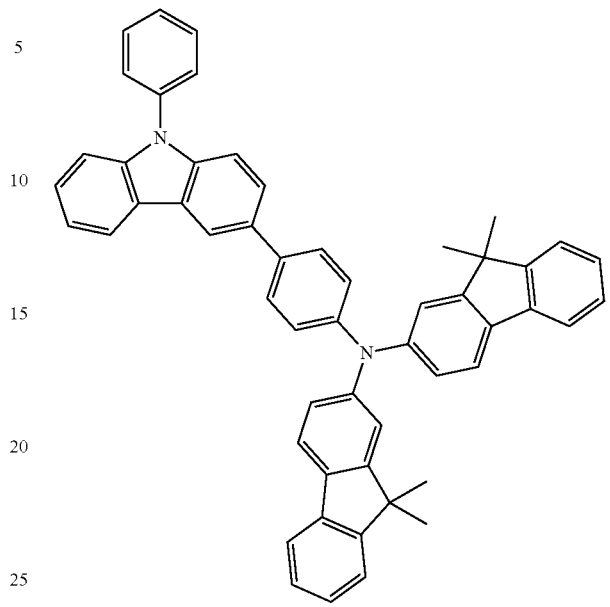
HT6
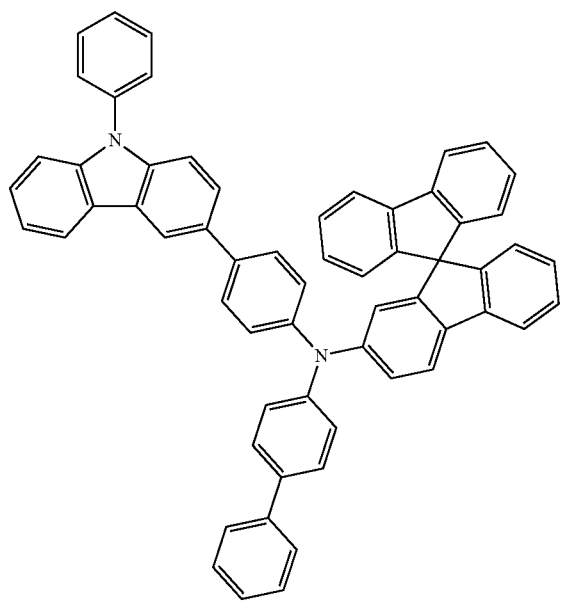
HT8
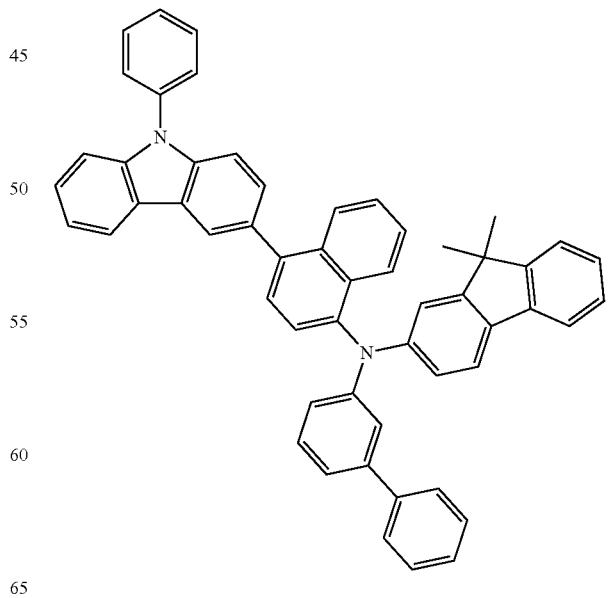

HT9
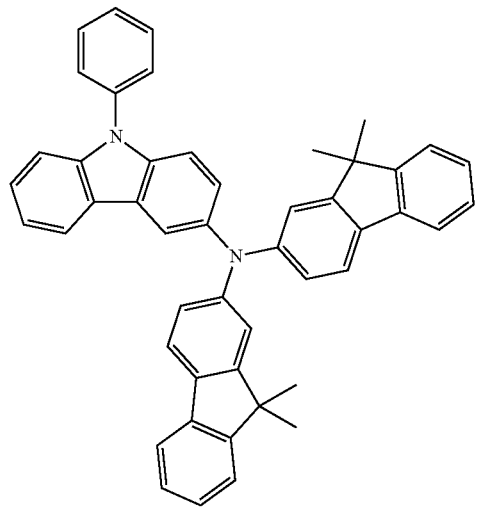
HT11
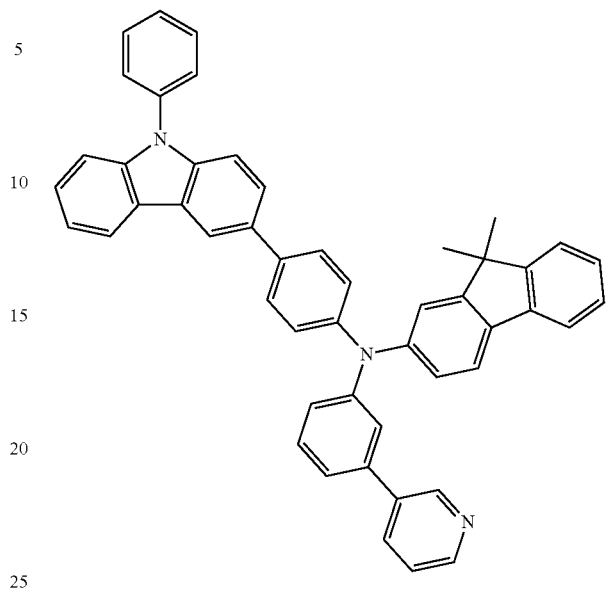
HT10
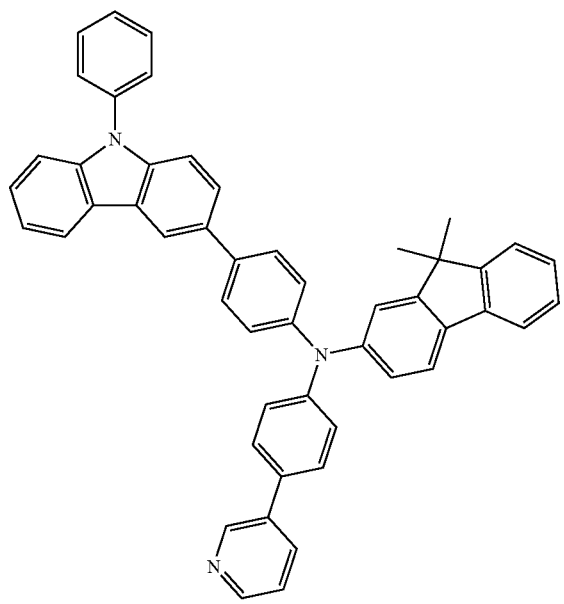
HT12
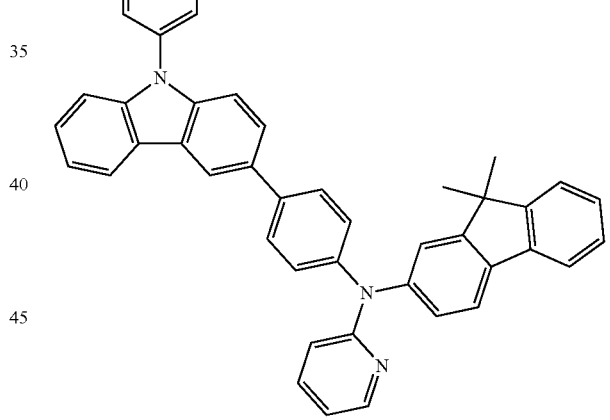
HT13
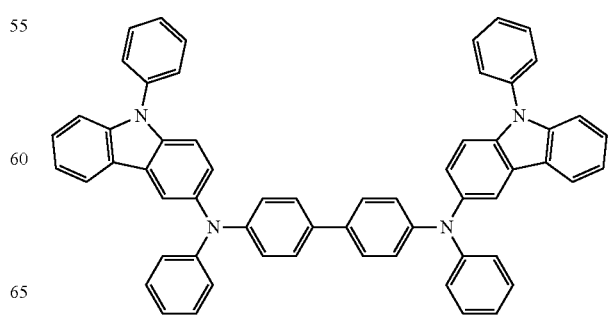

-continued

HT14
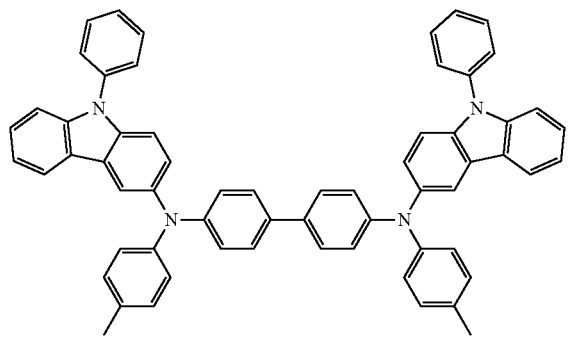

HT15
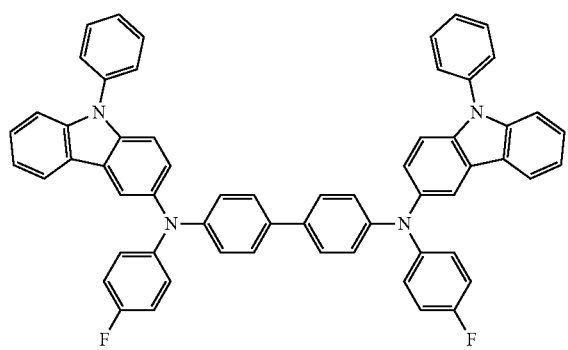

HT16
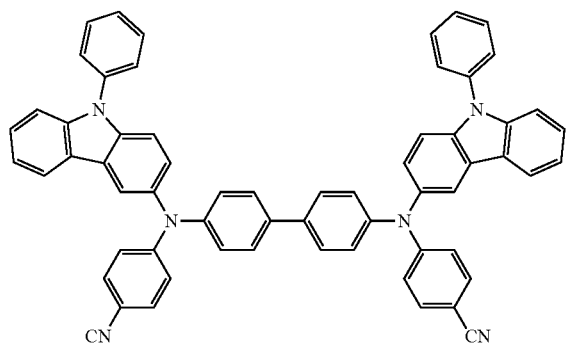

HT17
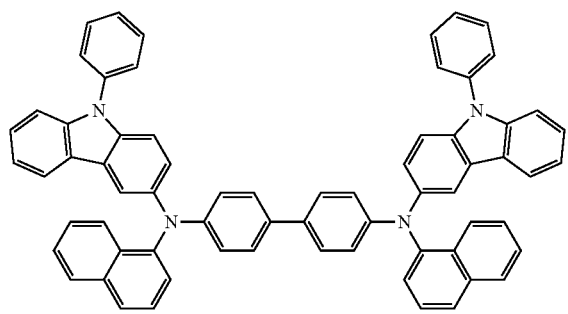

-continued

HT18
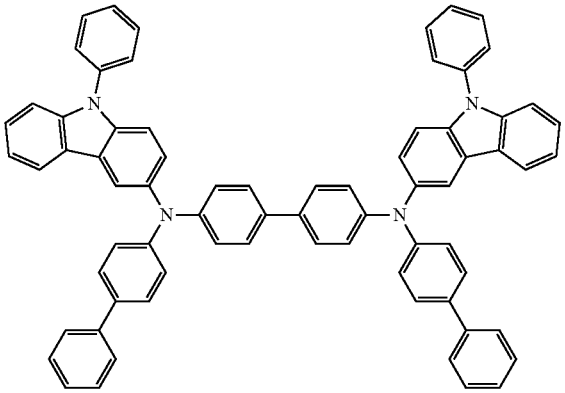

HT19
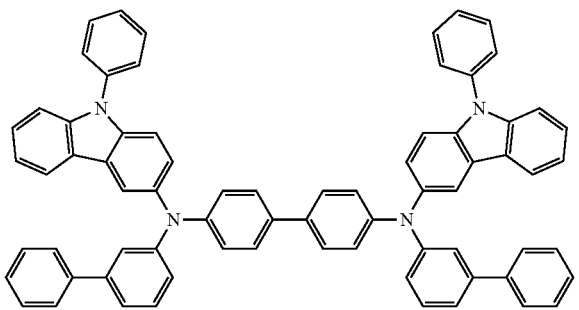

HT20
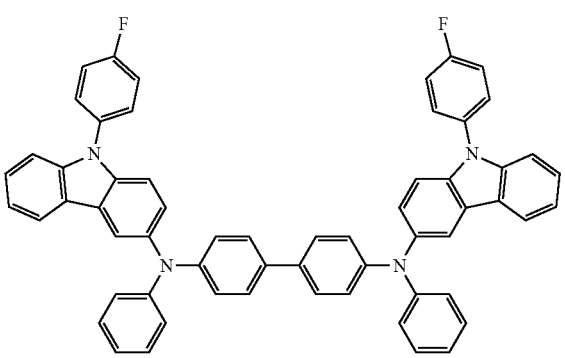

A thickness of the hole transport region may be in a range of about 100 Å to about 10000 Å, e.g., about 100 Å to about 1000 Å. When the hole transport region includes a hole injection layer and a hole transport layer, the thickness of the hole injection layer may be in a range of about 100 Å to about 10000 Å, e.g., about 100 Å to about 1000 Å, and the thickness of the hole transport layer may be in a range of about 50 Å to about 2000 Å, e.g., about 100 Å to about 1500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, e.g., a p-dopant. The p-dopant may be one selected from a quinone derivative, a metal oxide, and a cyano group-containing compound. For example, non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

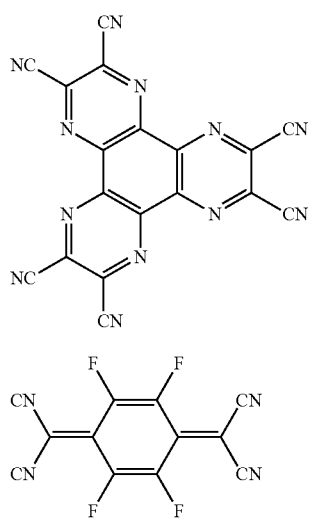

<Compound HT-D1>

<F4-TCNQ>

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer prevents injection of electrons from the electron transport region.

For example, a material for the electron blocking layer may be mCP.

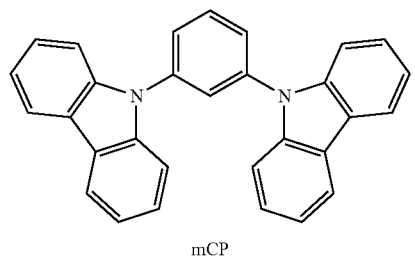 [SMILES: c1cc(-n2c3ccccc3c3ccccc32)cc(-n2c3ccccc3c3ccccc32)c1]

mCP

An emission layer may be formed on the first electrode 110 or the hole transport region by using various methods, e.g., vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include the condensed cyclic compound represented by Formula 1.

The emission layer may include a host and a dopant. The dopant may include the condensed cyclic compound represented by Formula 1.

The host may include, e.g., at least one selected from TPBi, TBADN, ADN (also referred to as "DNA"), CBP, CDBP, and TCP.

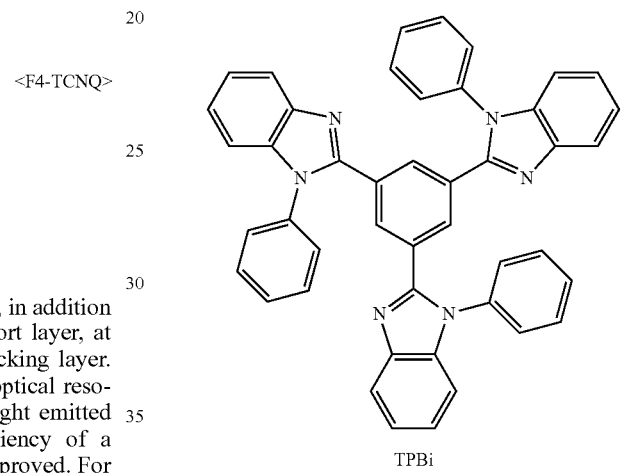

TPBi

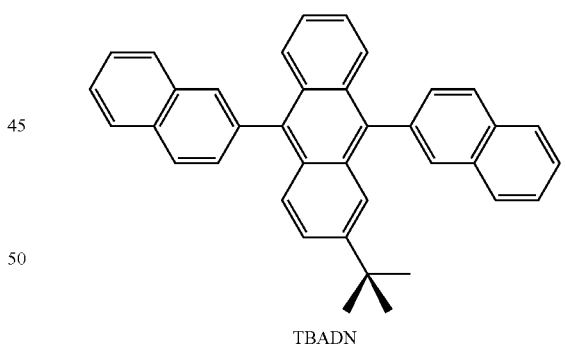

TBADN

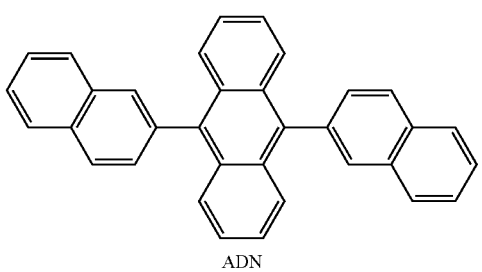

ADN

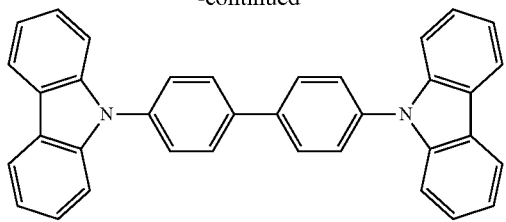

CBP

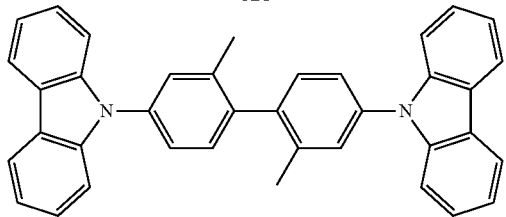

CDBP

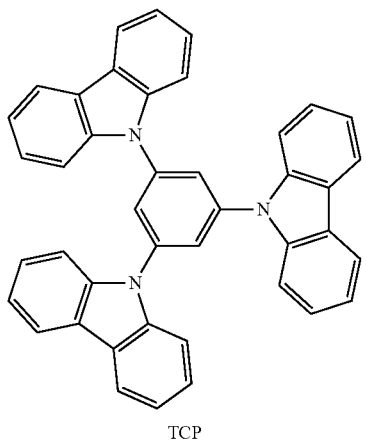

TCP

In some embodiments, the host may include a compound represented by Formula 301 below.

$$Ar_{301}\text{-}[(L_{301})_{xb1}\text{-}R_{301}]_{xb2}$$  <Formula 301>

In Formula 301, $Ar_{301}$ may be selected from a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$)

(wherein $Q_{301}$ to $Q_{303}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group);

$L_{301}$ may be the same as explained in connection with $L_1$;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

wherein in Formula 301, $L_{301}$ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

$R_{301}$ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but is not limited thereto.

For example, the host may include a compound represented by Formula 301A below.

<Formula 301A>

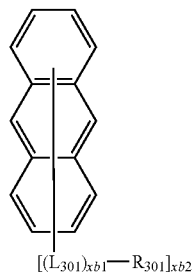

$[(L_{301})_{xb1}\text{—}R_{301}]_{xb2}$

Descriptions of substituents of Formula 301A may be understood by referring to the descriptions provided herein.

The compound represented by Formula 301 may include at least one of Compounds H1 to H42.

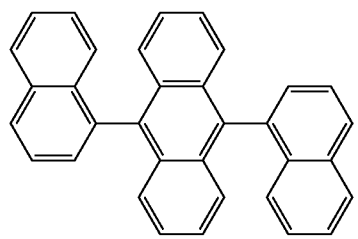

H1

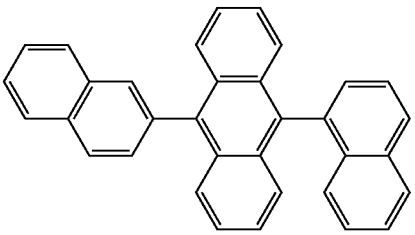

H2

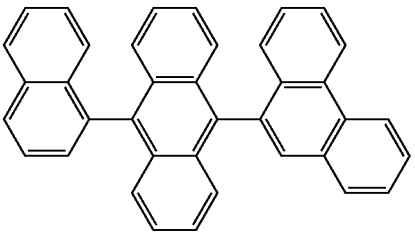

H3

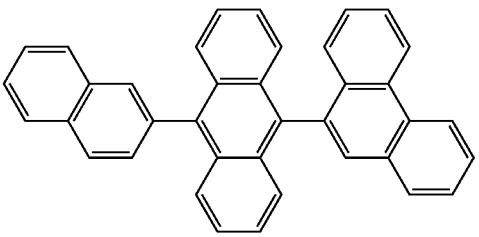

H4

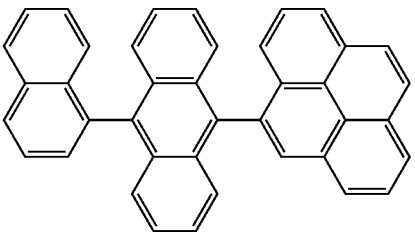

H5

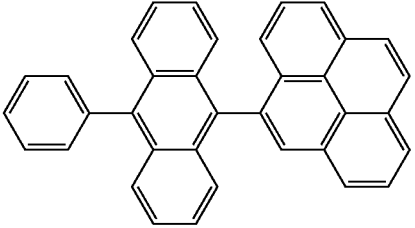

H6

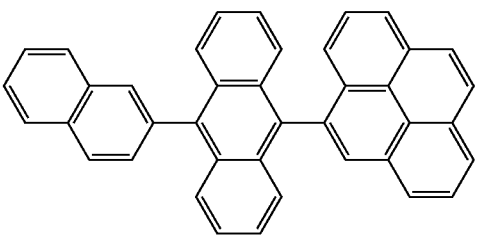

H7

-continued
H8
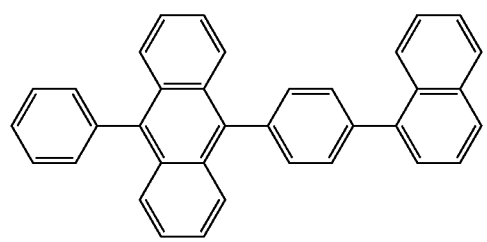
H9
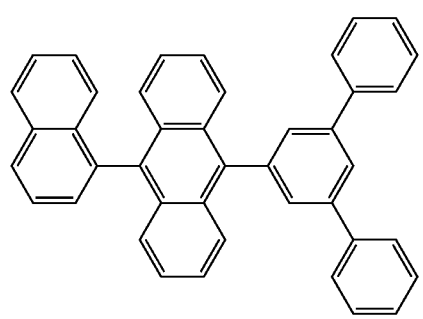
H10
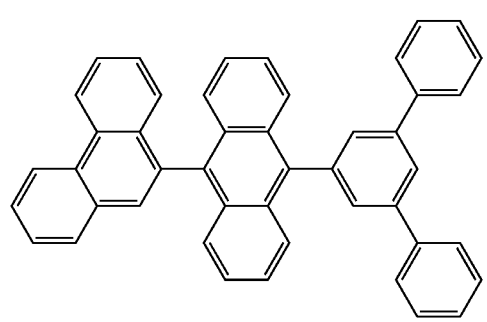
H11
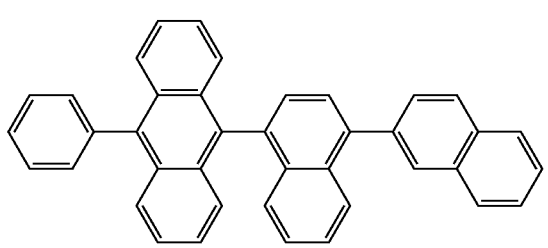
H12
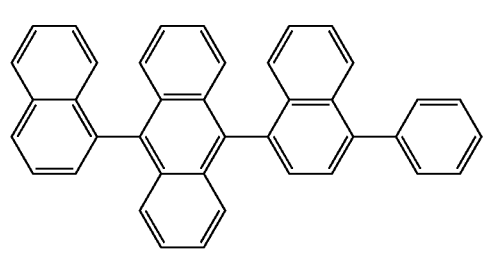
H13
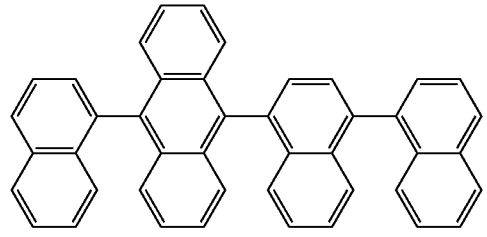
-continued
H14
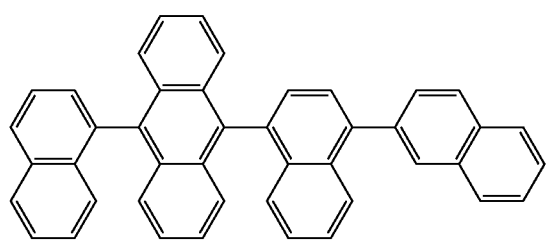
H15
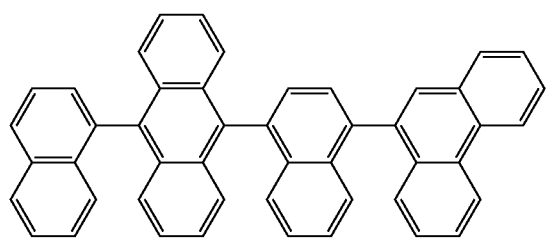
H16
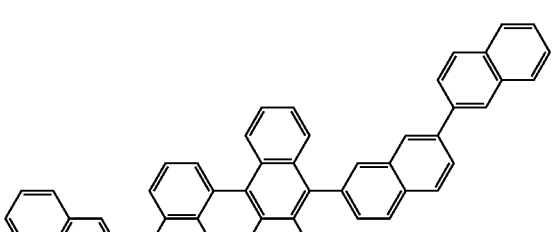
H17
H18
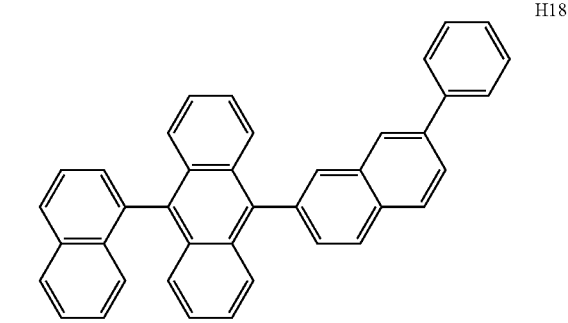

H19
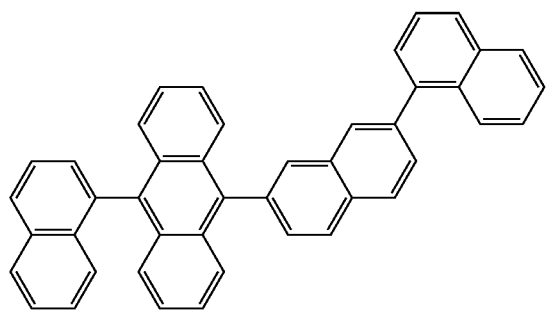
H20
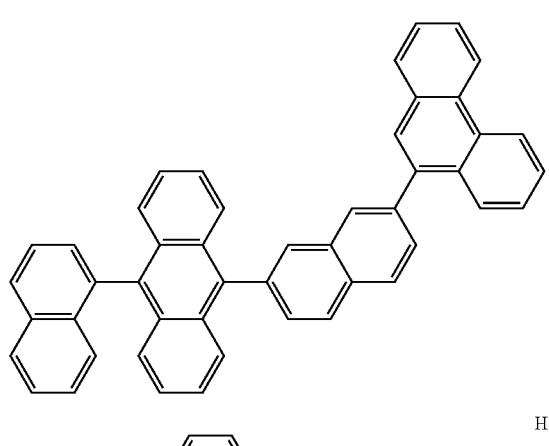
H21
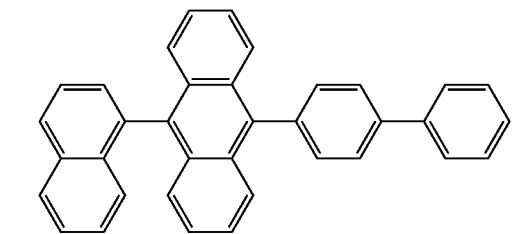
H22
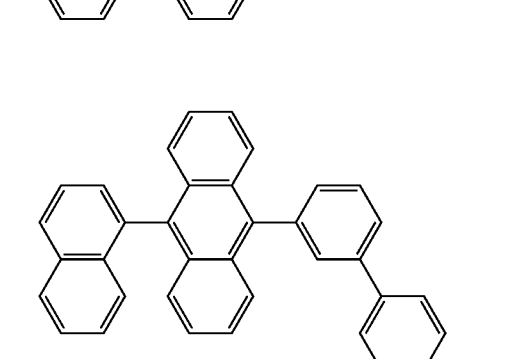
H23
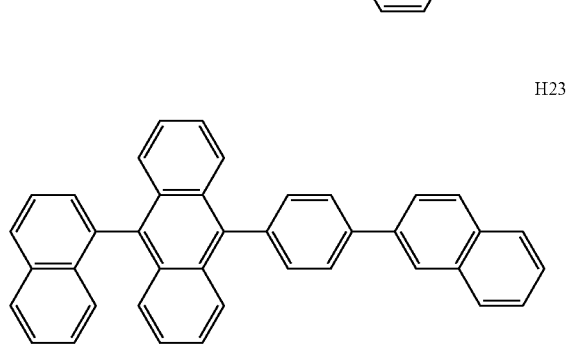
H24
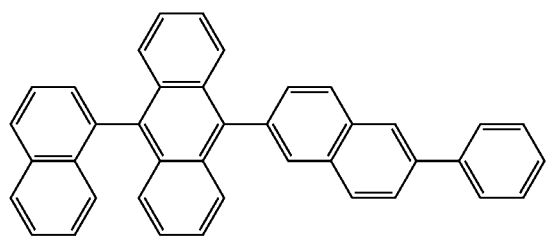
H25
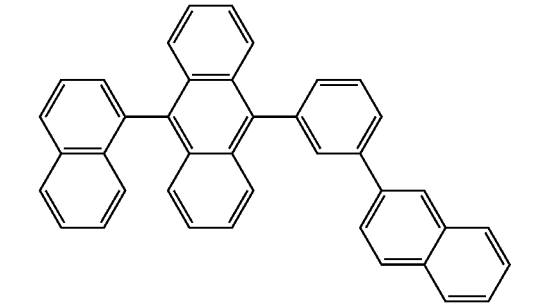
H26
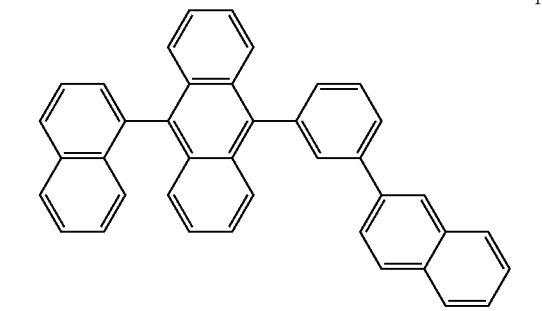
H27
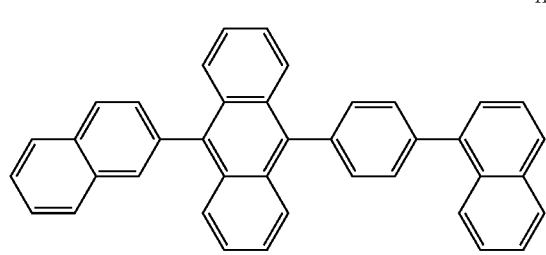
H28
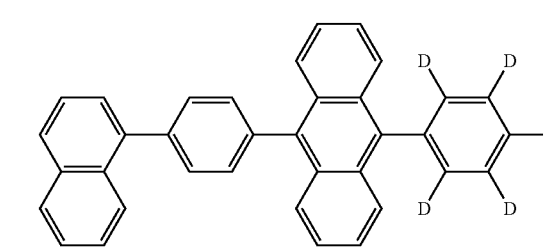
H29
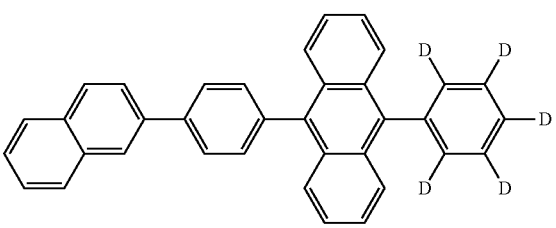

111
-continued
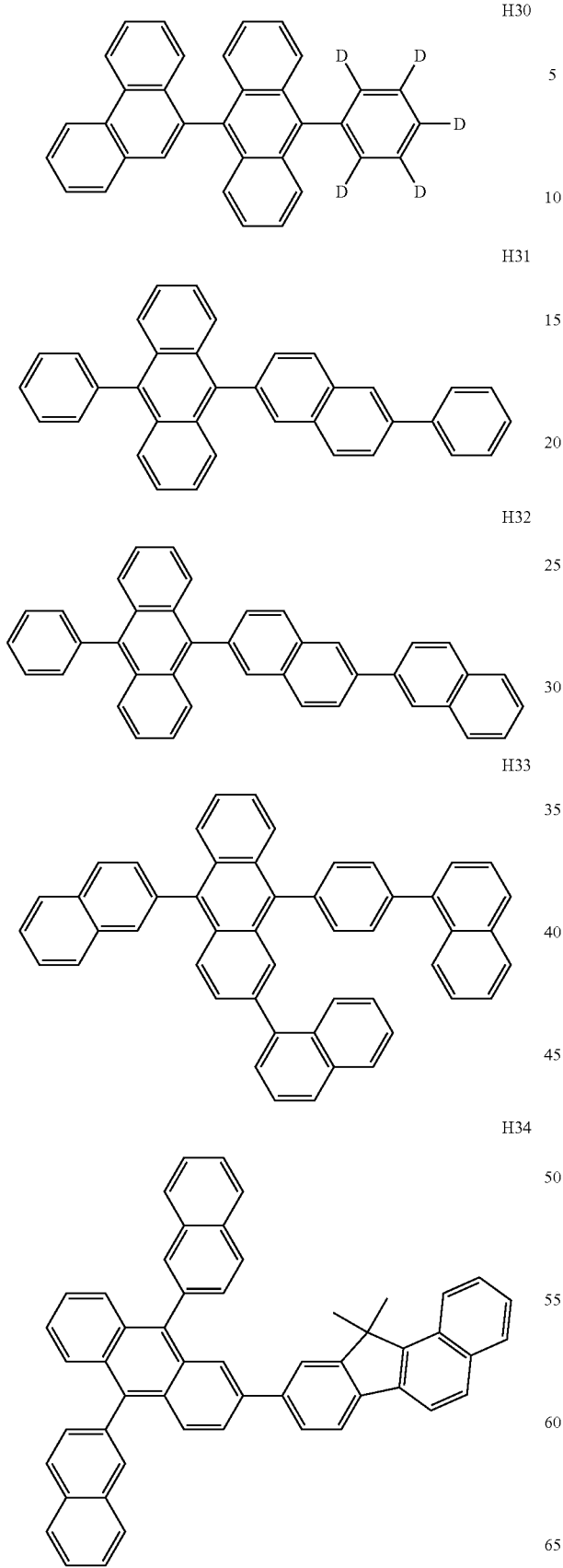
112
-continued
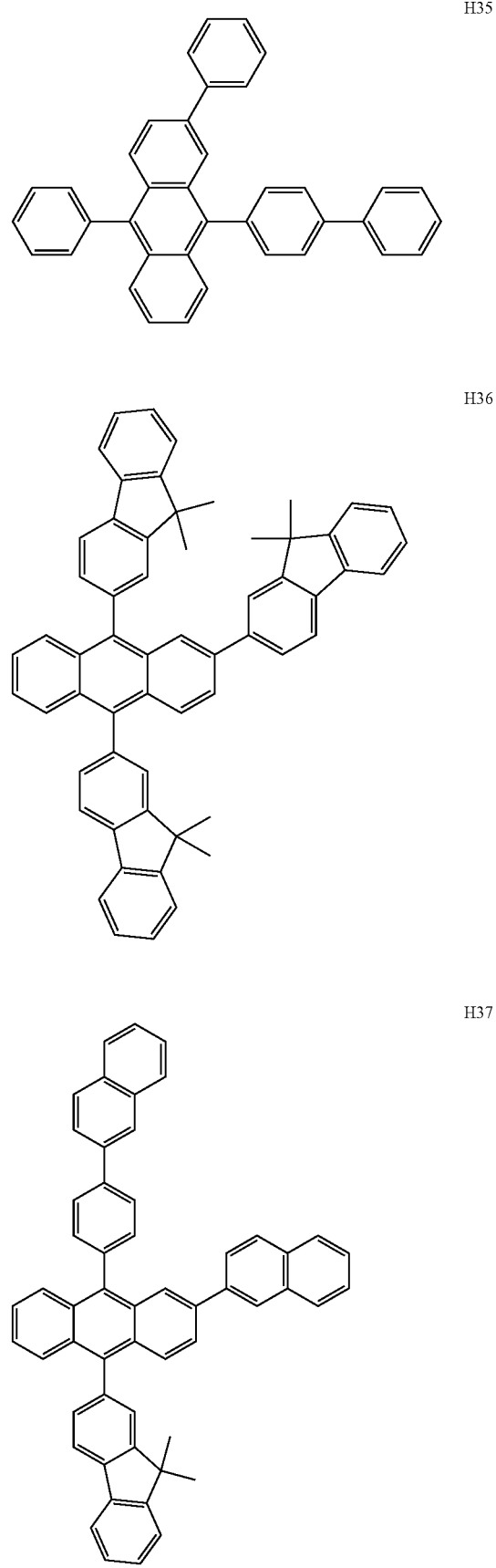

H38
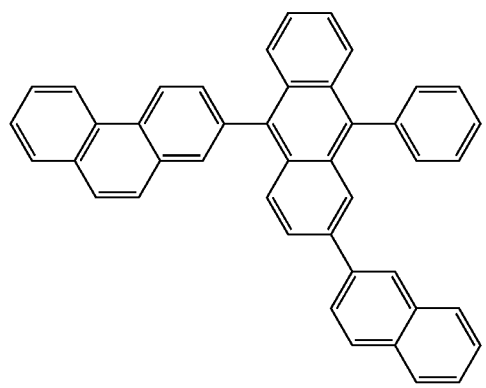
H39
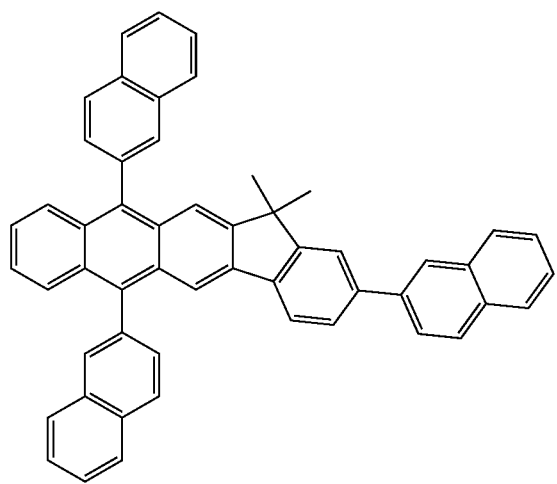
H40
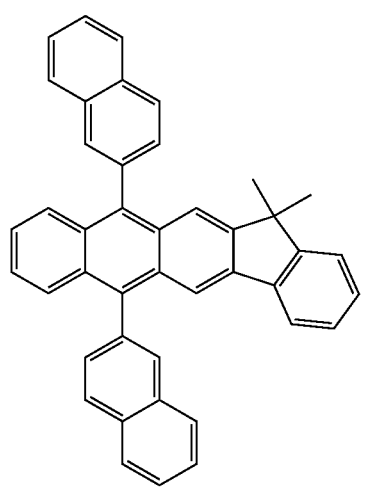
H41
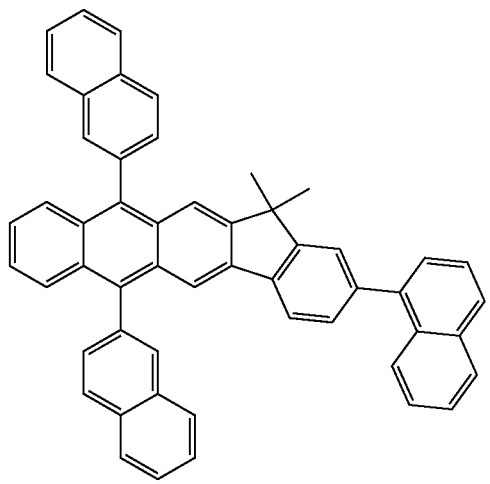
H42
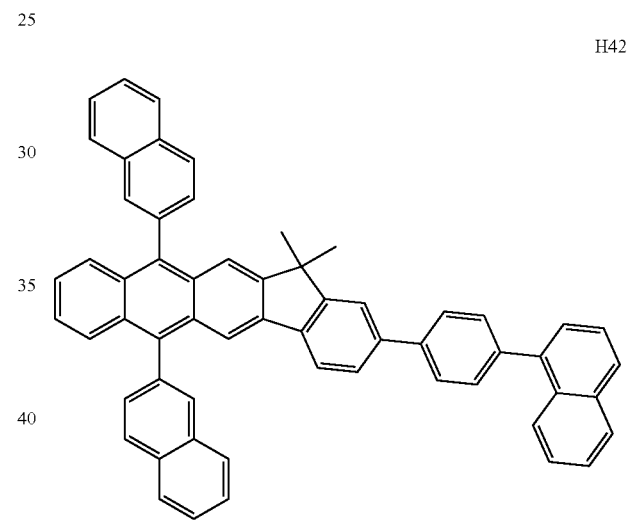
In some embodiments, the host may include at least one of Compounds H43 to H49 below.
H43
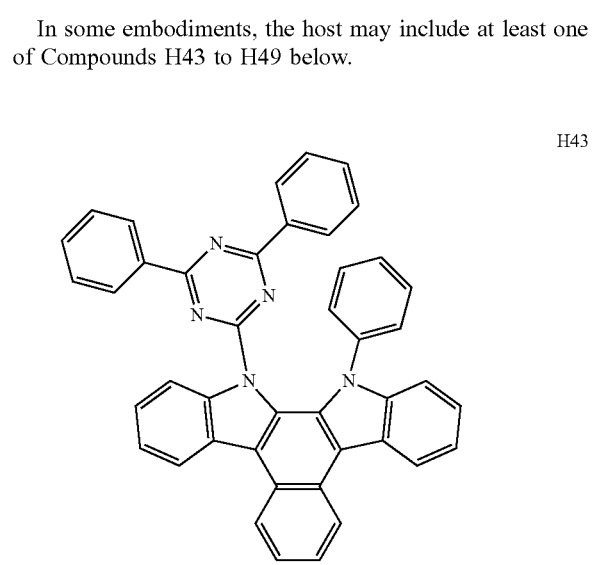

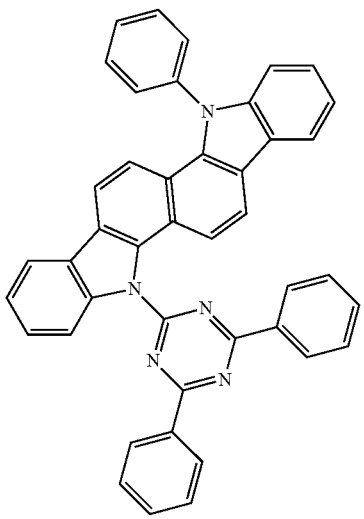
H44

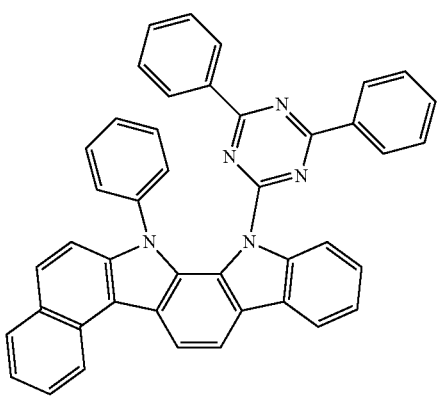
H45

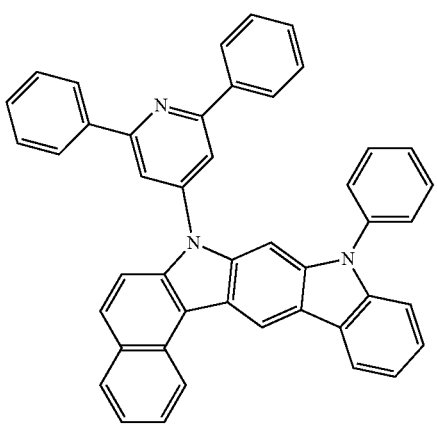
H46

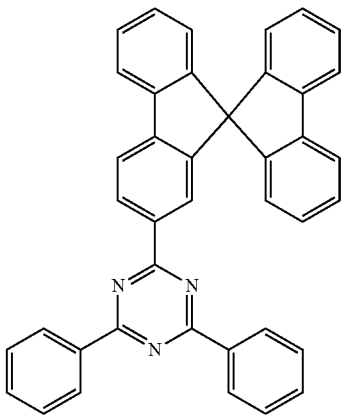
H47

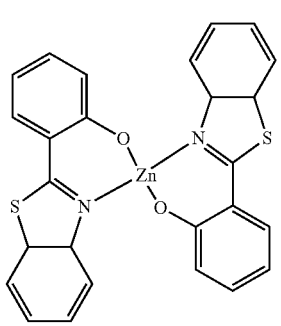
H48

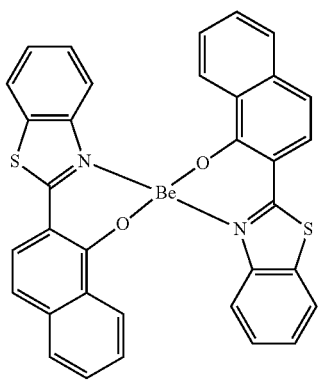
H49

The dopant may include at least one selected from a fluorescent dopant and a phosphorescent dopant. When the dopant includes a fluorescent dopant, the fluorescent dopant may include the condensed cyclic compound represented by Formula 1.

The fluorescent dopant may include, in addition to the condensed cyclic compound represented by Formula 1, at least one selected from DPAVBi, BDAVBi, TBPe, DCM, DCJTB, Coumarin 6, and C545T.

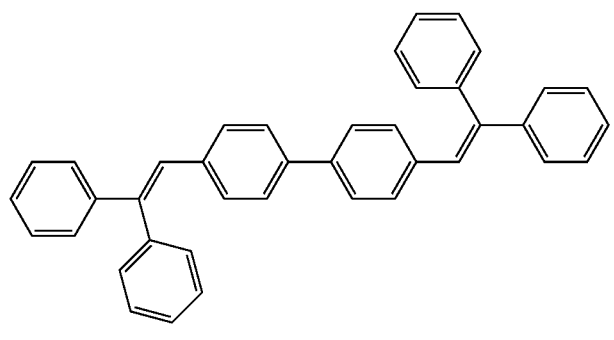
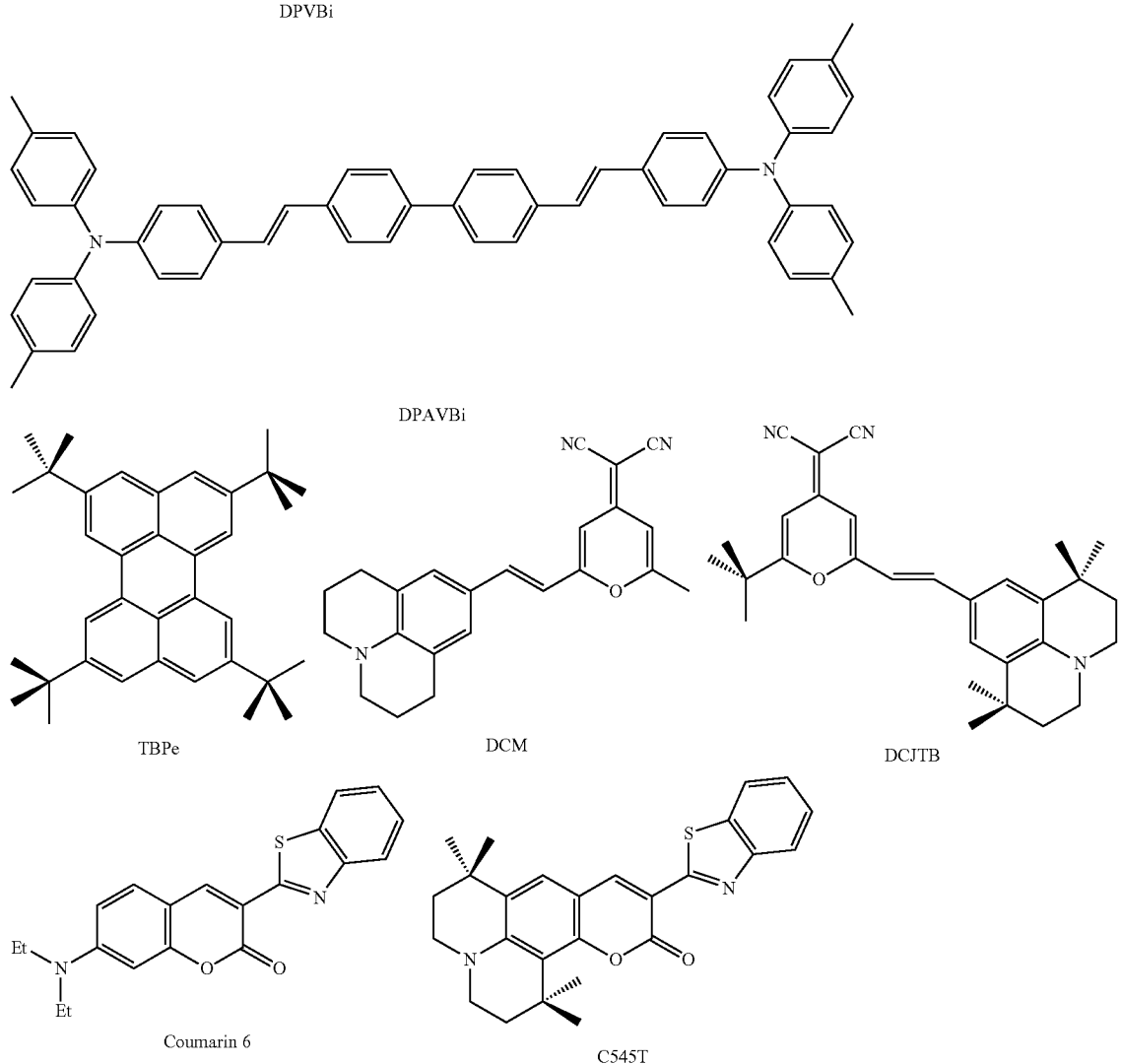

An amount of the dopant in the emission layer may be, e.g., in a range of about 0.01 to about 15 parts by weight based on 100 parts by weight of the host.

A thickness of the emission layer may be in a range of about 100 Å to about 1000 Å, for example, about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order, but is not limited thereto.

According to an embodiment, the organic layer 150 of the organic light-emitting device may include an electron transport region disposed between the emission layer and the second electrode 190.

When the electron transport region includes a hole blocking layer, the hole blocking layer may be formed on the emission layer by using various methods, such as vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, e.g., at least one of BCP and Bphen.

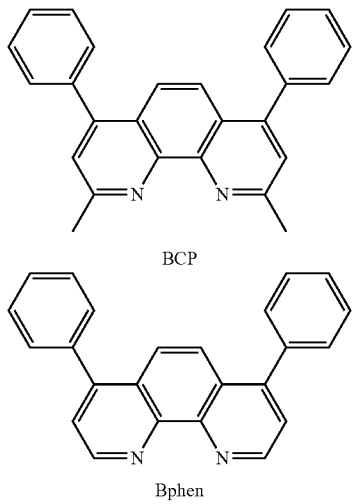

BCP

Bphen

A thickness of the hole blocking layer may be in a range of about 20 Å to about 1000 Å, e.g., about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, such as vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

In some embodiments, the electron transport layer may include at least one compound selected from a compound represented by Formula 601 and a compound represented by Formula 602 illustrated below.

$$Ar_{601}-[(L_{601})_{xe1}-E_{601}]_{xe2} \qquad <\text{Formula 601}>$$

In Formula 601, $Ar_{601}$ may be selected from:

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$cycloalkyl group, a $C_1$-$C_{10}$ heterocycloalkyl group, a $C_3$-$C_{10}$cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently a hydrogen, a $C_1$-$C_{60}$ alkyl group, a $C_2$-$C_{60}$ alkenyl group, a $C_6$-$C_{60}$ aryl group, or a $C_1$-$C_{60}$ heteroaryl group);

$L_{601}$ may be the same as explained in connection with $L_{201}$;

$E_{601}$ may be selected from:

a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

xe1 may be selected from 0, 1, 2, and 3; and
xe2 may be selected from 1, 2, 3, and 4.

<Formula 602>

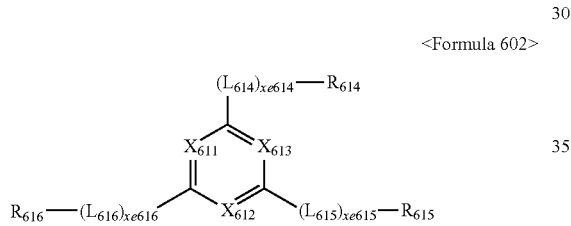

In Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$ and, at least one of $X_{611}$ to $X_{613}$ may be N;

$L_{11}$ to $L_{616}$ may be the same as explained in connection with $L_1$;

$R_{611}$ to $R_{616}$ may each independently be selected from
a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may each independently be selected from 0, 1, 2, and 3.

The compound represented by Formula 601 and the compound represented by Formula 602 may each independently be selected from Compounds ET1 to ET15 illustrated below:

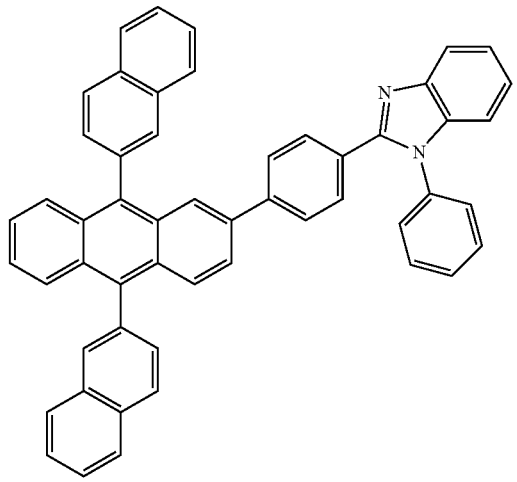

ET1

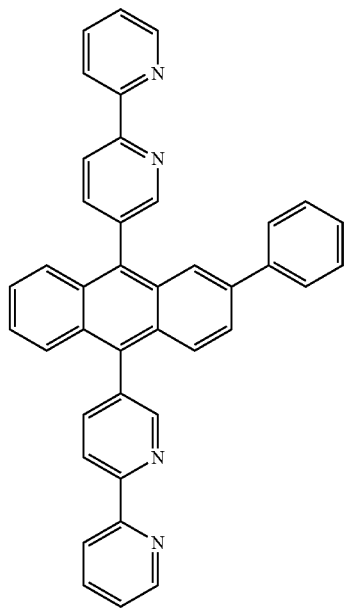

ET2

ET3
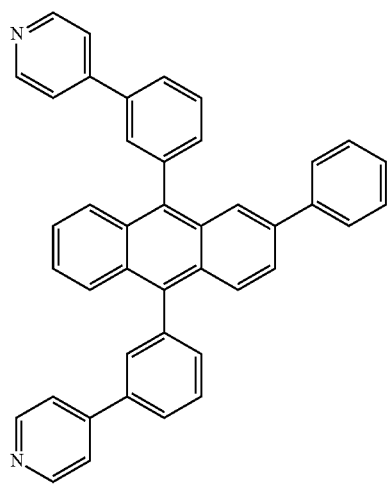
ET4
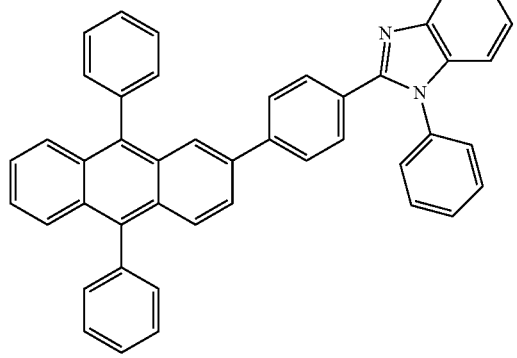
ET5
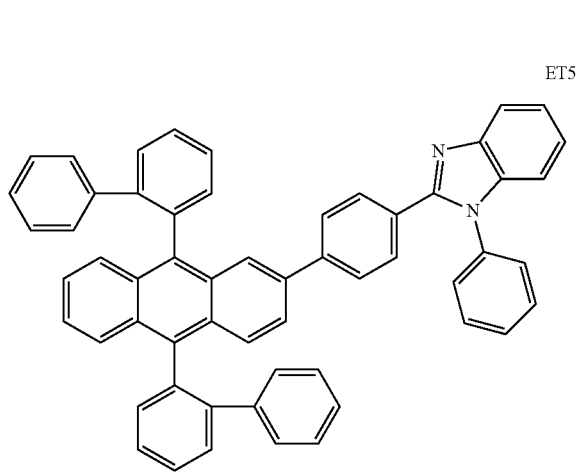
ET6
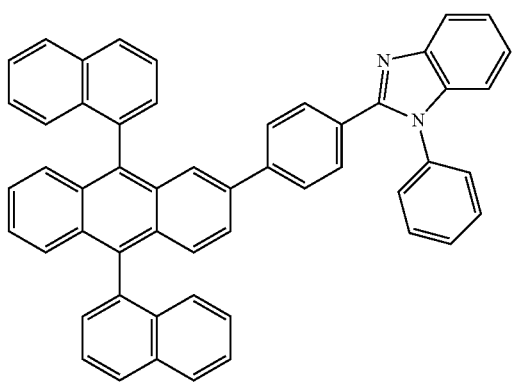
ET7
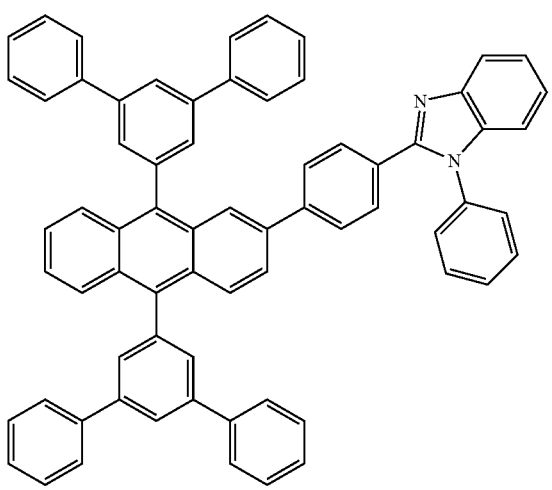
ET8
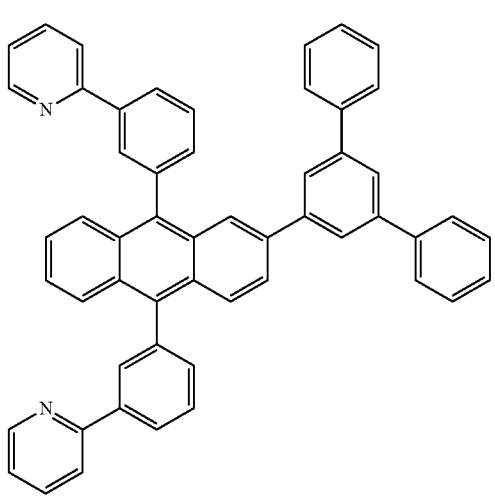

-continued
ET9
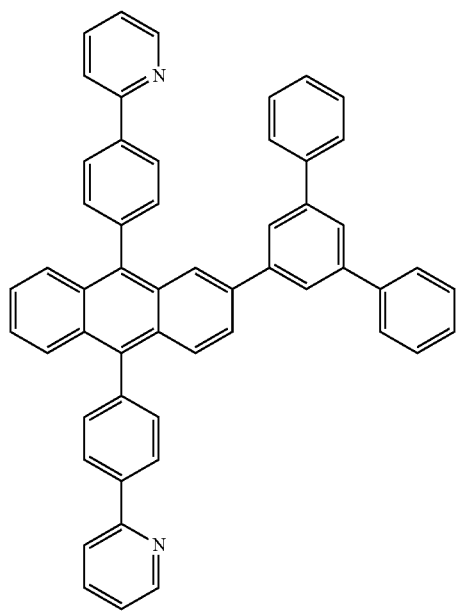
ET11
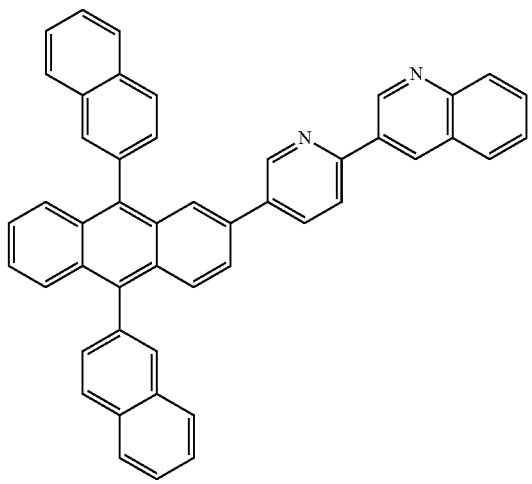
ET12
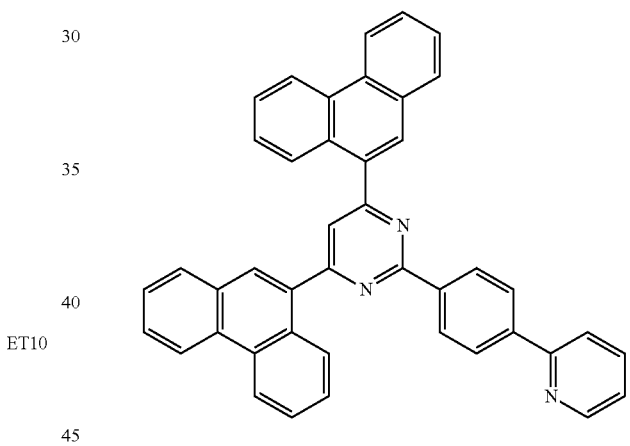
ET10
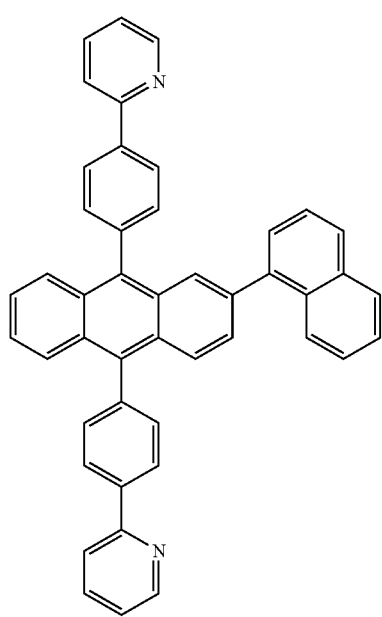
ET13
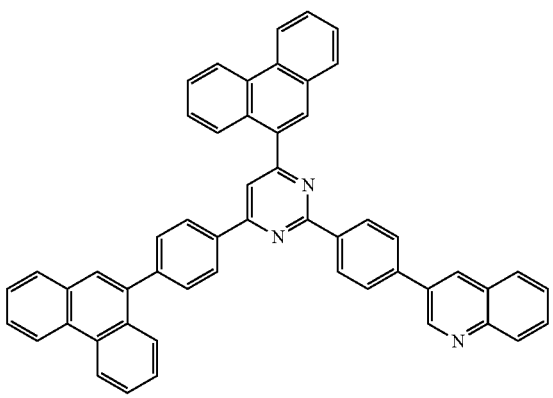

-continued

ET14

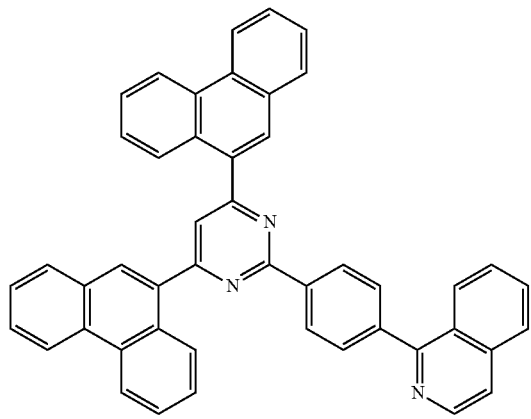

ET15

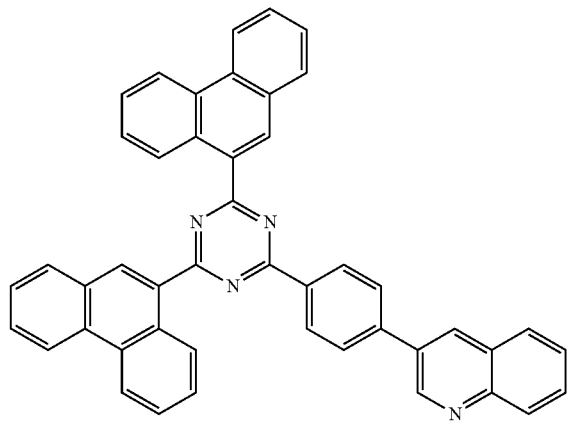

In some embodiments, the electron transport layer may further include at least one selected from BCP, Bphen, Alq$_3$, Balq, TAZ, and NTAZ.

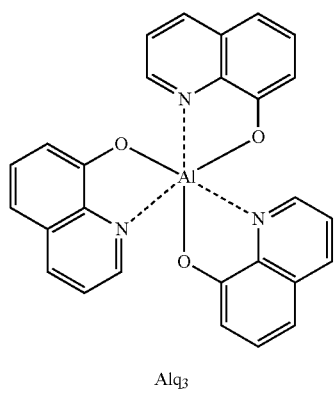

Alq$_3$

-continued

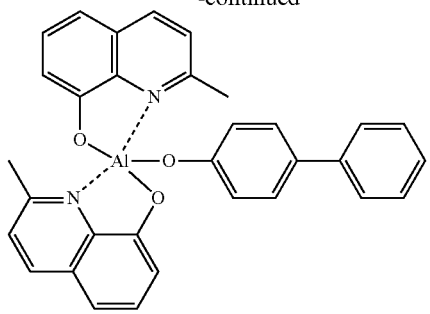

BAlq

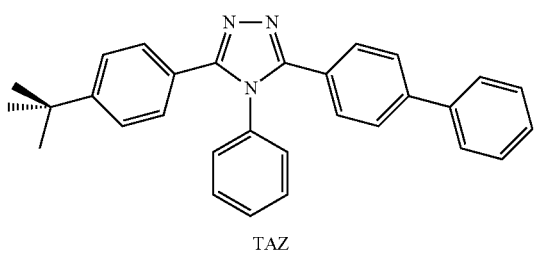

TAZ

NTAZ

A thickness of the electron transport layer may be in a range of about 100 Å to about 1000 Å, e.g., about 150 Å to about 500 Å. When the thickness of the electron transport layer is within the range described above, the electron transport layer may have satisfactory electron transport characteristics without a substantial increase in driving voltage.

In an implementation, the electron transport layer may further include, in addition to the materials described above, a metal-containing material.

The metal-containing material may include a Li complex. The Li complex may include, e.g., Compound ET-D1 (lithium quinolate, LiQ) or ET-D2.

ET-D1

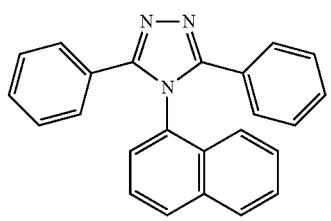

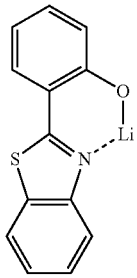
ET-D2

The electron transport region may include an electron injection layer that facilitates electron injection from the second electrode 190.

The electron injection layer may be formed on the electron transport layer by using various methods, such as vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, e.g., about 3 Å to about 90 Å. When the thickness of the electron injection layer is within the range described above, the electron injection layer may have satisfactory electron injection characteristics without a substantial increase in driving voltage.

The second electrode 190 may be disposed on the organic layer 150 having such a structure. The second electrode 190 may be a cathode that is an electron injection electrode, and in this regard, a material for forming the second electrode 190 may be a material having a low work function, and such a material may include metal, alloy, an electrically conductive compound, or a mixture thereof. Examples of the material for the second electrode 190 may include lithium (Li), magnesium (Mg), aluminum (Al), aluminum-lithium (Al—Li), calcium (Ca), magnesium-indium (Mg—In), or magnesium-silver (Mg—Ag). In some embodiments, the material for forming the second electrode 190 may be ITO or IZO. The second electrode 190 may be a semi-transmissive electrode or a transmissive electrode.

Hereinbefore, the organic light-emitting device has been described with reference to FIG. 1.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group, and detailed examples thereof are an ethenyl group, a prophenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group formed by substituting at least one carbon trip bond in the middle or at the terminal of the $C_2$-$C_{60}$ alkyl group, and detailed examples thereof are an ethynyl group, and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, Si, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carbocyclic aromatic system that has at least one hetero atom selected from N, O, Si, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 2 to 60 carbon atoms) that has two or more rings condensed to each other, has a heteroatom selected from N, O, Si, P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

at least one of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —$Si(Q_{11})(Q_{12})(Q_{13})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, —$Si(Q_{21})(Q_{22})(Q_{23})$, and —$B(Q_{24})(Q_{25})$; and —$Si(Q_{31})(Q_{32})(Q_{33})$, wherein $Q_1$ to $Q_3$, $Q_{11}$ to $Q_3$, $Q_{21}$ to $Q_{23}$, and $Q_{31}$ to $Q_{33}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

The term "Ph" used herein refers to a phenyl group, the term "Me" used herein refers to a methyl group, the term "Et" used herein refers to an ethyl group, and the term "ter-Bu" or "Bu$^t$" used herein refers to a tert-butyl group.

Hereinafter, an organic light-emitting device according to an embodiment will be described in detail with reference to Synthesis Examples and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

Synthesis of Compound 1

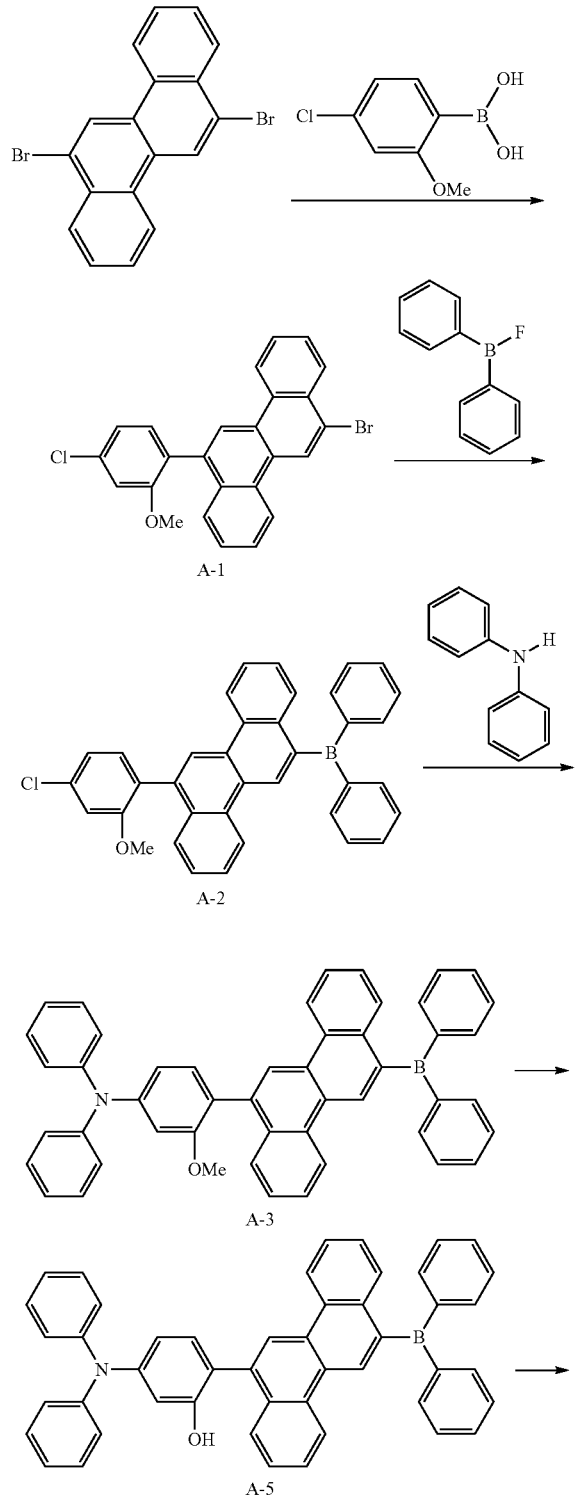

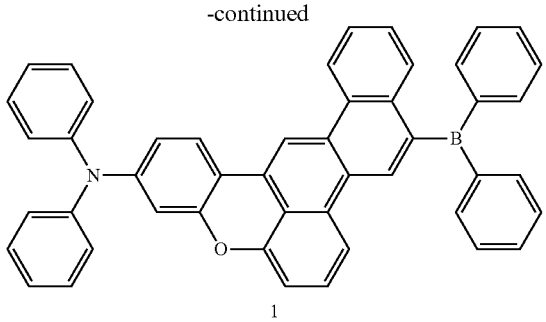

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon by using methylenechloride (MC). Column chromatography was performed thereon to obtain Intermediate A-1 (24.6 g, 55 mmol, yield of 55%).

Synthesis of Intermediate A-2

Intermediate A-1 (24.6 g, 55 mmol) was dissolved in 1.5 L of THF, and then, the result was cooled to a temperature of −78° C. n-BuLi was slowly added thereto, and then stirred for 1 hour. Fluorodiphenylborane (11.0 g, 60 mmol) dissolved in 300 ml of tetrahydrofuran (THF) was added to the mixture, and then, slowly heated to ambient temperature, the resultant solution was stirred for 12 hours. Once the reaction was complete, the resultant solution was neutralized by using a HCl aqueous solution until a pH thereof reached 5. Subsequently, a solvent was evaporated therefrom and an extraction process was performed thereon by using MC. A column chromatography was performed thereon to obtain Intermediate A-2 (20.5 g, 38 mmol, yield of 70%).

Synthesis of Intermediate A-3

Intermediate A-2 (10.6 g, 15 mmol), diphenylamine (3.0 g, 18 mmol), tris(dibenzylideneacetone)dipalladium(0) (275 mg, 0.3 mmol), tri(tert-butyl)phosphine (121 mg, 0.6 mmol), and sodium tert-butoxide (2.9 mg, 30 mmol) were dissolved in 50 ml of toluene, and then, the mixture was stirred at a temperature of 80° C. for 2 hours. The temperature was dropped to ambient temperature, and then an extraction process was performed thereon using ethyl acetate. Column chromatography was performed thereon to obtain Intermediate A-3 (8.0 g, 12 mmol, yield 80%).

Synthesis of Intermediate A-4

Intermediate A-3 (8.0 g, 12 mmol) and sodium ethanethiolate (2.0 g, 24 mmol) were dissolved in 100 mL of DMF, and then, the result was reflux-stirred at a temperature of 150° C. for 4 hours. The temperature was dropped to ambient temperature, and then an extraction process was performed thereon using ethyl acetate. Column chromatography was performed thereon to obtain Intermediate A-4 (5.4 g, 8.4 mmol, yield of 70%).

Synthesis of Compound 1

Intermediate A-4 (5.4 g, 8.4 mmol) and Cu$_2$O (6.0 g, 42 mmol) were dissolved in 50 mL of nitrobenzene, and then, the result was reflux-stirred at a temperature of 180° C. for 12 hours. The temperature was dropped to ambient temperature, and then an extraction process was performed thereon using ethyl acetate. Column chromatography was performed thereon to obtain Compound 1 (4.9 g, 7.6 mmol, yield of 90%).

Synthesis Example 2

Synthesis of Compound 4

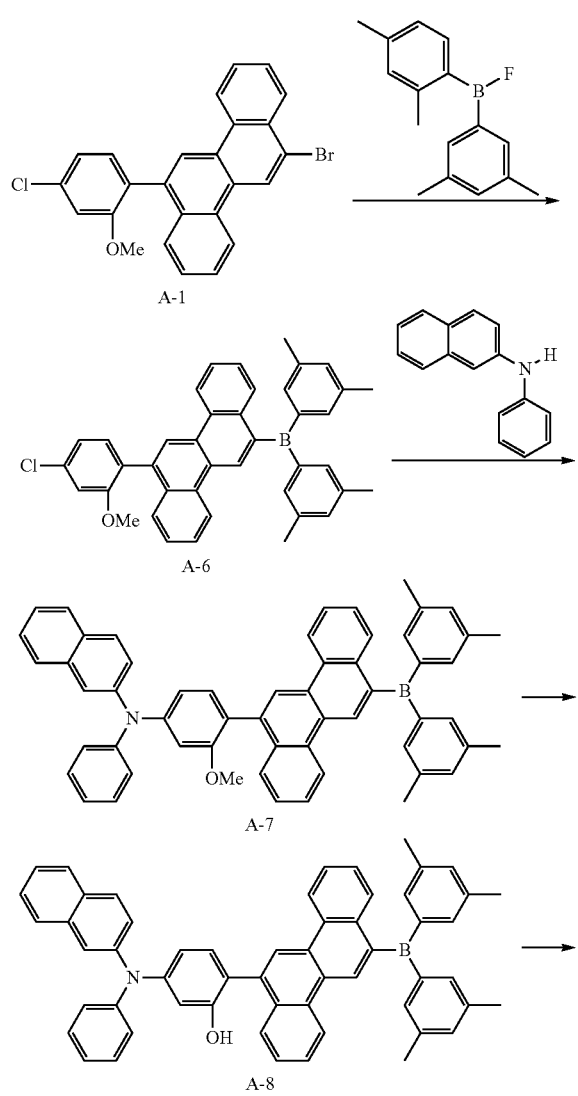

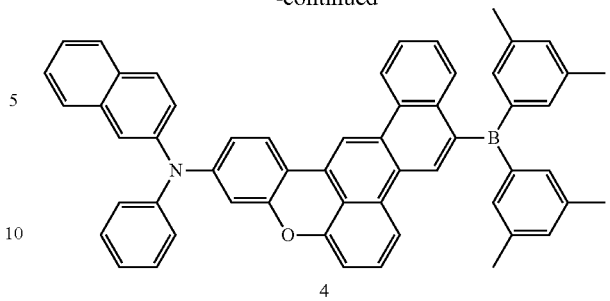

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-6

Intermediate A-6 was obtained in a yield of 70% in the same manner as used to synthesize Intermediate A-2, except that (2,4-dimethylphenyl)(3,5-dimethylphenyl)fluoroborane was used instead of fluorodiphenylborane.

Synthesis of Intermediate A-7

Intermediate A-7 was obtained in a yield of 83% in the same manner as used to synthesize Intermediate A-3, except that Intermediate A-6 was used instead of Intermediate A-2 and N-phenylnaphthalen-2-amine was used instead of diphenylamine.

Synthesis of Intermediate A-8

Intermediate A-8 was obtained in a yield of 70% in the same manner as used to synthesize Intermediate A-4, except that Intermediate A-7 was used instead of Intermediate A-3.

Synthesis of Compound 4

Compound 4 was obtained in a yield of 85% in the same manner as used to synthesize Compound 1, except that Intermediate A-8 was used instead of Intermediate A-4.

Synthesis Example 3

Synthesis of Compound 14

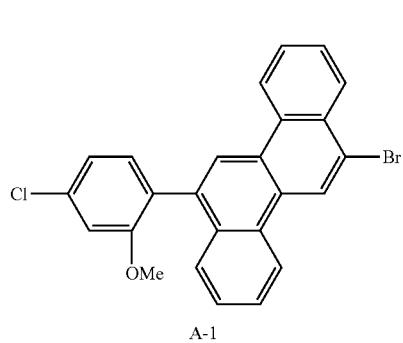

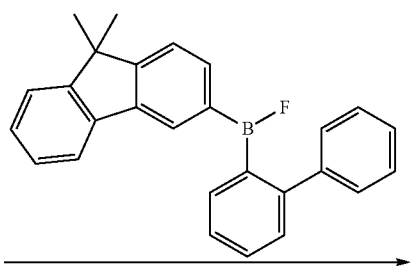

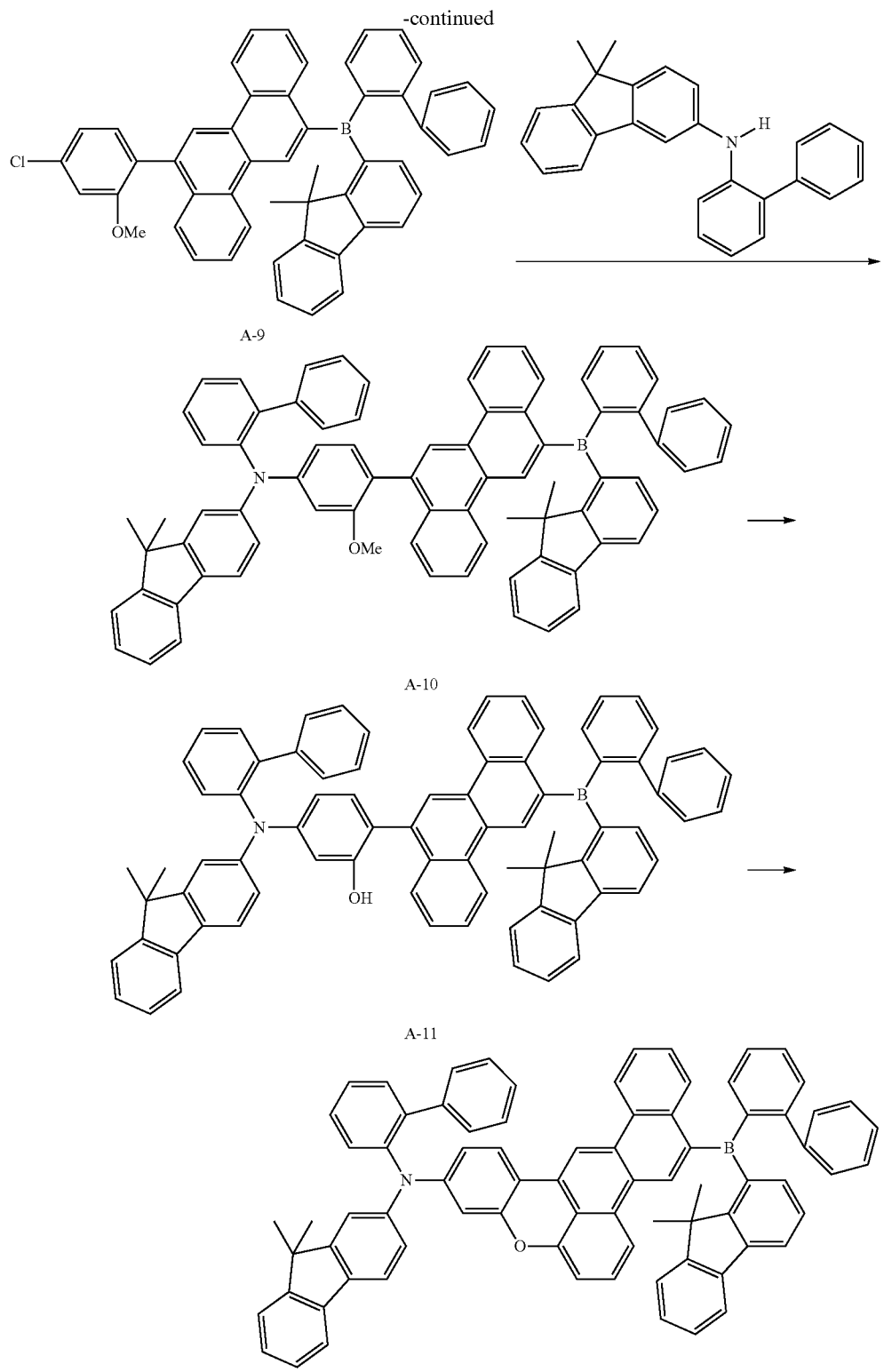

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh₄ (2.3 g, 5 mmol), K₃PO₄ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC).

Column chromatography was performed thereon to obtain Intermediate A-1 (24.6 g, 55 mmol, yield of 55%).

Synthesis of Intermediate A-9

Intermediate A-9 was obtained in a yield of 72% in the same manner as used to synthesize Intermediate A-2, except that [1,1'-biphenyl]-2-yl(9,9-dimethyl-9H-fluoren-3-yl)fluoroborane was used instead of fluorodiphenylborane.

Synthesis of Intermediate A-10

Intermediate A-10 was obtained in a yield of 79% in the same manner as used to synthesize Intermediate A-3, except that Intermediate A-9 was used instead of Intermediate A-2 and ([1,1'-biphenyl]-2-yl)-9,9-dimethyl-9H-fluoren-3-amine was used instead of diphenylamine.

Synthesis of Intermediate A-11

Intermediate A-11 was obtained in a yield of 73% in the same manner as used to synthesize Intermediate A-4, except that Intermediate A-10 was used instead of Intermediate A-3.

Synthesis of Compound 14

Compound 14 was obtained in a yield of 80% in the same manner as used to synthesize Compound 1, except that Intermediate A-11 was used instead of Intermediate A-4.

Synthesis Example 4

Synthesis of Compound 22

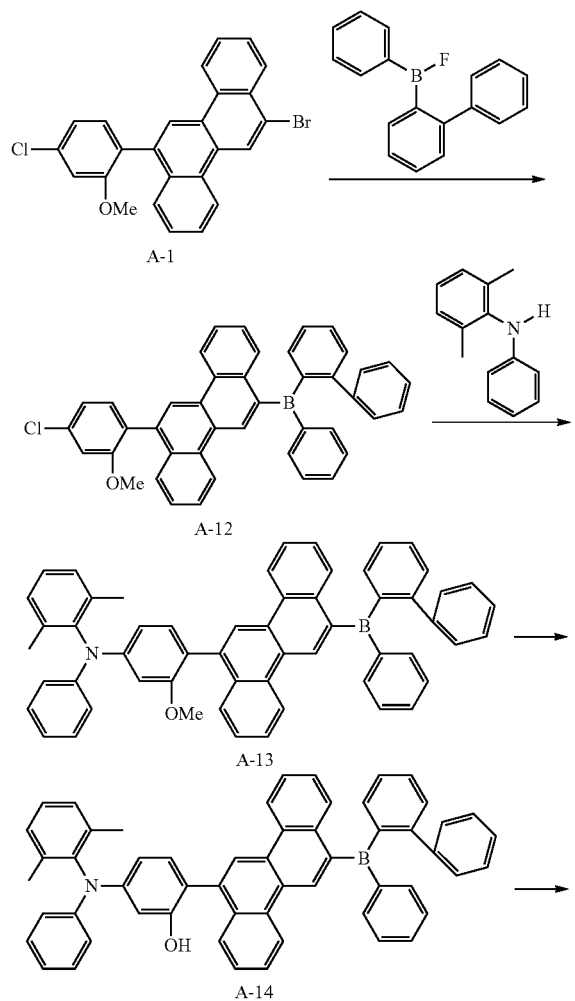

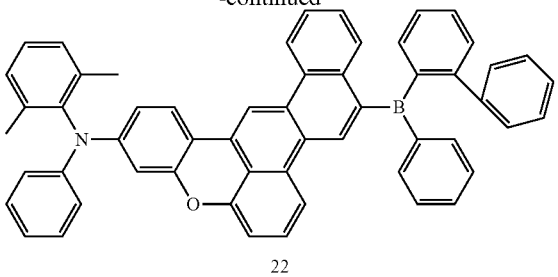

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-12

Intermediate A-12 was obtained in a yield of 75% in the same manner as used to synthesize Intermediate A-2, except that [1,1'-biphenyl]-2-ylfluoro(phenyl)borane was used instead of fluorodiphenylborane.

Synthesis of Intermediate A-13

Intermediate A-13 was obtained in a yield of 81% in the same manner as used to synthesize Intermediate A-3, except that Intermediate A-12 was used instead of Intermediate A-2 and 2,6-dimethyl-N-phenylaniline was used instead of diphenylamine.

Synthesis of Intermediate A-14

Intermediate A-14 was obtained in a yield of 77% in the same manner as used to synthesize Intermediate A-4, except that Intermediate A-13 was used instead of Intermediate A-3.

Synthesis of Compound 22

Compound 22 was obtained in a yield of 88% in the same manner as used to synthesize Compound 1, except that Intermediate A-14 was used instead of Intermediate A-4.

Synthesis Example 5

Synthesis of Compound 25

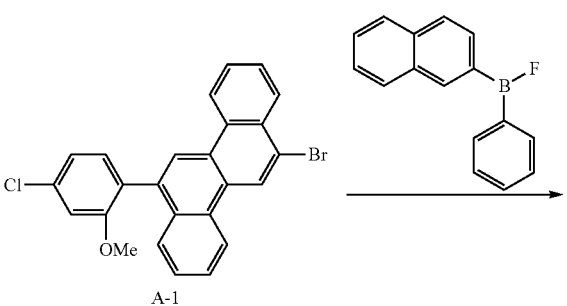

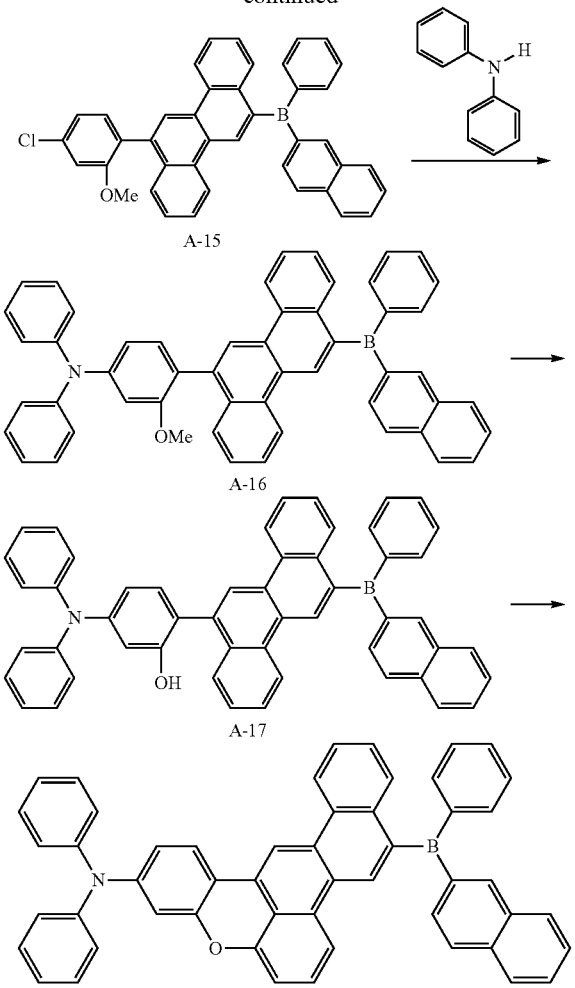

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-15

Intermediate A-15 was obtained in a yield of 80% in the same manner as used to synthesize Intermediate A-2, except that fluoro(naphthalen-2-yl)(phenyl)borane was used instead of fluorodiphenylborane.

Synthesis of Intermediate A-16

Intermediate A-16 was obtained in a yield of 88% in the same manner as used to synthesize Intermediate A-3, except that Intermediate A-12 was used instead of Intermediate A-2.

Synthesis of Intermediate A-17

Intermediate A-17 was obtained in a yield of 81% in the same manner as used to synthesize Intermediate A-4, except that Intermediate A-16 was used instead of Intermediate A-3.

Synthesis of Compound 25

Compound 25 was obtained in a yield of 87% in the same manner as used to synthesize Compound 1, except that Intermediate A-17 was used instead of Intermediate A-4.

Synthesis Example 6

Synthesis of Compound 33

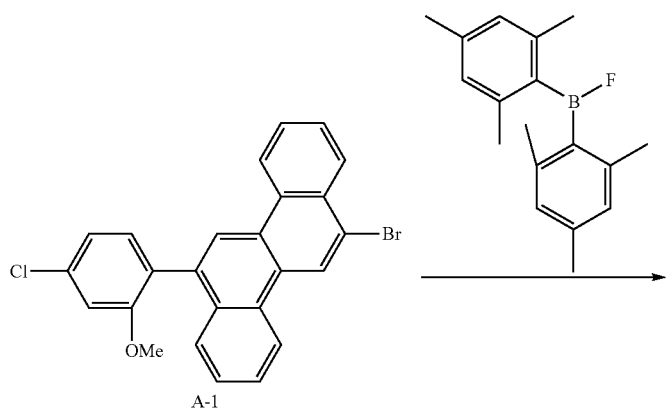

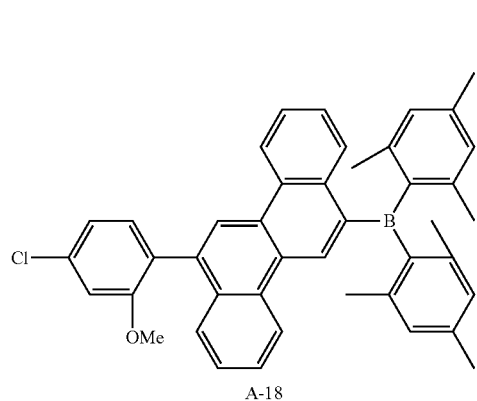
A-18
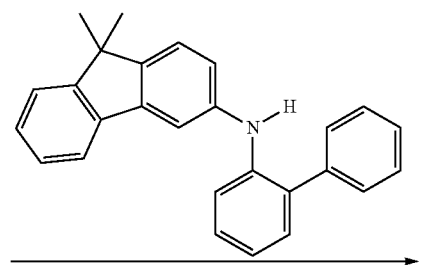
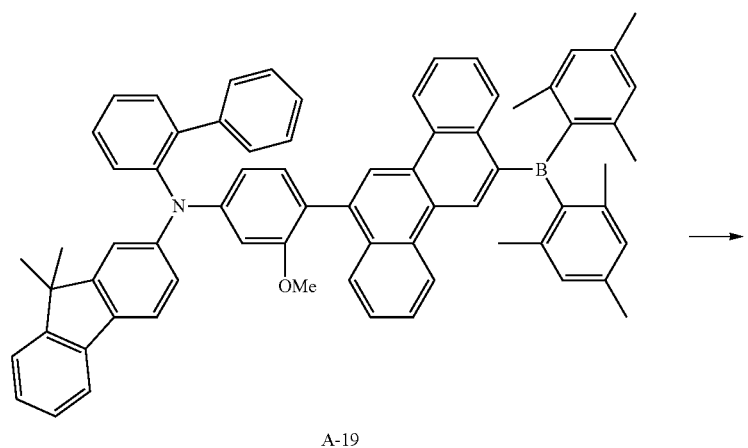
A-19
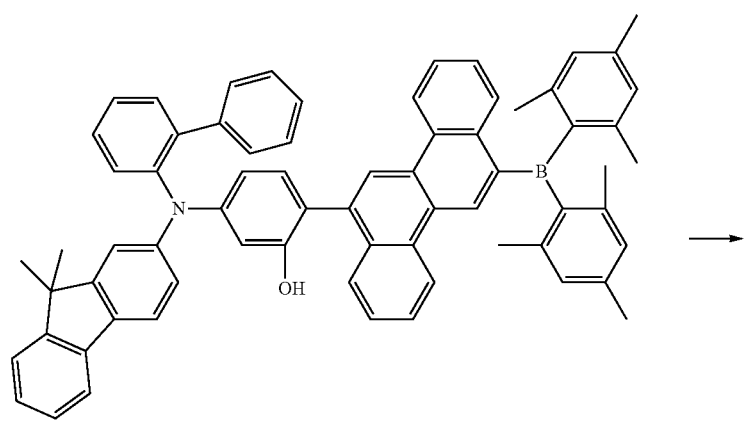
A-20

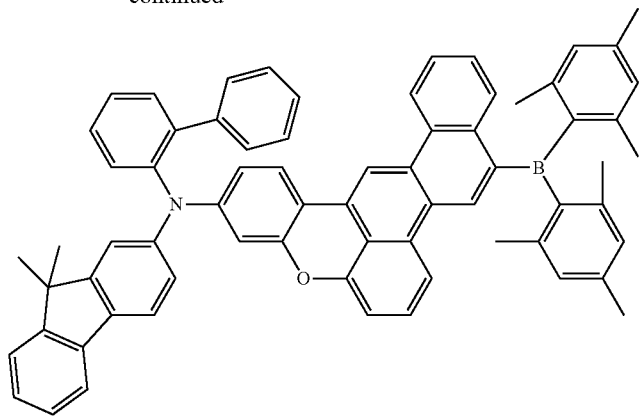

33

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh₄ (2.3 g, 5 mmol), K₃PO₄ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-18

Intermediate A-18 was obtained in a yield of 75% in the same manner as used to synthesize Intermediate A-2, except that fluorodimesitylborane was used instead of fluorodiphenylborane.

Synthesis of Intermediate A-19

Intermediate A-19 was obtained in a yield of 79% in the same manner as used to synthesize Intermediate A-3, except that Intermediate A-18 was used instead of Intermediate A-2 and N-([1,1'-biphenyl]-2-yl)-9,9-dimethyl-9H-fluoren-3-amine was used instead of diphenylamine.

Synthesis of Intermediate A-20

Intermediate A-20 was obtained in a yield of 75% in the same manner as used to synthesize Intermediate A-4, except that Intermediate A-19 was used instead of Intermediate A-3.

Synthesis of Compound 33

Compound 33 was obtained in a yield of 83% in the same manner as used to synthesize Compound 1, except that Intermediate A-20 was used instead of Intermediate A-4.

Synthesis Example 7

Synthesis of Compound 46

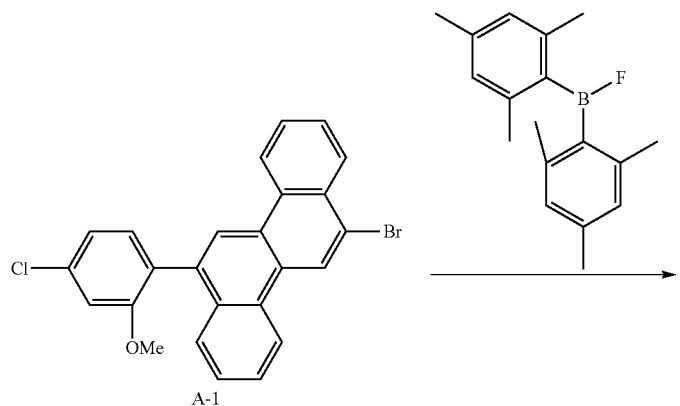

A-1

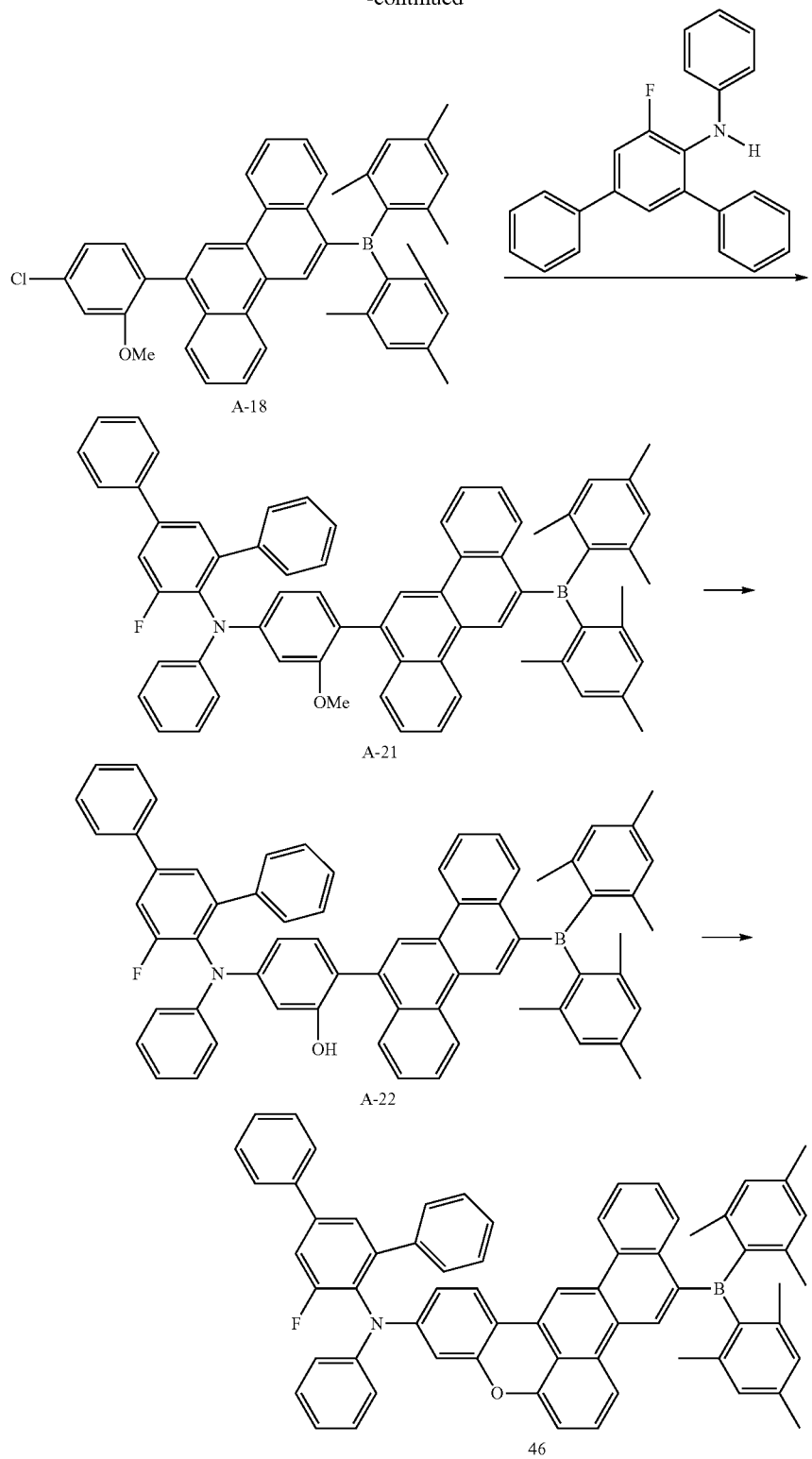

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-21

Intermediate A-21 was obtained in a yield of 70% in the same manner as used to synthesize Intermediate A-3, except that Intermediate A-18 was used instead of Intermediate A-2 and 5'-fluoro-N-phenyl-[1,1': 3',1"-terphenyl]-4'-amine was used instead of diphenylamine.

Synthesis of Intermediate A-22

Intermediate A-22 was obtained in a yield of 71% in the same manner as used to synthesize Intermediate A-4, except that Intermediate A-21 was used instead of Intermediate A-3.

Synthesis of Compound 46

Compound 46 was obtained in a yield of 72% in the same manner as used to synthesize Compound 1, except that Intermediate A-22 was used instead of Intermediate A-4.

Synthesis Example 8

Synthesis of Compound 53

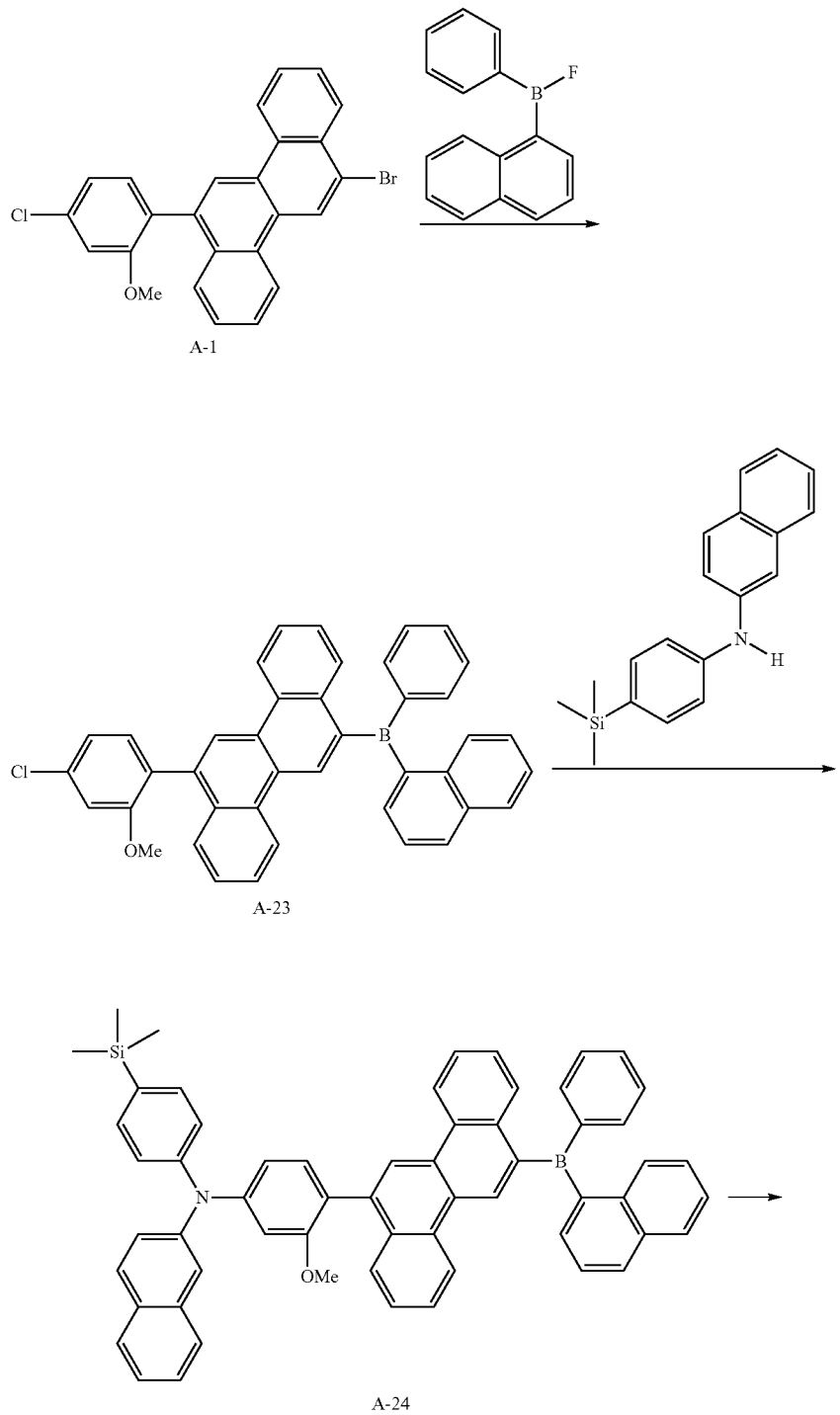

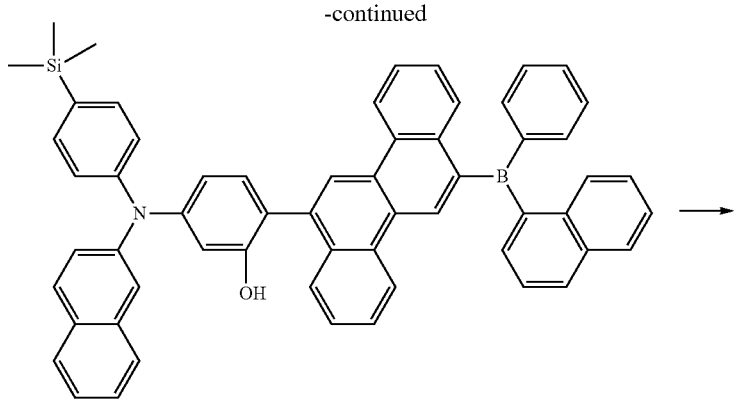

A-25

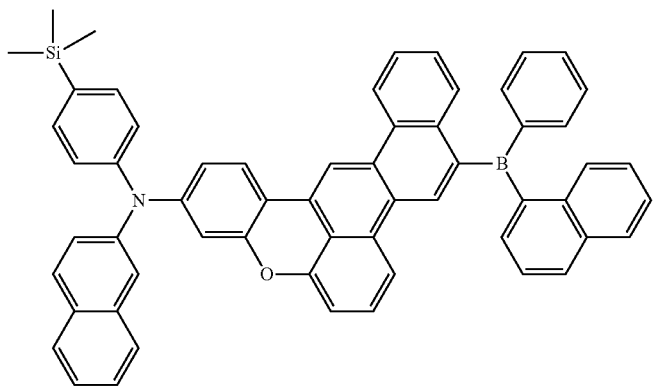

53

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-23

Intermediate A-23 was obtained in a yield of 78% in the same manner as used to synthesize Intermediate A-2, except that fluoro(naphthalen-1-yl)(phenyl)borane was used instead of fluorodiphenylborane.

Synthesis of Intermediate A-24

Intermediate A-24 was obtained in a yield of 76% in the same manner as used to synthesize Intermediate A-3, except that Intermediate A-23 was used instead of Intermediate A-2 and N-(4-(trimethylsilyl)phenyl)naphthalen-2-amine was used instead of diphenylamine.

Synthesis of Intermediate A-25

Intermediate A-25 was obtained in a yield of 79% in the same manner as used to synthesize Intermediate A-4, except that Intermediate A-24 was used instead of Intermediate A-3.

Synthesis of Compound 53

Compound 53 was obtained in a yield of 82% in the same manner as used to synthesize Compound 1, except that Intermediate A-25 was used instead of Intermediate A-4.

Synthesis Example 9

Synthesis of Compound 64

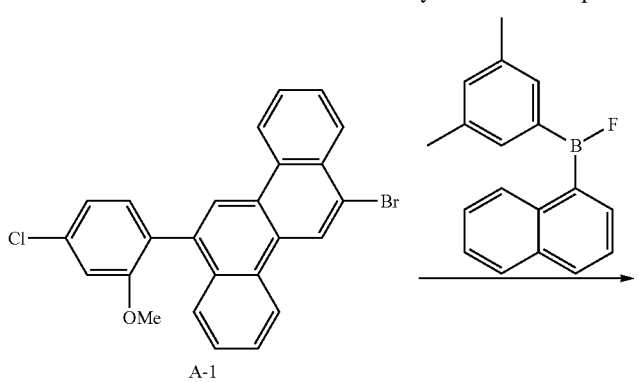

A-1

-continued
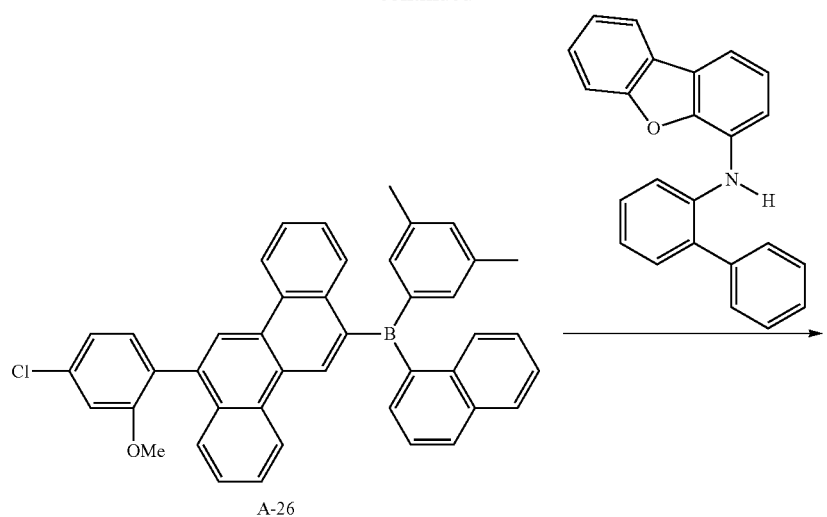
A-26
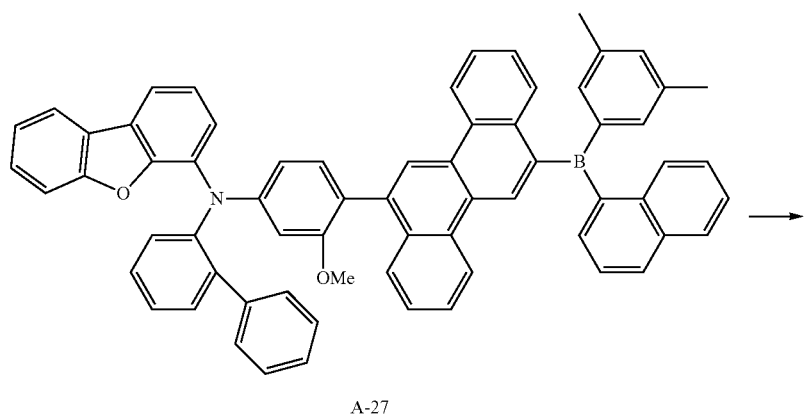
A-27
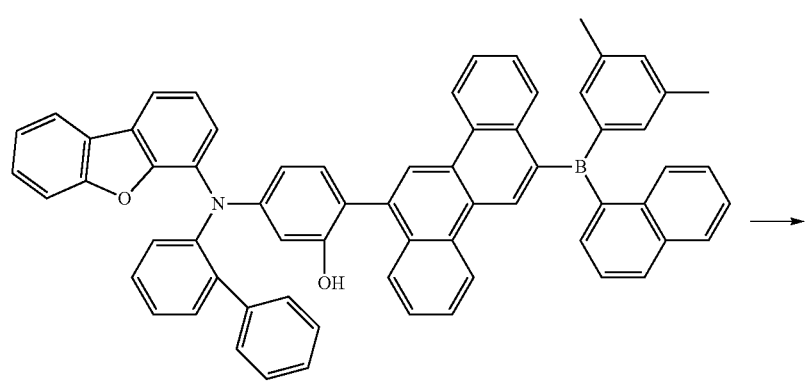
A-28

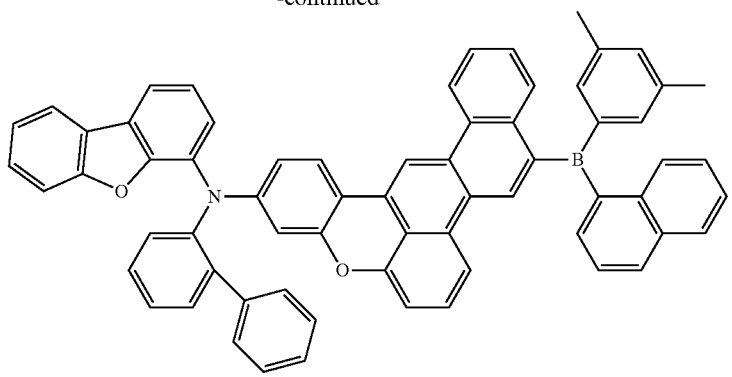

64

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate A-26

Intermediate A-26 was obtained in a yield of 81% in the same manner as used to synthesize Intermediate A-2, except that (3,5-dimethylphenyl)fluoro(naphthalen-1-yl)borane was used instead of fluorodiphenylborane.

Synthesis of Intermediate A-27

Intermediate A-27 was obtained in a yield of 76% in the same manner as used to synthesize Intermediate A-3, except that Intermediate A-26 was used instead of Intermediate A-2 and N-(4-(trimethylsilyl)phenyl)naphthalen-2-amine was used instead of diphenylamine.

Synthesis of Intermediate A-28

Intermediate A-28 was obtained in a yield of 80% in the same manner as used to synthesize Intermediate A-4, except that Intermediate A-27 was used instead of Intermediate A-3.

Synthesis of Compound 64

Compound 64 was obtained in a yield of 85% in the same manner as used to synthesize Compound 1, except that Intermediate A-28 was used instead of Intermediate A-4.

Synthesis Example 10

Synthesis of Compound 90

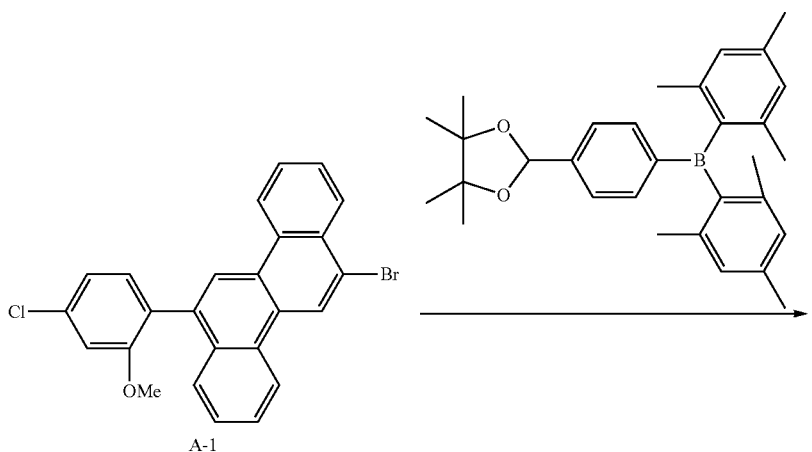

A-1

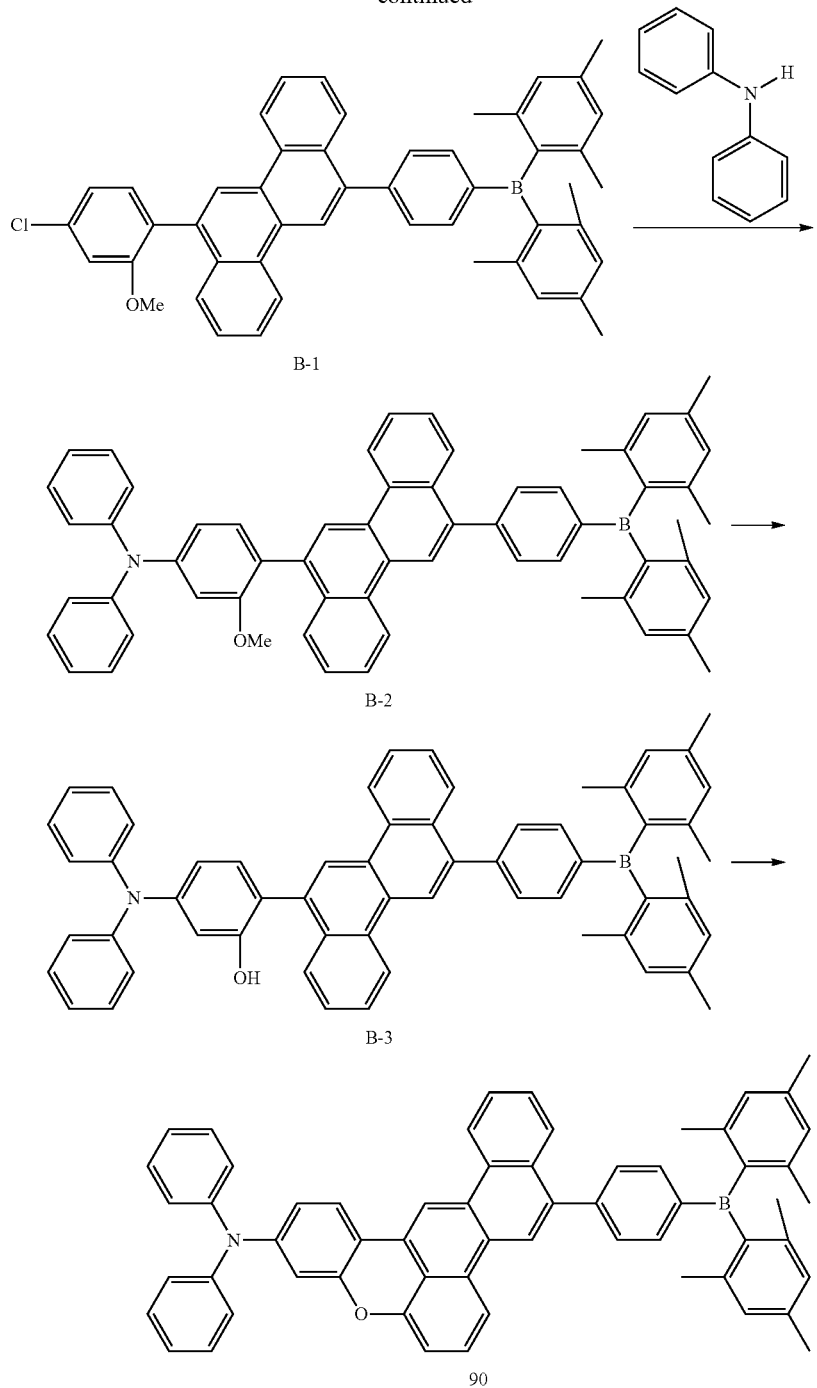

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh₄ (2.3 g, 5 mmol), K₃PO₄ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate B-1

Intermediate A-1 (4.5 g, 10 mmol) was dissolved in 100 mL of THF:H₂O (9:1 mixture) and then the mixture was heated. When Intermediate A-1 was completely dissolved, PdPPh₄ (222.9 mg, 0.5 mmol), K₂CO₃ (5.5 g, 40 mmol), dimesityl(4-(4,4,5,5-tetramethyl-1,3-dioxolan-2-yl)phenyl) borane (6.8 g, 15 mol) were added thereto, and then reflux-stirred for 1 hour at a temperature of 100° C. The temperature was dropped to ambient temperature, and then an extraction process was performed thereon using MC. Column chromatography was performed thereon to obtain Intermediate B-1 (4.5 g, 6.5 mmol, yield of 65%).

Synthesis of Intermediate B-2

Intermediate B-2 was obtained in a yield of 84% in the same manner as used to synthesize Intermediate A-3, except that Intermediate B-1 was used instead of Intermediate A-2.

Synthesis of Intermediate B-3

Intermediate B-3 was obtained in a yield of 88% in the same manner as used to synthesize Intermediate A-4, except that Intermediate B-2 was used instead of Intermediate A-3.

Synthesis of Compound 90

Compound 90 was obtained in a yield of 88% in the same manner as used to synthesize Compound 1, except that Intermediate B-3 was used instead of Intermediate A-4.

Synthesis Example 11

Synthesis of Compound 98

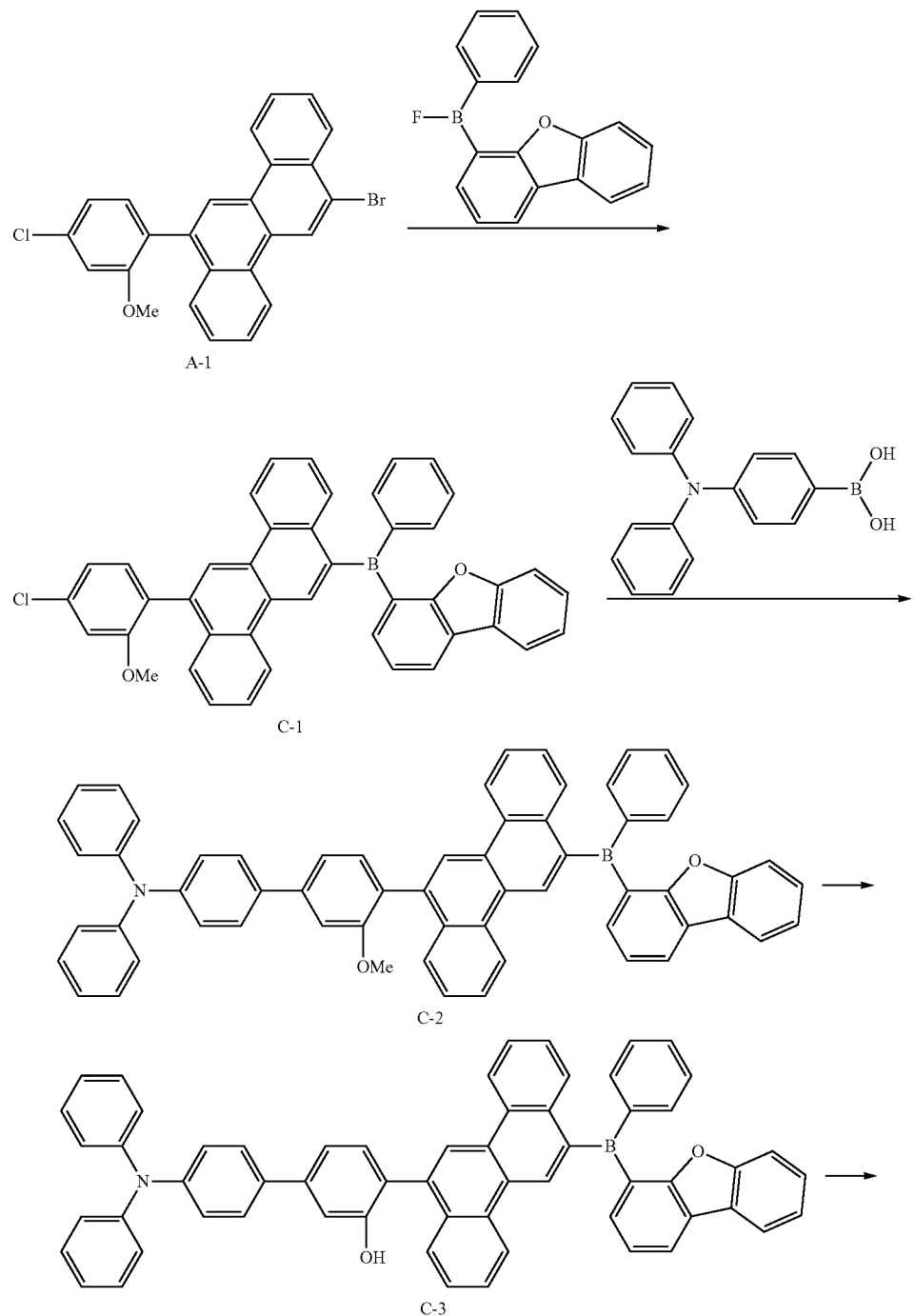

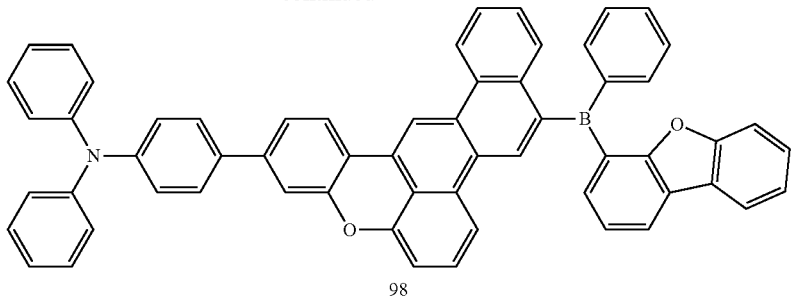

98

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate C-1

Intermediate C-1 was obtained in a yield of 83% in the same manner as used to synthesize Intermediate A-2, except that dibenzo[b,d]furan-4-ylfluoro(phenyl)borane was used instead of fluorodiphenylborane.

Synthesis of Intermediate C-2

Intermediate C-2 was obtained in a yield of 70% in the same manner as used to synthesize Intermediate A-3, except that Intermediate C-1 was used instead of Intermediate A-2 and (4-(diphenylamino)phenyl)boronic acid was used instead of diphenylamine.

Synthesis of Intermediate C-3

Intermediate C-3 was obtained in a yield of 81% in the same manner as used to synthesize Intermediate A-4, except that Intermediate C-2 was used instead of Intermediate A-3.

Synthesis of Compound 98

Compound 98 was obtained in a yield of 88% in the same manner as used to synthesize Compound 1, except that Intermediate C-3 was used instead of Intermediate A-4.

Synthesis Example 12

Compound 102

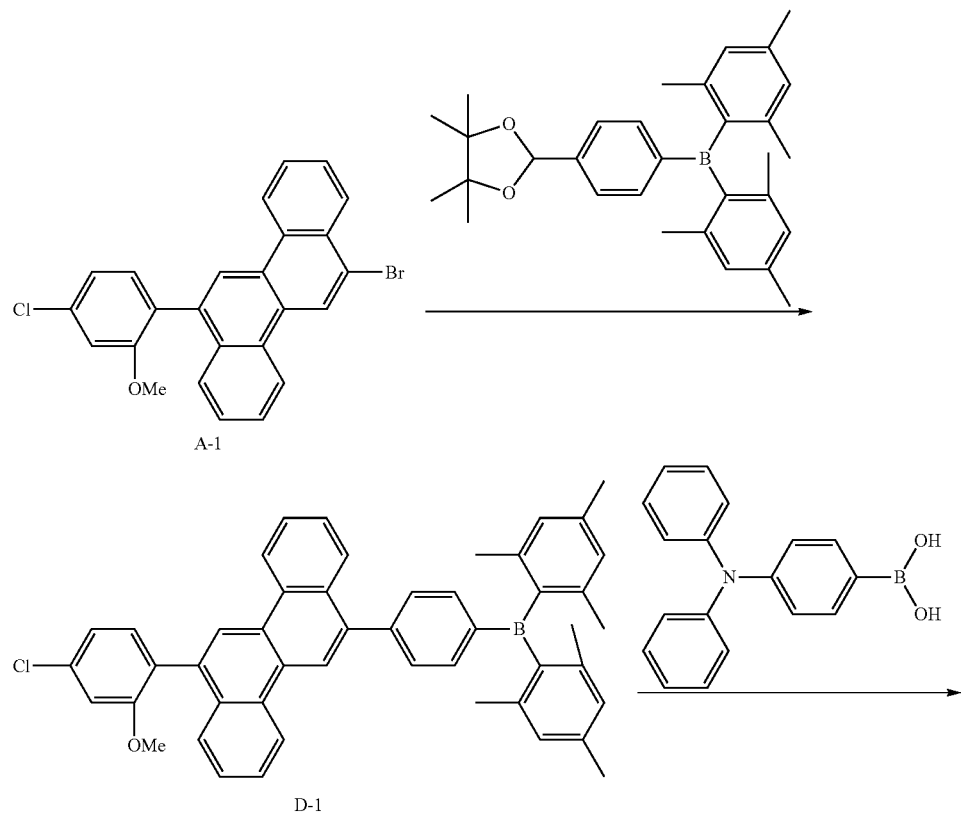

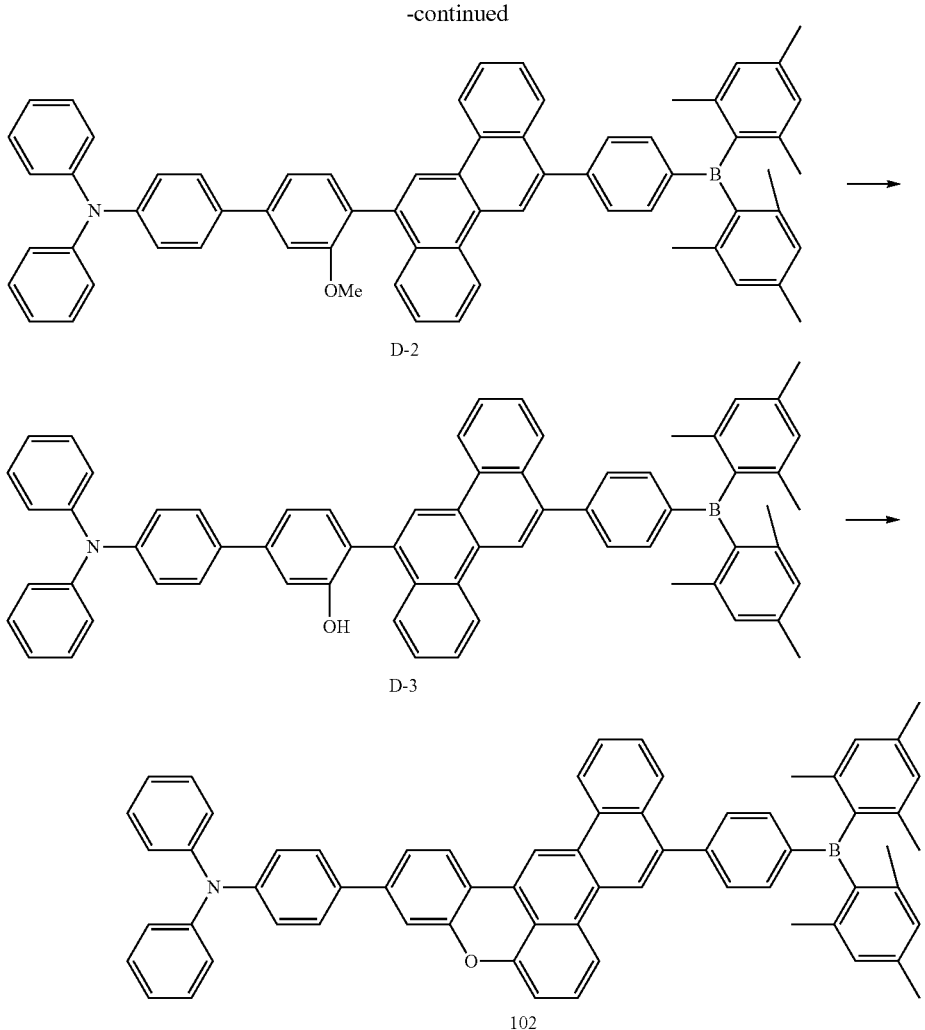

Synthesis of Intermediate A-1

6,12-dibromochrysene (38.6 g, 100 mmol) was dissolved in 1.5 L of o-xylene and then the result was heated. When 6,12-dibromochrysene was completely dissolved, PdPPh$_4$ (2.3 g, 5 mmol), K$_3$PO$_4$ (42.4 g, 200 mmol), and (4-chloro-2-methoxyphenyl)boronic acid (22.4 g, 120 mmol) were added thereto, and the resultant mixture was reflux-stirred for 1 hour at a temperature of 140° C. When the temperature was dropped to ambient temperature, an extraction process was performed thereon using methylene chloride (MC). Column chromatography was performed thereon to obtain Intermediate A-1 (24.6 g, 55 mmol, yield of 55%).

Synthesis of Intermediate D-1

Intermediate D-1 was obtained in a yield of 66% in the same manner as used to synthesize Intermediate B-1, except that dimesityl(4-(4,4,5,5-tetramethyl-1,3-dioxolan-2-yl)phenyl)borane was used instead of fluorodiphenylborane.

Synthesis of Intermediate D-2

Intermediate D-2 was obtained in a yield of 74% in the same manner as used to synthesize Intermediate A-3, except that Intermediate D-1 was used instead of Intermediate A-2 and (4-(diphenylamino)phenyl)boronic acid was used instead of diphenylamine.

Synthesis of Intermediate D-3

Intermediate D-3 was obtained in a yield of 85% in the same manner as used to synthesize Intermediate A-4, except that Intermediate D-2 was used instead of Intermediate A-3.

Synthesis of Compound 102

Compound 102 was obtained in a yield of 82% in the same manner as used to synthesize Compound 1, except that Intermediate D-3 was used instead of Intermediate A-4.

The compounds synthesized according to Synthesis Examples 1-12 were confirmed by $^1$H NMR and MS/FAB. Results thereof are shown in Table 1 below.

TABLE 1

| Compound | $^1$H NMR (CDCl$_3$, 400 MHz) | MS/FAB calc. | MS/FAB found |
|---|---|---|---|
| 1 | δ = 9.28(s, 1H), 8.94(s, 1H), 8.56(d, 1H), 8.4(d, 1H), 7.88(d, 1H), 7.68(dd, 1H), 7.59(d, 1H), 7.51-7.31(m, 8H), 7.30-7.02(m, 9H), 6.82-6.53(m, 4H), 6.43-6.42(m, 4H) | 649.60 | 649.26 |

TABLE 1-continued

| Compound | ¹H NMR (CDCl₃, 400 MHz) | MS/FAB calc. | MS/FAB found |
|---|---|---|---|
| 4 | δ = 9.15(s, 1H), 8.84(s, 1H), 8.5(d, 1H), 8.26(d, 1H), 7.96-7.87(m, 2H), 7.74-7.69(m, 2H), 7.65-7.56(m, 3H), 7.54-7.47(m, 4H), 7.38-7.16(m, 3H), 7.03(d, 1H), 6.99-6.9(m, 7H), 6.84-6.7(m, 2H), 6.54(d, 1H), 6.53(d, 1H), 2.81(s, 6H), 2.72(s, 6H) | 755.77 | 755.34 |
| 14 | δ = 9.15(d, 1H), 9.13(d, 1H), 8.48(d, 1H), 8.33(d, 1H), 7.98(d, 1H), 7.8(dd, 1H), 7.71-7.56(m, 8H), 7.54-7.45(m, 8H), 7.43-7.36(m, 5H), 7.34(d, 1H), 7.25-7.14(m, 7H), 7.1-7.03(m, 3H), 6.89(dd, 1H), 6.75(dd, 1H), 6.66-6.59(m, 2H), 6.57-6.53(m, 1H), 6.35(d, 1H), 2.35(s, 6H), 2.31(s, 6H) | 1033.45 | 1033.12 |
| 22 | δ = 9.16(s, 1H), 8.84(s, 1H), 8.49(d, 1H), 8.33(d, 1H), 7.98(d, 1H), 7.74(d, 1H), 7.68(dd, 1H), 7.64-7.53(m, 4H), 7.5-7.46(m, 3H), 7.44-7.4(m, 3H), 7.33-7.3(m, 5H), 7.24-7.22(m, 2H), 7.13-7.1(m, 3H), 6.95-6.91(m, 2H), 6.74(d, 1H), 6.59(d, 1H), 6.46(dd, 1H), 6.27(dd, 1H), 6.18(dd, 1H), 2.7(s, H) | 753.75 | 753.32 |
| 25 | δ = 9.16(s, 1H), 8.85(s, 1H), 8.49(d, 1H), 8.36(d, 1H), 7.94(d, H), 7.88-7.85(m, 2H), 7.86(d, 1H), 7.86(d, 1H), 7.68(d, 1H), 7.62-7.58(m, 2H), 7.57-7.4(m, 8H), 7.34-7.31(m, 3H), 7.15-7.13(m, 4H), 6.86(d, 1H), 6.77(d, 1H), 6.77(d, 1H), 6.64(d, 1H), 6.45-6.41(m, 4H) | 699.66 | 699.27 |
| 33 | δ = 9.24(s, 1H), 8.83(s, 1H), 8.54(d, 1H), 8.28(d, 1H), 8.1(d, 1H), 7.76(d, 1H), 7.69-7.66(m, 1H), 7.63-7.52(m, 7H), 7.5-7.45(m, 2H), 7.43-7.4(m, 1H), 7.31-7.25(m, 2H), 7.19-7.07(m, 3H), 7.05-6.78(m, 7H), 6.6(dd, 1H), 6.54(dd, 1H), 6.37(dd, 1H), 2.49(s, 3H), 2.49(s, 3H), 2.44(s, 3H), 2.44(s, 3H), 2.39(s, 3H), 2.39(s, 3H), 1.99(s, 6H) | 926.02 | 925.45 |
| 46 | δ = 8.84(s, 1H), 8.54(d, 1H), 8.29(d, 1H), 8.1(d, 1H), 7.72-7.62(m, 6H), 7.55-7.53(m, 5H), 7.48-7.43(m, 3H), 7.38-7.29(m, 2H), 7.17-7.08(m, 3H), 6.89-6.84(m, 4H), 6.7-6.29(m, 5H), 2.49(s, 3H), 2.49(s, 3H), 2.49(s, 3H), 2.49(s, 3H), 2.47(s, 3H), 2.47(s, 3H) | 903.95 | 903.40 |
| 53 | δ = 9.22(s, 1H), 8.89(s, 1H), 8.52(d, 1H), 8.35(d, 1H), 8.2(d, 1H), 7.99-7.74(m, 5H), 7.67-7.5(m, 5H), 7.48-7.42(m, 5H), 7.41-7.36(m, 5H), 7.31-7.26(m, 5H), 6.9-6.84(m, 2H), 6.79-6.76(m, 2H), 6.62(dd, 1H), 0.24(s, 9H) | 821.90 | 821.33 |
| 64 | δ = 9.23(s, 1H), 8.9(s, 1H), 8.53(d, 1H), 8.38(d, 1H), 8.23(d, 1H), 7.99-7.91(m, 2H), 7.82-7.75(m, 3H), 7.71-7.55(m, 8H), 7.5-7.36(m, 8H), 7.29-7.14(m, 3H), 7.14-6.85(m, 5H), 6.74-6.71(m, 2H), 6.52-6.38(m, 2H), 2.4(s, 6H) | 893.89 | 893.35 |
| 90 | δ = 9.24(s, 1H), 9.01(s, 1H), 8.83(d, 1H), 8.43(d, 1H), 7.83(d, 1H), 7.78-7.56(m, 6H), 7.43-7.29(m, 3H), 7.11-6.81(m, 9H), 6.72-6.58(m, 3H), 6.39-6.29(m, 4H), 2.19(s, 3H), 2.19(s, 3H), 2.19(s, 3H), 2.19(s, 3H), 2.18(s, 3H), 2.18(s, 3H) | 809.86 | 809.38 |
| 98 | δ = 9.42(s, 1H), 9.06(s, 1H), 8.56(d, 1H), 8.31(d, 1H), 8-7.83(m, 4H), 7.69-7.53(m, 7H), 7.49-7.42(m, 6H), 7.41-7.33(m, 6H), 7.29-7.24(m, 3H), 7.21-7.14(m, 3H), 7.06-6.85(m, 4H), 6.66(dd, 1H), 6.39-6.33(m, 2H), 6.1-6.04(m, 2H), 6.04(, H) | 891.88 | 891.33 |
| 102 | δ = 9.8(s, 1H), 9.04(s, 1H), 8.85(d, 1H), 8.44(d, 1H), 7.98(d, 1H), 7.82-7.51(m, 7H), 7.44-7.36(m, 5H), 7.17-7.07(m, 5H), 6.88-6.65(m, 8H), 6.19-6.14(m, 4H), 2.19(s, 3H), 2.19(s, 3H), 2.19(s, 3H), 2.19(s, 3H), 2.18(s, 3H), 2.18(s, 3H) | 885.96 | 885.41 |

Example 1

A 15 Ωcm² (1,200 Å) ITO glass substrate (a product of Corning) was cut to a size of 50 mm×50 mm×0.7 mm, and was ultrasonically cleaned by using isopropyl alcohol and pure water for 5 minutes each, and then UV light was irradiated thereto for 30 minutes and exposed to ozone to clean. Then, the resultant structure was loaded into a vacuum deposition apparatus.

4,4'-Bis[N-phenyl-N-(9-phenylcarbazol-3-yl)amino]-1,1'-biphenyl (HT13) was vacuum deposited on the ITO glass substrate to form a hole injection layer having a thickness of 600 Å, and N-[1,1'-biphenyl]-4-yl-9,9-dimethyl-N-[4-(9-phenyl-9H-carbazol-3-yl)phenyl]-9H-fluorene-2-amine (HT3) was vacuum deposited on the hole injection layer to form a hole transport layer having a thickness of 300 Å, thereby completing the formation of a hole transport region.

9,10-di-naphthalene-2-yl-anthracene (ADN), as a host, Compound 1, as a dopant, were co-deposited on the hole transport region at a weight ratio of 98:2 to form an emission layer having a thickness of 300 Å.

Alq₃ was vacuum-deposited on the emission layer to form an electron transport layer having a thickness of 300 Å, and LiF was deposited on the electron transport layer to form an electron injection layer having a thickness of 10 Å, thereby completing the formation of an electron transport region.

Al was vacuum-deposited on the electron transport region to form a cathode having a thickness of 3,000 Å, thereby completing the manufacture of an organic light-emitting device.

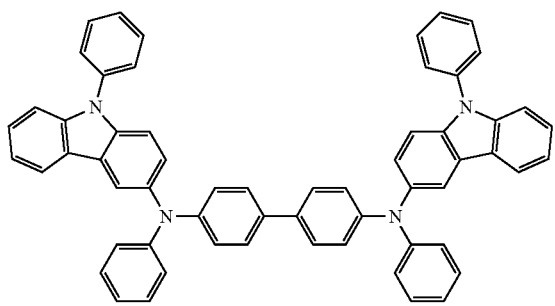

HT13

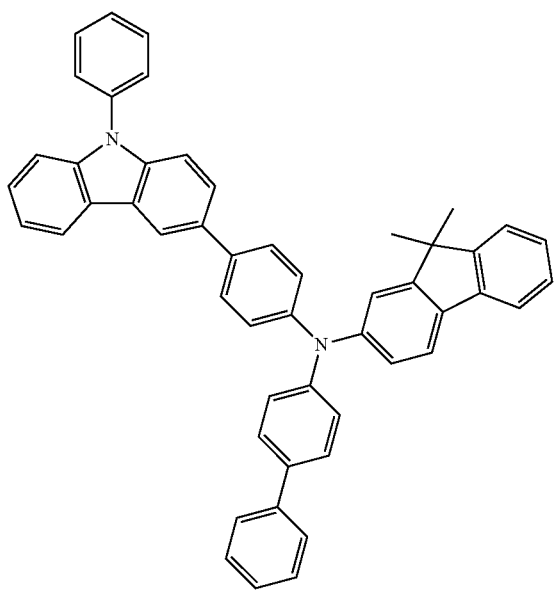

HT3

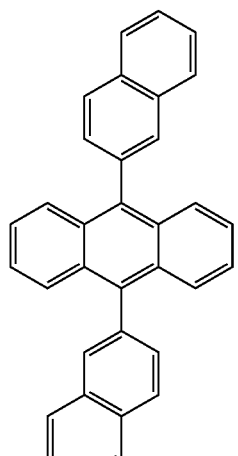

ADN

Example 2

An organic light-emitting device was manufactured in the same manner as in Example 1, except that in forming the emission layer, as a dopant, Compound 4 was used instead of Compound 1.

Example 3

An organic light-emitting device was manufactured in the same manner as in Example 1, except that in forming the emission layer, as a dopant, Compound 14 was used instead of Compound 1.

Example 4

An organic light-emitting device was manufactured in the same manner as in Example 1, except that in forming the emission layer, as a dopant, Compound 22 was used instead of Compound 1.

Example 5

An organic light-emitting device was manufactured in the same manner as in Example 1, except that in forming the emission layer, as a dopant, Compound 25 was used instead of Compound 1.

Example 6

An organic light-emitting device was manufactured in the same manner as in Example 1, except that in forming the emission layer, as a dopant, Compound 33 was used instead of Compound 1.

Example 7

An organic light-emitting device was manufactured in the same manner as in Example 1, except that in forming an emission layer, as a dopant, Compound 46 was used instead of Compound 1.

Example 8

An organic light-emitting device was manufactured in the same manner as in Example 1, except that in forming the emission layer, as a dopant, Compound 53 was used instead of Compound 1.

Example 9

An organic light-emitting device was manufactured in the same manner as in Example 1, except that in forming the emission layer, as a dopant, Compound 64 was used instead of Compound 1.

Example 10

An organic light-emitting device was manufactured in the same manner as in Example 1, except that in forming the emission layer, as a dopant, Compound 90 was used instead of Compound 1.

Example 11

An organic light-emitting device was manufactured in the same manner as in Example 1, except that in forming the emission layer, as a dopant, Compound 98 was used instead of Compound 1.

Example 12

An organic light-emitting device was manufactured in the same manner as in Example 1, except that in forming an emission layer, as a dopant, Compound 102 was used instead of Compound 1.

Comparative Example 1

An organic light-emitting device was manufactured in the same manner as in Example 1, except that in forming the emission layer, as a dopant, Compound A was used instead of Compound 1.

<Compound A>

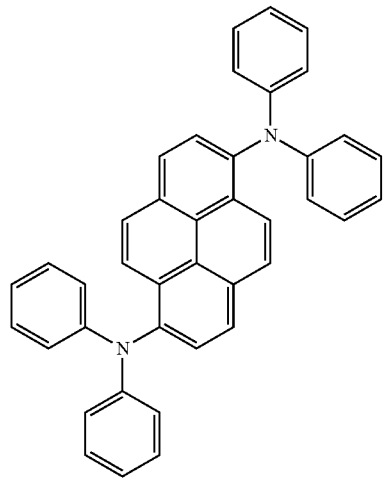

Comparative Example 2

An organic light-emitting device was manufactured in the same manner as in Example 1, except that in forming the emission layer, as a dopant, Compound B was used instead of Compound 1.

<Compound B>

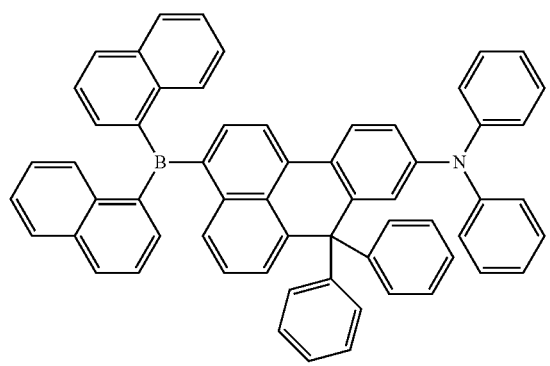

Evaluation Example 1

The driving voltage, current density, brightness, efficiency, and half-lifespan of the organic light-emitting devices manufactured according to Examples 1 to 12, and Comparative Examples 1 and 2 were measured by using Kethley SMU 236 and a brightness photometer PR650, and results thereof are shown in Table 2. The half-lifespan is a period of time that lapses until the brightness of the organic light-emitting device was 50% of initial brightness.

TABLE 2

|  | Emission layer | Driving voltage (V) | Current density (mA/cm$^2$) | Brightness (cd/m$^2$) | Efficiency (cd/A) | Emission color | Half lifespan (hr@100 mA/cm$^2$) |
|---|---|---|---|---|---|---|---|
| Example 1 | Compound 1 | 6.82 | 50 | 3,311 | 6.43 | Blue | 378 |
| Example 2 | Compound 4 | 6.67 | 50 | 3,429 | 6.65 | Blue | 351 |
| Example 3 | Compound 14 | 5.71 | 50 | 3,263 | 6.37 | Blue | 299 |
| Example 4 | Compound 22 | 5.88 | 50 | 3,443 | 6.66 | Blue | 354 |
| Example 5 | Compound 25 | 5.68 | 50 | 3,312 | 6.42 | Blue | 332 |
| Example 6 | Compound 33 | 6.65 | 50 | 3,388 | 6.57 | Blue | 362 |
| Example 7 | Compound 46 | 6.63 | 50 | 3,491 | 6.75 | Blue | 385 |
| Example 8 | Compound 53 | 6.60 | 50 | 3,483 | 6.73 | Blue | 390 |
| Example 9 | Compound 64 | 5.99 | 50 | 3,432 | 6.69 | Blue | 352 |
| Example 10 | Compound 90 | 5.85 | 50 | 3,369 | 6.51 | Blue | 365 |
| Example 11 | Compound 98 | 6.73 | 50 | 3,150 | 6.30 | Blue | 331 |
| Example 12 | Compound 102 | 6.76 | 50 | 3,170 | 6.34 | Blue | 309 |
| Comparative Example 1 | Compound A | 7.01 | 50 | 2,645 | 5.29 | Blue | 258 |
| Comparative Example 2 | Compound B | 6.99 | 50 | 2,950 | 5.3 | Blue | 295 |

From Table 2, it may be seen that the organic light-emitting devices manufactured according to Examples 1 to 11 had higher driving voltage, higher brightness, higher efficiency, and longer half-lifespan than the organic light-emitting devices manufactured according to Comparative Examples 1 and 2.

An organic light-emitting device including the compound according to an embodiment may have a low driving voltage, high efficiency, high brightness, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed cyclic compound represented by Formula 1 below:

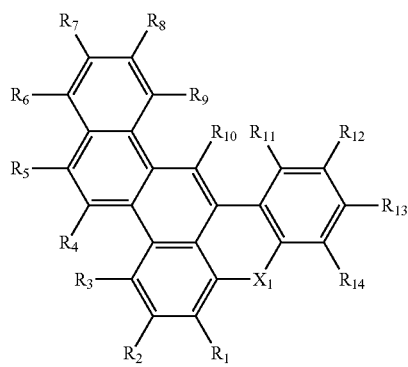

<Formula 1> wherein, in Formula 1, $X_1$ is O or S;

$R_1$ to $R_{14}$ are each independently selected from a group represented by the following Formula 2, a group represented by the following Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, and —Si($Q_1$)($Q_2$)($Q_3$);

at least one of $R_1$ to $R_{14}$ is a group represented by Formula 2, and at least one of $R_1$ to $R_{14}$ is a group represented by Formula 3:

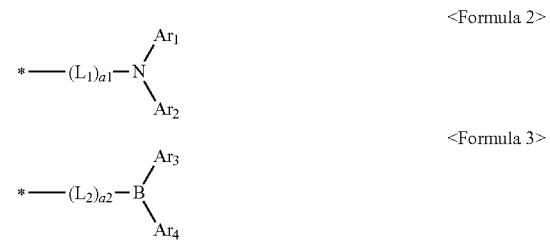

<Formula 2>

<Formula 3> wherein in Formulae 2 and 3, $L_1$ and $L_2$ are each independently selected from a substituted or unsubstituted $C_3$-$C_{10}$ cycloalkylene, a substituted or unsubstituted $C_1$-$C_{10}$ heterocycloalkylene, a substituted or unsubstituted $C_3$-$C_{10}$ cycloalkenylene, a substituted or unsubstituted $C_1$-$C_{10}$ heterocycloalkenylene, a substituted or unsubstituted $C_6$-$C_{60}$ arylene, a substituted or unsubstituted $C_1$-$C_{60}$ heteroarylene, a substituted or unsubstituted divalent non-aromatic condensed polycyclic group, and a substituted or unsubstituted divalent non-aromatic condensed heteropolycyclic group;

a1 and a2 are each independently selected from 0, 1, 2 and 3, when a1 is 2 or more, two or more $L_1$ are identical or different from one another, and when a2 is 2 or more, two or more $L_2$ are identical or different from one another;

$Ar_1$ to $Ar_4$ are each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group;

wherein at least one substituent of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from:

a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{11}$)($Q_{12}$)($Q_{13}$);

a $C_3$-$C_{10}$cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic heterocondensed polycyclic group, and —Si($Q_{21}$)($Q_{22}$)($Q_{23}$); and —Si($Q_{31}$)($Q_{32}$)($Q_{33}$), wherein $Q_1$ to $Q_3$, $Q_{11}$ to $Q_{13}$, $Q_{21}$ to $Q_{23}$, and $Q_{31}$ to $Q_{33}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$cycloalkyl group, a $C_1$-$C_{10}$ heterocycloalkyl group, a $C_3$-$C_{10}$cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, and a monovalent non-aromatic condensed heteropolycyclic group.

2. The condensed cyclic compound as claimed in claim 1, wherein $L_1$ and $L_2$ are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group; and a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, ovalenylene group, a pyrrolylene group, a thiophenylene group, a furanylene group, an imidazolylene group, a pyrazolylene group, a thiazolylene group, an isothiazolylene group, an oxazolylene group, a isoxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzoxazolylene group, an isobenzoxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, and an imidazopyrimidinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

3. The condensed cyclic compound as claimed in claim 1, wherein $L_1$ and $L_2$ are each independently a group represented by one of the following Formulae 3-1 to 3-35:

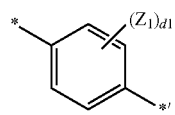

Formula 3-1

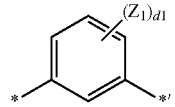

Formula 3-2

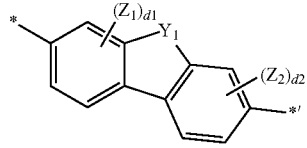

Formula 3-3

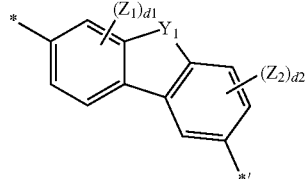

Formula 3-4

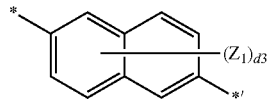

Formula 3-5

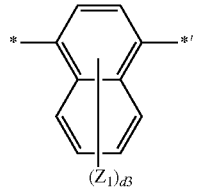

Formula 3-6

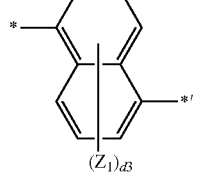

Formula 3-7

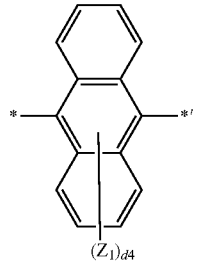

Formula 3-8

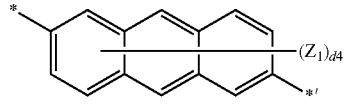

Formula 3-9

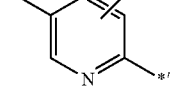

Formula 3-10

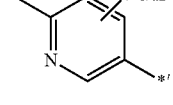

Formula 3-11

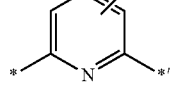

Formula 3-12

177
-continued
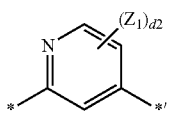
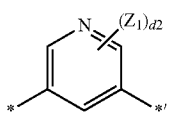
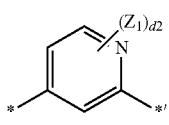
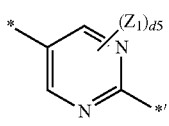
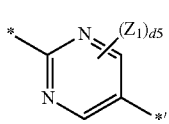
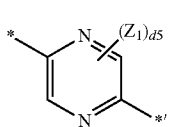
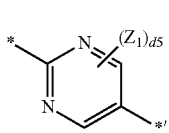
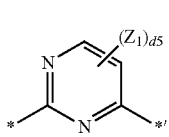
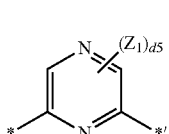
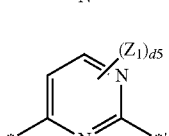
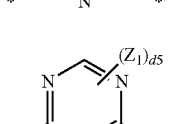
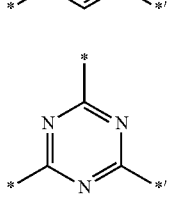
178
-continued
Formula 3-13
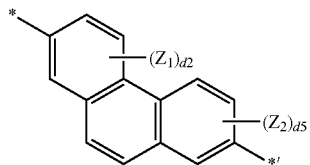
Formula 3-14
Formula 3-15
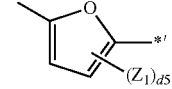
Formula 3-16
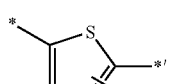
Formula 3-17
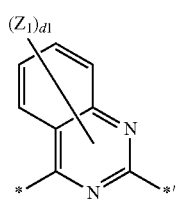
Formula 3-18
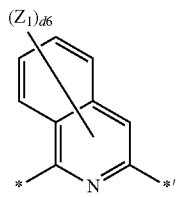
Formula 3-19
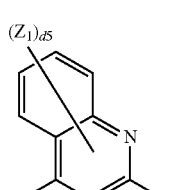
Formula 3-20
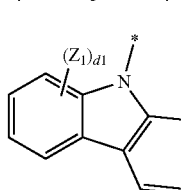
Formula 3-21
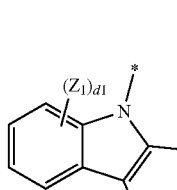
Formula 3-22
Formula 3-23
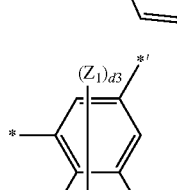
Formula 3-24
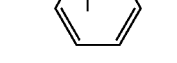
Formula 3-25
Formula 3-26
Formula 3-27
Formula 3-28
Formula 3-29
Formula 3-30
Formula 3-31
Formula 3-32
Formula 3-33

-continued

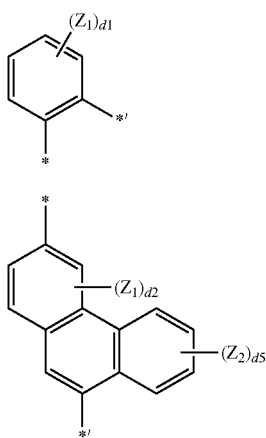
Formula 3-34

Formula 3-35

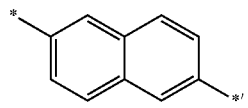
Formula 4-5

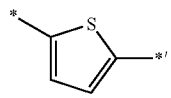
Formula 4-6

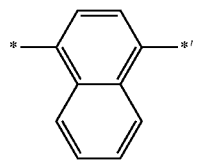
Formula 4-7

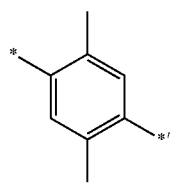
Formula 4-8 wherein, in Formulae 3-1 to 3-35,
$Y_1$ is O, S, $C(Z_3)(Z_4)$, $N(Z_5)$, or $Si(Z_6)(Z_7)$;
$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
d1 is an integer selected from 1, 2, 3, and 4, d2 is an integer selected from 1, 2, and 3, d3 is an integer selected from 1, 2, 3, 4, 5, and 6, d4 is an integer selected from 1, 2, 3, 4, 5, 6, 7, and 8, d5 is 1 or 2, and d6 is an integer selected from 1, 2, 3, 4, and 5, and * and *' indicate binding sites to a neighboring atom.

4. The condensed cyclic compound as claimed in claim 1, wherein $L_1$ and $L_2$ are each independently a group represented by one of the following Formulae 4-1 to 4-29:

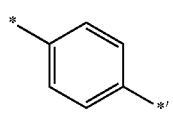
Formula 4-1

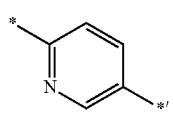
Formula 4-2

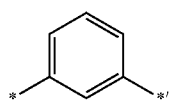
Formula 4-3

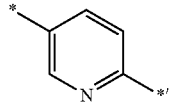
Formula 4-4

Formula 4-9

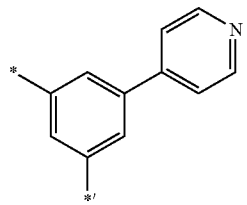
Formula 4-10

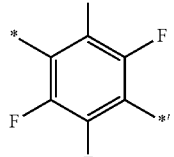
Formula 4-11

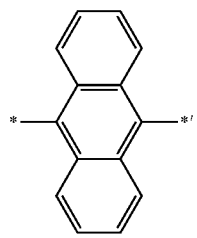
Formula 4-12

Formula 4-13

-continued

Formula 4-14
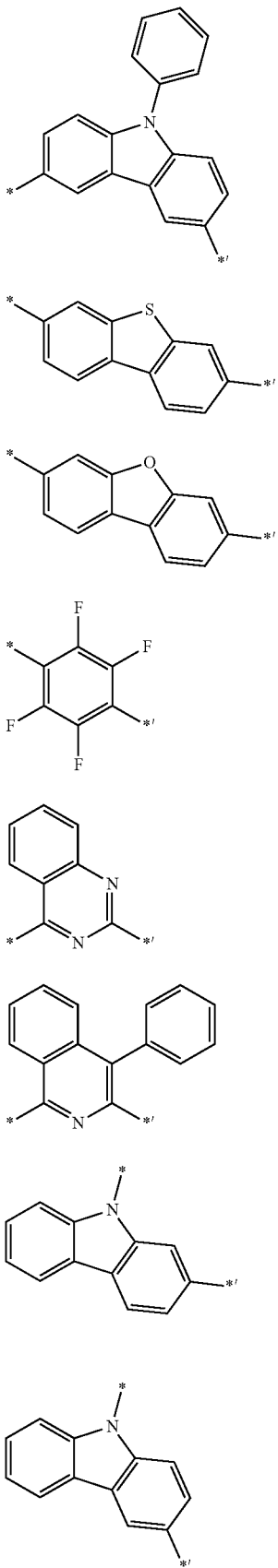

Formula 4-15

Formula 4-16

Formula 4-17

Formula 4-18

Formula 4-19

Formula 4-20

Formula 4-21

Formula 4-22
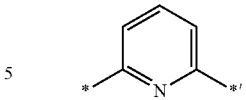

Formula 4-23
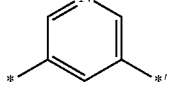

Formula 4-24
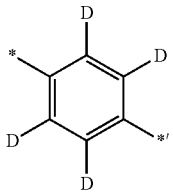

Formula 4-25
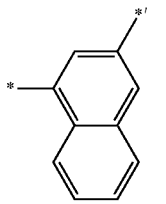

Formula 4-26
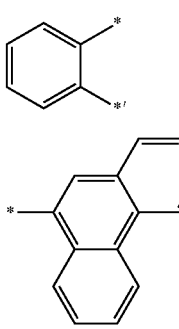

Formula 4-27
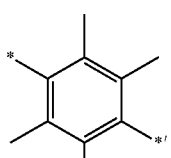

Formula 4-28
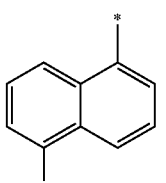

Formula 4-29
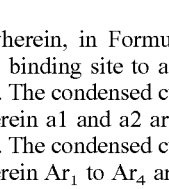

wherein, in Formulae 4-1 to 4-29, * and *' indicate a binding site to a neighboring atom.

5. The condensed cyclic compound as claimed in claim 1, wherein a1 and a2 are each independently 0 or 1.

6. The condensed cyclic compound as claimed in claim 1, wherein $Ar_1$ to $Ar_4$ are each independently selected from:
a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzosilolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group and a dibenzocarbazolyl group, a thiadiazolyl group, an imidazopyridinyl group, an imidazopyrimidinyl group, and —Si($Q_{31}$)($Q_{32}$)($Q_{33}$); and wherein $Q_{31}$ to $Q_{33}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, and an imidazopyrimidinyl group.

7. The condensed cyclic compound as claimed in claim 1, wherein $Ar_1$ to $Ar_4$ are each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group; and a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

8. The condensed cyclic compound as claimed in claim 1, wherein $Ar_1$ to $Ar_4$ are each independently selected from:

a phenyl group, a naphthyl group, a fluorenyl group, a phenanthrenyl group, a pyridinyl group, a pyrimidinyl group, a triazinyl group, a dibenzofuranyl group, and a dibenzothiophenyl group; and a phenyl group, a naphthyl group, a fluorenyl group, a phenanthrenyl group, a pyridinyl group, a pyrimidinyl group, a triazinyl group, a dibenzofuranyl group, and a dibenzothiophenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a phenanthrenyl group, a pyridinyl group, a pyrimidinyl group, a triazinyl group, a dibenzofuranyl group, a dibenzothiophenyl group, and —Si($Q_{31}$)($Q_{32}$)($Q_{33}$), wherein $Q_{31}$ to $Q_{33}$ are each independently selected from a $C_1$-$C_{10}$ alkyl group, a $C_1$-$C_{10}$ alkoxy group, a phenyl group, and a naphthyl group.

9. The condensed cyclic compound as claimed in claim 1, wherein $R_1$ to $R_{14}$ are each independently selected from:

a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group;

a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a benzoimidazolyl group, a benzofuranyl group, a benzothiophenyl group, an isobenzothiazolyl group, a benzoxazolyl group, an isobenzoxazolyl group, an oxadiazolyl group, a triazinyl group, a dibenzofuranyl group, a dibenzothiophenyl group, an imidazopyridinyl group, an imidazopyrimidinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

10. The condensed cyclic compound as claimed in claim 1, wherein $R_1$ to $R_{14}$ are each independently selected from
a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group;
a phenyl group, a naphthyl group, a pyrimidinyl group, and a triazinyl group;
a phenyl group, a naphthyl group, a pyridinyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, a $C_1$-$C_{10}$ alkoxy group, a phenyl group, a naphthyl group, a pyridinyl group, a pyrimidinyl group, a triazinyl group, and —Si($Q_{31}$)($Q_{32}$)($Q_{33}$); and —Si($Q_1$)($Q_2$)($Q_3$), wherein $Q_1$ to $Q_3$ and $Q_{31}$ to $Q_{33}$ are each independently selected from a $C_1$-$C_{10}$ alkyl group, a $C_1$-$C_{10}$ alkoxy group, a phenyl group, and a naphthyl group.

11. The condensed cyclic compound as claimed in claim 1, wherein
$Ar_1$ to $Ar_4$ are each independently a group represented by one of the following Formulae 5-1 to 5-43, and
$R_1$ to $R_{14}$ are each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —Si($Q_1$)($Q_2$)($Q_3$), and a group represented by one of the following Formulae 5-1 to 5-43, wherein $Q_1$ to $Q_3$ are each independently selected from a $C_1$-$C_{10}$ alkyl group, a $C_1$-$C_{10}$ alkoxy group, a phenyl group, and a naphthyl group:

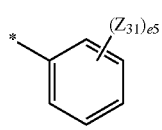

Formula 5-1

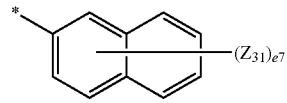

Formula 5-2

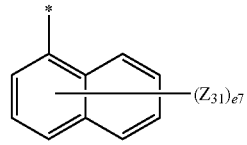

Formula 5-3

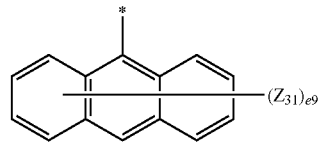

Formula 5-4

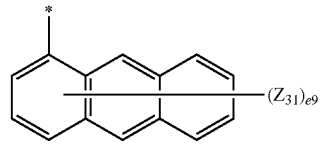

Formula 5-5

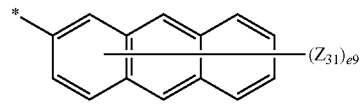

Formula 5-6

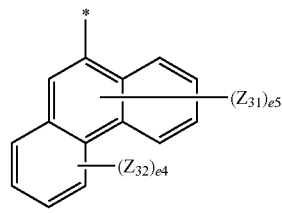

Formual 5-7

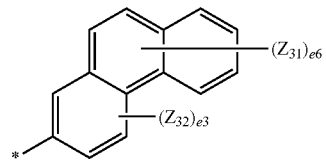

Formula 5-8

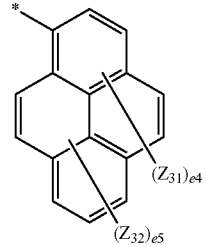

Formula 5-9

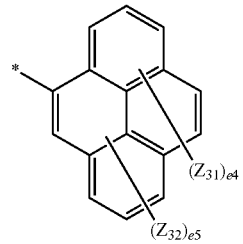

Formula 5-10

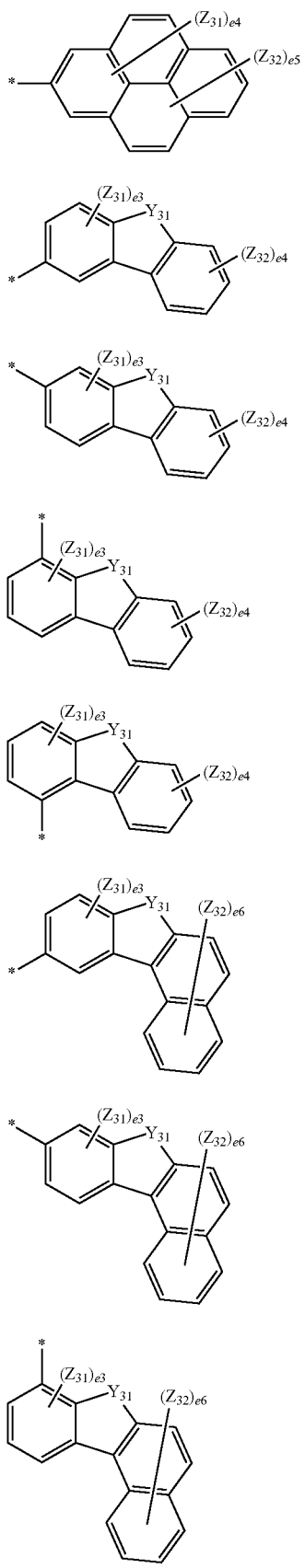
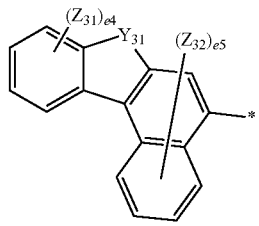 Formula 5-11
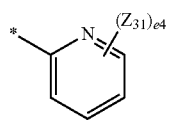 Formula 5-12
Formual 5-13
Formula 5-14
Formual 5-15
Formula 5-16
Formula 5-17
Formula 5-18
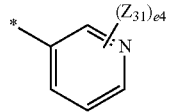 Formula 5-19
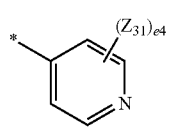 Formula 5-20
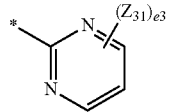 Formula 5-21
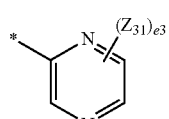 Formula 5-22
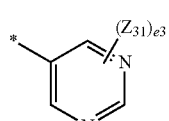 Formula 5-23
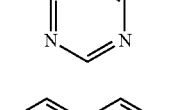 Formula 5-24
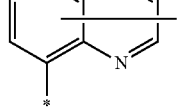 Formula 5-25
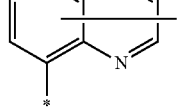 Formula 5-26
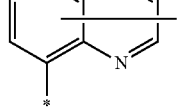 Formula 5-27
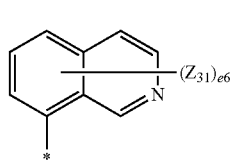 Formula 5-28
Formula 5-29

-continued

Formula 5-30
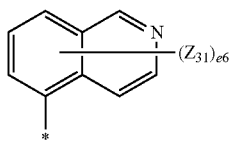

Formula 5-31
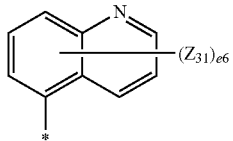

Formula 5-32
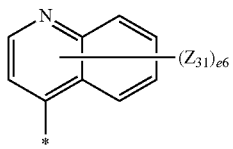

Formula 5-33
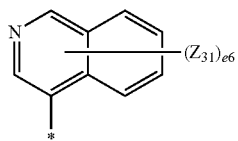

Formula 5-34
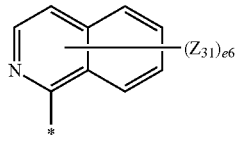

Formula 5-35
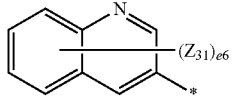

Formula 5-36
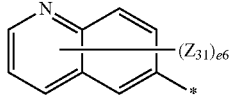

Formula 5-37
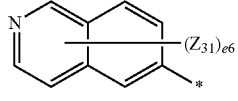

Formula 5-38
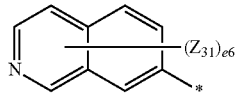

Formula 5-39
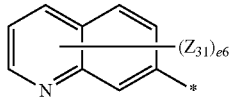

Formula 5-40
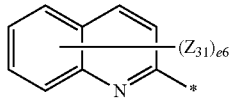

Formula 5-41
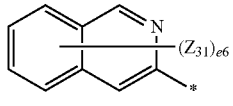

Formula 5-42
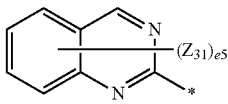

Formula 5-43
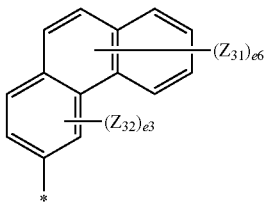

wherein, in Formulae 5-1 to 5-43, $Y_{31}$ is O, S, $C(Z_{33})(Z_{34})$, $N(Z_{35})$, or $Si(Z_{36})(Z_{37})$;

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spirofluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e3 is an integer selected from 1, 2, and 3, e4 is an integer selected from 1, 2, 3, and 4, e5 is an integer selected from 1, 2, 3, 4, and 5, e6 is an integer selected from 1, 2, 3, 4, 5, and 6, e7 is an integer selected from 1, 2, 3, 4, 5, 6, and 7, e8 is an integer selected from 1, 2, 3, 4, 5, 6, 7, and 8, e9 is an integer selected from 1, 2, 3, 4, 5, 6, 7, 8, and 9, and * indicates a binding site to a neighboring atom.

12. The condensed cyclic compound as claimed in claim 1, wherein:

$R_1$ to $R_{14}$ are each independently selected from a group represented by Formula 2, a group represented by Formula 3, a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, —$Si(Q_1)(Q_2)(Q_3)$, a phenyl group, a naphthyl group, a pyridinyl group, a pyrimidinyl group, and a triazinyl group, wherein $Q_1$ to $Q_3$ are each independently selected from a $C_1$-$C_{10}$ alkyl group, a $C_1$-$C_{10}$ alkoxy group, a phenyl group, and a naphthyl group, and $Ar_1$ to $Ar_4$ are each independently a group represented by one of the following Formulae 6-1 to 6-40, Formula 6-1
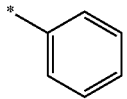

-continued
Formula 6-2
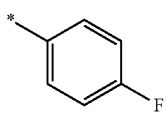
Formula 6-3
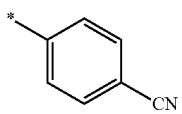
Formula 6-4
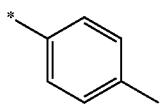
Formula 6-5
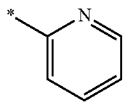
Formula 6-6
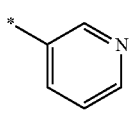
Formula 6-7
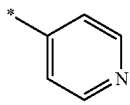
Formula 6-8
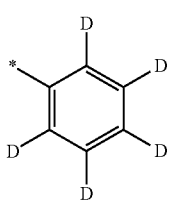
Formula 6-9
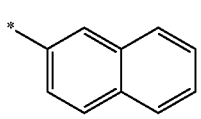
Formula 6-10
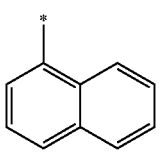
Formula 6-11
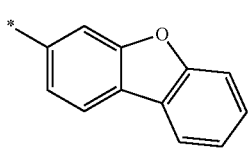
Formula 6-12
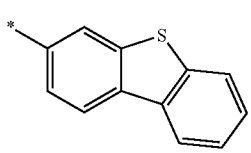
-continued
Formula 6-13
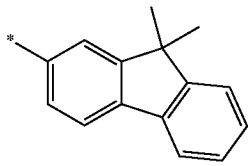
Formula 6-14
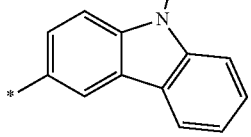
Formula 6-15
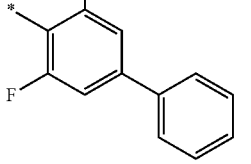
Formula 6-16
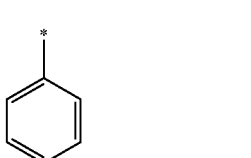
Formula 6-17
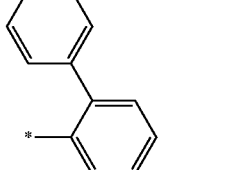
Formula 6-18
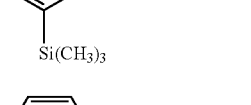
Formula 6-19
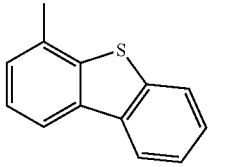
Formula 6-20
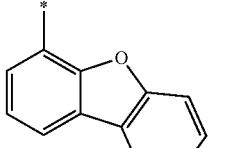

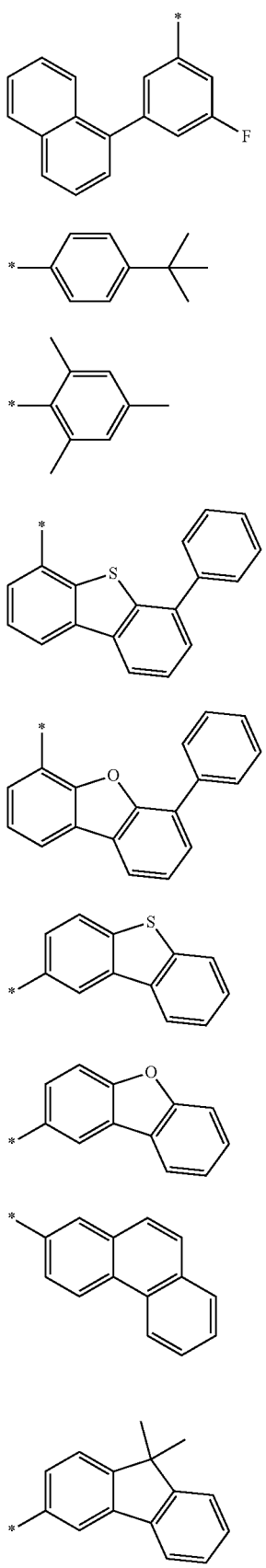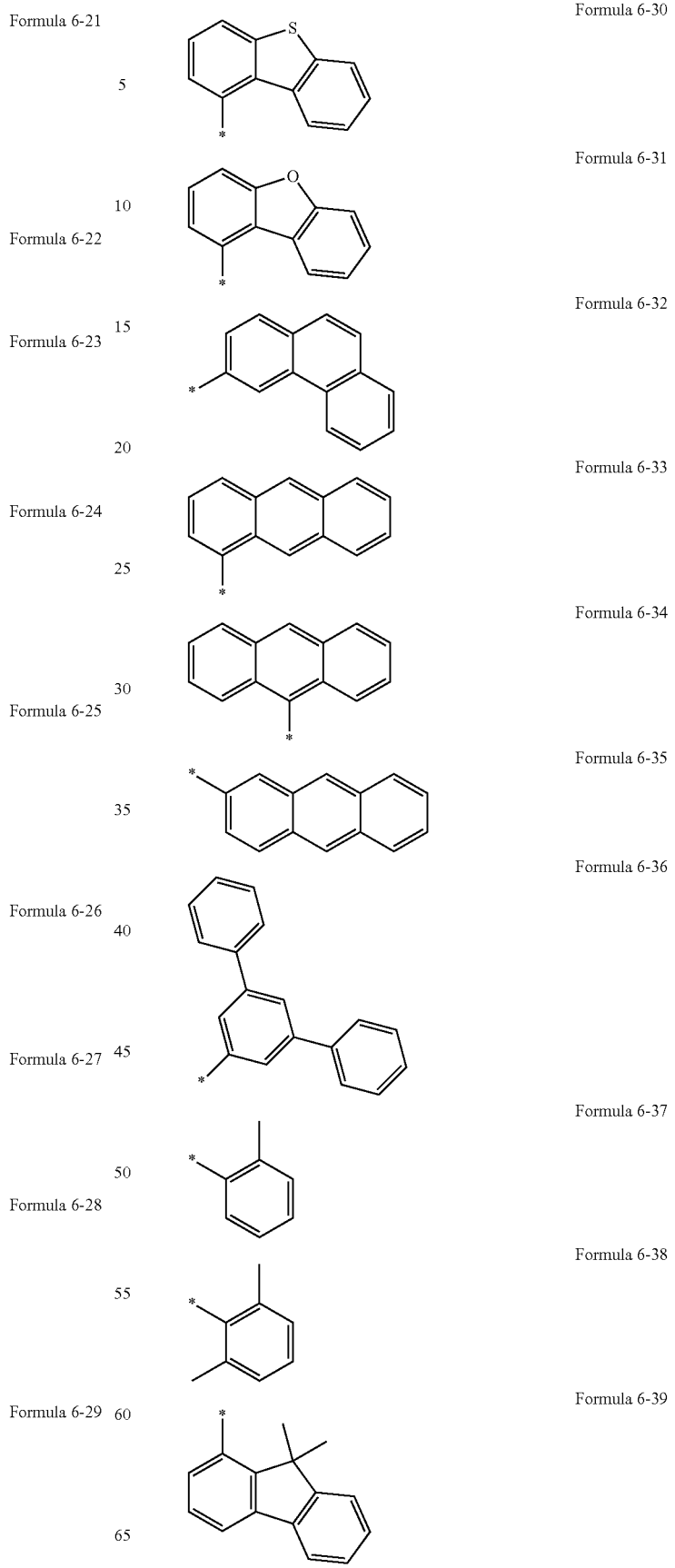

Formula 6-40
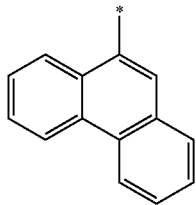
wherein, in Formulae 6-1 to 6-40, * indicates a binding site to a neighboring atom.
13. The condensed cyclic compound as claimed in claim 1, wherein the condensed cyclic compound represented by Formula 1 is represented by one of the following Formulae 1-1 to 1-8:
<Formula 1-1>
<Formula 1-2>
<Formula 1-3>
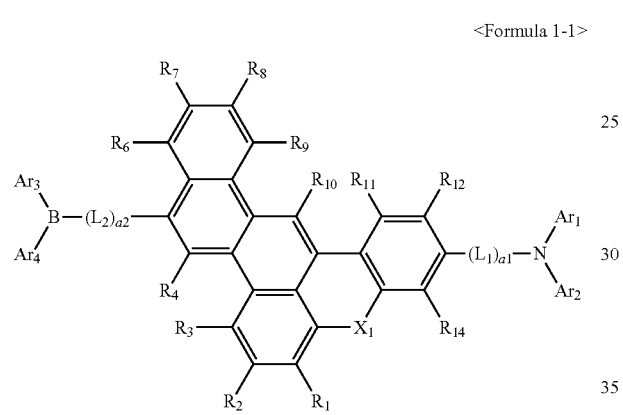
<Formula 1-4>
<Formula 1-5>
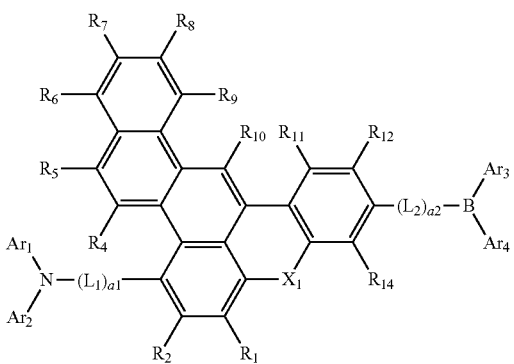
<Formula 1-6>
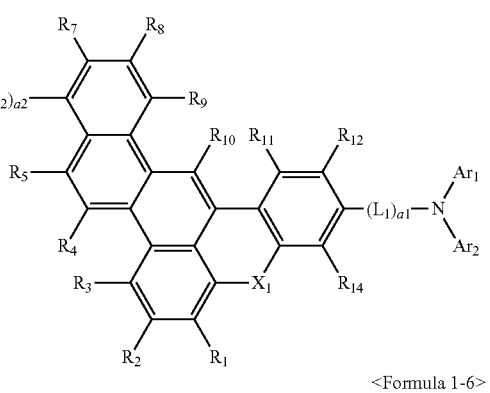
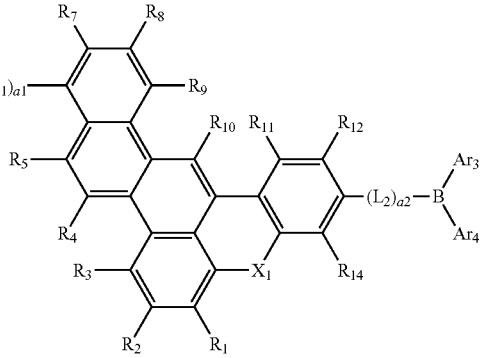
<Formula 1-7>
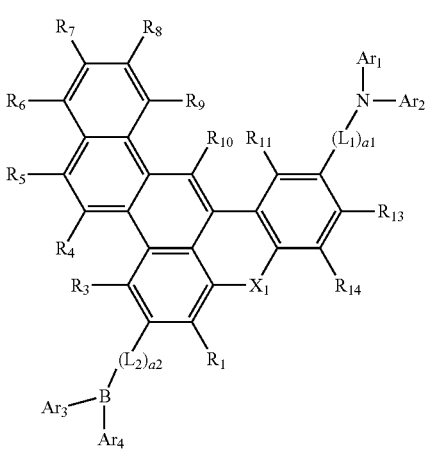

-continued

<Formula 1-8>

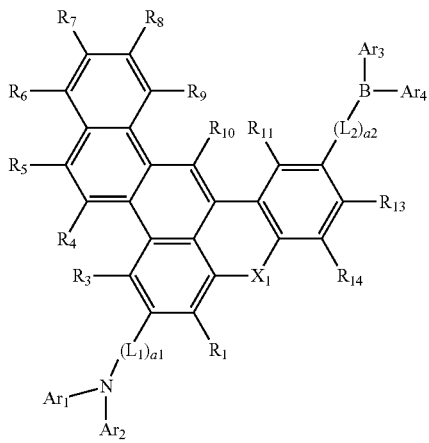

<Formula 1-1(3)>

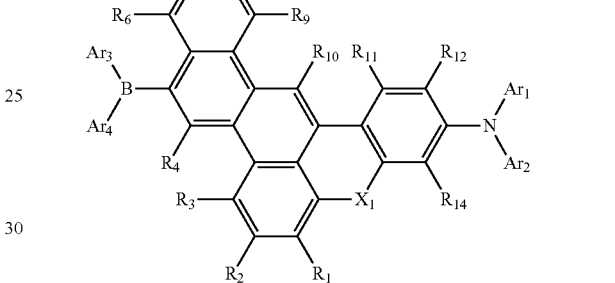

wherein, $X_1$, $L_1$, $L_2$, $a_1$, $a_2$, $Ar_1$ to $Ar_4$, and $R_1$ to $R_{14}$ in Formula 1-1 to Formula 1-8 are defined the same as $X_1$, $L_1$, $L_2$, $a_1$, $a_2$, $Ar_1$ to $Ar_4$, and $R_1$ to $R_{14}$ of Formulae 1 to 3.

14. The condensed cyclic compound as claimed in claim 1, wherein the condensed cyclic compound represented by Formula 1 is represented by one of the following Formulae 1-1(1) to 1-1(4):

<Formula 1-1(1)>

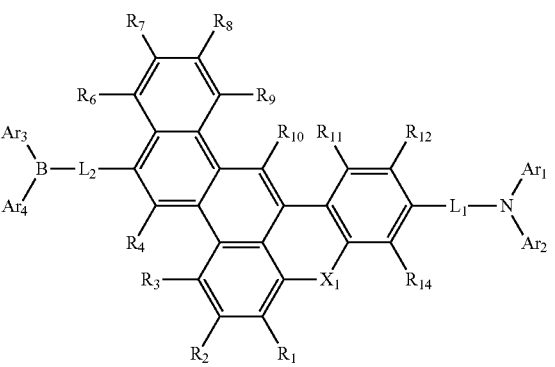

<Formula 1-1(4)>

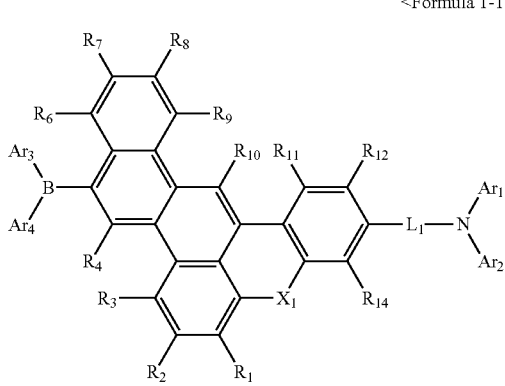

wherein, in Formulae 1-1(1) to 1-1(4), $X_1$, $L_1$, $L_2$, $Ar_1$ to $Ar_4$, $R_1$ to $R_4$, $R_6$ to $R_{12}$ and $R_{14}$ are defined the same as $X_1$, $L_1$, $L_2$, $Ar_1$ to $Ar_4$, $R_1$ to $R_4$, $R_6$ to $R_{12}$ and $R_{14}$ of Formulae 1 to 3.

15. The condensed cyclic compound as claimed in claim 14, wherein:

$R_1$ to $R_4$, $R_6$ to $R_{12}$, and $R_{14}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a pyridinyl group, a pyrimidinyl group, and a triazinyl group, $L_1$ and $L_2$ are each independently a group represented by one of the following Formulae 3-1 to 3-35, <Formula 1-1(2)>

Formula 3-1

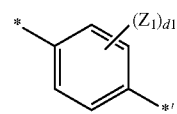

Formula 3-2

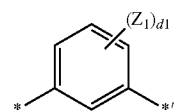

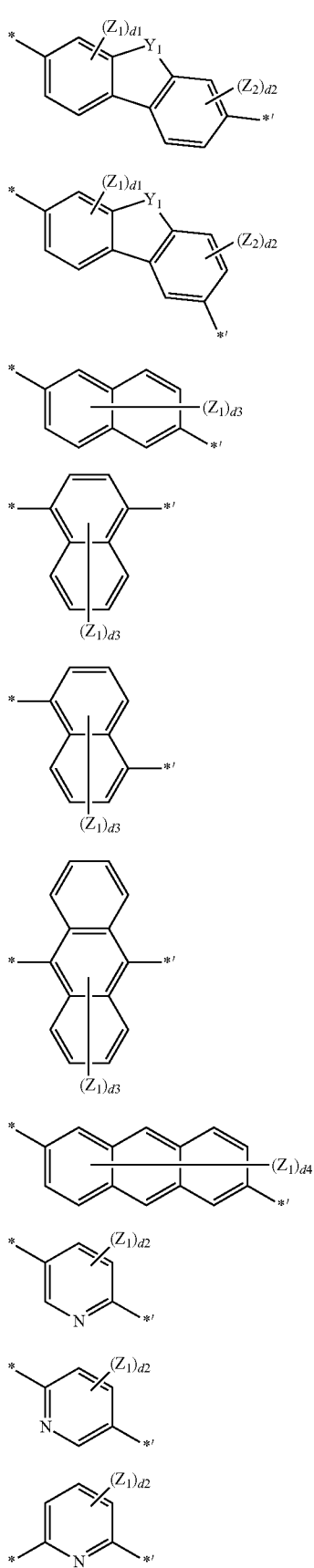
Formula 3-3
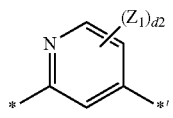
Formula 3-4
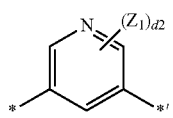
Formula 3-5
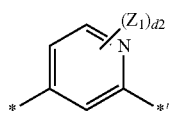
Formula 3-6
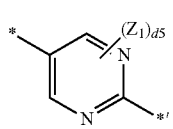
Formula 3-7
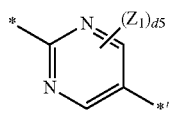
Formula 3-8
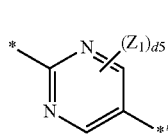
Formula 3-9
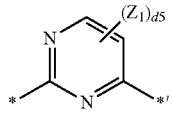
Formula 3-10
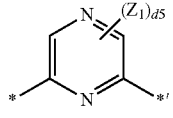
Formula 3-11
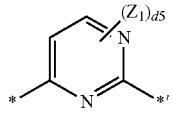
Formula 3-12
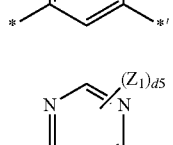
Formula 3-13
Formula 3-14
Formula 3-15
Formula 3-16
Formula 3-17
Formula 3-18
Formula 3-19
Formula 3-20
Formula 3-21
Formula 3-22
Formula 3-23
Formula 3-24

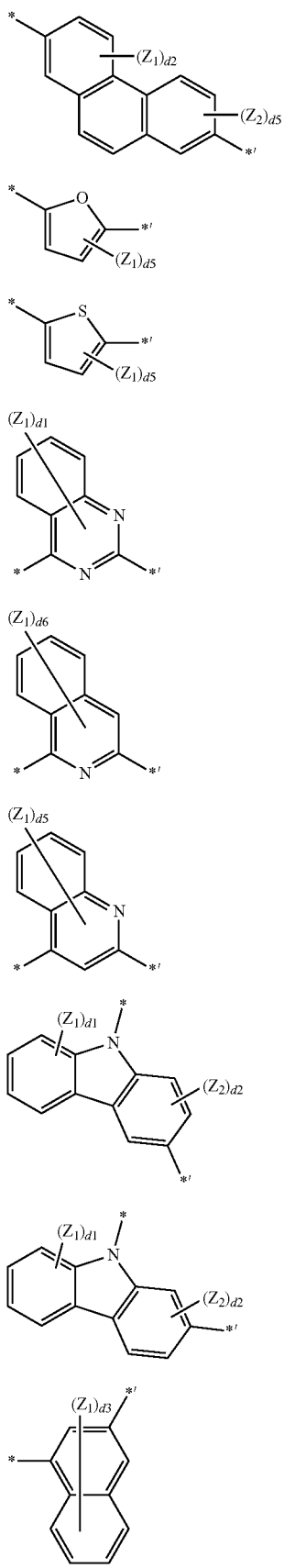

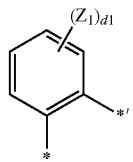

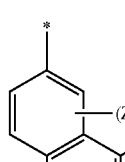

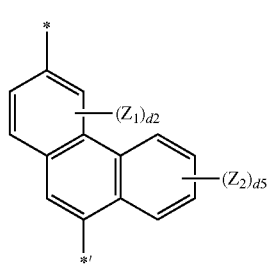

wherein, in Formulae 3-1 to 3-35,
Y₁ is O, S, C(Z₃)(Z₄), N(Z₅), or Si(Z₆)(Z₇);
Z₁ to Z₇ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group,
d1 is an integer selected from 1, 2, 3, and 4, d2 is an integer selected from 1, 2, and 3, d3 is an integer selected from 1, 2, 3, 4, 5, and 6, d4 is an integer selected from 1, 2, 3, 4, 5, 6, 7, and 8, d5 is 1 or 2, and d6 is an integer selected from 1, 2, 3, 4, and 5, and * and *' indicate binding sites to a neighboring atom,
a1 and a2 are each independently 0, 1, or 2; and
Ar₁ to Ar₄ are each independently a group represented by one of the following Formulae 5-1 to 5-43,

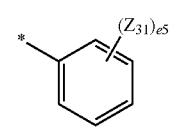

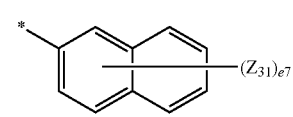

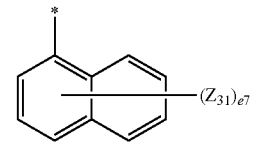

-continued
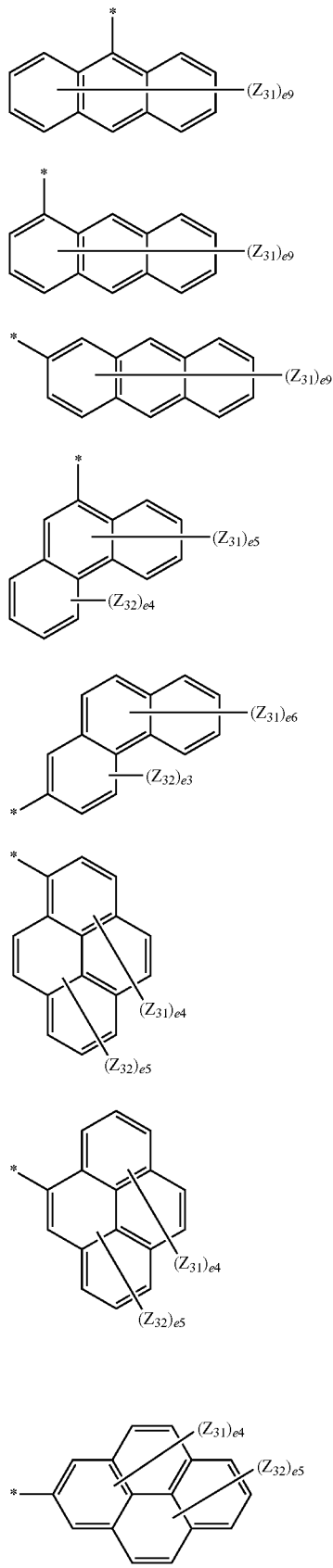
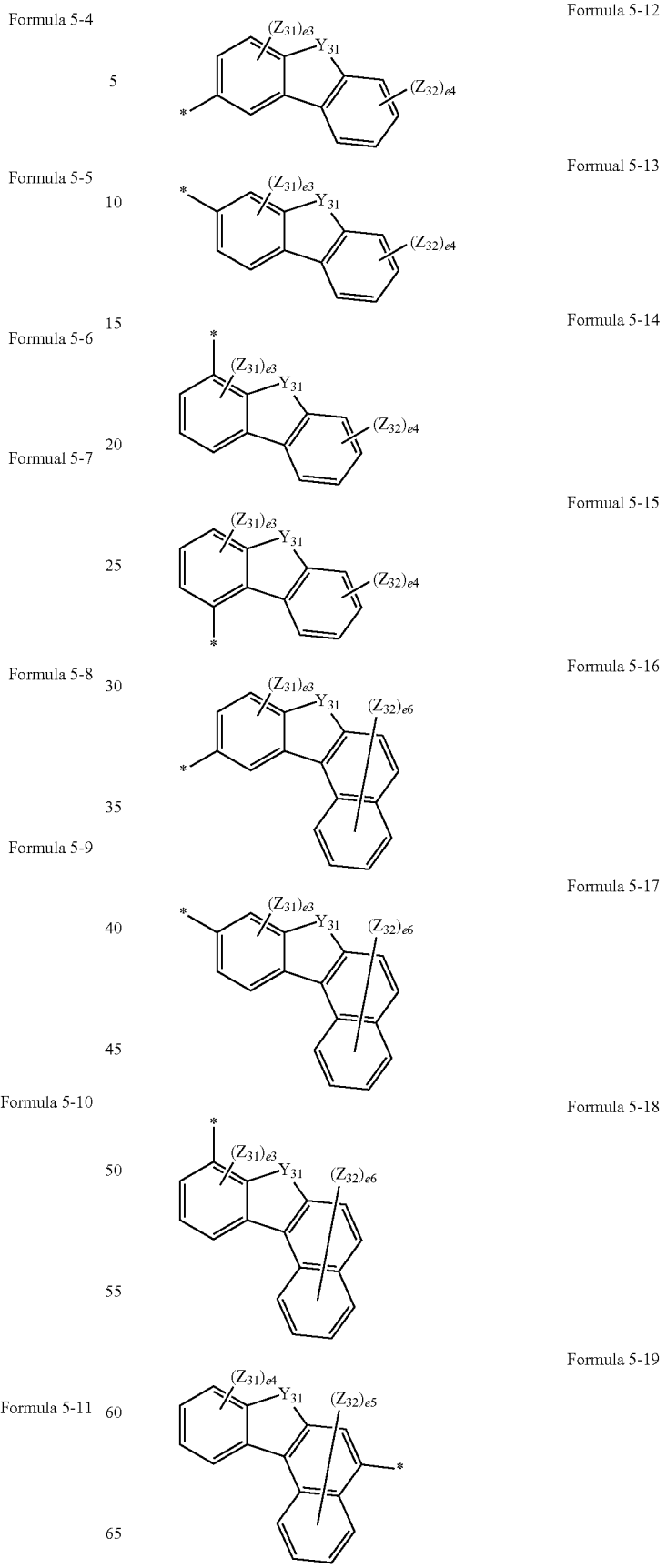
Formula 5-4
Formula 5-5
Formula 5-6
Formual 5-7
Formula 5-8
Formula 5-9
Formula 5-10
Formula 5-11
Formula 5-12
Formual 5-13
Formula 5-14
Formual 5-15
Formula 5-16
Formula 5-17
Formula 5-18
Formula 5-19

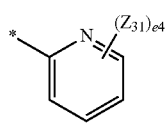 Formula 5-20
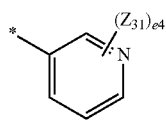 Formula 5-21
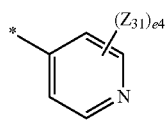 Formula 5-22
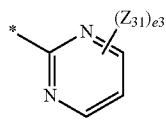 Formula 5-23
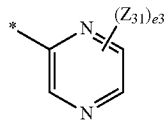 Formula 5-24
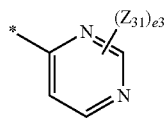 Formula 5-25
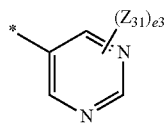 Formula 5-26
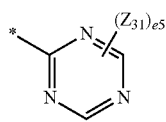 Formula 5-27
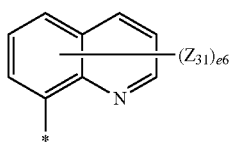 Formula 5-28
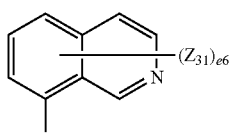 Formula 5-29
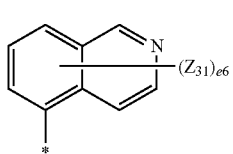 Formula 5-30
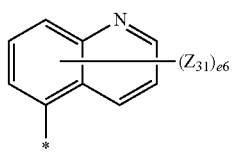 Formula 5-31
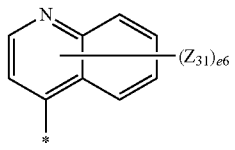 Formula 5-32
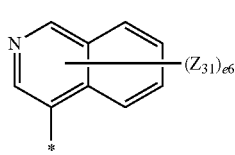 Formula 5-33
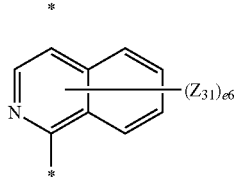 Formula 5-34
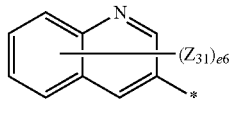 Formula 5-35
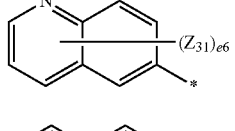 Formula 5-36
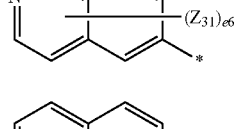 Formula 5-37
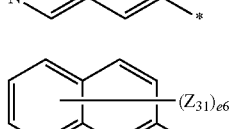 Formula 5-38
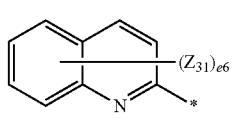 Formula 5-39
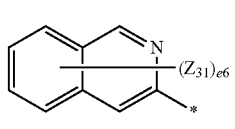 Formula 5-40
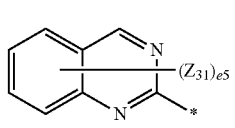 Formula 5-41
Formula 5-42

209
-continued

Formula 5-43

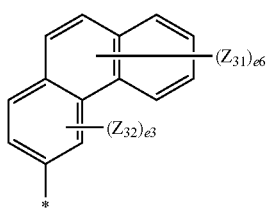

wherein, in Formulae 5-1 to 5-43,
$Y_{31}$ is O, S, C($Z_{33}$)($Z_{34}$), N($Z_{35}$), or Si($Z_{36}$)($Z_{37}$);

$Z_{31}$ to $Z_{37}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$ to $C_{20}$ alkyl group, a $C_1$ to $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, e3 is an integer selected from 1, 2, and 3, e4 is an integer selected from 1, 2, 3, and 4, e5 is an integer selected from 1, 2, 3, 4, and 5, e6 is an integer selected from 1, 2, 3, 4, 5, and 6, e7 is an integer selected from 1, 2, 3, 4, 5, 6, and 7, e8 is an integer selected from 1, 2, 3, 4, 5, 6, 7, and 8, e9 is an integer selected from 1, 2, 3, 4, 5, 6, 7, 8, and 9, and * indicates a binding site to a neighboring atom.

16. The condensed cyclic compound as claimed in claim 1, wherein the compound represented by Formula 1 is one of the following Compounds 1 to 104:

1

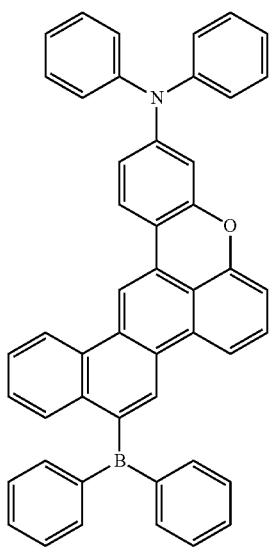

210
-continued

2

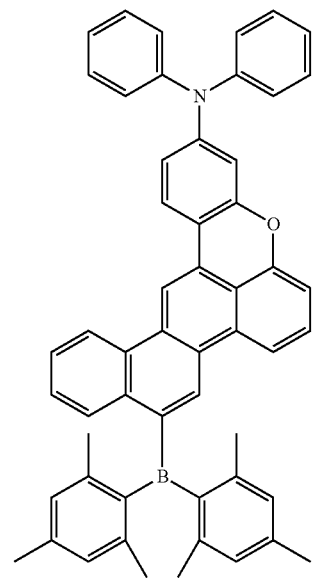

3

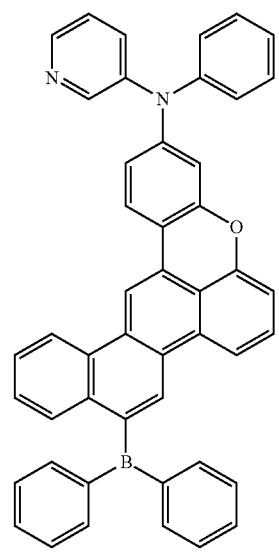

211
-continued
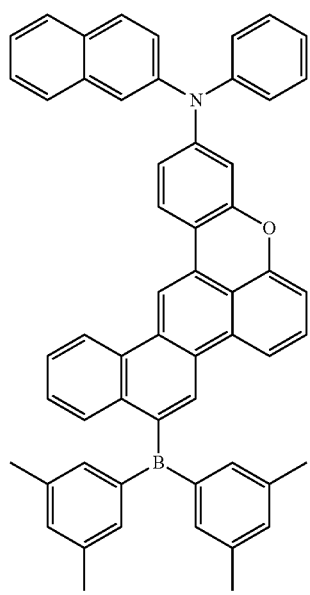
212
-continued
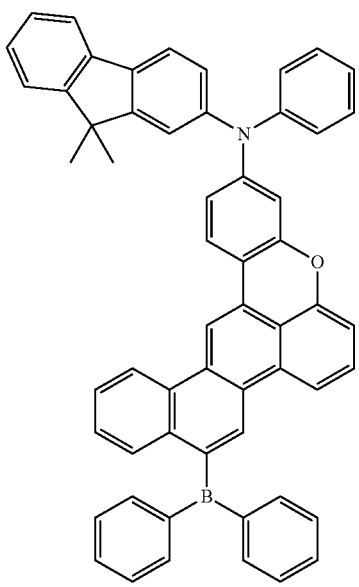
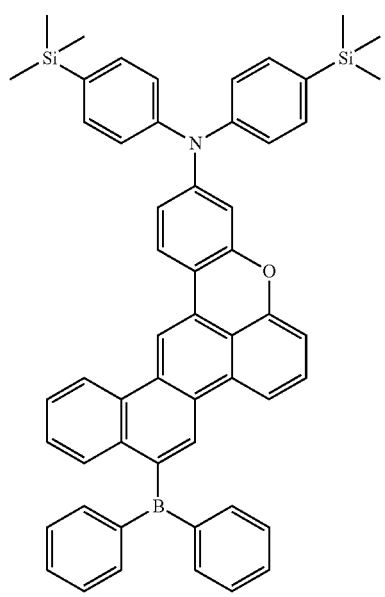
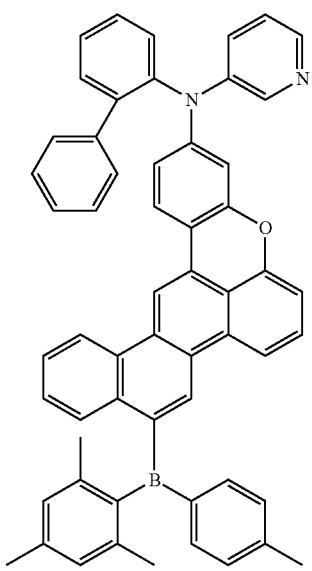

8
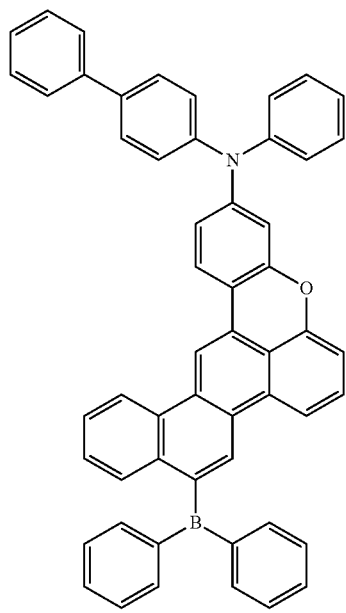
10
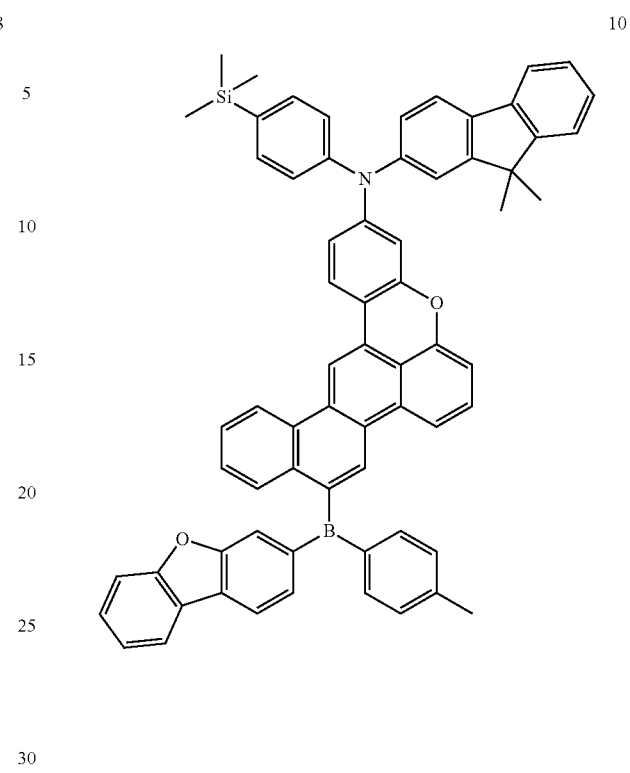
9
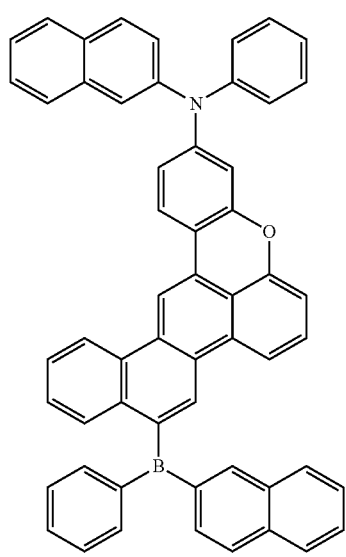
11
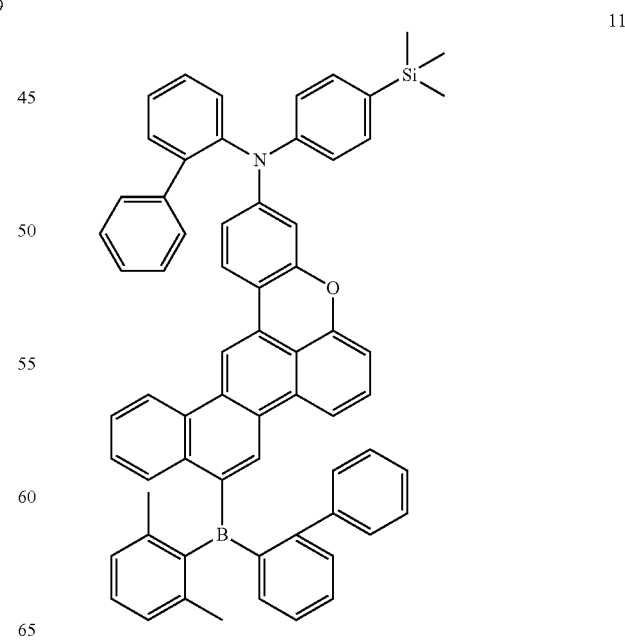

12
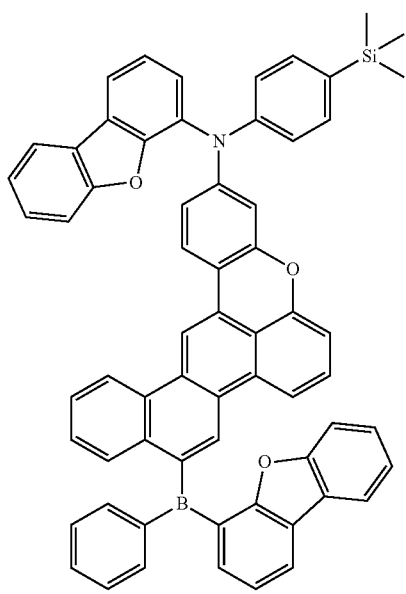
13
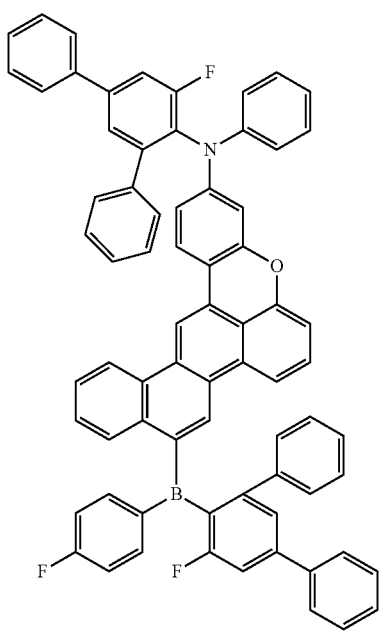
14
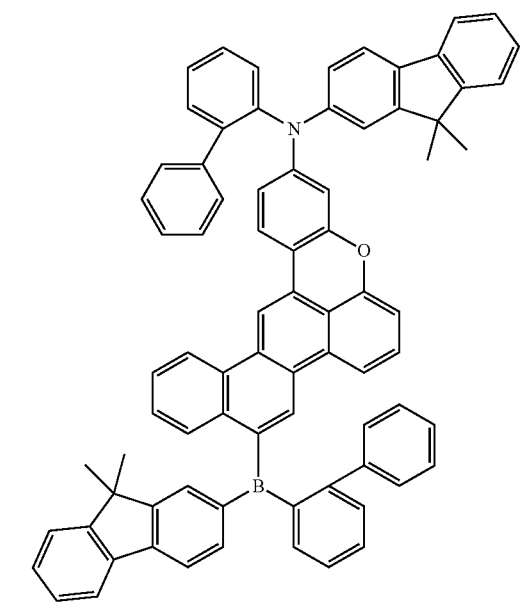
15
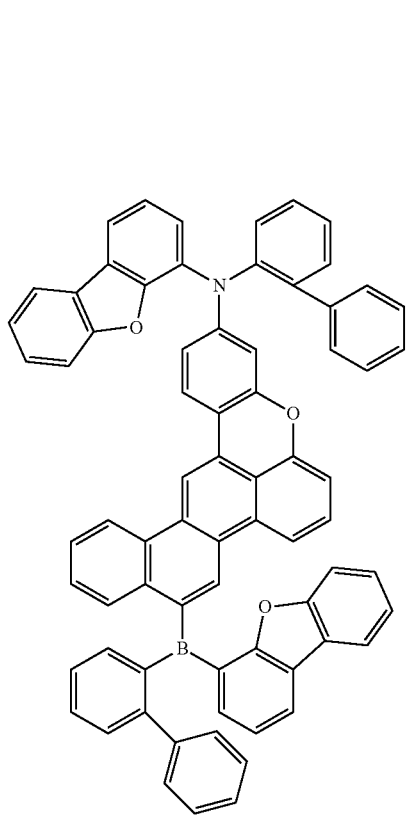

217
-continued
16
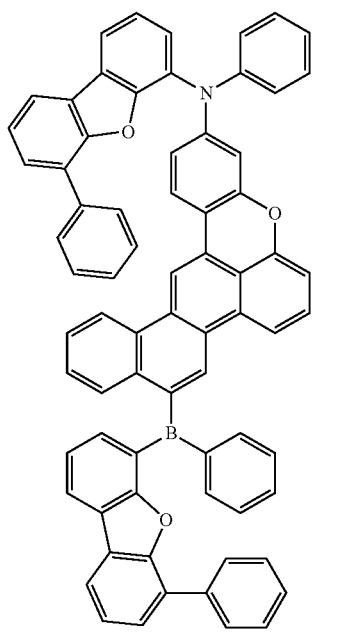
17
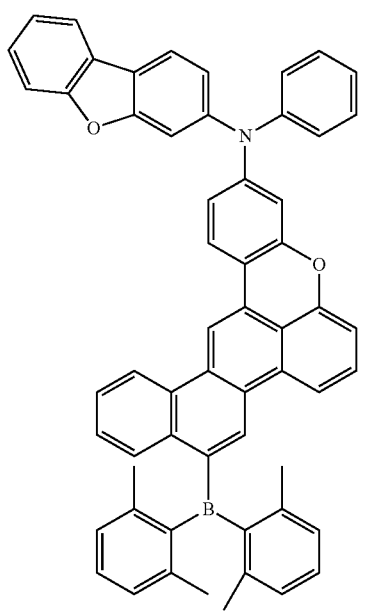
218
-continued
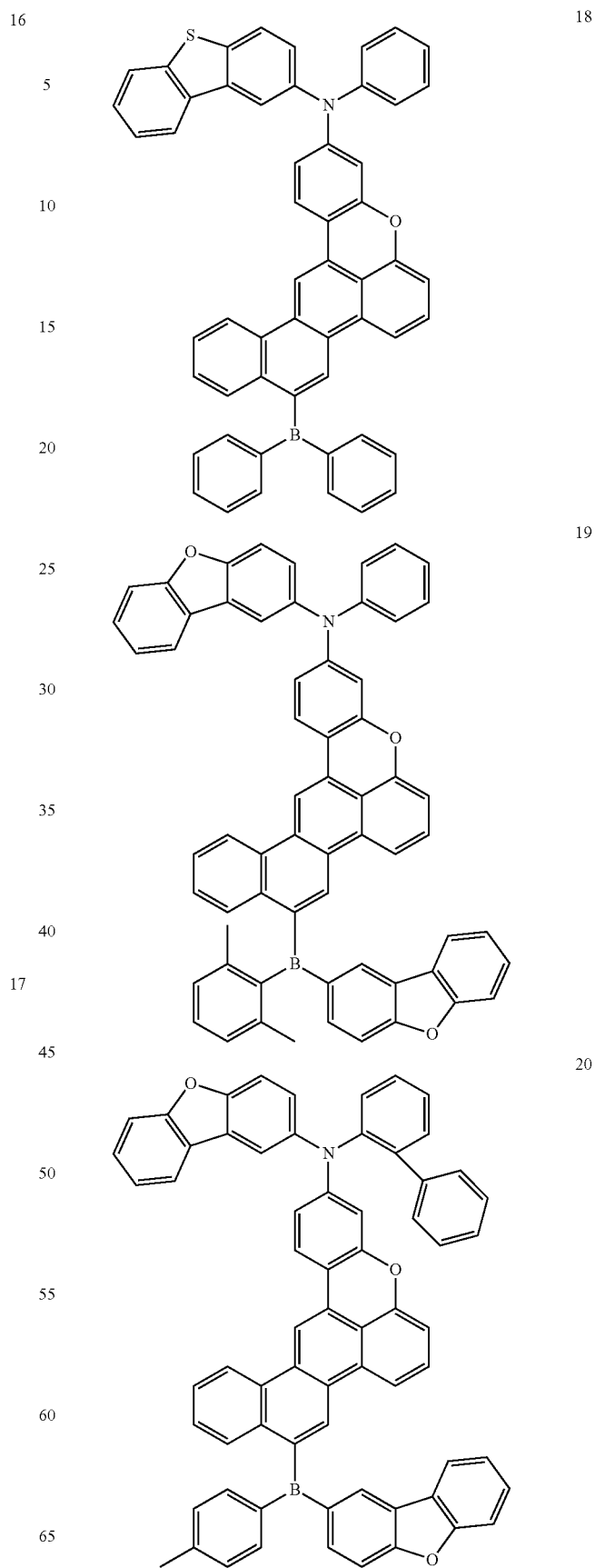

21
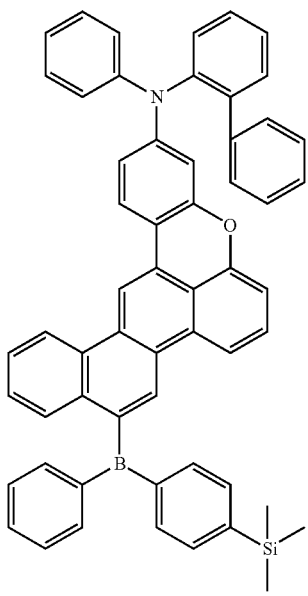
22
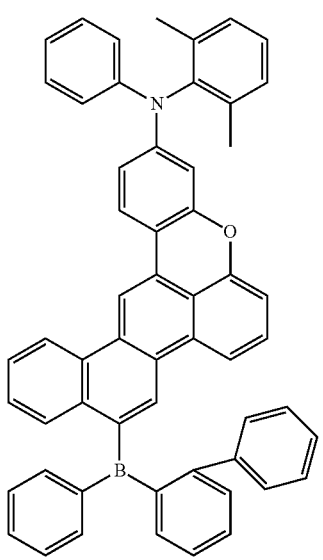
23
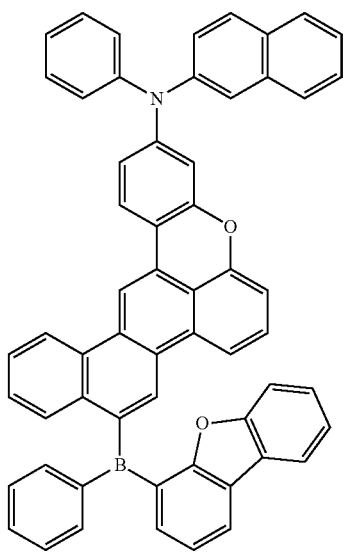
24
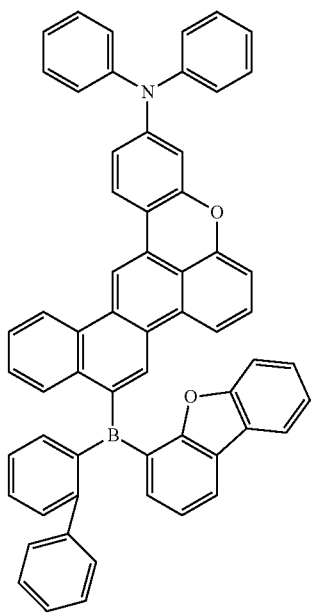

25
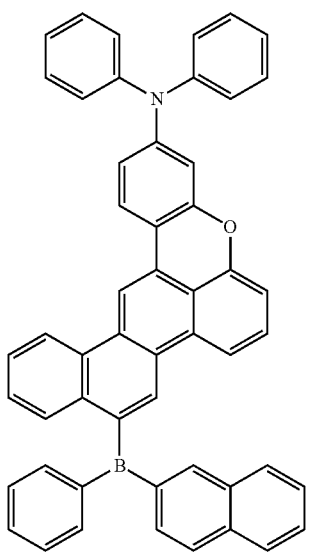
26
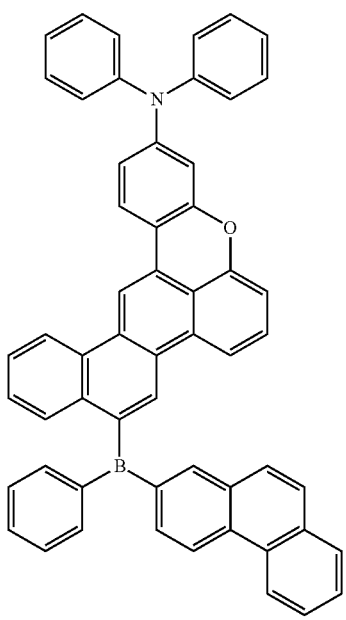
27
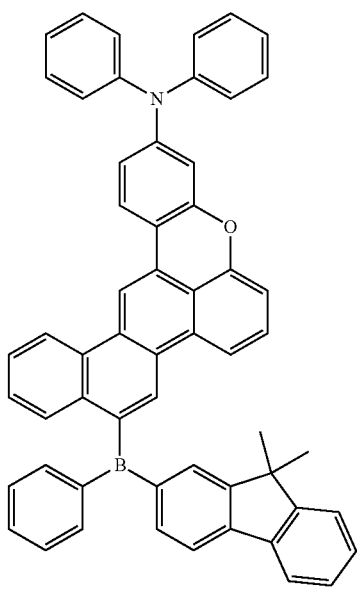
28
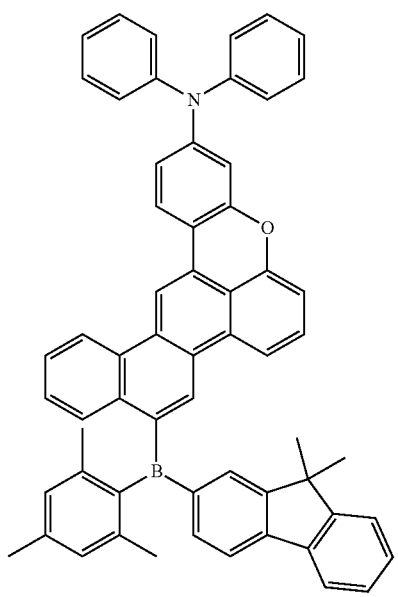

223
-continued
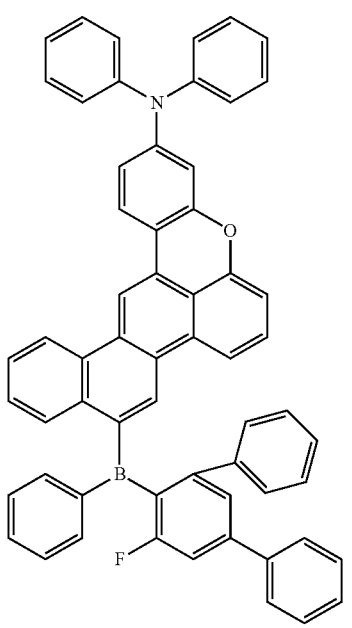
29
224
-continued
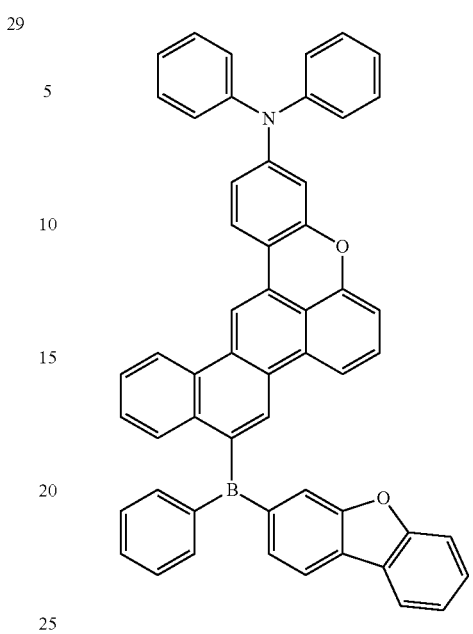
31
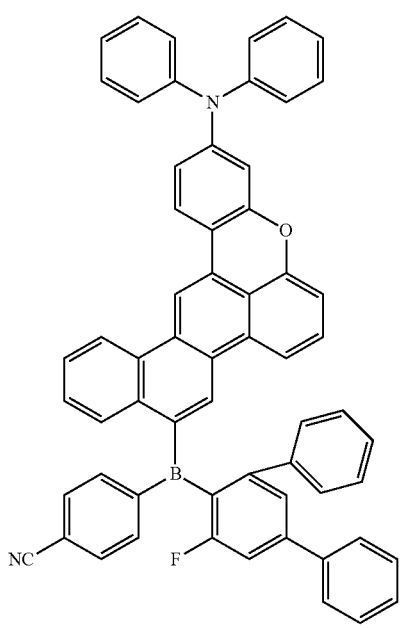
30
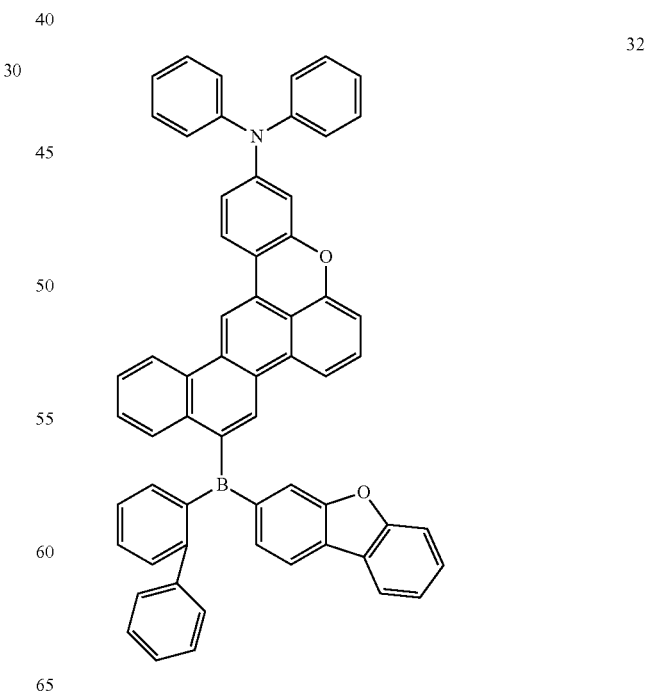
32

33
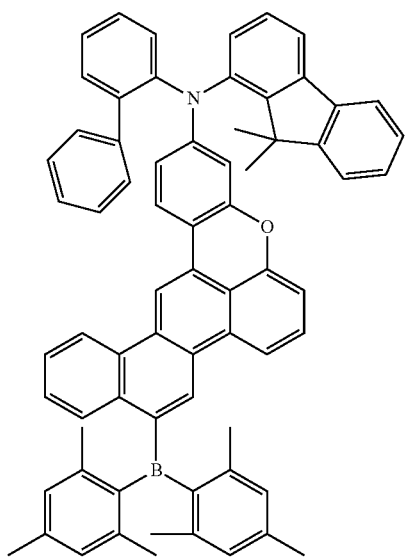
34
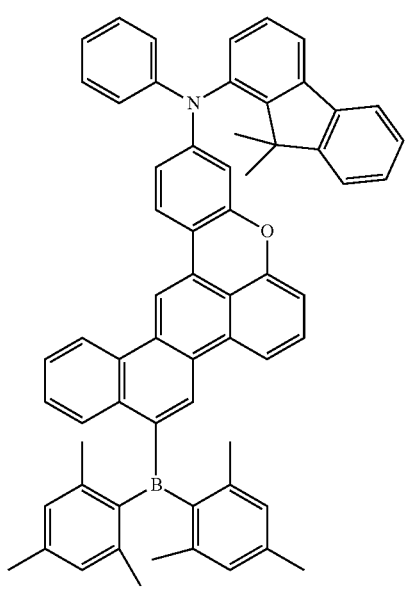
35
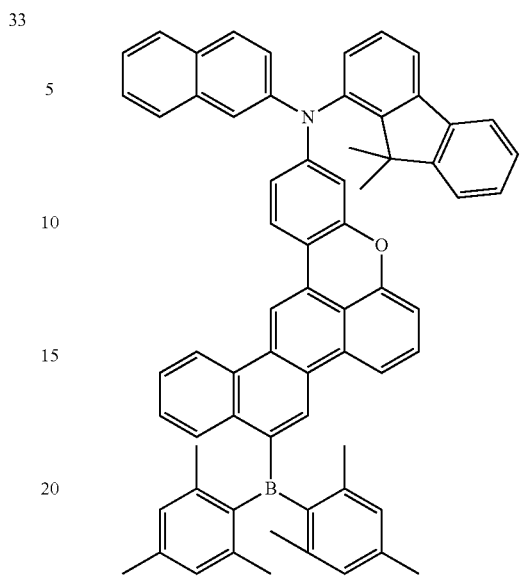
36
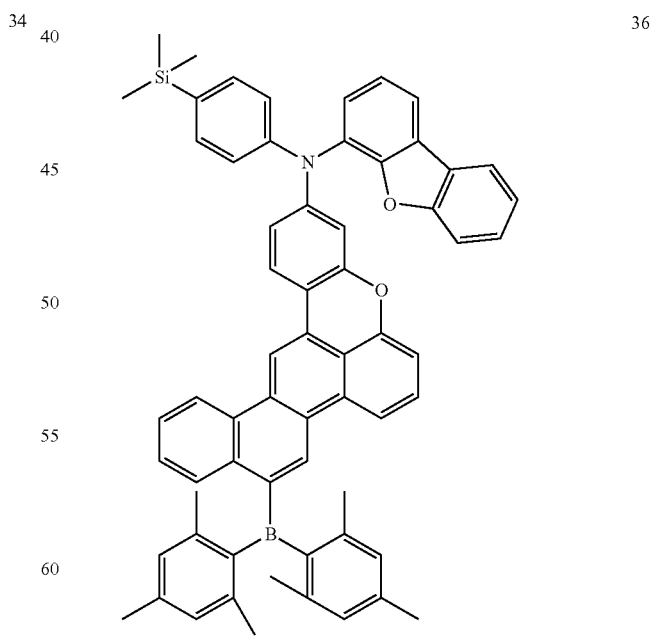

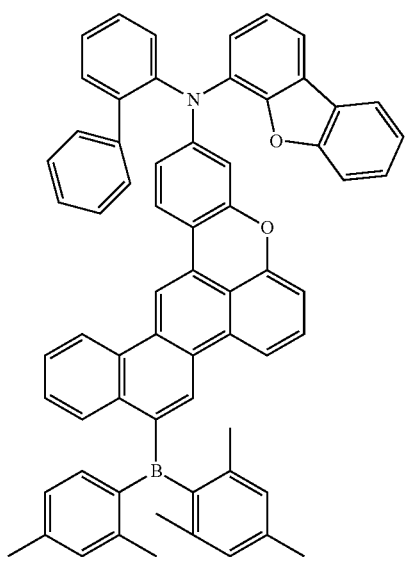
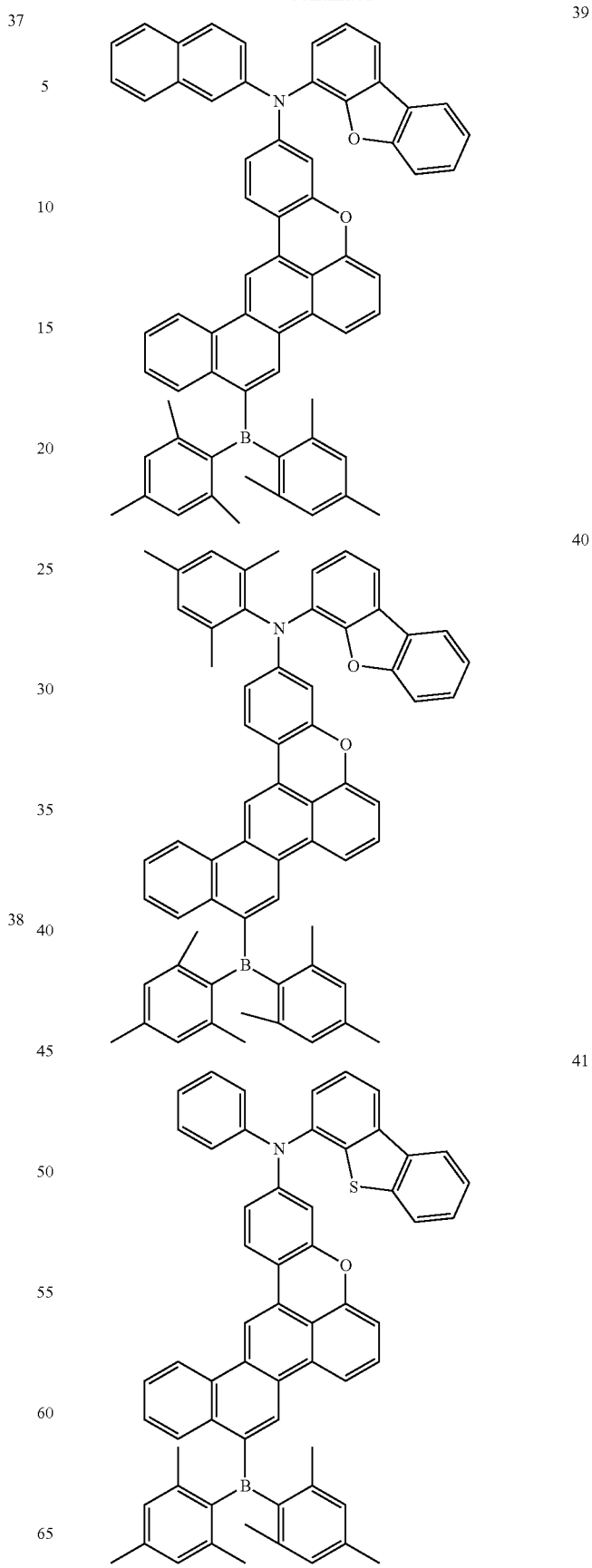

229
-continued
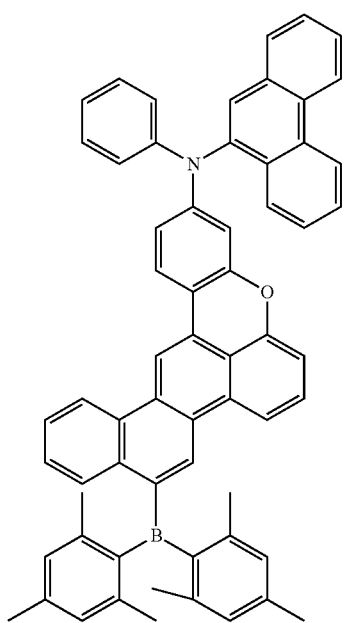
42
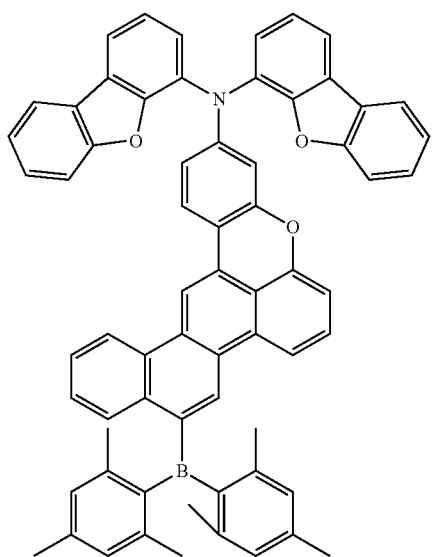
43
230
-continued
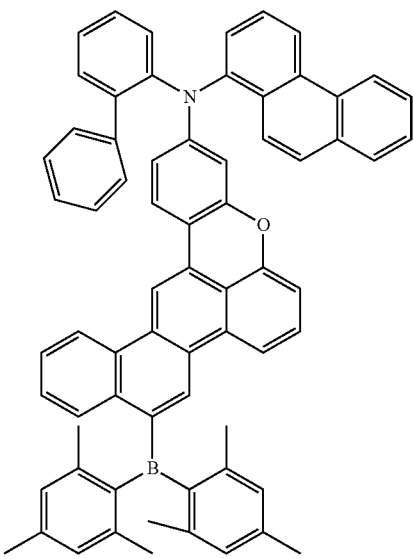
44
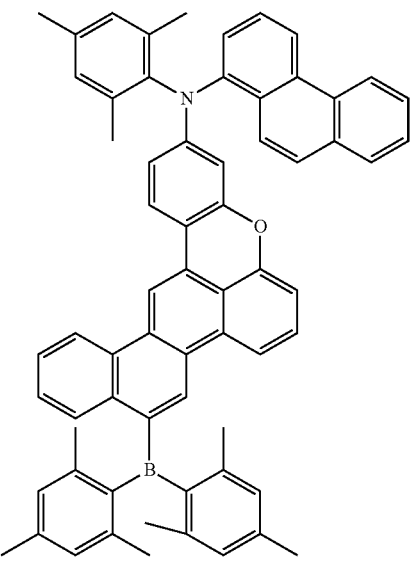
45

231
-continued
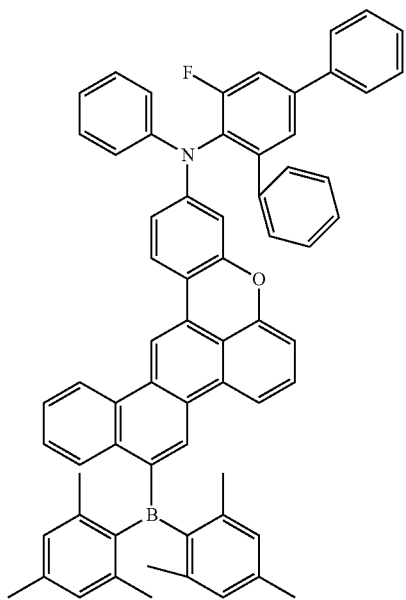
46
232
-continued
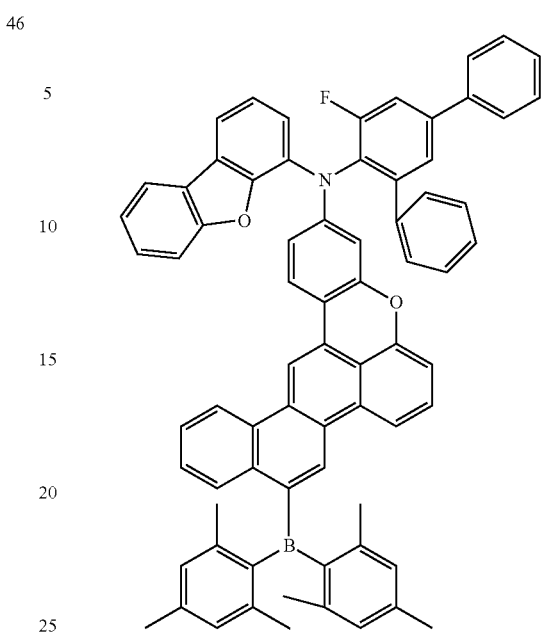
48
47
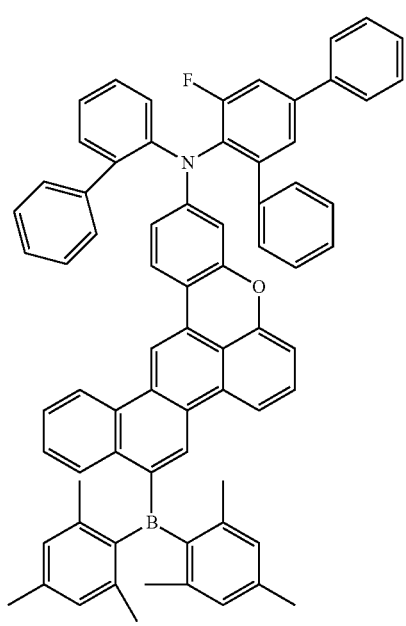
49
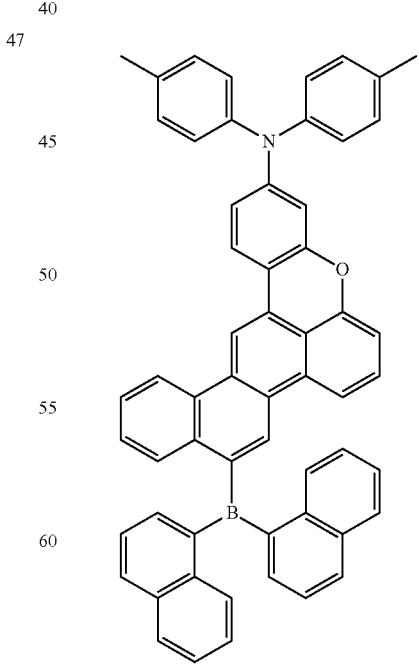

233
-continued
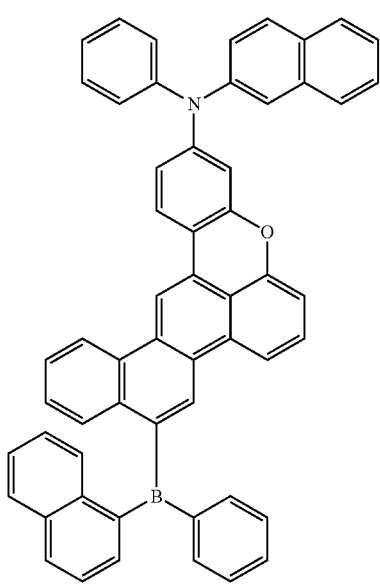
50
234
-continued
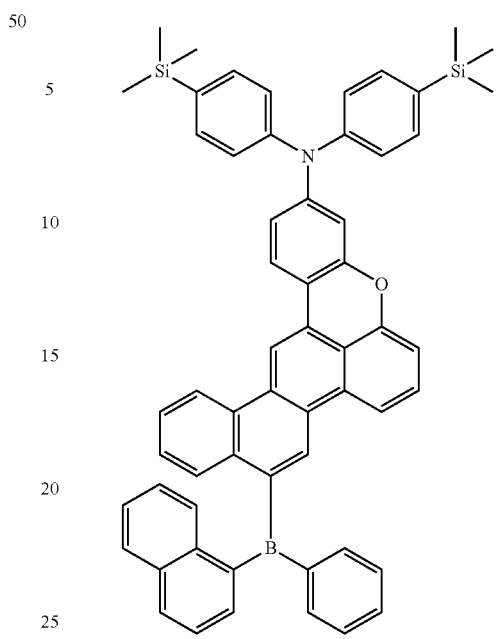
52
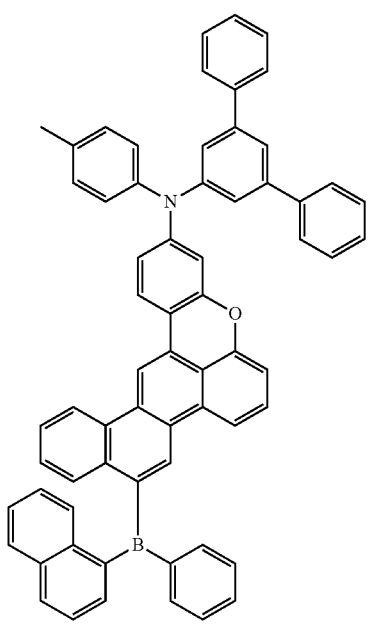
51
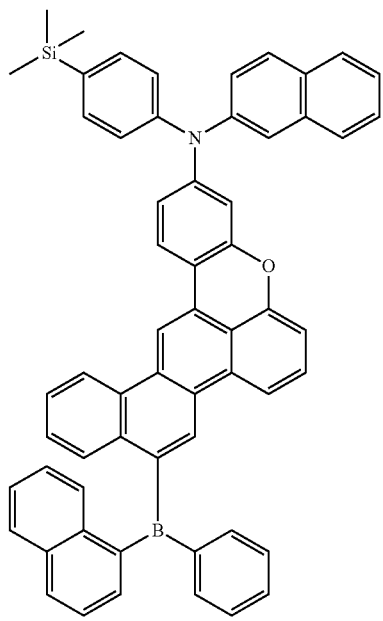
53

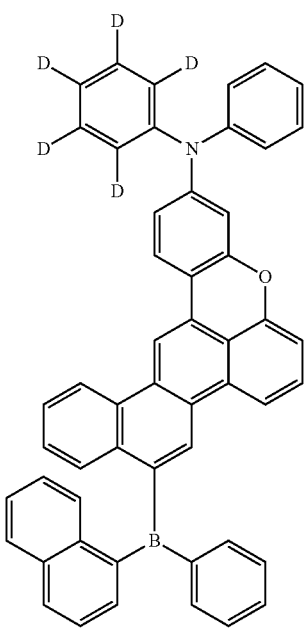
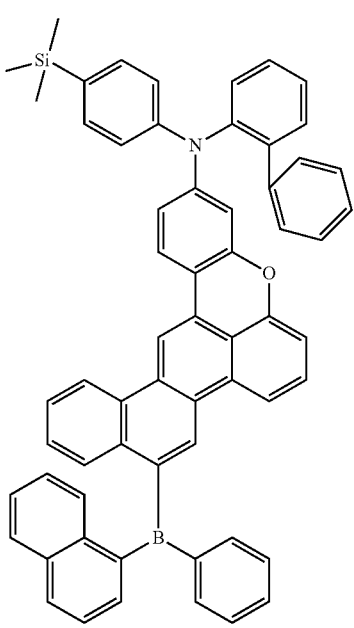
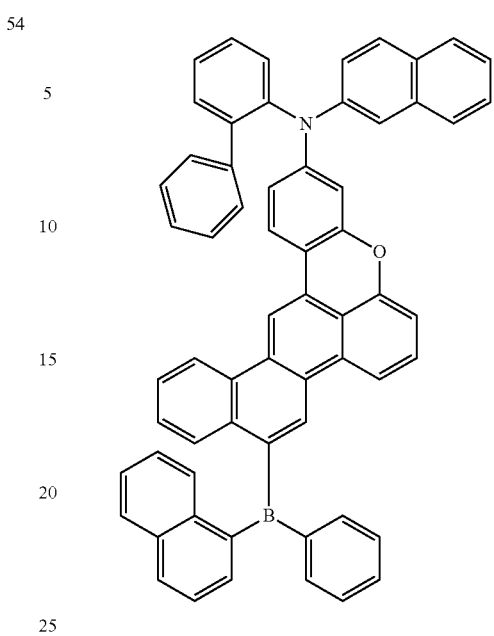

237
-continued
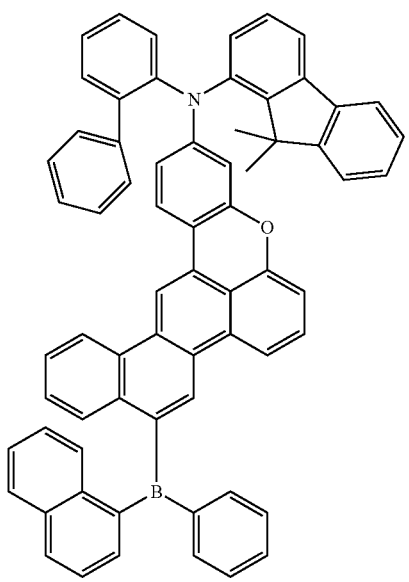
58
59
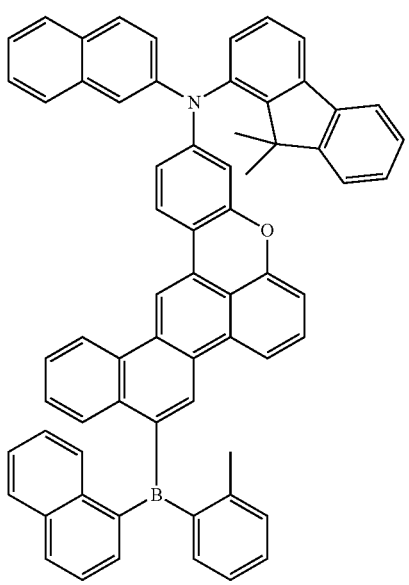
238
-continued
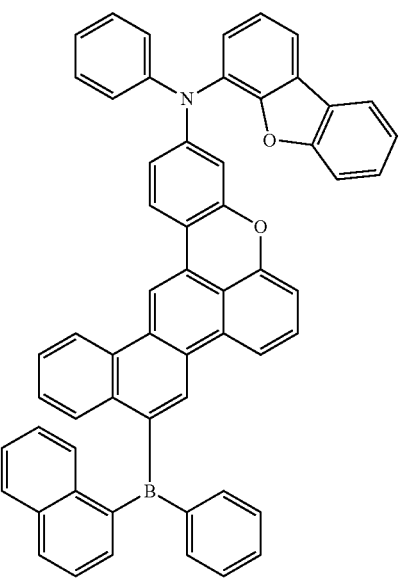
60
61

239
-continued
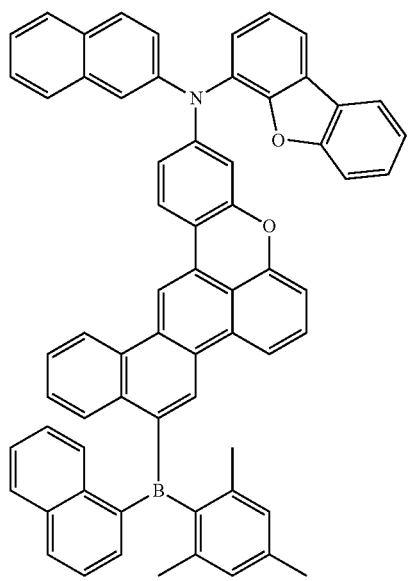
240
-continued
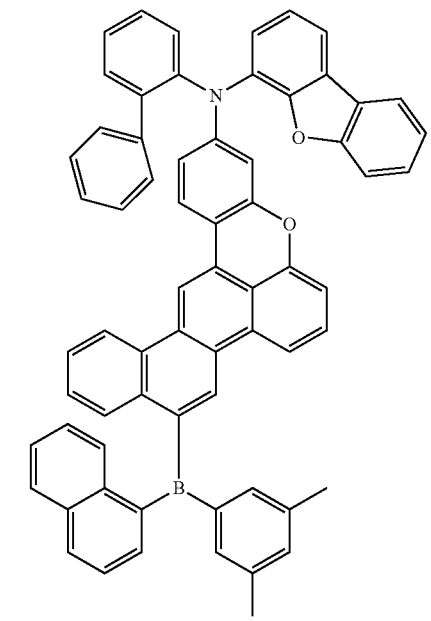
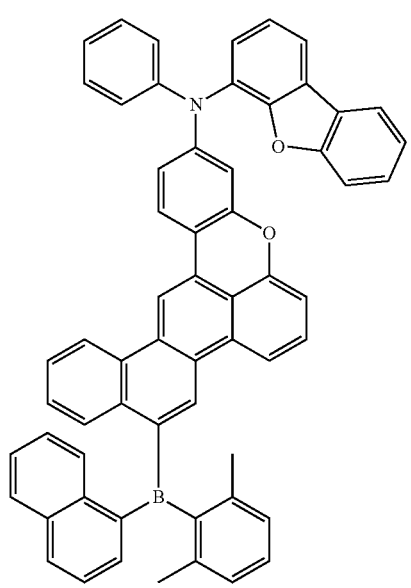
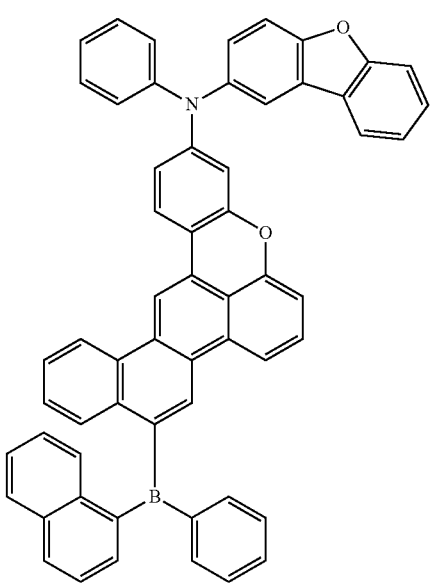

241
-continued
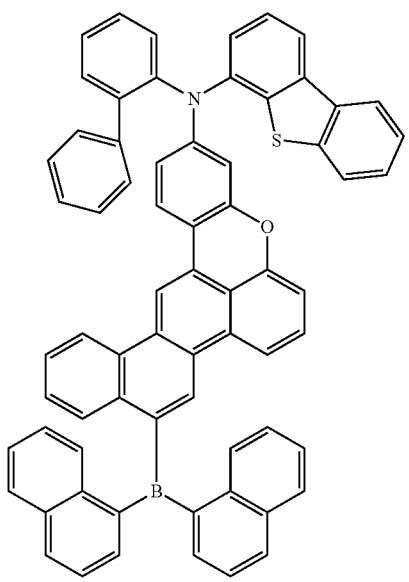
66
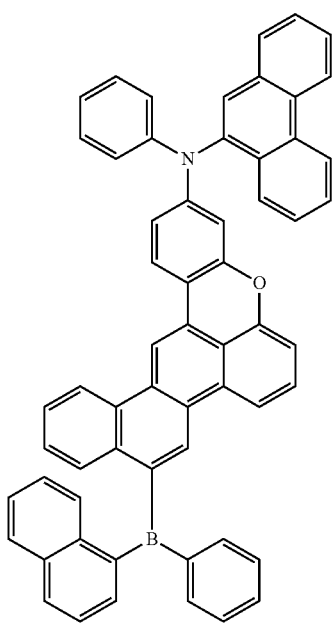
67
242
-continued
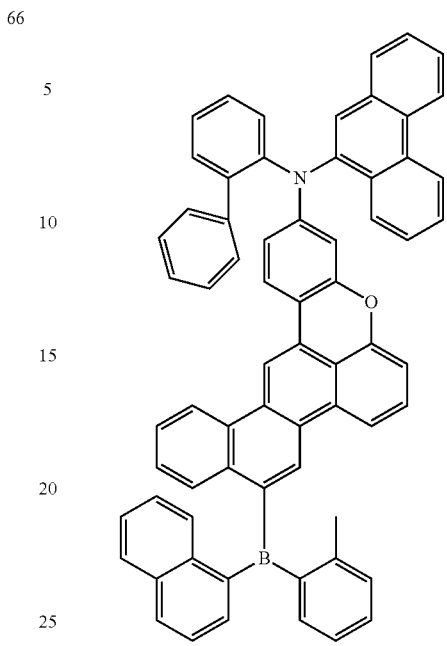
68
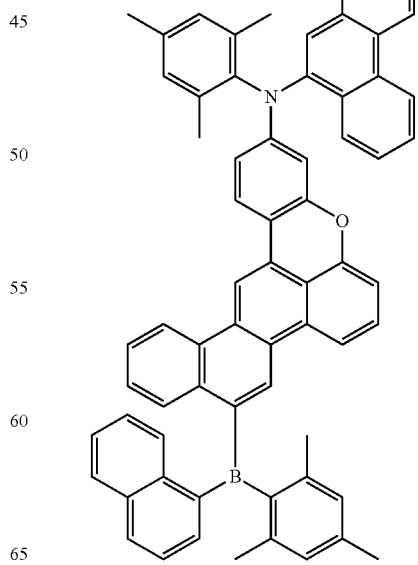
69

243
-continued
70
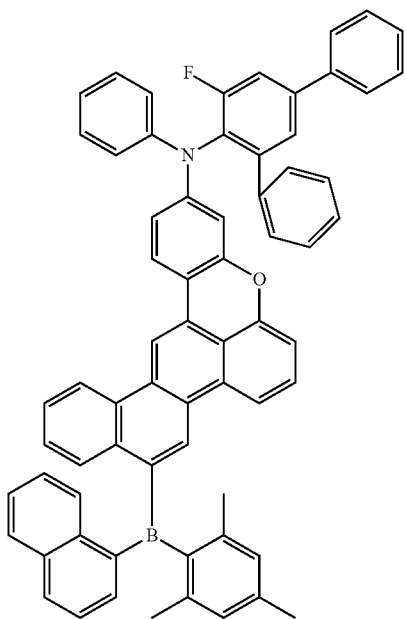
71
244
-continued
72
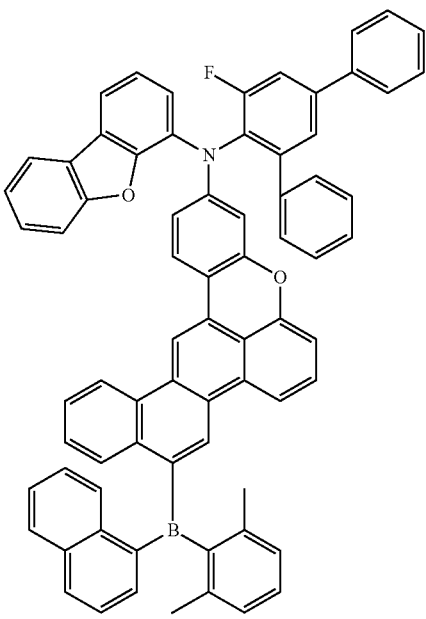
73
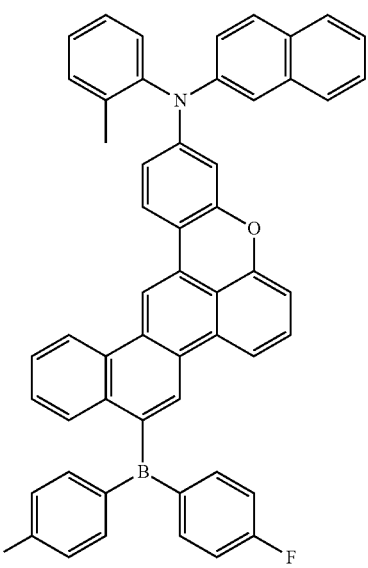

245
-continued
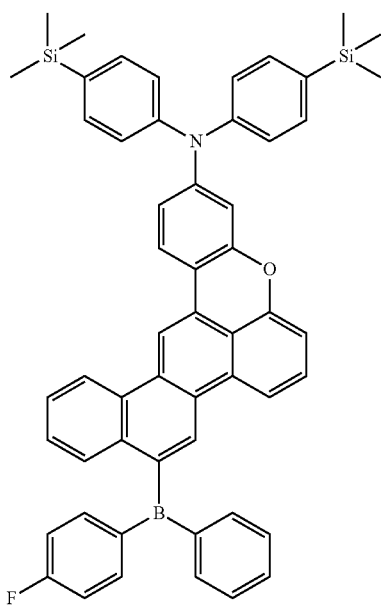
74
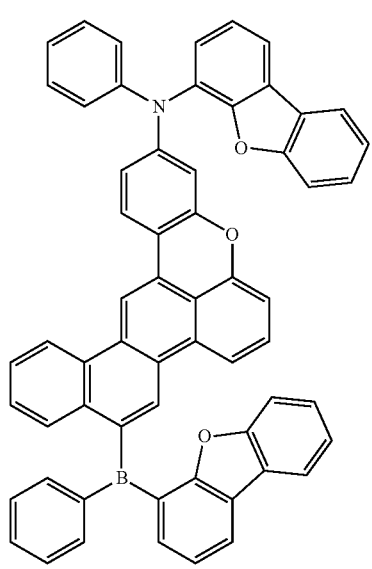
75
246
-continued
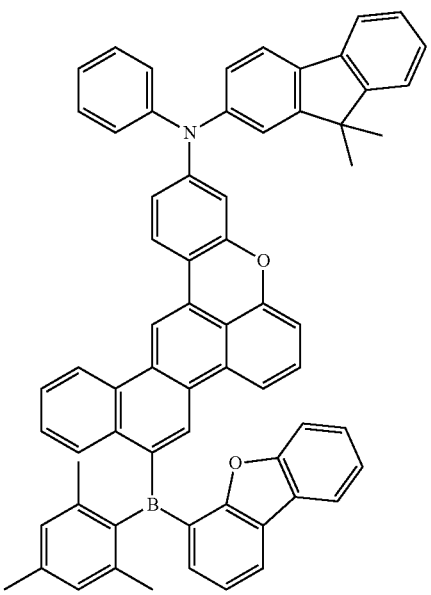
76
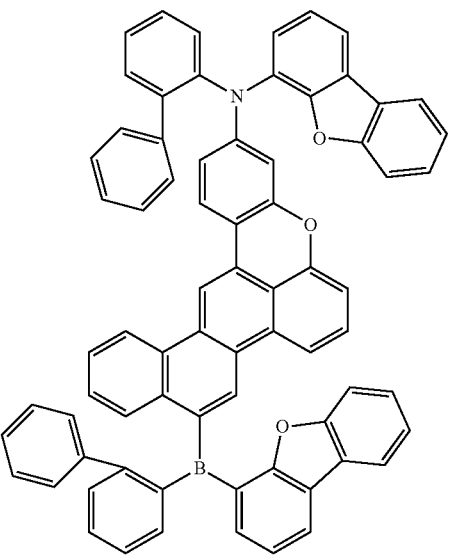
77

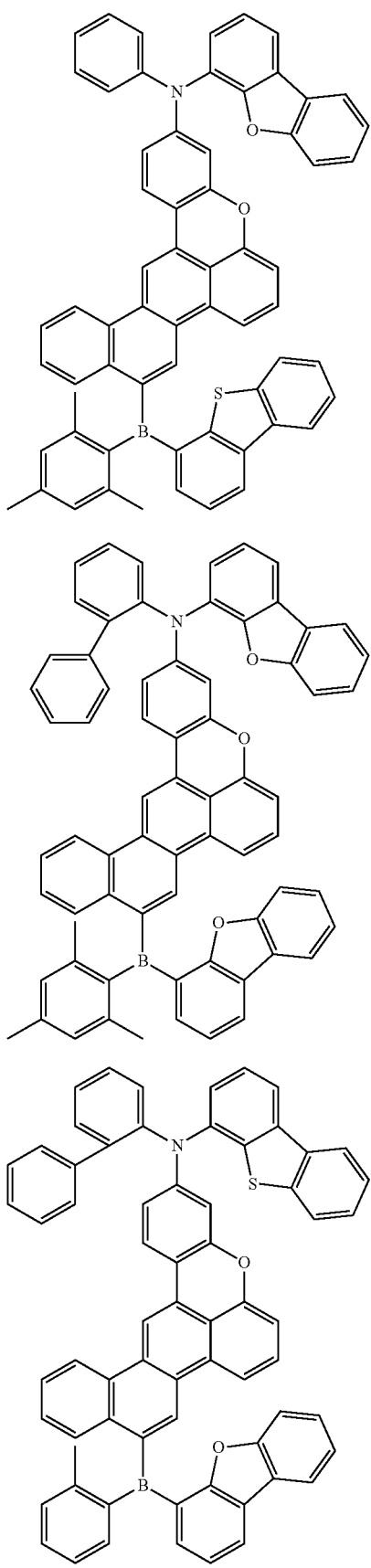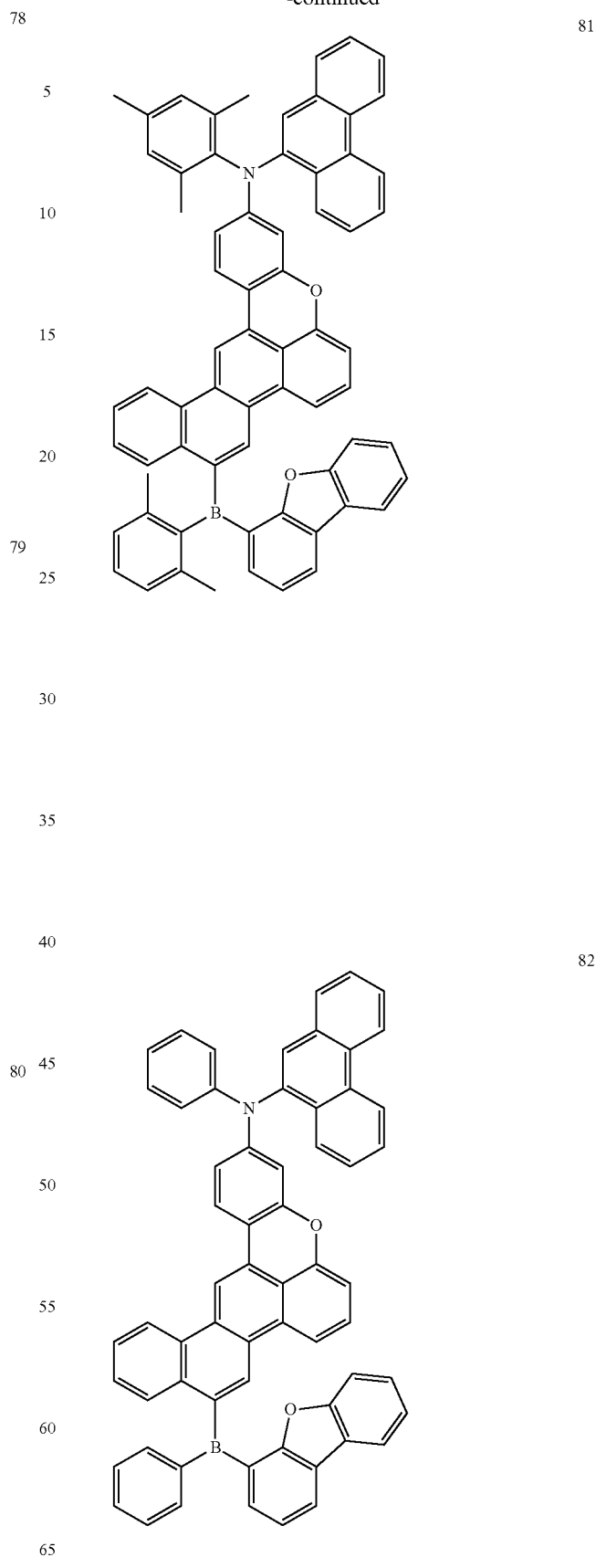

83
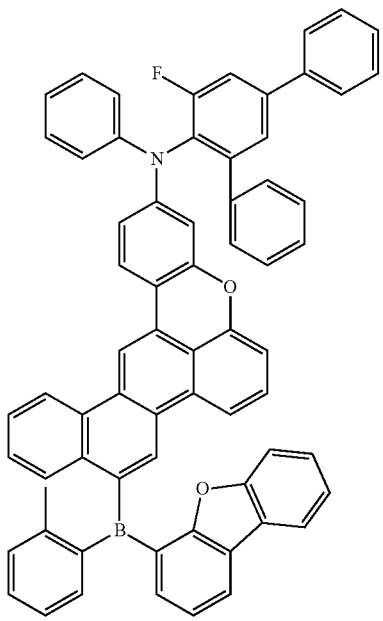
84
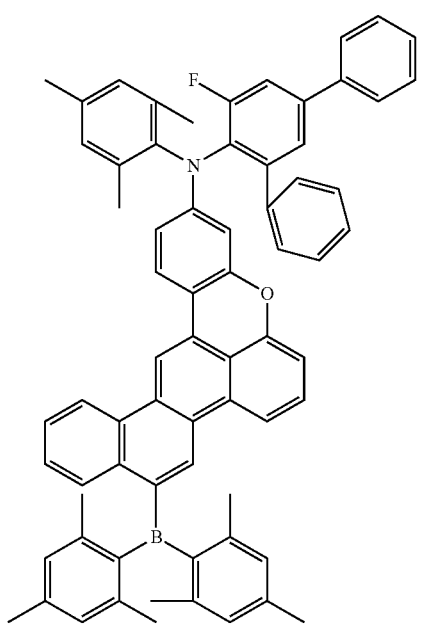
85
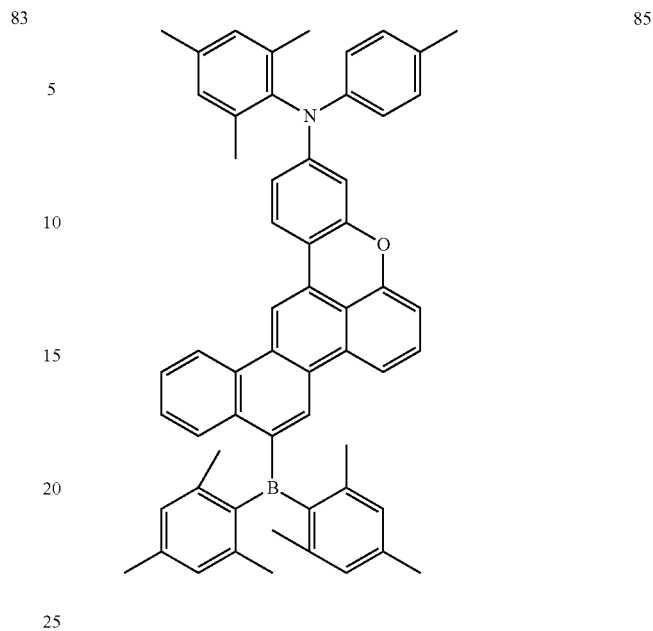
86
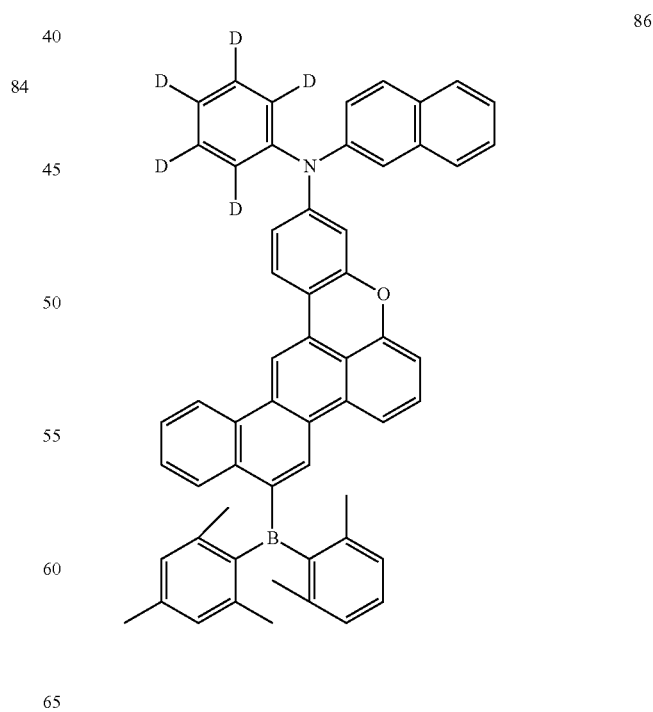

251
-continued
87
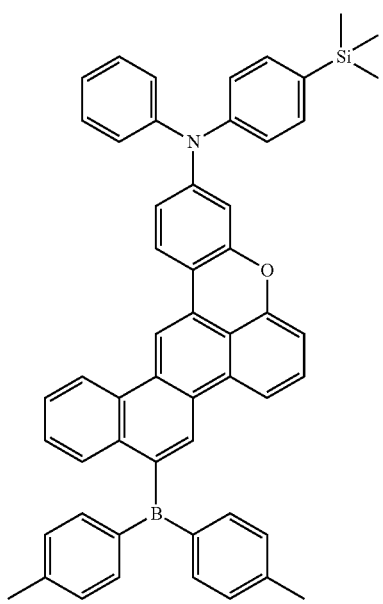
88
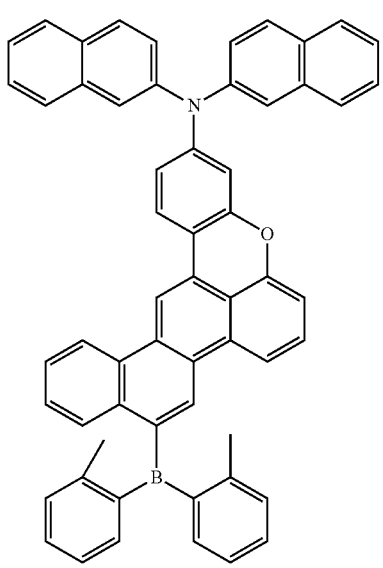
252
-continued
89
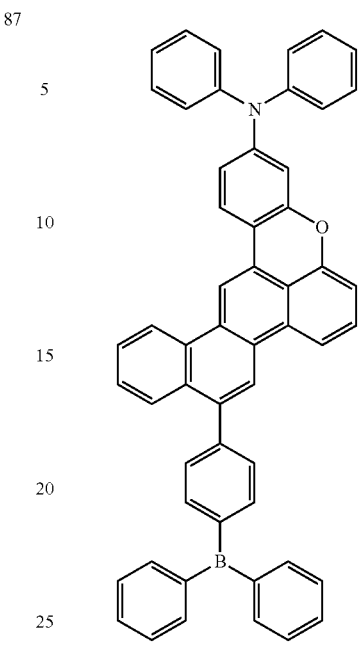
90
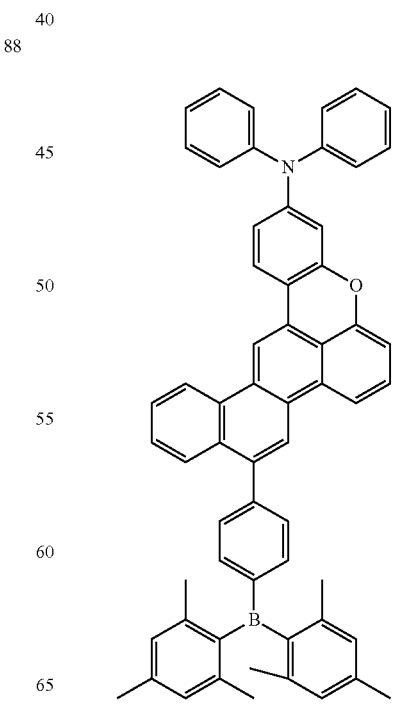

253
-continued
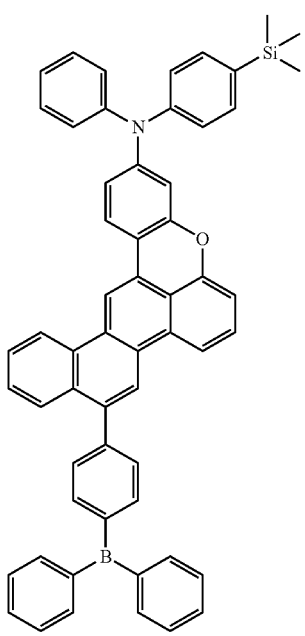
254
-continued
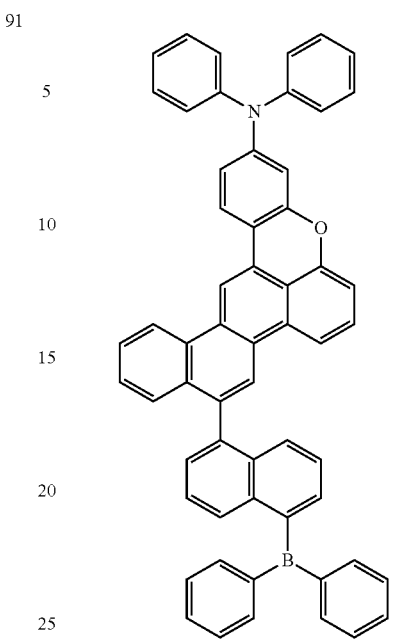
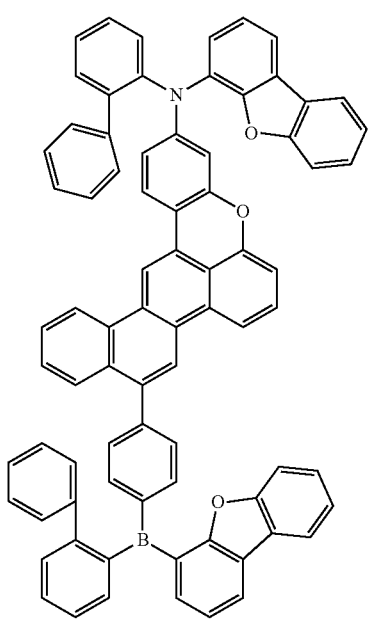
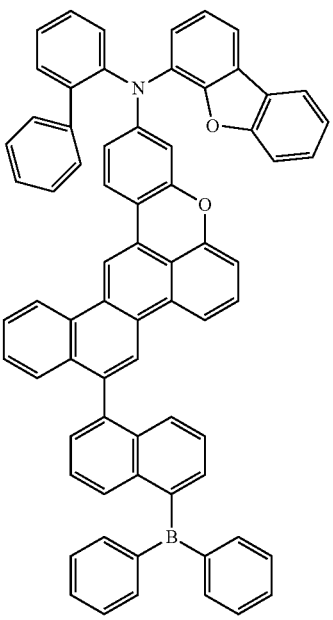

255
-continued
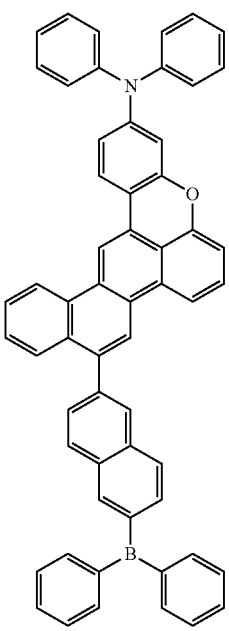
256
-continued
95
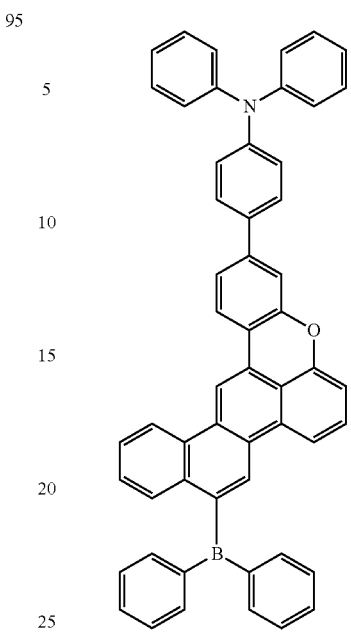
96
97
98
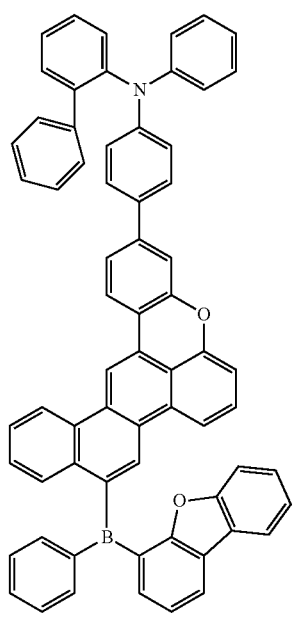

257
-continued
258
-continued
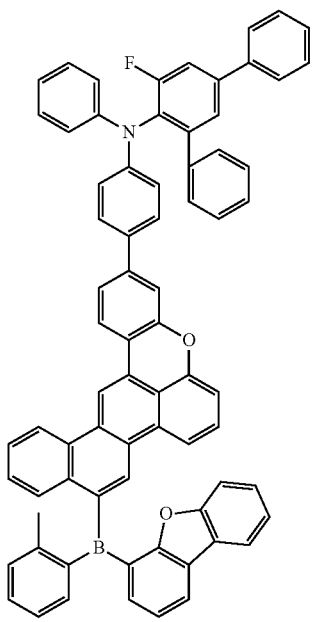
99
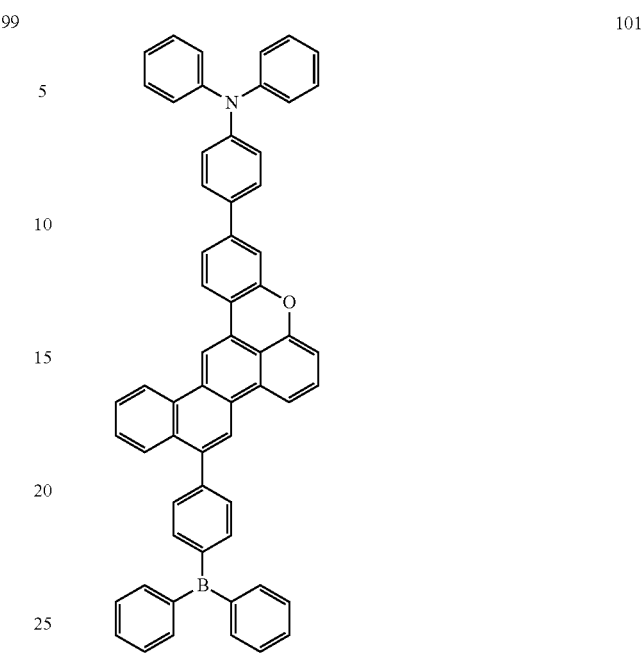
101
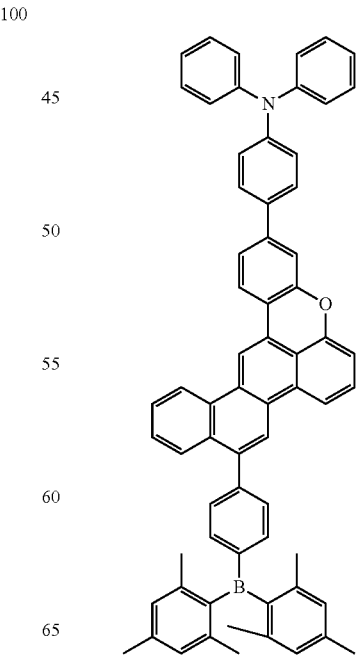
100
102

-continued

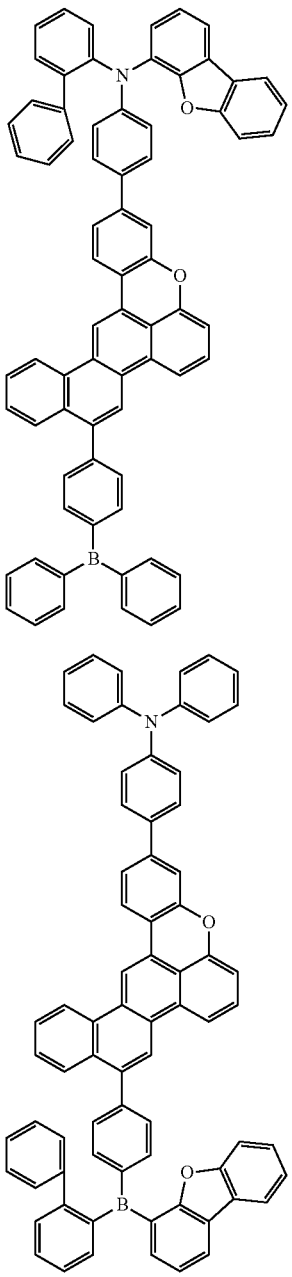

103

104

17. An organic light-emitting device, comprising:
a first electrode;
a second electrode facing the first electrode; and
an organic layer between the first electrode and the second electrode, the organic layer including an emission layer,
wherein the organic layer includes the condensed cyclic compound as claimed in claim 1.

18. The organic light-emitting device as claimed in claim 17, wherein
the first electrode is an anode,
the second electrode is a cathode, and
the organic layer includes:
a hole transport region between the first electrode and the emission layer, the hole transport region including at least one of a hole injection layer, a hole transport layer, a buffer layer, and an electron blocking layer, and
an electron transport region between the emission layer and the second electrode, the electron transport region including at least one selected from a hole blocking layer, an electron transport layer, and an electron injection layer.

19. The organic light-emitting device as claimed in claim 17, wherein the emission layer includes the condensed cyclic compound.

20. The organic light-emitting device as claimed in claim 19, wherein the emission layer further includes a compound represented by the following Formula 301:

$$Ar_{301}-[(L_{301})_{xb1}-R_{301}]_{xb2} \qquad \text{<Formula 301>}$$

wherein in Formula 301, $Ar_{301}$ is selected from:
a naphthalene, a heptalene, a fluorene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;
a naphthalene, a heptalene, a fluorene, a spiro-fluorenene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$), in which $Q_{301}$ to $Q_{303}$ are each independently selected from a hydrogen, a $C_1$-$C_{60}$ alkyl group, a $C_2$-$C_{60}$ alkenyl group, a $C_1$-$C_{60}$ aryl group, and a $C_1$-$C_{60}$ heteroaryl group;
each $L_{30}$ is independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;
$R_{301}$ is selected from:
a $C_1$-$C_{20}$ alkyl group and a $C_1$-$C_{20}$ alkoxy group;
a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 is selected from 0, 1, 2, and 3; and xb2 is selected from 1, 2, 3, and 4.

* * * * *